US008362203B2

(12) United States Patent
Cunningham et al.

(10) Patent No.: US 8,362,203 B2
(45) Date of Patent: Jan. 29, 2013

(54) NON-NATURAL PEPTIDES AS MODELS FOR THE DEVELOPMENT OF ANTIBIOTICS

(75) Inventors: Philip R. Cunningham, Troy, MI (US); Christine Sharon Chow, Detroit, MI (US); Nuwan Dinuka Abeydeera, College Station, TX (US); Tek Narayan Lamichhane, Silver Spring, MD (US)

(73) Assignee: Wayne State University, Detroit, MI (US)

( * ) Notice: Subject to any disclaimer, the term of this patent is extended or adjusted under 35 U.S.C. 154(b) by 196 days.

(21) Appl. No.: 12/703,255

(22) Filed: Feb. 10, 2010

(65) Prior Publication Data
US 2011/0021748 A1    Jan. 27, 2011

Related U.S. Application Data

(60) Provisional application No. 61/151,412, filed on Feb. 10, 2009.

(51) Int. Cl.
*C07K 7/00*    (2006.01)
(52) U.S. Cl. ....................................................... 530/329
(58) Field of Classification Search ................... 530/329
See application file for complete search history.

(56) References Cited

U.S. PATENT DOCUMENTS

| 4,772,555 | A | | 9/1988 | De Boer | |
|---|---|---|---|---|---|
| 4,873,316 | A | | 10/1989 | Meade et al. | |
| 5,821,058 | A | | 10/1998 | Smith et al. | |
| 5,981,280 | A | | 11/1999 | Fang et al. | |
| 6,136,558 | A | * | 10/2000 | Ballinger et al. | 435/69.1 |
| 7,081,341 | B2 | | 7/2006 | Cunningham | |
| 7,786,264 | B2 | * | 8/2010 | Xia et al. | 530/387.1 |
| 2004/0031072 | A1 | * | 2/2004 | La Rosa et al. | 800/278 |
| 2004/0053425 | A1 | * | 3/2004 | Link et al. | 436/526 |
| 2007/0271630 | A1 | * | 11/2007 | Boukharov et al. | 800/279 |

FOREIGN PATENT DOCUMENTS

| WO | WO-96/06106 | | 2/1996 |
|---|---|---|---|
| WO | WO-00/32619 | | 6/2000 |
| WO | WO-01/42445 | | 6/2001 |
| WO | WO-02/29019 | | 4/2002 |
| WO | WO-03/029459 | | 4/2003 |
| WO | WO 03/040172 A2 | * | 5/2003 |
| WO | WO 03/040187 A1 | * | 5/2003 |
| WO | WO-2004/003511 | | 1/2004 |
| WO | WO-2006/115570 | | 11/2006 |

OTHER PUBLICATIONS

Adachi, J. A., et al. (2002) "Natural history of enteroaggregative and enterotoxigenic *Escherichia coli* infection among US travelers to Guadalajara, Mexico"; *J Infect Dis* 185:1681-3.
Adang, A. E. P., et al. (1994) "Case Histories of Peptidomimetics: Progression from Peptides to Drugs"; *Recl. Trav. Chim. Pays-Bas* 113:63-78.

Agalarov, S. C., et al. (2000) "Structure of the S15,S6,S18-rRNA complex: assembly of the 30S ribosome central domain"; *Science* 288:107-112.
Ahn, J. M., et al. (2002) "Peptidomimetics and Peptide Backbone Modifications"; *Mini Rev. Med. Chem.* 2:463-473.
Andersson, D. I., et al. (1998) "Antibiotic resistance here to stay? Compensatory mutations restore virulence of resistant bacteria"; *Lakartidningen* 95:3940, 3943-4.
Ang, J. Y., et al. (2004) "Antibacterial resistance"; *Indian J Pediatr* 71:229-39.
Aoki, H., et al. (2002) "Oxazolidinone antibiotics target the P site on *Escherichia coli* ribosomes"; *Antimicrob Agents Chemother* 46:1080-5.
Asai, T., (1999) "Construction and initial characterization of *Escherichia coli* strains with few or no intact chromosomal rRNA operons"; *J. Bacteriol.* 181: 3803-3809.
Baldari et al. (1987) "A novel leader peptide which allows efficient secretion of a fragment of human interleukin 1β in *Saccharomyces cerevisiae*"; *EMBO J.* 6:229-234.
Banerji et al. (1983) "A lymphocyte-specific cellular enhancer is located downstream of the joining region in immunoglobulin heavy chain genes," *Cell* 33:729-740.
Barrick, J. E., et al. (2001) "Selection of RNA-Binding Peptides Using mRNA-Peptide Fusions"; *Methods* 3:287-293.
Barrick, J. E. & Roberts, R. W. (2002) "Sequence Analysis of an Artifical Family of RNA-Binding Peptides"; *Protein Sci.* 11:2688-2696.
Batey, R. T., et al. (1992) "Preparation of isotopically labeled ribonucleotides for multidimensional NMR spectroscopy of RNA"; *Nucleic Acids Res.* 20:4515-4523.
Batey, R. T. & Williamson, J. R. (1996) "Interaction of the *Bacillus stearothermophilus* ribosomal protein S15 with 16 S rRNA: II. Specificity determinants of RNA-protein recognition"; *J Mol Biol* 261:550-67.
Bhattacharya, S. K., et al. (2003) "Multidrug-resistant *Shigella dysenteriae* type 1 in south Asia"; *Lancet Infect Dis* 3:755.
Bjorkman, J., et al. (2000) "Effects of environment on compensatory mutations to ameliorate costs of antibiotic resistance"; *Science* 287:1479-82.
Bodhidatta, L., et al. (2002) "Bacterial enteric pathogens in children with acute dysentery in Thailand: increasing importance of quinolone-resistant Campylobacter"; *Southeast Asian J Trop Med Public Health* 33:752-7.
Boettger, E., et al., "Resistance to drugs targeting protein synthesis in mycobacteria," Trends in Microbiology; 2(10):416-421 (1994).
Brodersen, D. E., et al. (2002) "Crystal structure of the 30 S ribosomal subunit from *Thermus thermophilus*: structure of the proteins and their interactions with 16 S RNA"; *J Mol Biol* 316:725-68.
Brosius, J., et al. (1981); "Construction and fine mapping of recombinant plasmids containing the *rrnB* ribosomal RNA operon of *Escherichia coil*"; *Plasmid* 6:112-118.
Brow, D. A. & Noller, H. F. (1983) "Protection of ribosomal RNA from Kethoxal in polyribosomes"; *J. Mol. Biol.* 163:27-46.

(Continued)

*Primary Examiner* — Amber D. Steele
(74) *Attorney, Agent, or Firm* — Senniger Powers LLP

(57) ABSTRACT

Described herein are methods of screening one of the RNA hairpins in the small ribosomal subunit of bacteria to identify peptides that bind to it. The RNA hairpin target may be the 970 loop (aka helix 31 (h31)) or a modified version thereof. The identified peptides may inhibit protein synthesis and, therefore, may be used as a model for new antibiotics.

3 Claims, 93 Drawing Sheets

OTHER PUBLICATIONS

Bursavich, M. G. & Rich, D. H. (2002) "Designing Non-Peptide Peptidomimetics in the 21st Century: Inhibitors Targeting Conformational Ensembles"; *J. Med. Chem.* 45(3):541-558.

Byrne and Ruddle (1989) "Multiplex gene regulation: a two-tiered approach to transgene regulation in transgenic mice"; *Proc. Natl. Acad. Sci. USA* 86:5473-5477.

Calame and Eaton (1988) "Transcriptional controlling elements in the immunoglobulin and T cell receptor loci," *Adv. Immunol.* 43:235-275.

Calos, M.P. (1978) "DNA sequence for a low-level promoter of the *lac* repressor gene and an 'up' promoter mutation"; *Nature* 274:762-765.

Cannone, J. J., et al. (2002) "The Comparative RNA Web (CRW) Site: an online database of comparative sequence and structure information for ribosomal, intron, and other RNAs: Correction"; *BMC Bioinformatics* 3:15.

Capaldi, D. & Reese, C. (1994) "Use of the 1-(2-fluorophenyl)-4-methoxypiperidin-4-yl (Fpmp) and related protecting groups in oligoribonucleotide synthesis: stability of internucleotide linkages to aqueous acid"; *Nucl. Acids Res.* 22:2209-2216.

Carter, A. P., et al. (2001) "Crystal structure of an initiation factor bound to the 30S ribosomal subunit"; *Science* 291:498-501.

Carter, A. P., et al. (2000) "Functional insights from the structure of the 30S ribosomal subunit and its interactions with antibiotics"; *Nature* 407:340-8.

Carter-Muenchau, P. & Wolf, R. E. (1989) "Growth-rate dependent regualtion of 6-phosphogluconate dehydrogenase level mediated by an anti-Shine-Dalgarno sequence located within the *Escherichia coli* gnd structural gene"; *Proc. Natl. Acad. Sci. USA* 86:1138-1142.

Castagnoli, L., et al. (2001) "Alternative bacteriophage display systems"; *Comb Chem High Throughput Screen* 4:121-33.

Cha, J., et al. (1993) "New vectors for direct cloning of PCR products"; *Gene* 136:369-70.

Chen, H., et al. (1994) "Determination of the optimal aligned spacing between the Shine-Dalgarno sequence and the translation initiation codon of *Escherichia coli* mRNAs"; *Nucl. Acids Res.* 22: 4953-4957.

Chopra, I., et al. (2003) "The role of mutators in the emergence of antibiotic-resistant bacteria"; *Drug Resist Updat* 6:137-45.

Chow, C. S. & Bogdan, F. M. (1997) "A Structural Basis for RNA-Ligand Interactions"; *Chem. Rev.* 97:1489-1513.

Clarke, S. C., et al. (2003) "Virulence of enteropathogenic *Escherichia coli*, a global pathogen"; *Clin Microbiol Rev* 16(3):365-78.

Clarke, S. C., et al. (2002) "Enteropathogenic *Escherichia coli* infection: history and clinical aspects"; *Br J Biomed Sci* 59:123-7.

Collins, M. & Tami, T. A. (2003) "Methicillin-resistant *Staphylococcus aureus* (MRSA) in the practice of otolaryngology—an emerging community acquired organism?"; *Curr Opin Otolaryngol Head Neck Surg* 11:179-83.

Cunningham, P., et al. (1993) "Functional effects of base changes which further define the decoding center of *Escherichia coli* 16S ribosomal RNA: mutation of C1404, G1405, C1496, G1497, and U1498," *Biochemistry* 32: 7172-7180.

Cunningham, P. R., et al. (1988) "The role of 16S RNA in ribosome function: single base alterations and their effect on in vitro protein synthesis"; *Arch Biol Med Exp* (Santiago) 21:393-401.

Danner, S. & Belasco, J. G. (2001) "T7 phage display: a novel genetic selection system for cloning RNA-binding proteins from cDNA libraries"; *Proc Natl Acad Sci U S A* 98:12954-9.

de Boer, H. A., et al. (1983) "The tac promoter: a functional hybrid derived from the *trp* and *lac* promoters"; *Proc. Natl Acad. Sci. USA* 80:21-25.

De Stasio, E. A., et al. (1989) "Mutations in 16S ribosomal RNA disrupt antibiotic—RNA interactions"; *EMBO J* 8:1213-6.

Denman, R. et al. (1989) "In vitro assembly of 30S and 70S bacterial ribosomes from 16S RNA containing single base substitutions, insertions, and deletions around the decoding site (C1400)," *Biochemistry* 28:1002-1011.

Depardieu, F., et al. (2003) "VanD-type vancomycin-resistant *Enterococcus faecium* 10/96A"; *Antimicrob Agents Chemother* 47:7-18.

Dessen, A., et al. (2001) "Molecular mechanisms of antibiotic resistance in gram-positive pathogens"; *Curr Drug Targets Infect Disord* 1:63-77.

Dower, W. J., et al. (1988) "High efficiency transformation of *Escherichia coli* by high voltage electroporation"; *Nucl. Acids Res.* 16: 6127.

Edlund et al. (1985) "Cell-specific expression of the rat insulin gene: evidence for role f two distinct 5' flanking elements"; *Science* 230:912-916.

Enright, M. C. (2003) "The evolution of a resistant pathogen—the case of MRSA"; *Curr Opin Pharmacol* 3:474-9.

Evans, G. A. (2002) "The Oxazolidinones"; *Curr Infect Dis Rep* 4:17-27.

Fauci, A. S., et al.; (2005) "Emerging infectious diseases: a 10-year perspective from the national institute of allergy and infectious diseases." *Emerg Infect Dis*; 11: 519-25.

Fourmy, D., et al. (1996) "Structure of the A site of *Escherichia coli* 16S Ribosomal RNA Complexed with an Aminoglycoside Antibiotic"; *Science* 274:1367-1371.

Gabashvili, I. S., et al. (1999) "Major rearrangements in the 70S ribosomal 3D structure caused by a conformational switch in 16S ribosomal RNA"; *Embo J* 18:6501-7.

Goeddel (1990) "Systems for heterologous gene expression"; *Methods Enzymol.* 185:3-7.

Gomi, H., et al. (2001) "In vitro antimicrobial susceptibility testing of bacterial enteropathogens causing traveler's diarrhea in four geographic regions"; *Antimicrob Agents Chemother* 45:212-6.

Gonzales, R. D., et al. (2001) "Infections due to vancomycin-resistant *Enterococcus faecium* resistant to linezolid"; *Lancet* 357:1179.

Gottesman, S. (1990) "Minimizing proteolysis in *Escherichia coli*: genetic solutions"; *Methods Enzymol.* 185:119-128.

Govantes, F. et al. (1998) "Mechanism of translational coupling in the nifLA operon of *Klebsiella pneumoniae*"; *EMBO J.* 17(8):2368-2377.

Guerrant, R. L., et al. (2002) "Magnitude and impact of diarrheal diseases"; *Arch Med Res* 33:351-5.

Gutell, R. R. (1994) "Collection of small subunit (16S- and 16S-like) ribosomal RNA structures"; *Nucl. Acids Res.* 22: 3502-3507.

Gutell, R. R., et al. (1992) "Identifying constraints on the higher-order structure of RNA: continued development and application of comparative sequence analysis methods"; *Nucleic Acids Res* 20(21):5785-95.

Haddad, J., et al. (2002) "Design of Novel Antibiotics that Bind to the Ribosomal Acyltransfer Site"; *J. Am. Chem. Soc.* 124:3229-3237.

Hanahan, D. (1983) "Studies on transformation of *Escherichia coli* with plasmids"; *J. Mol. Biol.* 166:557-580.

Hancock, R. E. & Chapple, D. S. (1999) "Peptide Antibiotics"; *Antimicrob. Agents Chemother.* 43(6):1317-1323.

Harms, J., et al. (2001) "High Resolution Structure of the Large Ribosomal Subunit from a Mesophilic Eubacterium"; *Cell* 107:679-688.

Hartman, A. B., et al. (2003) "Epidemiology of tetracycline resistance determinants in *Shigella* spp. and enteroinvasive *Escherichia coli*: characterization and dissemination of tet(A)-1"; *J Clin Microbiol* 41:1023-32.

Herr, W., et al. (1979) "Mechanism of ribosomal subunit association: discrimination of specific sites in 16S RNA essential for association activity"; *J. Mol. Biol.* 130: 433-449.

Herrero, I. A., et al. (2002) "Nosocomial spread of linezolid-resistant, vancomycin-resistant *Enterococcus faecium*"; *N Engl J Med* 346:867-9.

Higuchi, R. (1989) "Using PCR to engineer DNA"; PCR Technology (Erlich, H.A., ed.), pp. 61-70, Stockton Press, New York.

Hui, A., et al. (1987) "Specialized ribosome system: preferential translation of a single mRNA species by a subpopulation of a mutated ribosome in *Escherichia coli*"; *Proc. Natl. Acad. Sci. U.S.A.* 84: 4762-4766.

Hui, A., et al. (1987) "Directing ribosomes to a single mRNA species: a method to study ribosomal RNA mutations and their effects on translation of a single messenger in *Escherichia coli*"; *Methods Enzymol.* 153: 432-452.

Hwang, S., et al. (1999) "Inhibition of Gene Expression in Human Cells Through Small-Molecule-RNA Interactions"; *Proc. Natl. Acad. Sci. USA* 96:12997-13002.

International Search Report dated Nov. 28, 2007 from PCT/US06/18320.

John, T. J. (1996) "Emerging & re-emerging bacterial pathogens in India"; *Indian J Med Res* 103:4-18.

Jones, R. N., et al. (2002) "Linezolid-resistant *Enterococcus faecium* isolated from a patient without prior exposure to an oxazolidinone: report from the SENTRY Antimicrobial Surveillance Program"; *Diagn Microbiol Infect Dis* 42:137-9.

Kaufman, et al. (1987) "Translation efficiency of polycistronic mRNAs and their utilization to express heterologous genes in Mammalian Cells"; *EMBO J.* 6:187-195.

Keren-Zur, M., et al. (1979) "Localization of the decoding region on the 30S *Escherichia coli* ribosomal subunit by affinity immunoelectron microscopy"; *Proc Natl Acad Sci U S A* 76:1054-8.

Kessel and Gruss (1990) "Murine developmental control genes"; *Science* 249:374-379.

Khan, W. A., et al. (1996) "Randomised controlled comparison of single-dose ciprofloxacin and doxycycline for cholera caused by *Vibrio cholerae* 01 or 0139"; *Lancet* 348:296-300.

Kieber-Emmons, T., et al. (1997) "Therapeutic Peptides and Peptidomimetics"; *Curr Opin. Biotech.* 8:435-441.

Kloss, P., et al. (1999) "Resistance mutations in 23 S rRNA identify the site of action of the protein synthesis inhibitor linezolid in the ribosomal peptidyl transferase center"; *J Mol Biol* 294:93-101.

Klostermeier, D., et al. (2004) "A three-fluorophore FRET assay for high-throughput screening of small-molecule inhibitors of ribosome assembly"; *Nucleic Acids Res.*; May 17; 32(9); pp. 2707-15.

Koosha, H., et al. (2000) "Alterations in the peptidyltransferase and decoding domains of ribosomal RNA suppress mutations in the elongation factor G gene"; *RNA.* 6: 1166-1173.

Kozak, M., "Regulation of translation via mRNA structure in prokaryotes and eukaryotes," Gene, 361:13-37 (2005).

Krzyzosiak, W., et al. (1987) "In vitro synthesis of 16S ribosomal RNA containing single base changes and assembly into a functional 30S ribosome"; *Biochemistry* 26:2353-64.

Kurjan and Herskowitz (1982) "Structure of a yeast pheromone gene (MF alpha): a putative alpha-factor precursor contains four tandem copies of mature alpha-factor," *Cell* 30:933-943.

Laios, E., et al. (2004) "Combinatorial genetic technology for the development of new anti-infectives"; *Arch Pathol Lab Med.*; Dec.; 128 (12); pp. 1351-9.

Lam, K. S., et al. (1995) "Application of a Dual Color Detection Scheme in the Screening of a Random Combinatorial Peptide Library"; *J. Immunol. Methods* 180:219-223.

Lee, K., et al. (2001) "Genetic approaches to studying protein synthesis: effects of mutations at Psi516 and A535 in *Escherichia coli* 16S rRNA"; *J Nutr* 131:2994S-3004S.

Lee, K., et al. (1997) "In vivo determination of RNA structure-function relationships: analysis of the 790 loop in ribosomal RNA"; *J. Mol. Biol.* 269:732-743.

Lee, K., et al. (1996) "Genetic analysis of the Shine-Dalgarno interaction: selection of alternative functional mRNA-rRNA combinations"; *RNA* 2: 1270-1285.

Lesley, S. A., et al. (1991) "Use of in vitro protein synthesis from polymerase chain reaction-generated templates to study interaction of *Escherichia coli* transcription factors with core RNA polymerase and for epitope mapping of monoclonal antibodies"; *J Biol Chem* 266(4): 2632-8.

Levy, S. B., et al. (2004) "Antibacterial resistance worldwide: causes, challenges and responses." *Nat Med.*; 10:S122-9.

Levy, S. B. (2001) "Antibiotic resistance: consequences of inaction"; *Clin Infect Dis* 33 Suppl 3:S124-9.

Lin-Goerke, J. L., et al. (1997) "PCR-based random mutagenesis using manganese and reduced dNTP concentration"; *Biotechniques* 23:409-12.

Lind, K. E., et al. (2002) "Structure-Based Computational Database Screening, In Vitro Assay, and NMR Assessment of Compunds that Target TAR RNA"; *Chem. Biol.* 9:185-193.

Lindenbaum, J., et al. (1967) "Antibiotic therapy of cholera in children"; *Bull World Health Organ* 37:529-38.

Llano-Sotelo, B., et al. (2002) "Aminoglycosides Modified by Resistance Enzymes Display Diminished Binding to the Bacterial Ribosomal Acyl-Transfer Site"; *Chemistry & Biology* 9:455-463.

Lodmell, J. S. & Dahlberg, A. E. (1997) "A conformational switch in *Escherichia coli* 16S ribosomal RNA during decoding of messenger RNA"; *Science* 277:1262-7.

Luria, S.E. & Burrous, J.W. (1957); "Hybridization between *Escherichia coli* and *Shigella*"; *J. Bacteriol.* 74:461-476.

Lynch, S. R., et al. (2003) "Comparison of X-Ray Crystal Structure of the 30S Subunit-Antibiotic Complex with NMR Structure of Decoding Site Oligonucleotide-Paromomycin Complex"; *Structure* 11:43-53.

Maden, B. E. (1990); "The numerous modified nucleotides in eukaryotic ribosomal RNA"; *Prog. Nucleic Acid Res. Mol. Biol.* 39: 241-303.

Magnet, S. & Blanchard, J.S. (2005) "Molecular insights into aminoglycoside action and resistance"; *Chem Rev*; 105:477-98.

Maidak, B. L. et al. (1996); "The ribosomal database project (RDP)"; *Nucl. Acids Res.* 24: 82-85.

Makosky, P. C. et al. (1987) "Spectinomycin resistance at site 1192 in 16S ribosomal RNA of *E. coli*: an analysis of three mutants," *Biochimie* 69: 885-889.

McManus, M. C. (1997) "Mechanisms of bacterial resistance to antimicrobial agents"; *Am J Health Syst Pharm* 54:1420-33; quiz pp. 1444-1446.

Miller, B. T., et al. (1997) "Peptide Biotinylation with Amine-Reactive Esters: Differential Side Chain Reactivity"; *Peptides* 18:1585-1595.

Miller, J.H. (1992) "Procedures for Working with lac," In *A Short Course in Bacterial Genetics*, (Miller, J. H., ed.), pp. 71-80, Cold Spring Harbor Laboratory Press, Cold Spring Harbor, NY.

Mirza, S. H., et al. (1996) "Multi-drug resistant typhoid: a global problem"; *J Med Microbiol* 44:317-9.

Moazed, D. & Noller, H.F. (1986) "Interconversion of active and inactive 30S ribosomal subunits is accompanied by a conformation change in the decoding region of 16S rRNA"; *J. Mol. Biol.* 191:483-493.

Morosyuk S. V., et al. (2001) "Structure and function of the conserved 690 hairpin in *Escherichia coli* 16S ribosomal RNA. II. NMR solution structure"; *J. Mol. Biol.* 307 (1):197-211.

Morosyuk S. V., et al. (2001) "Structure and function of the conserved 690 hairpin in *Escherichia coli* 16S ribosomal RNA. III. Functional analysis of the 690 loop"; *J. Mol. Biol.* 307 (1):213-228.

Morosyuk S. V., et al. (2000) "Structure and function of the conserved 690 hairpin in *Escherichia coli* 16S ribosomal RNA"; *J. Mol. Biol.* 300 (1):113-126.

Mucha, P., et al. (2002) "Interaction of RNA with Phage-Display Selected Peptides Analyzed by Capillary Electrophoresis Mobility Shift Assay"; *RNA* 8:698-704.

Mucha, P., et al. (2001) "Anticodon Domain Methylated Nucleosides of Yeast tRNA Phe are Significant Recognition Determinants in the Building of a Phage Display Selected Peptide"; *Biochemistry* 40:14191-14199.

Nandi, S., et al. (2004) "Gram-positive bacteria are a major reservoir of Class 1 antibiotic resistance integrons in poultry litter"; *Proc Natl Acad Sci U S A* 101:7118-22.

Nataro, J. P. & Kaper, J. B. (1998) "Diarrheagenic *Escherichia coli*"; *Clin Microbiol Rev* 11(1):142-201.

Nielsen, D. A. et al. (1989) "A highly sensitive, mixed-phase assay for chloramphenicol acetyltransferase activity in transfected cells," *Anal. Biochem.* 179: 19-23.

Nikonowicz, E. P., et al. (1992) "Preparation of 13C and 15N labelled RNAs for heteronuclear multi-dimensional NMR studies"; *Nucleic Acids Res.* 20(17):4507-4513.

O'Connor, M., et al. (2001) "Enhancement of translation by the epsilon element is independent of the sequence of the 460 region of 16S rRNA"; *Nucl. Acids Res.* 29: 1420-1425.

O'Connor, M., et al. (2001) "Mutagenesis of the peptidyltransferase center of 23S rRNA: the invariant U2449 is dispensable"; *Nucl. Acids Res.* 29: 710-715.

Ogle, J. M., et al. (2001) "Recognition of cognate transfer RNA by the 30S ribosomal subunit"; *Science* 292:897-902.

Oldfield, E. C., 3rd & Wallace, M. R. (2001) "The role of antibiotics in the treatment of infectious diarrhea"; *Gastroenterol Clin North Am* 30:817-36.

Orr, J. W., et al. (1998) "Protein and Mg(2+)-induced conformational changes in the S15 binding site of 16 S ribosomal RNA"; *J. Mol. Biol.* 275:453-464.

Papich, M. G. (2003) "Antimicrobial therapy for gastrointestinal diseases"; *Vet Clin North Am Equine Pract* 19:645-63.

Pelham, H. R. & Jackson, R. J. (1976) "An efficient mRNA-dependent translation system from reticulocyte lysates"; *Eur J Biochem* 67:247-56.

Peske, F., et al. (2004) "Conformational changes of the small ribosomal subunit during elongation factor G-dependent tRNA-mRNA translocation"; *J Mol Biol* 343:1183-94.

Pinkert, et al. (1987) "An albumin enhancer located 10 kb upstream functions along with its promoter to direct efficient, liver-specific expression in transgenic mice"; *Genes Dev.* 1:268-277.

Pioletti, M., et al. (2001) "Crystal structures of complexes of the small ribosomal subunit with tetracycline, edeine and IF3"; *Embo J* 20:1829-39.

Powers, T. et al. (1991) "A functional pseudoknot in 16S ribosomal RNA"; *EMBO J.* 10: 2203-2214.

Prince, J. B., et al. (1982) "Covalent crosslinking of tRNA1Val to 16S RNA at the ribosomal P site: identification of crosslinked residues"; *Proc Natl Acad Sci U S A* 79:5450-4.

Queen, C. & Baltimore, D. (1983) "Immunoglobulin gene transcription is activated by downstream sequence elements." *Cell* 33:741-748.

Recht, M. I., et al. (1999) "Effect of mutations in the A site of 16 S rRNA on aminoglycoside antibiotic-ribosome interaction"; *J Mol Biol;* 286:33-43.

Rodriguez-Correa, D. & Dahlberg, A. E. (2004) "Genetic evidence against the 16S ribosomal RNA helix 27 conformational switch model"; *RNA* 10:28-33.

Rothman, J. H. & Still, W. C. (1997) "Peptide-Binding Antibiotics: A Solid-Phase Assay for Screening Libraries of Vancomycin Mimics for Selective d-Ala-d-Ala Binding"; *Bioorg. Med. Chem. Lett.* 7:3159-3164.

Sander, P., et al. (2002) "Ribosomal and non-ribosomal resistance to oxazolidinones: species-specific idiosyncrasy of ribosomal alterations"; *Mol Microbiol* 46:1295-304.

Schottel, J. L., et al. (1984) "Effects of alterations in the translational control region on bacterial gene expression: use of *cat* gene constructs transcribed from the *lac* promoter as a model system"; *Gene* 28: 177-193.

Schultz et al. (1987) "Expression and secretion in yeast of a 400-kDa envelope glycoprotein derived from Epstein-Barr virus"; *Gene* 54:113-123.

Seed, B. (1987) "An LFA-3 cDNA encodes a phospholipid-linked membrane protein homologous to its receptor CD2"; *Nature* 329:840.

Serganov, A. A., et al. (1996) "The 16S rRNA binding site of *Thermus thermophilus* ribosomal protein S15: comparison with *Escherichia coli* S15, minimum site and structure"; *RNA* 2:1124-1138.

Sergiev, P. V., et al. (2000) "Mutations at position A960 of *Escherichia coli* 23S ribosomal RNA influence the structure of 5S ribosomal RNA and the peptidyltransferase region of 23 S ribosomal RNA"; *J. Mol. Biol.* 299:379-389.

Shine, J. & Dalgarno, L. (1974) "The 3'-terminal sequence of *Escherichia coli* 16S ribosomal RNA: complementarity to nonsense triplets and ribosome binding sites"; *Proc Natl Acad Sci U S A*; 71:1342-6.

Sigmund, C. D., et al. (1988) "Antibiotic resistance mutations in ribosomal RNA genes of *Escherichia coil*"; *Methods Enzymol.* 164: 673-690.

Sigmund, C. D., et al. (1984) "Antibiotic resistance in 16S and 23S ribosomal RNA genes of *Escherichia coli*"; *Nucl. Acids Res.* 12(11):4653-4663.

Sigmund, C. D. et al. (1982) "Erythromycin resistance due to a mutation in a ribosomal RNA operon of *Escherichia coli*"; *Proc. Natl. Acad. Sci. U.S.A.* 79: 5602-5606.

Sirinavin, S. & Garner, P. (2000) "Antibiotics for treating *Salmonella* gut infections"; *Cochrane Database Syst Rev*, CD001167.

Smith, D.B. and Johnson, K.S. (1988); "Single-step purification of polypeptides expressed in *Escherichia coli* as fusions with glutathione S-transferase"; *Gene* 67:31-40.

Stormo, G. D., et al. (1982) "Characterization of translational initiation sites in *Escherichia coli*"; *Nucleic Acids Res.* 10:2971-2996.

Tapprich, W., et al. (1989) "Mutation at position 791 *Escherichia coli* 16S ribosomal RNA affects processes involved in the initiation of protein synthesis"; *Proc. Natl Acad. Sci. USA* 86: 4927-4931.

Tapprich, W. & Hill, W. (1986); "Involvement of bases 787-795 of *Escherichia coli* 16S ribosomal RNA in ribosomal subunit association"; *Proc. Natl Acad. Sci. USA* 83: 556-560.

Triman, K., et al. (1989) "Isolation of temperature-sensitive mutants of 16S rRNA in *Escherichia coli*"; *J. Mol. Biol.* 209:645-653.

Tsiodras, S., et al. (2001) "Linezolid resistance in a clinical isolate of *Staphylococcus aureus*"; *Lancet* 358:207-8.

Vicens, Q. & Westhof, E. (2003) "Crystal structure of geneticin bound to a bacterial 16S ribosomal RNA A site oligonucleotide"; *J Mol Biol* 326:1175-88.

Vicens, Q. & Westhof, E. (2001) "Crystal Structure of Paromomycin Docked into the Eubacterial Ribosomal Decoding A Site"; *Structure* 9:647-658.

Vila-Sanjurjo, A. et al. (2001) "Mutational analysis of the conserved bases C1402 and A1500 in the center of the decoding domain of *Escherichia coli* 16S rRNA reveals an important tertiary interaction"; *J. Mol. Biol.* 308: 457-463.

Vila-Sanjurjo, A., et al. (1999) "Isolation of kasugamycin resistant mutants in the 16 S ribosomal RNA of *Escherichia coli*"; *J Mol Biol* 293:1-8.

Voulgaris, J., et al. (1999) "Increased *rrn* gene dosage causes intermittent transcription of rRNA in *Escherichia coli*"; *J. Bacteriol.* 181: 4170-4175.

Wada et al. (1992) "Codon usage tabulated from the Genbank genetic sequence data"; *Nucl. Acids Res.* 20:2111-2118.

Wallace, C. K., et al. (1968) "Optimal antibiotic therapy in cholera"; *Bull World Health Organ* 39:239-45.

Wang, Y., et al. (1997) "Specificity of Aminoglycoside Binding to RNA Constructs Derived from the 16S rRNA Decoding Region and the HIV-RRE Activator Region"; *Biochemistry* 36:768-779.

Wanke, C. A. (2001) "To know *Escherichia coli* is to know bacterial diarrheal disease"; *Clin Infect Dis* 32:1710-2.

Wilson, K. S. & Noller, H. F. (1998) "Mapping the position of translational elongation factor EF-G in the ribosome by directed hydroxyl radical probing"; *Cell* 92:131-9.

Wimberly, B. T., et al. (2000) "Structure of the 30S ribosomal subunit"; *Nature* 407:327-39.

Winkler, F. K., et al. (2001) "Structure-Based Approaches in Modern Drug Discovery Research"; *Ernst Schering Res. Found. Workshop* 34:123-142.

Winoto and Baltimore (1989) "A novel, inducible and T cell-specific enhancer located at the 3' end of the T cell receptor α locus"; *EMBO J.* 8:729-733.

Xiong, L., et al. (2000) "Oxazolidinone resistance mutations in 23S rRNA of *Escherichia coli* reveal the central region of domain V as the primary site of drug action"; *J Bacteriol* 182(19):5325-31.

Yanisch-Perron, C., et al. (1985) "Improved M13 phage cloning vectors and host strains: nucleotide sequences of the M13mp18 and pUC19 vectors"; *Gene* 33:103-119.

Yoshizawa, S., et al. (1998) "Structural Origins of Gentamicin Antibiotic Action"; *EMBO J.* 17:6437-6448.

Yusupov, M. M., et al. (2001) "Crystal Structure of the Ribosome at 5.5 Å Resolution"; *Science* 292:883-896.

Yusupova, G. Z., et al. (2001) "The path of messenger RNA through the ribosome"; *Cell* 106:233-41.

Zhang, K. & Zhao, H. (2000) "Assessing reliability of gene clusters from gene expression data"; *Funct Integr Genomics* 1:156-73.

Zhang, X., et al. (2000) "Quinolone antibiotics induce Shiga toxin-encoding bacteriophages, toxin production, and death in mice"; *J Infect Dis* 181:664-70.

Supplementary European Search Report dated Oct. 25, 2005 from EP 03 76 2329.

Supplementary European Search Report dated Dec. 23, 2008 from EP 06 75 9609.

\* cited by examiner

Figure 7
(A) ECh31WT    Predicted mass- 5783.5;   Observed mass- 5784.1
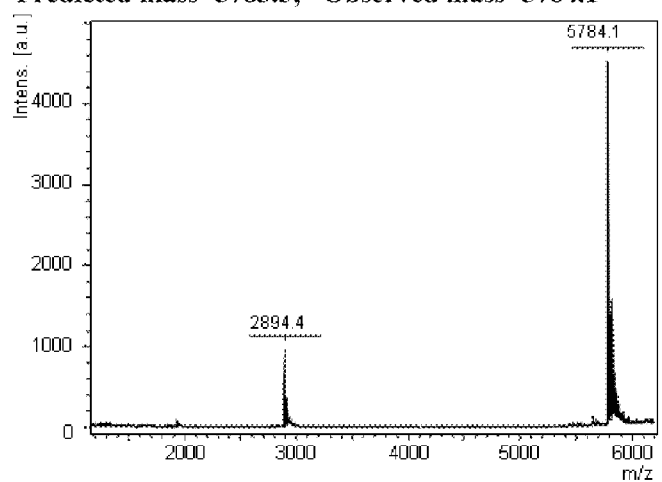
(B) ECh31M2G   Predicted mass- 5768.5;   Observed mass- 5767.4
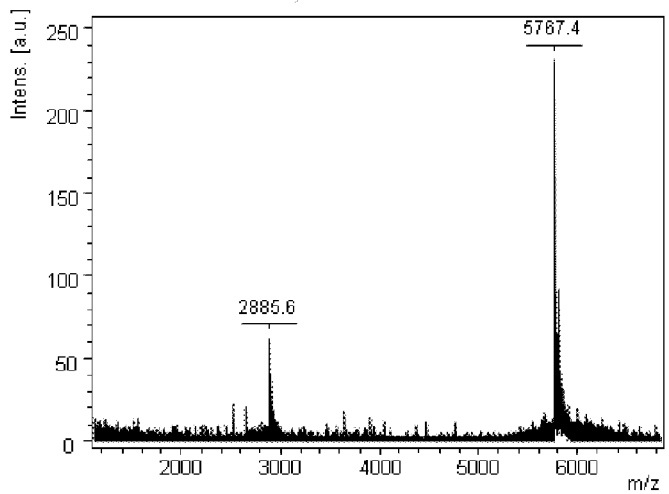

Figure 14
A
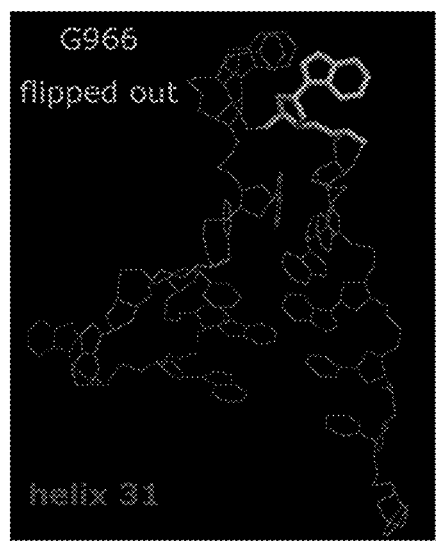
B
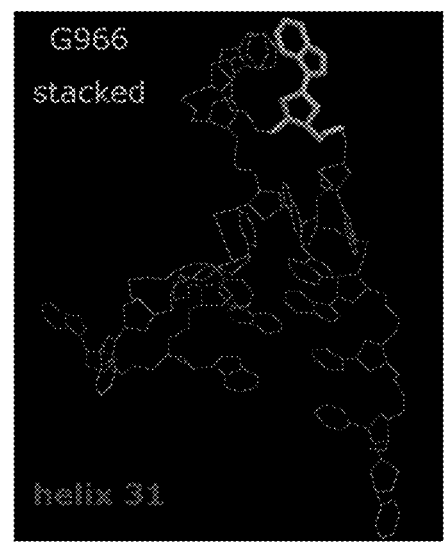

| Base Pair (960:975) | | | | | | | | | | | | | | | | Collective Score | |
|---|---|---|---|---|---|---|---|---|---|---|---|---|---|---|---|---|---|
| Aln | GC | CG | UA | AU | GU | UG | AA | AC | AG | CA | CC | CU | GA | GG | UC | UU | gap | Seq |
| T | -- | -- | 61.8* | 14.8* | -- | 22.4 | 0.2 | -- | 0.1 | -- | -- | -- | -- | -- | 0.2 | 0.2 | 0.3 | 6871 |
| 3 | -- | -- | 72.2 | -- | -- | 27.5 | -- | -- | -- | -- | -- | -- | -- | -- | -- | -- | 0.1 | 5561 |
| B | -- | -- | 92.1 | -- | -- | 7.5 | -- | -- | -- | -- | -- | -- | -- | -- | -- | -- | 0.2 | 4347 |
| A | -- | -- | -- | -- | -- | 100.0 | -- | -- | -- | -- | -- | -- | -- | -- | -- | -- | -- | 208 |
| C | -- | -- | 96.9 | -- | -- | -- | -- | -- | -- | -- | -- | -- | -- | -- | -- | 3.1 | -- | 162 |
| E | -- | -- | 0.7 | -- | -- | 99.0 | -- | -- | 0.1 | -- | -- | -- | -- | 0.2 | -- | -- | -- | 1006 |
| M | -- | -- | 6.5* | 89.1* | -- | 0.6 | 0.9 | 0.3 | 0.6 | -- | 0.1* | 0.3 | -- | -- | 1.0 | 0.7 | 0.1 | 1153 |

| Base Pair (961:974) | | | | | | | | | | | | | | | | Collective Score | |
|---|---|---|---|---|---|---|---|---|---|---|---|---|---|---|---|---|---|
| Aln | GC | CG | UA | AU | GU | UG | AA | AC | AG | CA | CC | CU | GA | GG | UC | UU | gap | Seq |
| T | 0.1* | 0.1 | 66.4* | 0.1 | 0.1 | 16.8 | 0.3 | -- | -- | 0.6 | 0.2 | 2.1* | -- | -- | 8.7 | 4.1 | 0.3 | 6856 |
| 3 | 0.1 | 0.1 | 68.1* | -- | -- | 20.8 | -- | -- | -- | -- | 0.2* | -- | -- | -- | 8.9 | 1.5 | 0.3 | 5546 |
| B | 0.1* | -- | 86.4* | -- | -- | 0.3 | -- | -- | -- | -- | 0.1 | -- | -- | -- | 11.3 | 1.2 | 0.4 | 4330 |
| A | -- | 3.3 | 3.3 | -- | -- | 78.5 | -- | -- | -- | -- | -- | -- | -- | -- | -- | 14.8 | -- | 209 |
| C | -- | -- | 96.9 | -- | -- | -- | -- | -- | -- | 2.5 | -- | -- | -- | -- | -- | 0.6 | -- | 163 |
| E | -- | 0.1 | 2.4 | -- | -- | 96.7* | -- | -- | -- | 0.4* | -- | -- | -- | 0.1 | 0.3 | -- | -- | 1007 |
| M | 0.6* | -- | 54.6* | 0.6 | 0.4 | 0.1 | 1.5 | 0.1 | -- | 3.3 | 0.3 | 12.3* | 0.1 | -- | 8.9 | 17.3 | -- | 1151 |

| Base Pair (962:973) | | | | | | | | | | | | | | | | Collective Score | |
|---|---|---|---|---|---|---|---|---|---|---|---|---|---|---|---|---|---|
| Aln | GC | CG | UA | AU | GU | UG | AA | AC | AG | CA | CC | CU | GA | GG | UC | UU | gap | Seq |
| T | 3.1* | 80.5* | 0.5* | -- | -- | 15.3 | -- | -- | -- | 0.1 | -- | -- | 0.1 | -- | -- | 0.3 | 6863 |
| 3 | 3.8* | 77.0* | 0.1* | -- | -- | 18.6 | -- | -- | -- | 0.1 | -- | -- | 0.1 | -- | -- | 0.2 | 5552 |
| B | 0.2* | 97.9* | -- | -- | -- | 1.2 | -- | -- | 0.2 | -- | -- | -- | 0.1 | -- | -- | 0.2 | 4339 |
| A | 100.0 | -- | -- | -- | -- | -- | -- | -- | -- | -- | -- | -- | -- | -- | -- | -- | 205 |
| C | -- | 95.7* | 1.8* | -- | -- | 2.5 | -- | -- | -- | -- | -- | -- | -- | -- | -- | -- | 163 |
| E | -- | 2.2 | 0.5 | -- | -- | 97.2 | -- | -- | -- | -- | -- | -- | -- | -- | 0.1 | -- | 1007 |
| M | 0.3* | 95.7* | 1.9* | 0.1* | 0.1 | 1.7 | -- | -- | -- | 0.1 | 0.1 | -- | -- | -- | -- | -- | 1151 |

| Base Pair (963:972) | | | | | | | | | | | | | | | | Collective Score | |
|---|---|---|---|---|---|---|---|---|---|---|---|---|---|---|---|---|---|
| Aln | GC | CG | UA | AU | GU | UG | AA | AC | AG | CA | CC | CU | GA | GG | UC | UU | gap | Seq |
| T | 99.4 | -- | -- | -- | -- | -- | -- | 0.1 | -- | -- | -- | -- | -- | -- | -- | -- | 0.4 | 6866 |
| 3 | 99.5 | -- | -- | -- | -- | -- | -- | 0.1 | -- | -- | 0.1 | -- | -- | -- | -- | -- | 0.3 | 5549 |
| B | 99.5 | -- | -- | -- | -- | -- | -- | 0.1 | -- | -- | -- | -- | -- | -- | -- | -- | 0.2 | 4342 |
| A | 100.0 | -- | -- | -- | -- | -- | -- | -- | -- | -- | -- | -- | -- | -- | -- | -- | -- | 201 |
| C | 100.0 | -- | -- | -- | -- | -- | -- | -- | -- | -- | -- | -- | -- | -- | -- | -- | -- | 163 |
| E | 99.5 | -- | -- | -- | -- | -- | -- | 0.2 | -- | -- | 0.1 | -- | -- | -- | -- | -- | 0.2 | 1006 |
| M | 99.9 | -- | -- | -- | 0.1 | -- | -- | -- | -- | -- | -- | -- | -- | -- | -- | -- | -- | 1153 |

```
      C A              C A              C A
   U     A          U     A          G     A
  C       C        C       C        U       C
   A     A          A     A          A     G
    G - C            G - C            G - C
    U · G            c - g            C - G
    U · G            u - a            U - A
    U · G            u - a            U - A
    g - c            g - c            g - c
    5'  3'           5'  3'           5'  3'
  HSh31UNMOD       HSh31ECstem       ECh31UNMOD
```

Figure 39

| Peptide sequences | | | | | | Frequency |
|---|---|---|---|---|---|---|
| A | A | L | A | S | S | R | 1 |
| A | A | N | M | N | I | S | 1 |
| A | H | S | S | L | V | H | 1 |
| A | L | I | P | K | P | R | 1 |
| A | M | I | N | P | Q | P | 1 |
| A | P | P | S | T | S | G | 1 |
| A | P | P | Q | P | L | K | 1 |
| A | Q | W | S | L | Y | Q | 1 |
| A | S | A | D | A | T | S | 1 |
| A | S | P | G | Y | A | R | 1 |
| A | T | P | L | W | L | K | 5 |
| A | T | P | T | Q | R | E | 3 |
| A | T | P | L | Y | L | R | 2 |
| A | W | L | F | T | S | E | 1 |
| D | H | S | P | I | L | R | 1 |
| D | I | R | T | Q | R | E | 4 |
| D | I | R | T | Q | T | R | 2 |
| D | I | R | A | T | Q | A | 2 |
| D | L | G | L | N | K | V | 1 |
| D | R | M | P | H | Y | F | 1 |
| D | T | L | A | I | H | Y | 1 |
| E | A | H | Y | P | L | N | 1 |
| E | P | L | Q | L | K | M | 2 |
| F | H | Q | H | T | S | K | 2 |
| F | P | N | V | K | D | P | 1 |
| F | P | S | T | I | T | P | 2 |
| F | V | R | P | F | P | L | 6 |
| F | V | R | P | F | A | L | 4 |
| F | V | R | P | Y | A | P | 2 |
| F | V | R | T | I | A | P | 2 |

| Peptide sequences | | | | | | Frequency |
|---|---|---|---|---|---|---|
| G | A | Y | A | A | N | K | 1 |
| G | G | P | Q | H | R | D | 1 |
| G | L | M | H | Q | A | A | 2 |
| H | I | L | P | W | P | H | 1 |
| H | L | E | N | H | P | M | 3 |
| H | L | Q | S | S | T | H | 1 |
| H | P | F | L | V | A | G | 2 |
| H | T | V | T | A | M | R | 1 |
| H | T | W | L | R | S | A | 1 |
| H | Y | A | D | S | M | V | 1 |
| I | P | T | L | P | S | S | 2 |
| I | S | R | L | F | S | L | 1 |
| K | H | D | V | Q | T | F | 1 |
| K | P | A | S | E | L | W | 1 |
| L | A | F | S | N | P | G | 2 |
| L | T | F | P | S | N | L | 1 |
| L | T | M | N | S | M | P | 1 |
| N | P | P | T | P | T | P | 2 |
| N | Q | P | H | V | R | A | 1 |
| Q | D | L | F | P | F | H | 1 |
| Q | G | Y | Y | R | P | P | 1 |
| Q | L | R | P | L | L | A | 1 |
| S | A | L | L | P | S | F | 1 |
| S | A | P | S | S | K | N | 1 |
| S | I | L | P | Y | P | Y | 4 |
| S | L | H | Y | F | S | P | 2 |
| S | L | L | L | H | A | P | 1 |
| S | S | F | P | P | L | L | 1 |

Figure 40A

| Peptide sequences | | | | | | | Frequency |
|---|---|---|---|---|---|---|---|
| S | T | P | R | P | P | T | 1 |
| S | V | L | P | P | P | L | 1 |
| T | A | K | P | M | V | A | 1 |
| T | A | N | L | W | R | L | 1 |
| T | A | P | G | A | N | R | 1 |
| T | E | V | Q | S | P | R | 1 |
| T | F | A | K | S | A | Y | 2 |
| T | F | N | F | Q | S | L | 1 |
| T | F | P | L | P | G | T | 1 |
| T | F | R | I | S | L | L | 1 |
| T | F | T | Q | M | H | Q | 1 |
| T | F | T | A | L | K | W | 1 |
| T | F | W | F | S | S | L | 1 |
| T | F | Y | Y | K | P | K | 1 |
| T | H | G | H | S | K | H | 1 |
| T | H | P | V | P | P | P | 1 |
| T | H | P | L | L | L | S | 1 |
| T | H | P | Q | I | K | A | 1 |
| T | H | P | L | Y | S | H | 1 |
| T | I | A | F | P | A | H | 1 |
| T | I | K | P | F | L | R | 2 |
| T | I | L | D | A | K | S | 1 |
| T | I | S | R | A | T | M | 1 |
| T | I | T | N | P | R | P | 2 |
| T | L | E | R | L | K | N | 1 |
| T | L | G | P | P | R | S | 1 |
| T | L | H | S | L | P | P | 1 |
| T | L | P | N | A | L | S | 1 |
| T | L | P | A | P | S | H | 1 |
| T | L | R | S | G | S | I | 1 |

| Peptide sequences | | | | | | | Frequency |
|---|---|---|---|---|---|---|---|
| T | L | T | T | L | T | N | 1 |
| T | L | T | F | F | H | R | 2 |
| T | L | W | D | L | I | P | 5 |
| T | L | W | S | F | M | P | 3 |
| T | L | W | V | P | S | R | 2 |
| T | L | T | T | L | T | N | 2 |
| T | M | L | Y | K | S | L | 1 |
| T | M | P | T | R | P | Q | 1 |
| T | Y | L | P | W | P | A | 5 |
| T | Y | L | P | W | P | P | 2 |
| T | Y | L | R | A | R | L | 2 |
| T | Y | P | F | A | P | W | 2 |
| V | H | S | T | W | R | G | 1 |
| V | N | H | F | A | Y | Y | 1 |
| W | S | W | K | Q | L | V | 2 |
| W | S | W | K | Q | L | V | 1 |
| Y | L | T | M | P | T | P | 1 |
| Y | Q | D | S | A | P | T | 1 |
| Y | W | W | Q | P | D | S | 1 |

Figure 40B

| Peptide sequences | Frequency |
|---|---|
| C V R P F A L | 5 |
| C V R A P T L | 2 |
| T V R P F T L | 2 |
| T L W D L I P | 2 |
| T L W P L S P | 2 |

Figure 41

| Peptide sequence | Frequency | Peptide sequence | Frequency |
|---|---|---|---|
| A A K I A L L | 1 | L N T L R S P | 1 |
| A D S D T A L | 1 | L P S C D F P | 2 |
| A F Y Y Y A A | 1 | L P V L P Q L | 1 |
| A H W Y P K T | 2 | L R F P S S P | 1 |
| A I H L T P L | 1 | L S Q S V G S | 1 |
| A P A V A T S | 1 | L S S L T M T | 1 |
| A P R I T N G | 1 | L S T I D L R | 1 |
| A R G P S A P | 2 | M H L P S R P | 1 |
| A S V F A L G | 1 | M T K Y A S Q | 1 |
| D A C P I S Y | 1 | N P M P P Y K | 1 |
| D P I A S H P | 1 | N Q Y N L S H | 1 |
| F I D H L S H | 2 | N T P S T S A | 1 |
| F L A R T P Q | 2 | P E T S Q S P | 1 |
| F L L T R Q P | 1 | Q L Q K L P P | 1 |
| F S T I N D A | 1 | Q N N Q A A T | 1 |
| G D A P K L H | 1 | Q P R L Y L G | 1 |
| G D G A L A R | 1 | Q R L S L D H | 1 |
| G H E Y K Q T | 1 | R D L R L T A | 2 |
| G L P A M A L | 1 | R L V A L S L | 1 |
| H H H P P L A | 5 | R Y G P E Q A | 1 |
| H H P P F P P | 2 | S A I N P T L | 1 |
| H P P S W G D | 2 | S F L N P R G | 1 |
| H P P H F P N | 2 | S H Y S L P L | 1 |
| H P T G L F R | 2 | S L Q L N H K | 1 |
| H P T G L F R | 1 | S L Y R V L L | 1 |
| H N H L G V H | 2 | S M I Y S K M | 1 |
| H S Q T Y L L | 2 | S M P S H Y P | 2 |
| H W V Q G G A | 1 | S N H G L P S | 2 |
| I A S Y T L R | 1 | S N L P S L T | 1 |
| I K N T D L L | 2 | S T V Q H A T | 1 |
| I L A P L S L | 1 | S W S M S L Q | 1 |
| I P I L T S A | 1 | S Y I S A Q P | 1 |
| I P P Q R P A | 1 | S Y L N R A L | 1 |
| I T P L L F T | 1 | T A L P R F F | 1 |
| K P F H N S T | 5 | T F F T P S L | 1 |
| K P V H H P R | 3 | T F F H V I L | 1 |
| K P G Y S S A | 2 | T G S S Y Q L | 1 |
| K P P Q V P L | 2 | T L N V S P Q | 1 |
| K P P H V P Y | 1 | T L S T P P R | 1 |
| K P V K V P R | 2 | T P A S L T T | 1 |
| L L G K P T H | 1 | | |
| L N A E T H P | 1 | | |

Figure 42

| Peptide sequence | | | | | | Frequency |
|---|---|---|---|---|---|---|
| T | P | P | G | T | S | L | 1 |
| T | Q | S | P | P | L | K | 1 |
| T | R | P | L | S | I | V | 1 |
| T | S | P | P | Y | A | P | 1 |
| T | S | R | S | C | P | R | 1 |
| T | T | A | E | Y | T | R | 1 |
| T | T | K | M | S | M | A | 1 |
| T | T | S | E | F | R | H | 1 |
| T | W | Q | I | S | M | Q | 1 |
| T | W | S | P | L | R | S | 1 |
| T | Y | Q | R | M | S | L | 1 |
| V | C | C | H | M | V | E | 1 |
| V | D | P | W | P | L | V | 1 |
| V | G | L | G | P | M | F | 1 |
| V | P | A | I | S | K | S | 1 |
| V | P | G | Y | P | S | Q | 1 |
| V | T | R | A | P | L | L | 1 |
| W | L | W | G | P | F | I | 1 |
| W | T | P | F | Q | V | F | 1 |
| W | V | V | S | P | T | P | 1 |
| Y | D | F | P | K | C | L | 1 |
| Y | I | W | L | P | S | S | 2 |
| Y | P | T | L | F | P | L | 1 |
| Y | Q | M | Q | C | A | S | 1 |
| Y | S | S | A | M | V | P | 2 |
| Y | T | V | P | P | L | R | 1 |
| Y | Y | V | N | P | S | S | 1 |

Figure 43

| Peptides | | | | | | |
|---|---|---|---|---|---|---|
| T | L | Q | P | G | G | A |
| S | L | L | A | H | P | H |
| H | L | E | N | H | P | M |
| S | L | V | S | H | P | M |
| H | L | E | N | H | P | M |
| G | L | D | H | H | P | P |
| I | P | E | W | H | P | Q |
| S | L | L | S | H | P | Q |
| T | L | L | A | H | P | Q |
| N | L | V | S | H | P | Q |
| I | P | E | W | H | P | Q |
| H | L | A | N | H | P | Q |
| S | L | L | A | H | P | Q |
| T | L | I | A | H | P | Q |
| S | L | I | A | H | P | Q |
| N | L | V | N | H | P | Q |
| N | L | L | N | H | P | Q |
| S | L | I | A | H | P | Q |
| I | S | S | T | H | P | Q |
| T | L | L | A | H | P | Q |
| I | P | E | W | H | P | Q |
| N | L | V | N | H | P | Q |
| T | L | L | A | H | P | Q |
| T | L | L | N | H | P | Q |
| T | L | L | A | H | P | Q |
| N | L | L | N | H | P | Q |
| T | L | I | S | H | P | Q |
| H | F | T | N | H | P | Q |
| I | A | P | N | H | P | Q |
| I | P | E | W | H | P | Q |
| T | L | L | N | H | P | Q |
| S | L | L | A | H | P | Q |
| T | L | I | S | H | P | Q |
| S | L | L | A | H | P | Q |
| N | L | L | N | H | P | Q |

| Peptides | | | | | | |
|---|---|---|---|---|---|---|
| S | L | L | A | H | P | Q |
| I | P | E | W | H | P | Q |
| N | L | L | N | H | P | Q |
| N | L | L | N | H | P | Q |
| P | L | L | A | H | P | Q |
| S | L | L | A | H | P | Q |
| N | L | L | N | H | P | Q |
| S | L | L | A | H | P | Q |
| T | L | L | A | H | P | Q |
| I | P | E | W | H | P | Q |
| T | L | I | S | H | P | Q |
| T | L | I | S | H | P | Q |
| N | L | V | N | H | P | Q |
| S | L | I | A | H | P | Q |
| N | L | L | N | H | P | Q |
| G | Y | D | K | H | P | Q |
| S | L | I | A | H | P | Q |
| N | L | L | N | H | P | Q |
| I | P | E | W | H | P | Q |
| I | P | Y | W | H | P | Q |
| H | L | I | A | H | P | Q |
| S | L | L | S | H | P | Q |
| N | L | L | N | H | P | Q |
| T | L | L | A | H | P | Q |
| S | L | L | A | H | P | Q |
| N | L | V | N | H | P | Q |
| Y | L | V | N | H | P | Q |
| N | L | I | S | H | P | Q |
| N | L | L | N | H | P | Q |
| H | Y | E | G | H | P | Q |

| Peptides | | | | | | |
|---|---|---|---|---|---|---|
| H | Y | E | G | H | P | Q |
| I | P | Y | W | H | P | Q |
| T | L | I | S | H | P | Q |
| I | P | Y | W | H | P | Q |
| T | L | L | A | H | P | Q |
| T | L | L | A | H | P | Q |
| I | A | P | N | H | P | Q |
| H | L | Y | A | H | P | Q |
| H | F | T | N | H | P | Q |
| N | L | L | N | H | P | Q |
| I | P | E | W | H | P | Q |
| H | L | Y | A | H | P | Q |
| N | P | T | K | H | Q | M |
| T | P | S | P | L | A | G |
| V | T | P | T | M | H | P |
| A | P | R | D | P | L | S |
| M | Q | S | H | Q | D | S |
| S | P | T | Y | Q | R | L |
| Y | M | E | H | S | R | V |
| H | R | I | S | W | P | S |
| D | P | F | F | Y | T | P |

Figure 44

| Sequences | Homology with | Position |
|---|---|---|
| TYLPWPA | ATP dependent RNA helicase, Dead/DeaH box family | 2 YLPWA 7 |
| | | 42 YLPWA 47 |
| FVRPFPL | Glycine tRNA synthetase, beta subunit | 1 FVRP 4 |
| | | 157 FVRP 160 |
| TLWDLIP | 23S rRNA m(5)U747 methyl transferase | 2 LWDL 5 |
| | | 237 LWDL 240 |
| | Leucyl-tRNA synthetase | 1 TLW 3 |
| | | 771 TLW 773 |
| CVRPFAL | Glycine tRNA synthetase, beta subunit | 4 PFAL 7 |
| | | 477 PFAL 480 |
| DIRTQRE | Predicted methyltransferase | 4 TQRE 7 |
| | | 224 TQRE 227 |
| | Valyl tRNA synthetase | 2 IRTQR 7 |
| | | 63 IR - QR 67 |
| ATPLWLK | Phenylalanine tRNA synthetase | 2 TPLWLK 7 |
| | | 230 TPLWLK 235 |
| HHHPPLA | Fused glutamine amidotransferase | 3 HPPLA 7 |
| | | 384 HPPLA 388 |
| KPFHNST | 16S rRNA m$^2$G1207 methylase | 2 PFHN 5 |
| | | 270 PFHD 273 |

14 (TLWDLIP)

15 (CVRPFAL)

16 (FVRPFPL)

17 (TYLPWPA)

18 (DIRTQRE)

Figure 70
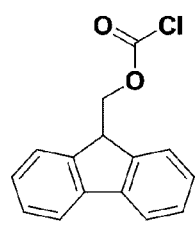
9-fluorenylmethoxycarbonyl chloride
(Fmoc-Cl)
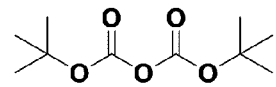
di-tert-butyl pyrocarbonate
(Boc)

Figure 73
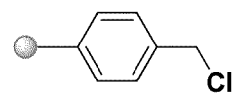
Merrifield resin
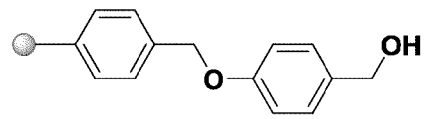
Wang resin
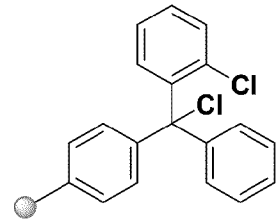
2-chlorotrityl resin
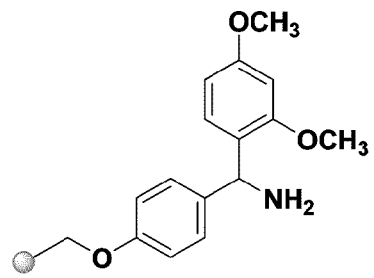
Rink amide resin

SEQUENCE LISTING

<160> NUMBER OF SEQ ID NOS: 283

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Tyr Leu Pro Trp Pro Ala
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Leu Trp Asp Leu Ile Pro
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Val Arg Pro Phe Ala Leu
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Thr Pro Leu Trp Leu Lys
1               5

<210> SEQ ID NO 6
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 6

Asp Ile Arg Thr Gln Arg Glu
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Phe Val Arg Pro Phe Ala Leu
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

His His His Pro Pro Leu Ala
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Pro Phe His Asn Ser Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Thr or Asn
<220> FEATURE:
<221> NAME/KEY: MOD_RES
<222> LOCATION: (3)..(3)
<223> OTHER INFORMATION: Leu, Ile or Val
<220> FEATURE:
<221> NAME/KEY: MOD_RES
<222> LOCATION: (4)..(4)
<223> OTHER INFORMATION: Ala or Asn

<400> SEQUENCE: 10

Xaa Leu Xaa Xaa His Pro Gln
1               5

<210> SEQ ID NO 11
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 11

Ser Ile Leu Pro Tyr Pro Tyr
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Pro Leu Thr Pro Leu Pro
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

His Ala Ile Tyr Pro Arg His
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Phe Val Arg Pro Phe Pro Leu
1               5

<210> SEQ ID NO 15
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2-N-methylguanosine
<220> FEATURE:
<221> NAME/KEY: modified_base
<222> LOCATION: (9)..(9)
<223> OTHER INFORMATION: 5-methylcytidine

<400> SEQUENCE: 15
guucgaugca acgcgaac                                                 18

<210> SEQ ID NO 16
<211> LENGTH: 18
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 16
guucgaugca acgcgaac                                                    18

<210> SEQ ID NO 17
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: 5-methylcytidine

<400> SEQUENCE: 17
guucgaugca acgcgaac                                                    18

<210> SEQ ID NO 18
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2-N-methylguanosine

<400> SEQUENCE: 18
guucgaugca acgcgaac                                                    18

<210> SEQ ID NO 19
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 2-N-methylguanosine
<220> FEATURE:
<221> NAME/KEY: modified_base
<222> LOCATION: (8)..(8)
<223> OTHER INFORMATION: 5-methylcytidine

<400> SEQUENCE: 19
uucgaugcaa cgcgaa                                                      16

<210> SEQ ID NO 20
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)
<223> OTHER INFORMATION: 1-methyl-3-(3-amino-3-carboxypropyl)-
      pseudouridine

<400> SEQUENCE: 20
uuugacucaa cacggg                                                      16

-continued

```
<210> SEQ ID NO 21
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
guuugacuca acacgggc                                                 18

<210> SEQ ID NO 22
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
guucgacuca acacgaac                                                 18

<210> SEQ ID NO 23
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
uuugacucaa cacggg                                                   16

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Ala Leu Ala Ser Ser Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Ala Asn Met Asn Ile Ser
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala His Ser Ser Leu Val His
1               5
```

```
<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Leu Ile Pro Lys Pro Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Met Ile Asn Pro Gln Pro
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Pro Pro Ser Thr Ser Gly
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Pro Pro Gln Pro Leu Lys
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Gln Trp Ser Leu Tyr Gln
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32
```

Ala Ser Ala Asp Ala Thr Ser
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Ser Pro Gly Tyr Ala Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Thr Pro Thr Gln Arg Glu
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Thr Pro Leu Tyr Leu Arg
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Trp Leu Phe Thr Ser Glu
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp His Ser Pro Ile Leu Arg
1               5

<210> SEQ ID NO 38
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 38

Asp Ile Arg Thr Gln Thr Arg
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Ile Arg Ala Thr Gln Ala
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Leu Gly Leu Asn Lys Val
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Arg Met Pro His Tyr Phe
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Thr Leu Ala Ile His Tyr
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Glu Ala His Tyr Pro Leu Asn
1               5

<210> SEQ ID NO 44

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Glu Pro Leu Gln Leu Lys Met
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Phe His Gln His Thr Ser Lys
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Phe Pro Asn Val Lys Asp Pro
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Phe Pro Ser Thr Ile Thr Pro
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Phe Val Arg Pro Tyr Ala Pro
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Phe Val Arg Thr Ile Ala Pro
```

```
<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Ala Tyr Ala Ala Asn Lys
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Gly Pro Gln His Arg Asp
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Leu Met His Gln Ala Ala
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

His Ile Leu Pro Trp Pro His
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

His Leu Glu Asn His Pro Met
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 55

His Leu Gln Ser Ser Thr His
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

His Pro Phe Leu Val Ala Gly
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

His Thr Val Thr Ala Met Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

His Thr Trp Leu Arg Ser Ala
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

His Tyr Ala Asp Ser Met Val
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ile Pro Thr Leu Pro Ser Ser
1               5

<210> SEQ ID NO 61
<211> LENGTH: 7
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 61

Ile Ser Arg Leu Phe Ser Leu
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys His Asp Val Gln Thr Phe
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Lys Pro Ala Ser Glu Leu Trp
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Ala Phe Ser Asn Pro Gly
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Thr Phe Pro Ser Asn Leu
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Thr Met Asn Ser Met Pro
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asn Pro Pro Thr Pro Thr Pro
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asn Gln Pro His Val Arg Ala
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Asp Leu Phe Pro Phe His
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Gly Tyr Tyr Arg Pro Pro
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Leu Arg Pro Leu Leu Ala
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ser Ala Leu Leu Pro Ser Phe
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Ala Pro Ser Ser Lys Asn
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Leu His Tyr Phe Ser Pro
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ser Leu Leu Leu His Ala Pro
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Ser Phe Pro Pro Leu Leu
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Thr Pro Arg Pro Pro Thr
1               5

<210> SEQ ID NO 78
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 78

Ser Val Leu Pro Pro Leu
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Ala Lys Pro Met Val Ala
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Ala Asn Leu Trp Arg Leu
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Thr Ala Pro Gly Ala Asn Arg
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Glu Val Gln Ser Pro Arg
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Phe Ala Lys Ser Ala Tyr
1               5

<210> SEQ ID NO 84
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Thr Phe Asn Phe Gln Ser Leu
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Thr Phe Pro Leu Pro Gly Thr
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Phe Arg Ile Ser Leu Leu
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Thr Phe Thr Gln Met His Gln
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Thr Phe Thr Ala Leu Lys Trp
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Thr Phe Trp Phe Ser Ser Leu
```

```
<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Thr Phe Tyr Tyr Lys Pro Lys
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Thr His Gly His Ser Lys His
1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Thr His Pro Val Pro Pro Pro
1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Thr His Pro Leu Leu Leu Ser
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Thr His Pro Gln Ile Lys Ala
1               5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 95

Thr His Pro Leu Tyr Ser His
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Thr Ile Ala Phe Pro Ala His
1               5

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Thr Ile Lys Pro Phe Leu Arg
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Thr Ile Leu Asp Ala Lys Ser
1               5

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Ile Ser Arg Ala Thr Met
1               5

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Thr Ile Thr Asn Pro Arg Pro
1               5

<210> SEQ ID NO 101
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 101

Thr Leu Glu Arg Leu Lys Asn
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Thr Leu Gly Pro Pro Arg Ser
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Thr Leu His Ser Leu Pro Pro
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Thr Leu Pro Asn Ala Leu Ser
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Thr Leu Pro Ala Pro Ser His
1               5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Thr Leu Arg Ser Gly Ser Ile
1               5
```

```
<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Thr Leu Thr Thr Leu Thr Asn
1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Thr Leu Thr Phe Phe His Arg
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Thr Leu Trp Ser Phe Met Pro
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Thr Leu Trp Val Pro Ser Arg
1               5

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Thr Met Leu Tyr Lys Ser Leu
1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112
```

```
Thr Met Pro Thr Arg Pro Gln
1               5

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Thr Tyr Leu Pro Trp Pro Pro
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Thr Tyr Leu Arg Ala Arg Leu
1               5

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Thr Tyr Pro Phe Ala Pro Trp
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Val His Ser Thr Trp Arg Gly
1               5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Val Asn His Phe Ala Tyr Tyr
1               5

<210> SEQ ID NO 118
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 118

Trp Ser Trp Lys Gln Leu Val
1               5

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Tyr Leu Thr Met Pro Thr Pro
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Tyr Gln Asp Ser Ala Pro Thr
1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Tyr Trp Trp Gln Pro Asp Ser
1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Cys Val Arg Ala Pro Thr Leu
1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Thr Val Arg Pro Phe Thr Leu
1               5

<210> SEQ ID NO 124
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Thr Leu Trp Pro Leu Ser Pro
1               5

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ala Ala Lys Ile Ala Leu Leu
1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ala Asp Ser Asp Thr Ala Leu
1               5

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ala Phe Tyr Tyr Tyr Ala Ala
1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ala His Trp Tyr Pro Lys Thr
1               5

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ala Ile His Leu Thr Pro Leu
```

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ala Pro Ala Val Ala Thr Ser
1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Pro Arg Ile Thr Asn Gly
1               5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ala Arg Gly Pro Ser Ala Pro
1               5

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Ser Val Phe Ala Leu Gly
1               5

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Asp Ala Cys Pro Ile Ser Tyr
1               5

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 135

Asp Pro Ile Ala Ser His Pro
1               5

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Phe Ile Asp His Leu Ser His
1               5

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Phe Leu Ala Arg Thr Pro Gln
1               5

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Phe Leu Leu Thr Arg Gln Pro
1               5

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Phe Ser Thr Ile Asn Asp Ala
1               5

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly Asp Ala Pro Lys Leu His
1               5

<210> SEQ ID NO 141
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 141

Gly Asp Gly Ala Leu Ala Arg
1               5

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly His Glu Tyr Lys Gln Thr
1               5

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Leu Pro Ala Met Ala Leu
1               5

<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

His His Pro Pro Phe Pro Pro
1               5

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

His Pro Pro Ser Trp Gly Asp
1               5

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

His Pro Pro His Phe Pro Asn
1               5
```

```
<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

His Pro Thr Gly Leu Phe Arg
1               5

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

His Asn His Leu Gly Val His
1               5

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

His Ser Gln Thr Tyr Leu Leu
1               5

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

His Trp Val Gln Gly Gly Ala
1               5

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ile Ala Ser Tyr Thr Leu Arg
1               5

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152
```

```
Ile Lys Asn Thr Asp Leu Leu
1               5

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ile Leu Ala Pro Leu Ser Leu
1               5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ile Pro Ile Leu Thr Ser Ala
1               5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ile Pro Pro Gln Arg Pro Ala
1               5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ile Thr Pro Leu Leu Phe Thr
1               5

<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Lys Pro Val His His Pro Arg
1               5

<210> SEQ ID NO 158
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 158

Lys Pro Gly Tyr Ser Ser Ala
1               5

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Lys Pro Pro Gln Val Pro Leu
1               5

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Lys Pro Pro His Val Pro Tyr
1               5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Lys Pro Val Lys Val Pro Arg
1               5

<210> SEQ ID NO 162
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Leu Leu Gly Lys Pro Thr His
1               5

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Leu Asn Ala Glu Thr His Pro
1               5

<210> SEQ ID NO 164
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Leu Asn Thr Leu Arg Ser Pro
1               5

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Leu Pro Ser Cys Asp Phe Pro
1               5

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Leu Pro Val Leu Pro Gln Leu
1               5

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Leu Arg Phe Pro Ser Ser Pro
1               5

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Leu Ser Gln Ser Val Gly Ser
1               5

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Leu Ser Ser Leu Thr Met Thr
```

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Leu Ser Thr Ile Asp Leu Arg
1               5

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Met His Leu Pro Ser Arg Pro
1               5

<210> SEQ ID NO 172
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Met Thr Lys Tyr Ala Ser Gln
1               5

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Asn Pro Met Pro Pro Tyr Lys
1               5

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Asn Gln Tyr Asn Leu Ser His
1               5

<210> SEQ ID NO 175
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 175

Asn Thr Pro Ser Thr Ser Ala
1               5

<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Pro Glu Thr Ser Gln Ser Pro
1               5

<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gln Leu Gln Lys Leu Pro Pro
1               5

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gln Asn Asn Gln Ala Ala Thr
1               5

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gln Pro Arg Leu Tyr Leu Gly
1               5

<210> SEQ ID NO 180
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gln Arg Leu Ser Leu Asp His
1               5

<210> SEQ ID NO 181
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 181

Arg Asp Leu Arg Leu Thr Ala
1               5

<210> SEQ ID NO 182
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Arg Leu Val Ala Leu Ser Leu
1               5

<210> SEQ ID NO 183
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Arg Tyr Gly Pro Glu Gln Ala
1               5

<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ser Ala Ile Asn Pro Thr Leu
1               5

<210> SEQ ID NO 185
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ser Phe Leu Asn Pro Arg Gly
1               5

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ser His Tyr Ser Leu Pro Leu
1               5
```

```
<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ser Leu Gln Leu Asn His Lys
1               5

<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ser Leu Tyr Arg Val Leu Leu
1               5

<210> SEQ ID NO 189
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ser Met Ile Tyr Ser Lys Met
1               5

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ser Met Pro Ser His Tyr Pro
1               5

<210> SEQ ID NO 191
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ser Asn His Gly Leu Pro Ser
1               5

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192
```

Ser Asn Leu Pro Ser Leu Thr
1               5

<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ser Thr Val Gln His Ala Thr
1               5

<210> SEQ ID NO 194
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ser Trp Ser Met Ser Leu Gln
1               5

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Ser Tyr Ile Ser Ala Gln Pro
1               5

<210> SEQ ID NO 196
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ser Tyr Leu Asn Arg Ala Leu
1               5

<210> SEQ ID NO 197
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Thr Ala Leu Pro Arg Phe Phe
1               5

<210> SEQ ID NO 198
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 198

Thr Phe Phe Thr Pro Ser Leu
1               5

<210> SEQ ID NO 199
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Thr Phe Phe His Val Ile Leu
1               5

<210> SEQ ID NO 200
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Thr Gly Ser Ser Tyr Gln Leu
1               5

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Thr Leu Asn Val Ser Pro Gln
1               5

<210> SEQ ID NO 202
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Thr Leu Ser Thr Pro Pro Arg
1               5

<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Thr Pro Ala Ser Leu Thr Thr
1               5

<210> SEQ ID NO 204

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Thr Pro Pro Gly Thr Ser Leu
1               5

<210> SEQ ID NO 205
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Thr Gln Ser Pro Pro Leu Lys
1               5

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Thr Arg Pro Leu Ser Ile Val
1               5

<210> SEQ ID NO 207
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Thr Ser Pro Pro Tyr Ala Pro
1               5

<210> SEQ ID NO 208
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Thr Ser Arg Ser Cys Pro Arg
1               5

<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Thr Thr Ala Glu Tyr Thr Arg
```

<210> SEQ ID NO 210
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Thr Thr Lys Met Ser Met Ala
1               5

<210> SEQ ID NO 211
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Thr Thr Ser Glu Phe Arg His
1               5

<210> SEQ ID NO 212
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Thr Trp Gln Ile Ser Met Gln
1               5

<210> SEQ ID NO 213
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Thr Trp Ser Pro Leu Arg Ser
1               5

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Thr Tyr Gln Arg Met Ser Leu
1               5

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 215

Val Cys Cys His Met Val Glu
1               5

<210> SEQ ID NO 216
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Val Asp Pro Trp Pro Leu Val
1               5

<210> SEQ ID NO 217
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Val Gly Leu Gly Pro Met Phe
1               5

<210> SEQ ID NO 218
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Val Pro Ala Ile Ser Lys Ser
1               5

<210> SEQ ID NO 219
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Val Pro Gly Tyr Pro Ser Gln
1               5

<210> SEQ ID NO 220
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Val Thr Arg Ala Pro Leu Leu
1               5

<210> SEQ ID NO 221
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 221

Trp Leu Trp Gly Pro Phe Ile
1               5

<210> SEQ ID NO 222
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Trp Thr Pro Phe Gln Val Phe
1               5

<210> SEQ ID NO 223
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Trp Val Val Ser Pro Thr Pro
1               5

<210> SEQ ID NO 224
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Tyr Asp Phe Pro Lys Cys Leu
1               5

<210> SEQ ID NO 225
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Tyr Ile Trp Leu Pro Ser Ser
1               5

<210> SEQ ID NO 226
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Tyr Pro Thr Leu Phe Pro Leu
1               5
```

```
<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Tyr Gln Met Gln Cys Ala Ser
1               5

<210> SEQ ID NO 228
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Tyr Ser Ser Ala Met Val Pro
1               5

<210> SEQ ID NO 229
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Tyr Thr Val Pro Pro Leu Arg
1               5

<210> SEQ ID NO 230
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Tyr Tyr Val Asn Pro Ser Ser
1               5

<210> SEQ ID NO 231
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Thr Leu Gln Pro Gly Gly Ala
1               5

<210> SEQ ID NO 232
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232
```

```
Ser Leu Leu Ala His Pro His
1               5

<210> SEQ ID NO 233
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ser Leu Val Ser His Pro Met
1               5

<210> SEQ ID NO 234
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Gly Leu Asp His His Pro Pro
1               5

<210> SEQ ID NO 235
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ile Pro Glu Trp His Pro Gln
1               5

<210> SEQ ID NO 236
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ser Leu Leu Ser His Pro Gln
1               5

<210> SEQ ID NO 237
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Thr Leu Leu Ala His Pro Gln
1               5

<210> SEQ ID NO 238
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 238

Asn Leu Val Ser His Pro Gln
1               5

<210> SEQ ID NO 239
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

His Leu Ala Asn His Pro Gln
1               5

<210> SEQ ID NO 240
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Ser Leu Leu Ala His Pro Gln
1               5

<210> SEQ ID NO 241
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Thr Leu Ile Ala His Pro Gln
1               5

<210> SEQ ID NO 242
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ser Leu Ile Ala His Pro Gln
1               5

<210> SEQ ID NO 243
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Asn Leu Val Asn His Pro Gln
1               5

<210> SEQ ID NO 244

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Asn Leu Leu Asn His Pro Gln
1               5

<210> SEQ ID NO 245
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ile Ser Ser Thr His Pro Gln
1               5

<210> SEQ ID NO 246
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Thr Leu Leu Asn His Pro Gln
1               5

<210> SEQ ID NO 247
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Thr Leu Ile Ser His Pro Gln
1               5

<210> SEQ ID NO 248
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

His Phe Thr Asn His Pro Gln
1               5

<210> SEQ ID NO 249
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ile Ala Pro Asn His Pro Gln
```

<210> SEQ ID NO 250
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Pro Leu Leu Ala His Pro Gln
1               5

<210> SEQ ID NO 251
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Gly Tyr Asp Lys His Pro Gln
1               5

<210> SEQ ID NO 252
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ile Pro Tyr Trp His Pro Gln
1               5

<210> SEQ ID NO 253
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

His Leu Ile Ala His Pro Gln
1               5

<210> SEQ ID NO 254
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Tyr Leu Val Asn His Pro Gln
1               5

<210> SEQ ID NO 255
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Asn Leu Ile Ser His Pro Gln
1               5

<210> SEQ ID NO 256
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

His Tyr Glu Gly His Pro Gln
1               5

<210> SEQ ID NO 257
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

His Leu Tyr Ala His Pro Gln
1               5

<210> SEQ ID NO 258
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Asn Pro Thr Lys His Gln Met
1               5

<210> SEQ ID NO 259
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Thr Pro Ser Pro Leu Ala Gly
1               5

<210> SEQ ID NO 260
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Val Thr Pro Thr Met His Pro
1               5

<210> SEQ ID NO 261
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 261

Ala Pro Arg Asp Pro Leu Ser
1               5

<210> SEQ ID NO 262
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Met Gln Ser His Gln Asp Ser
1               5

<210> SEQ ID NO 263
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Ser Pro Thr Tyr Gln Arg Leu
1               5

<210> SEQ ID NO 264
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Tyr Met Glu His Ser Arg Val
1               5

<210> SEQ ID NO 265
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

His Arg Ile Ser Trp Pro Ser
1               5

<210> SEQ ID NO 266
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Asp Pro Phe Phe Tyr Thr Pro
1               5
```

```
<210> SEQ ID NO 267
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Asp Glu Ala Asp
1

<210> SEQ ID NO 268
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Asp Glu Ala His
1

<210> SEQ ID NO 269
<211> LENGTH: 5
<212> TYPE: PRT
<213> ORGANISM: Escherichia coli

<400> SEQUENCE: 269

Tyr Leu Pro Trp Ala
1               5

<210> SEQ ID NO 270
<211> LENGTH: 4
<212> TYPE: PRT
<213> ORGANISM: Escherichia coli

<400> SEQUENCE: 270

Phe Val Arg Pro
1

<210> SEQ ID NO 271
<211> LENGTH: 4
<212> TYPE: PRT
<213> ORGANISM: Escherichia coli

<400> SEQUENCE: 271

Leu Trp Asp Leu
1

<210> SEQ ID NO 272
<211> LENGTH: 4
<212> TYPE: PRT
<213> ORGANISM: Escherichia coli

<400> SEQUENCE: 272

Pro Phe Ala Leu
1

<210> SEQ ID NO 273
<211> LENGTH: 4
<212> TYPE: PRT
<213> ORGANISM: Escherichia coli

<400> SEQUENCE: 273
```

Thr Gln Arg Glu
1

<210> SEQ ID NO 274
<211> LENGTH: 5
<212> TYPE: PRT
<213> ORGANISM: Escherichia coli

<400> SEQUENCE: 274

Ile Arg Thr Gln Arg
1               5

<210> SEQ ID NO 275
<211> LENGTH: 5
<212> TYPE: PRT
<213> ORGANISM: Escherichia coli

<400> SEQUENCE: 275

Ile Arg Tyr Gln Arg
1               5

<210> SEQ ID NO 276
<211> LENGTH: 6
<212> TYPE: PRT
<213> ORGANISM: Escherichia coli

<400> SEQUENCE: 276

Thr Pro Leu Trp Leu Lys
1               5

<210> SEQ ID NO 277
<211> LENGTH: 5
<212> TYPE: PRT
<213> ORGANISM: Escherichia coli

<400> SEQUENCE: 277

His Pro Pro Leu Ala
1               5

<210> SEQ ID NO 278
<211> LENGTH: 4
<212> TYPE: PRT
<213> ORGANISM: Escherichia coli

<400> SEQUENCE: 278

Pro Phe His Asn
1

<210> SEQ ID NO 279
<211> LENGTH: 4
<212> TYPE: PRT
<213> ORGANISM: Escherichia coli

<400> SEQUENCE: 279

Pro Phe His Asp
1

<210> SEQ ID NO 280
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280

-continued

```
gcaagctgat aaaccgatac aat                                         23

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
ccctcatagt tagcgtaacg                                             20

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
tccagacgtt agtaaatgaa                                             20

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
tccagacgtt agtaaatgaa                                             20
```

NON-NATURAL PEPTIDES AS MODELS FOR THE DEVELOPMENT OF ANTIBIOTICS

RELATED APPLICATIONS

This application claims the benefit of priority to U.S. Provisional Patent Application Ser. No. 61/151,412, filed Feb. 10, 2009, which is hereby incorporated by reference in its entirety.

BACKGROUND

The increasing emergence of antibiotic resistant bacteria is a global problem. [Fauci, A. S., Touchette, N. A. & Folkers, G. K. (2005). Emerging infectious diseases: a 10-year perspective from the national institute of allergy and infectious diseases. *Emerg Infect Dis* 11, 519-25.] Antibiotic resistant bacteria were responsible for 17 million deaths world-wide in 1996 with an estimated cost of $30 billion dollars in the United States alone. [Levy, S. B. & Marshall, B. (2004). Antibacterial resistance worldwide: causes, challenges and responses. *Nat Med* 10, S122-9.] Funding for new research by major pharmaceutical companies has steadily decreased, as has the development of new antimicrobials. Furthermore, the rapid emergence of resistance to new classes of antimicrobials has limited their use in clinical settings. These trends, if continued, will result in a lack of effective antimicrobials for a majority of bacterial infections in the years to come.

The mechanism of resistance for all currently-used therapeutics has been determined. There are several general mechanisms of bacterial resistance: 1) reduction of antibiotic uptake, 2) transport of the antibiotic out of the cell, 3) enzymatic inactivation of the antibiotic, 4) use of an alternative metabolic pathway, 5) titration of the antibiotic by overproduction of the target, and 6) target modification so that it is no longer recognized by the antibiotic. [Laios, E., Waddington, M., Saraiya, A. A., Baker, K. A., O'Connor, E., Pamarathy, D. & Cunningham, P. R. (2004). Combinatorial genetic technology for the development of new anti-infectives. *Arch Pathol Lab Med* 128, 1351-9.] Of these mechanisms, target modification is the most common mechanism of resistance for newly-developed antibiotics. The specificity of antibiotic-target binding involves the structure as well as the sequence of the target. Mutations that affect the sequence or structure of the target without affecting function may reduce or eliminate antibiotic binding and result in resistance. For example, aminoglycoside antibiotics target the A-site of bacterial 16 S ribosomal RNA and increase the translational error rate. [Magnet, S. & Blanchard, J. S. (2005). Molecular insights into aminoglycoside action and resistance. *Chem Rev* 105, 477-98.] A single A1408G mutation reduces ribosome function by approximately 30% but completely disrupts binding of certain aminoglycoside antibiotics. [Recht, M. I., Douthwaite, S., Dahlquist, K. D. & Puglisi, J. D. (1999). Effect of mutations in the A site of 16 S rRNA on aminoglycoside antibiotic-ribosome interaction. *J Mol Biol* 286, 33-43.] Therefore, targeting an antibiotic to all possible mutants of a particular ribosomal region that maintain function would eliminate this mechanism of resistance.

Nearly half of all naturally-occurring antibiotics target an aspect of protein synthesis and more specifically the ribosome. The 70 S bacterial ribosome is responsible for the translation of messenger RNA (mRNA) into protein. Ribosome crystal structures and biochemical studies have shown that the RNA is the catalytically-active component of the ribosome, therefore, the ribosome is a ribozyme. [Yusupov, M. M., Yusupova, G. Z., Baucom, A., Lieberman, K., Earnest, T. N., Cate, J. H. & Noller, H. F. (2001). Crystal structure of the ribosome at 5.5 A resolution. *Science* 292, 883-96; Wimberly, B. T., Brodersen, D. E., Clemons, W. M., Jr., Morgan-Warren, R. J., Carter, A. P., Vonrhein, C., Hartsch, T. & Ramakrishnan, V. (2000). Structure of the 30S ribosomal subunit. *Nature* 407, 327-39.] The essential nature of the protein synthesis process makes the ribosomal RNA (rRNA) an ideal drug target.

Studies of the rRNA sequences from numerous different organisms have shown that the overall structure of the ribosome is conserved within all three domains of life. Phylogenetic analysis of rRNA sequences has provided much information about pairing interactions and nucleotide conservation. Each of these analyses, however, employs genomic or organelle rRNA sequences. These sequences are constrained by their essential role in protein synthesis. As a result, very little or no sequence variation is observed in rRNA regions believed to be functionally important, since even subtle changes to the structure surrounding critical residues may reduce function and affect fidelity. Additionally, these conserved sites may be structurally important rather than functionally important. Therefore, drugs that target these sites would allow for resistance if the sequence can mutate but maintain the functional structure. An ideal drug would target all possible functional mutations at the target site.

SUMMARY

In certain embodiments, the invention relates to screening one of the RNA hairpins in the small ribosomal subunit of bacteria to identify peptides that bind to it and therefore have the potential to serve as leads for further development into antibiotics.

In certain embodiments, the invention relates to the peptides so identified.

In certain other embodiments, the invention relates to the use of the RNA hairpin, 970 loop aka helix 31 (h31), as a target, and the peptides identified herein.

In certain further embodiments, the invention relates to derivatives of the identified peptides.

In certain other embodiments, the invention relates to peptides that inhibit protein synthesis.

In certain other embodiments, the invention relates to methods of using the peptides to create new antibiotics.

TOMCl, room temperature, 3 h; (iii) 2-cyanoethyldiisopropylphosphoramido-chloridite, iPr$_2$NEt, dichloromethane, room temperature, 2 h.

Figure 5:
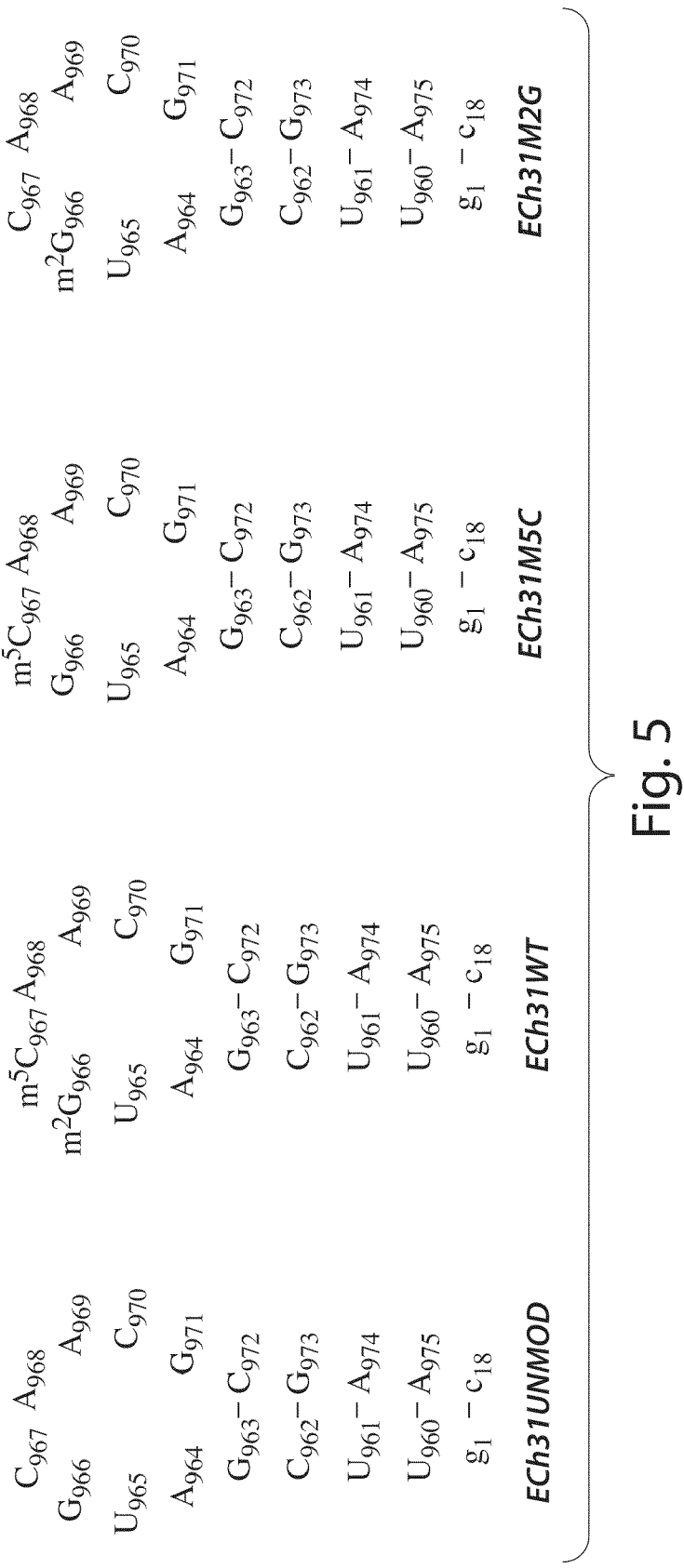

FIG. 5 depicts secondary structure representations of the synthetic RNA hairpins derived from positions 960-975 (based on the h31 stem-loop region) of *E. coli* 16S rRNA, in which positions 966 and/or 967 are modified. FIG. 5 discloses SEQ ID NOS 16, 15 and 17-18, respectively, in order of appearance.

Figure 6:
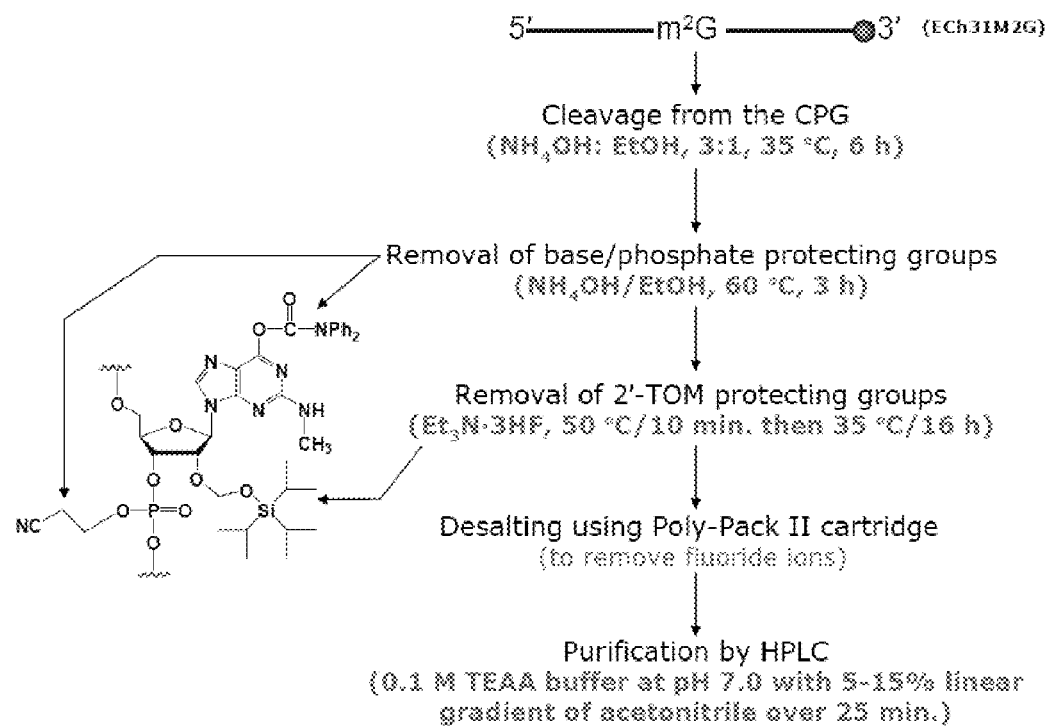
Figure 8A:
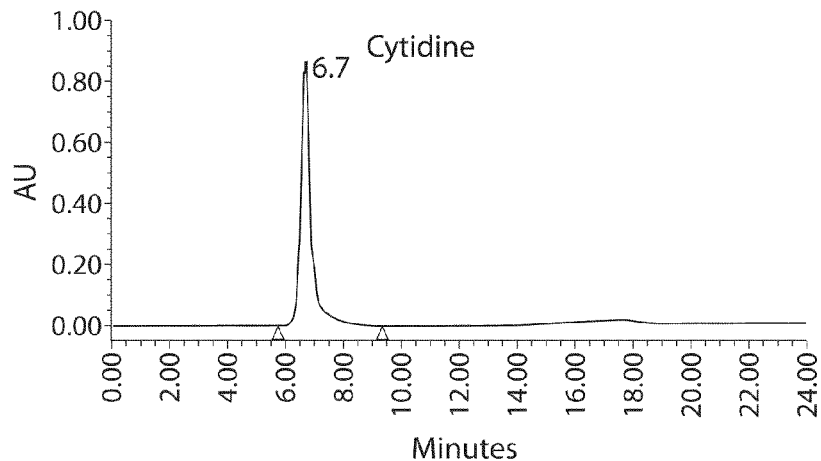
Figure 8B:
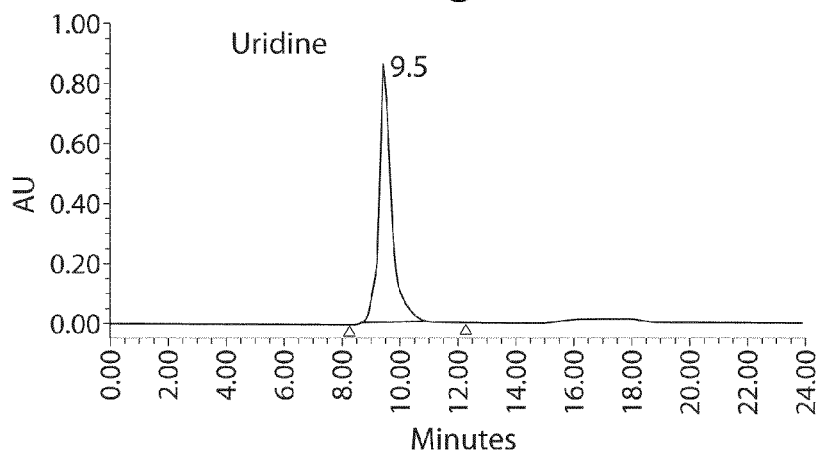
Figure 8C:
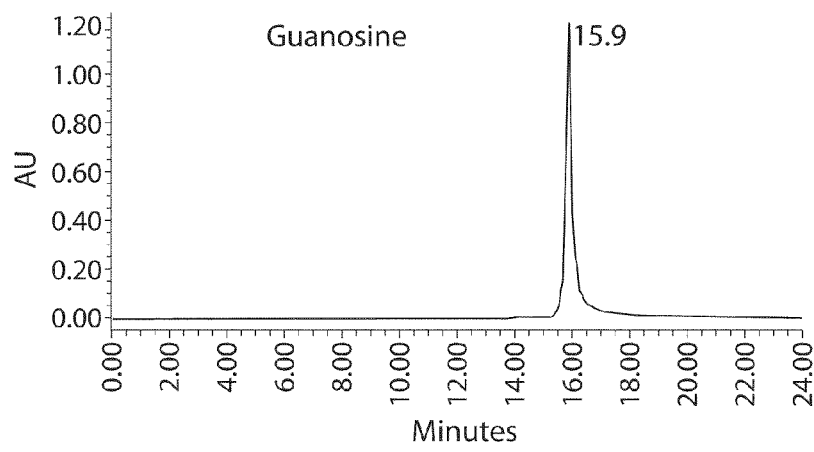
Figure 8D:
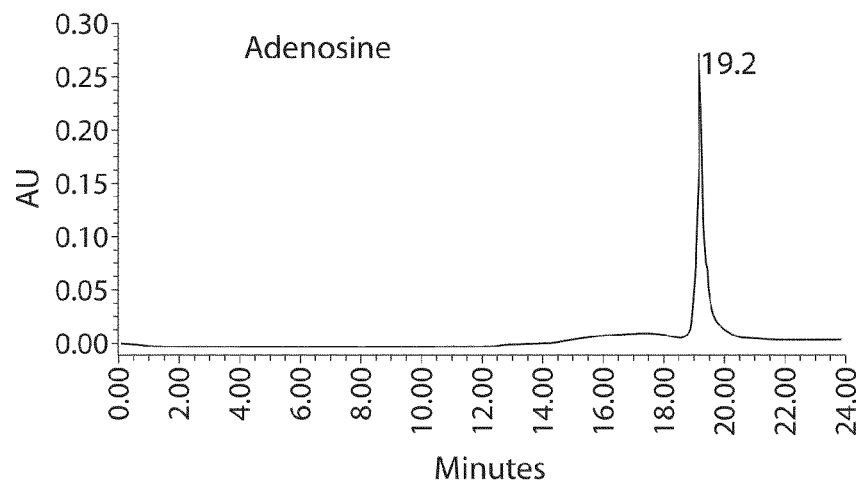
Figure 8E:
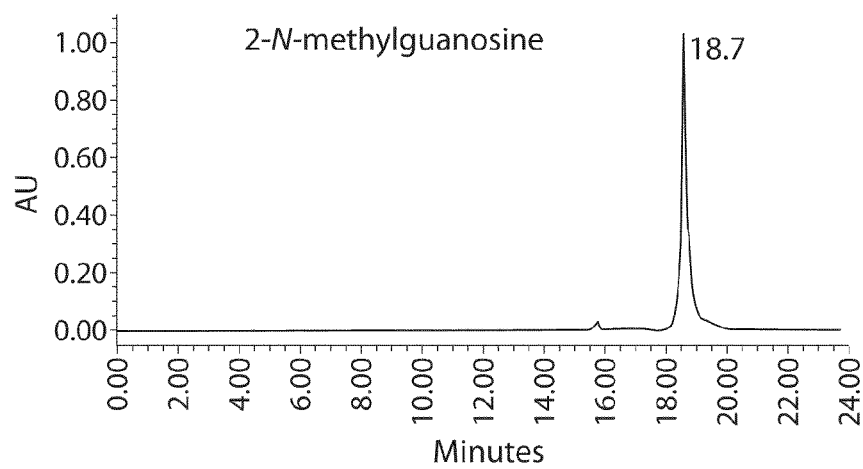
Figure 8F:
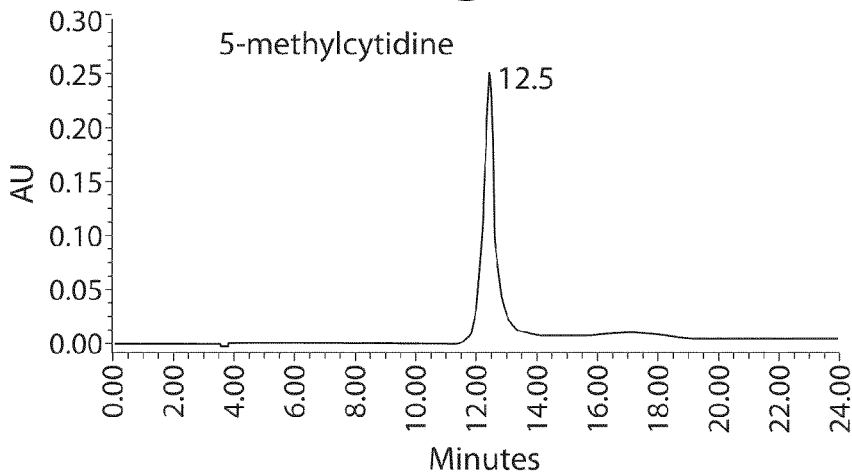

FIG. 6 depicts the post-synthetic processing steps of RNA constructs containing the modified nucleoside m$^2$G.

FIG. 7 depicts the MALDI-TOF mass spectra of helix 31 RNA constructs containing m2G modification: (A) ECh31WT (SEQ ID NO: 16), (B) ECh31M2G (SEQ ID NO: 18). The RNA samples were analyzed on a Bruker Ultraflex MALDI-TOF under negative ion mode and linear acquisition operation mode (Predicted masses for ECh31WT and ECh31M2G are 5783.5 and 5768.5 respectively).

FIG. 8 depicts HPLC analyses of authentic nucleoside standards: (A) cytidine, (B) uridine, (C) guanosine, (D) adenosine, (E) 2-N-methylguanosine, and (F) 5-methylcytidine.

Figure 9:
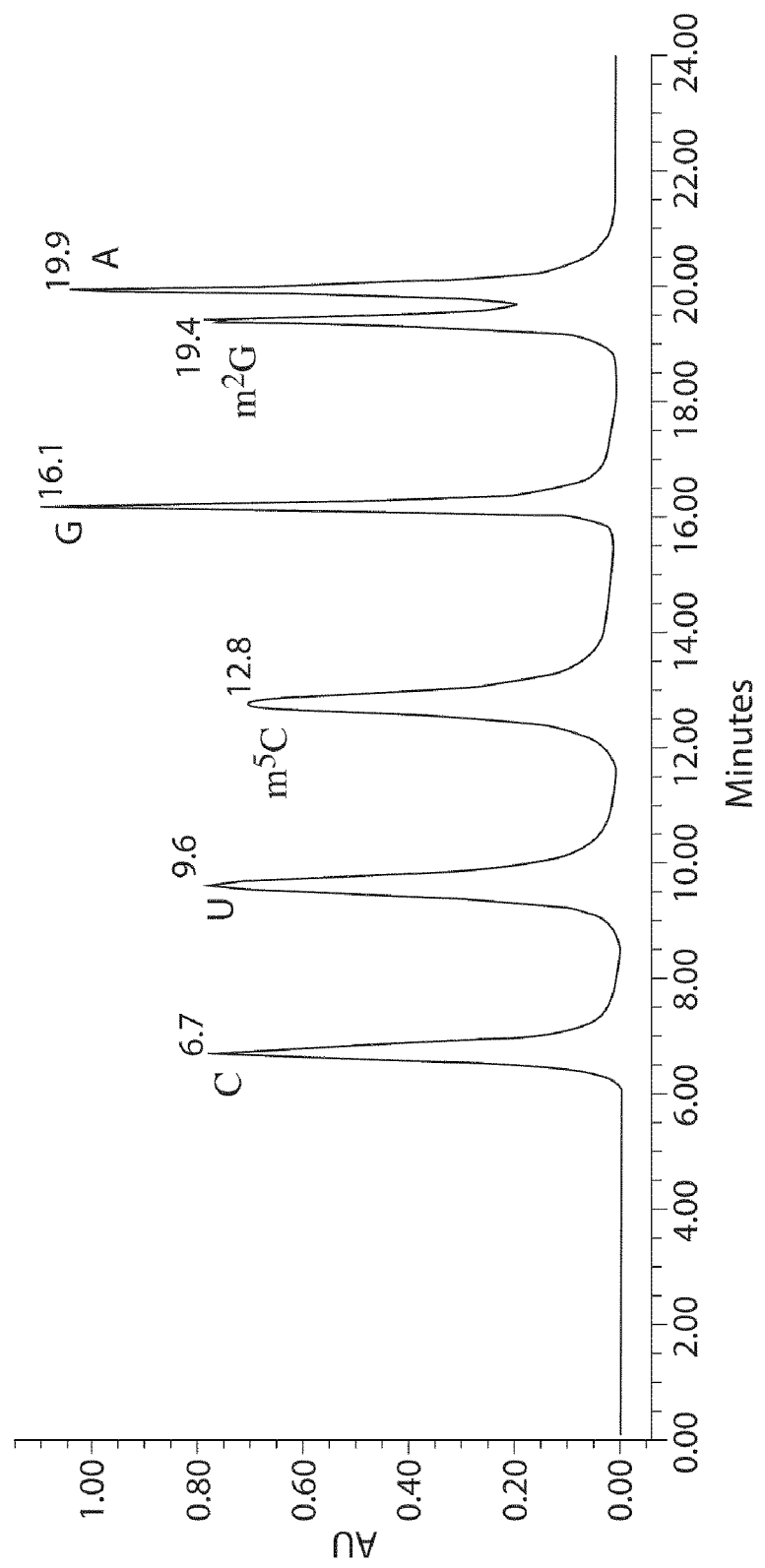

FIG. 9 depicts an HPLC analysis of a mixture of nucleoside standards.

Figure 10A:
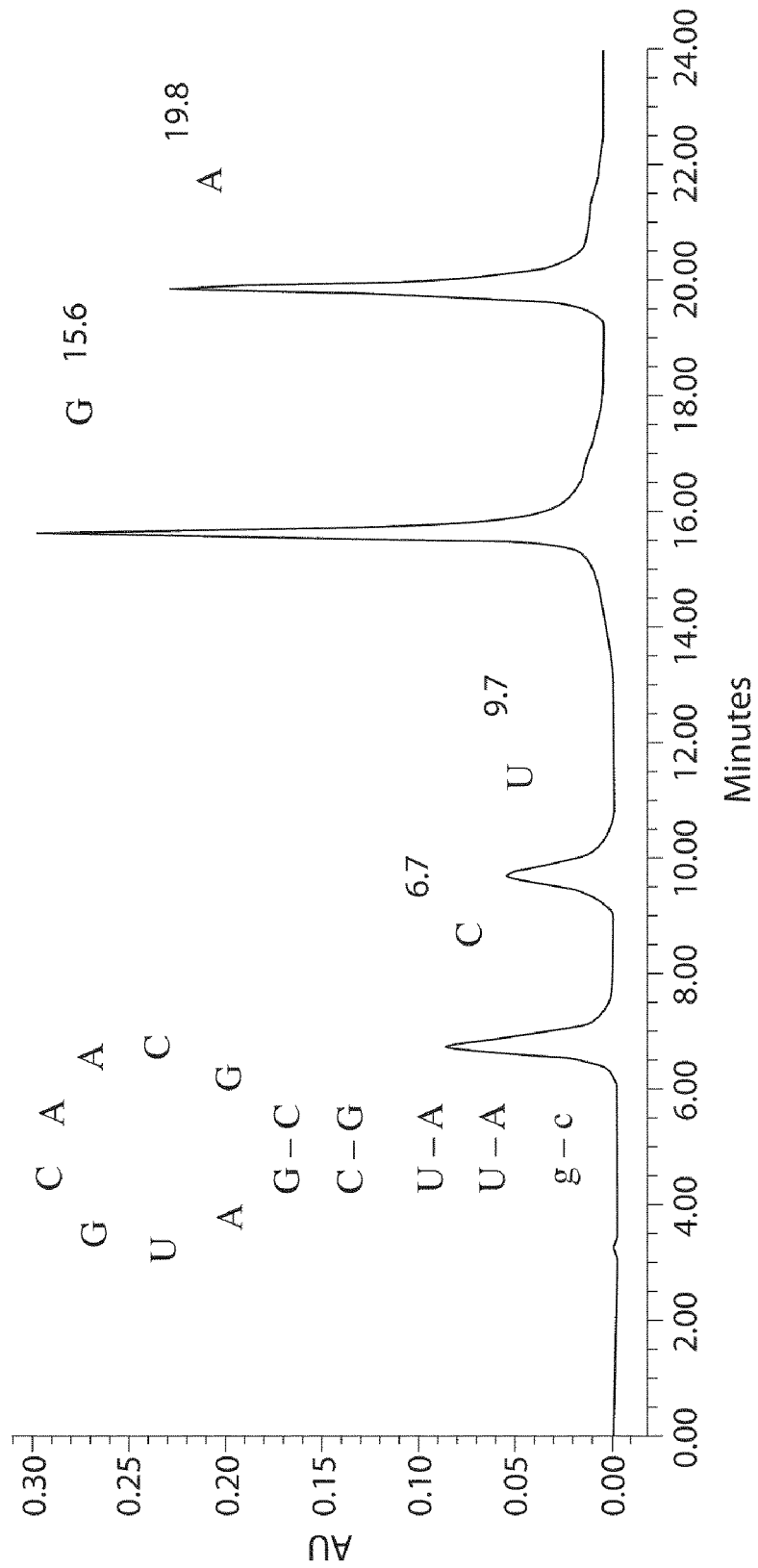
Figure 10B:
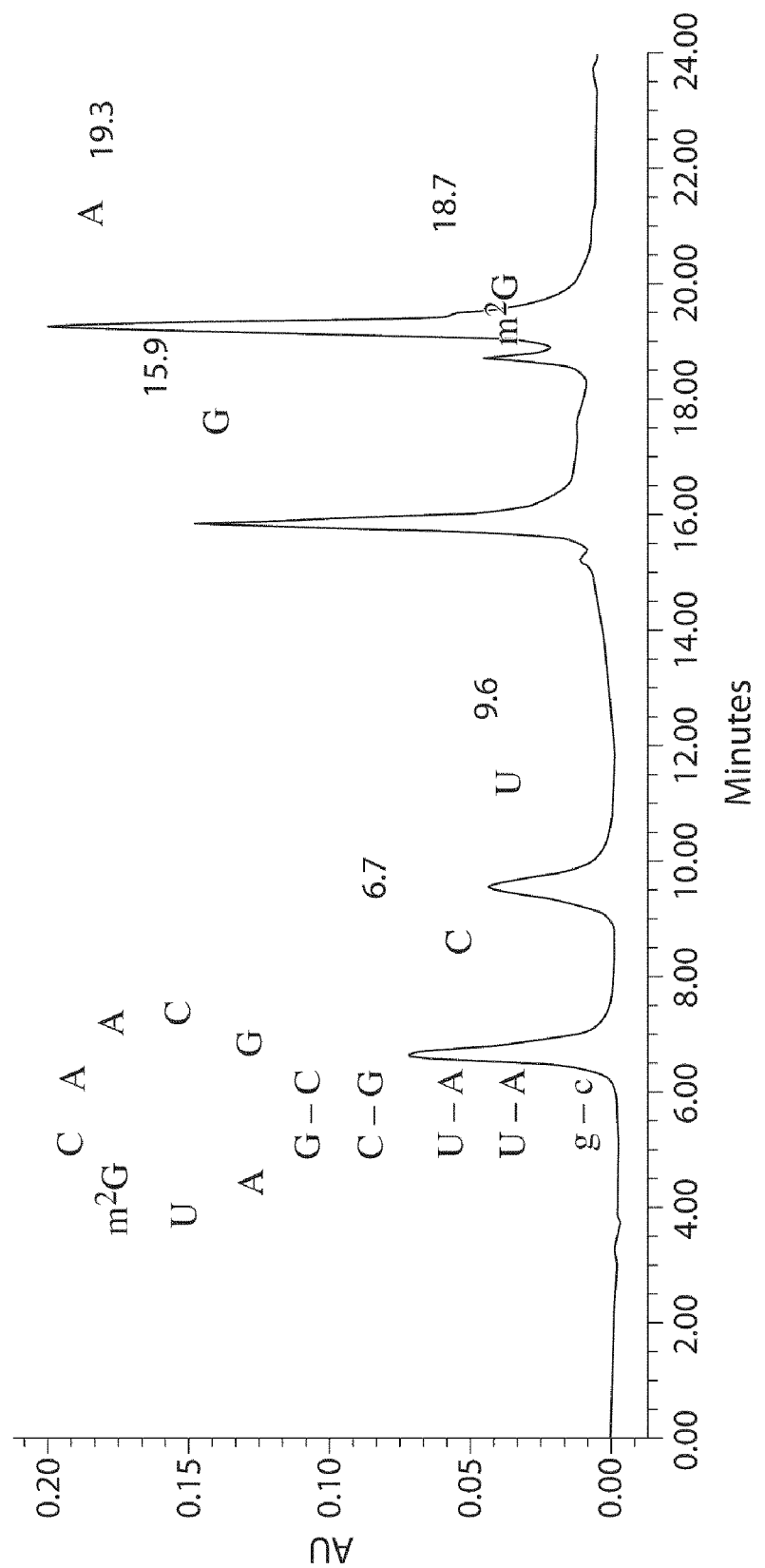
Figure 10C:
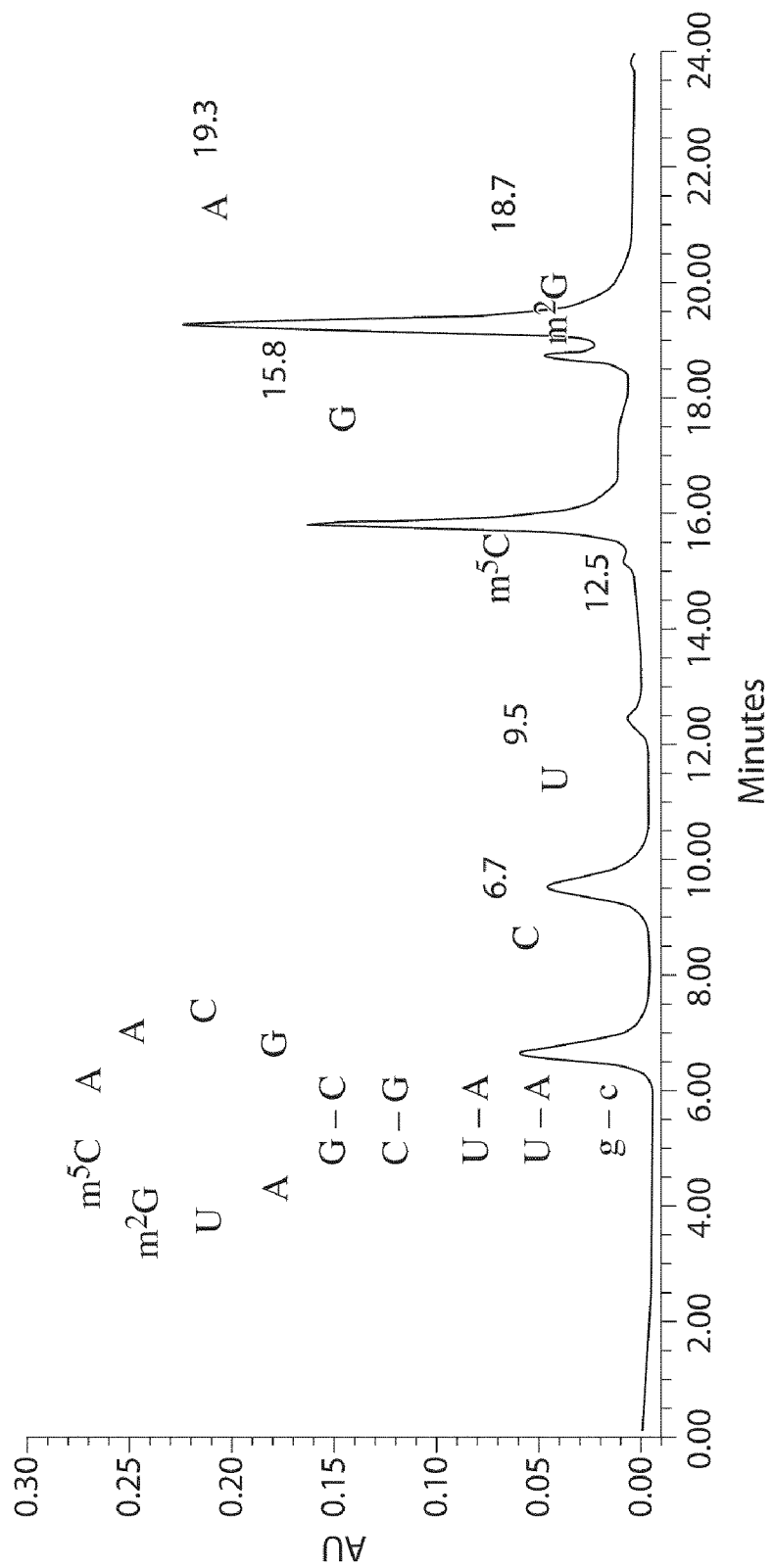
Figure 11A:
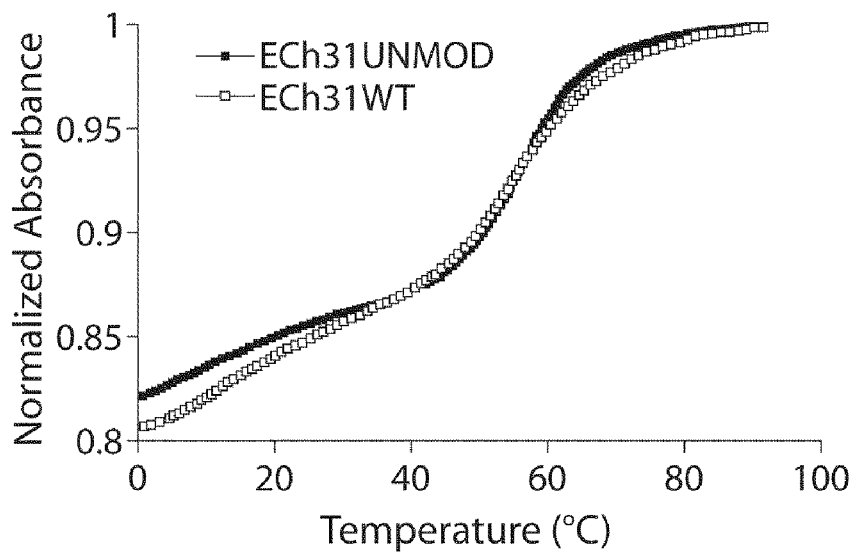
Figure 11B:
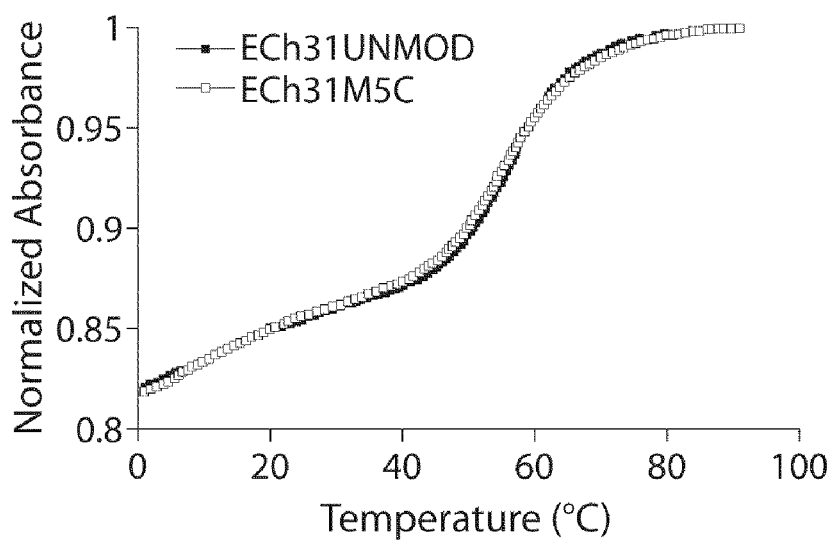
Figure 11C:
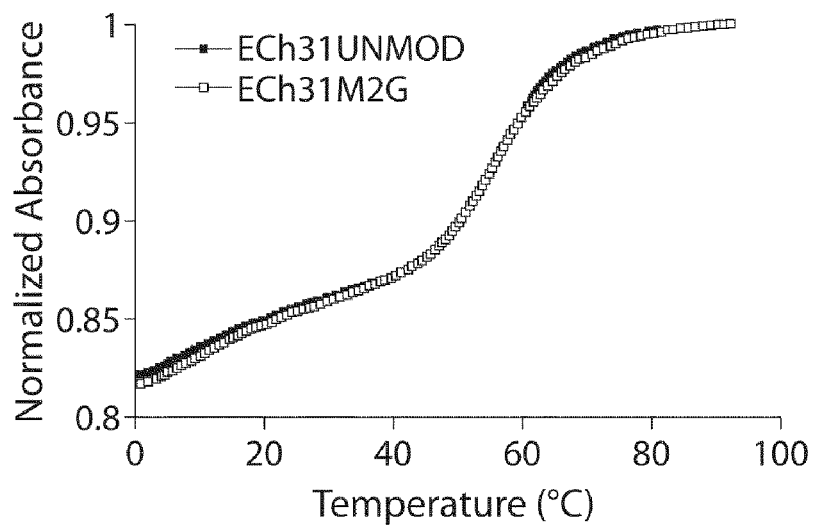
Figure 11D:
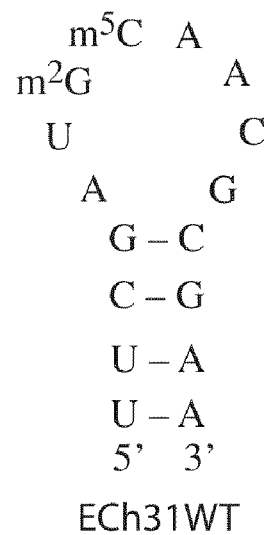

FIG. 10 depicts the HPLC analyses of helix 31 RNA constructs: (A) ECh31UNMOD (SEQ ID NO: 16), (B) ECh31M2G (SEQ ID NO: 18), and (C) ECh31WT (SEQ ID NO: 15).

FIG. 11 depicts representative normalized UV melting curves of the modified RNAs with their unmodified RNA counterpart are compared in panels A-C. The RNA sequence for h31 is shown in panel D (SEQ ID NO: 19).

Figure 12:
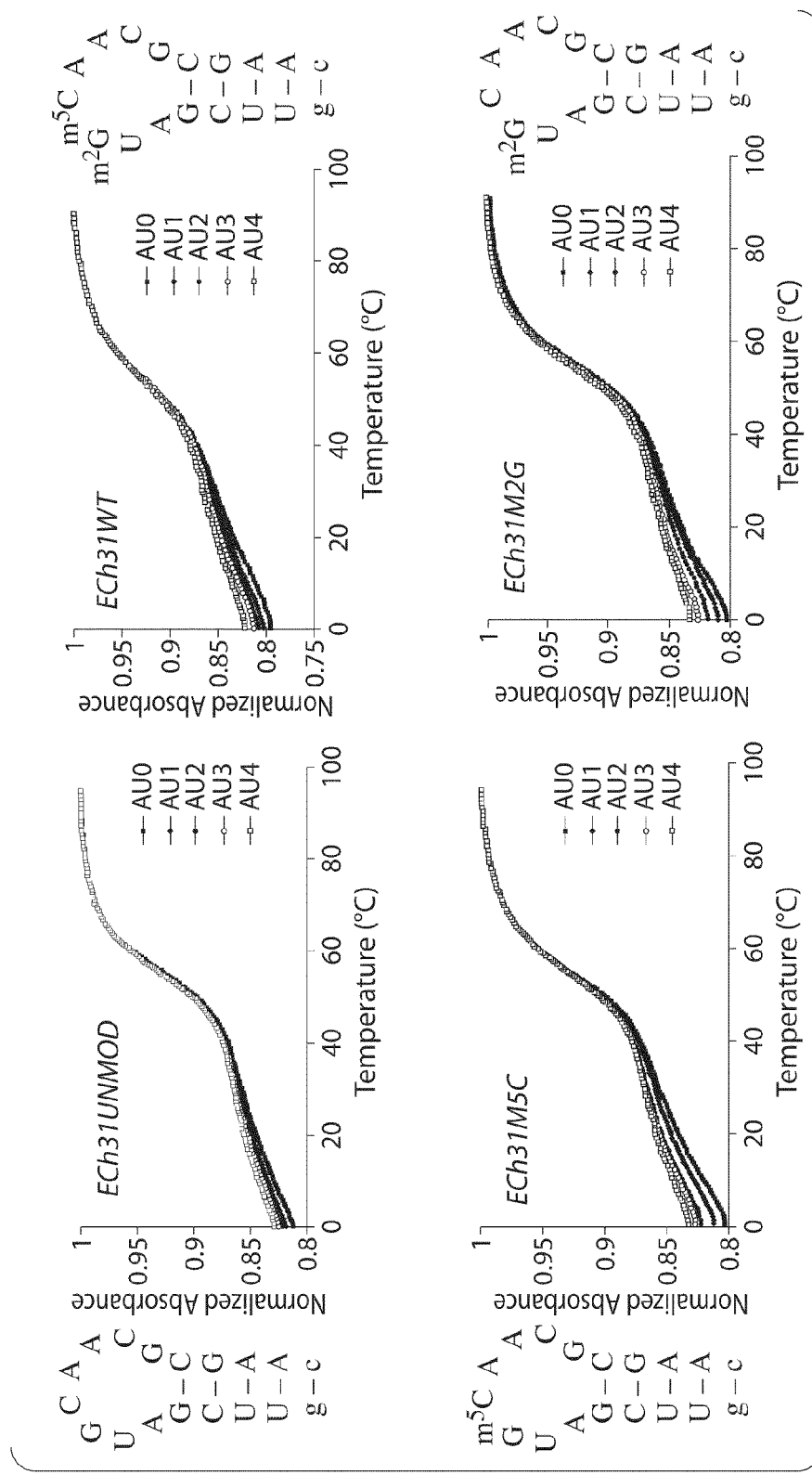

FIG. 12 depicts the UV melting profiles representing the melting transitions of the four RNAs are shown (SEQ ID NOS 16, 15 and 17-18, respectively, in order of appearance). AU0-AU4 represent profiles corresponding to different dilutions of each RNA.

Figure 13:
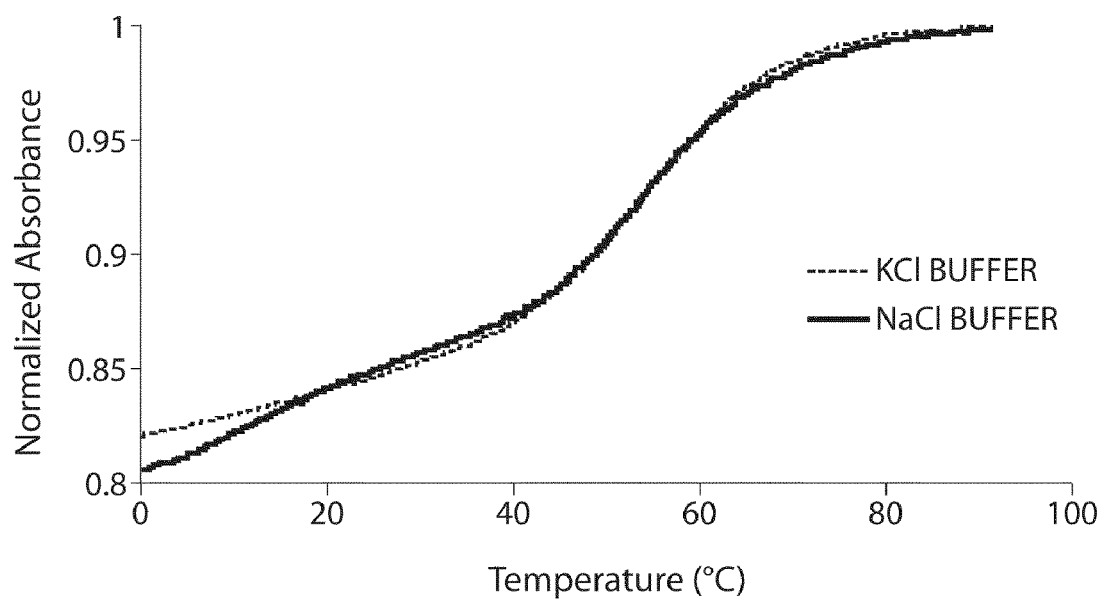

FIG. 13 depicts representative normalized UV melting curves of the ECh31WT RNA taken in Na$^+$ and K$^+$ buffers.

FIG. 14 depicts the structures of h31, showing the flipped out (A) and stacked (B) conformations of residue G966 (PDB accession IDs—1FJF$^9$ and 2J00$^6$).

FIG. 15 depicts CD spectra of the modified and unmodified RNA constructs. FIG. 15A depicts the CD spectrum of ECh31M5C, FIG. 15B depicts the spectrum of ECh31M2G, FIG. 15C depicts the CD spectrum of ECh31WT, and FIG. 15D depicts the CD spectrum of ECh31UNMOD.

Figure 16:
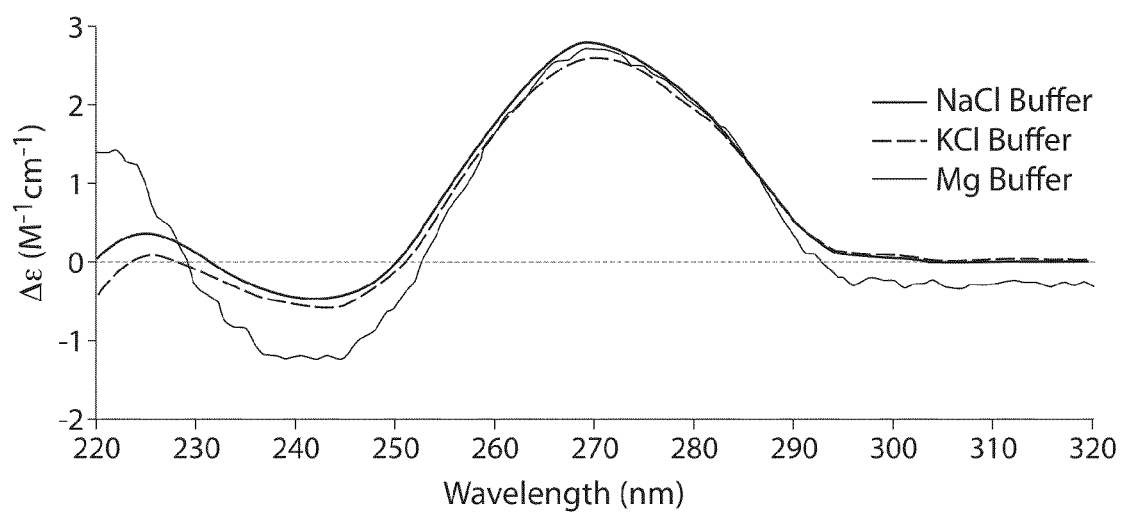

FIG. 16 depicts CD spectra of the ECh31WT RNA construct acquired in Na$^+$, K$^+$, and Mg$^{2+}$ containing buffers.

Figure 17:
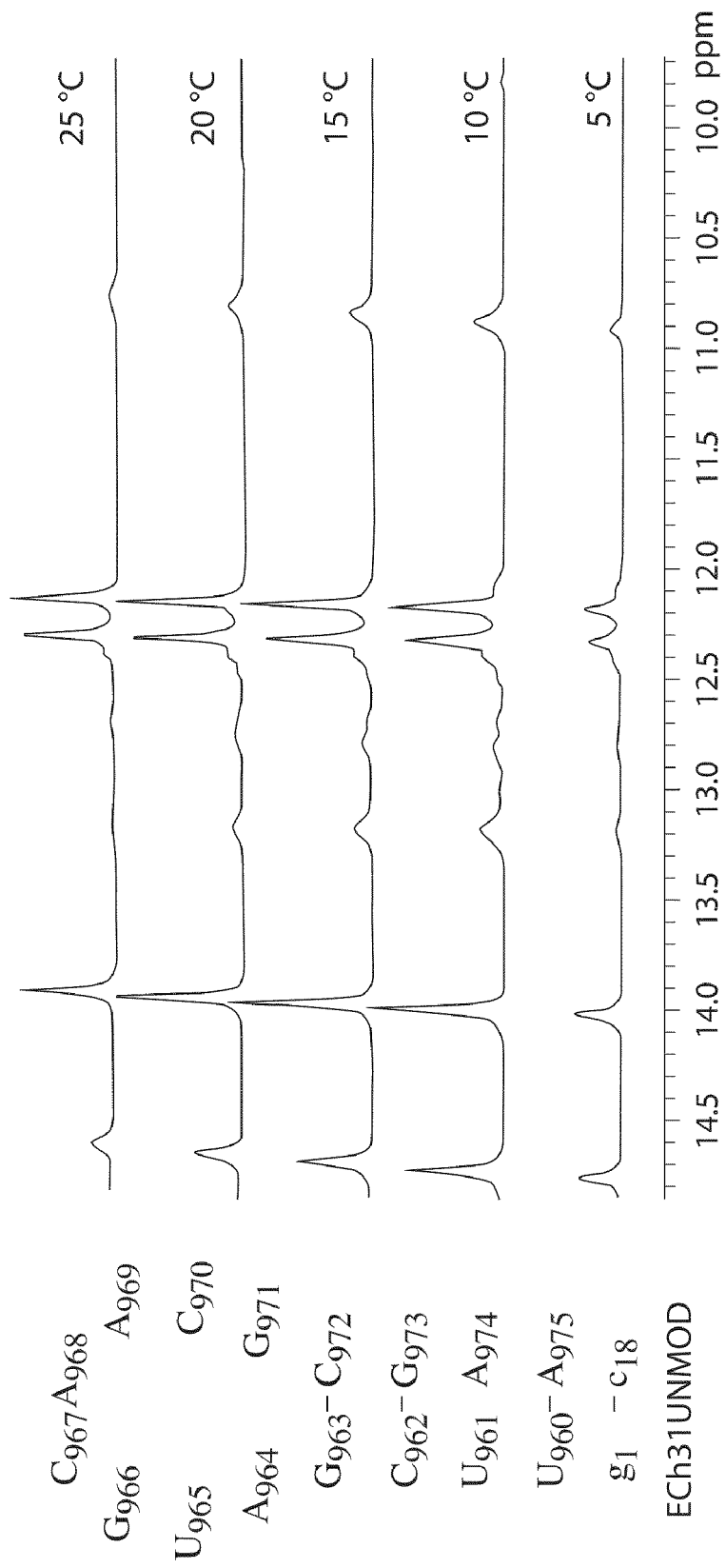

FIG. 17 depicts the temperature dependence of the imino region of ECh31UNMOD RNA sequence (SEQ ID NO: 16).

Figure 18:
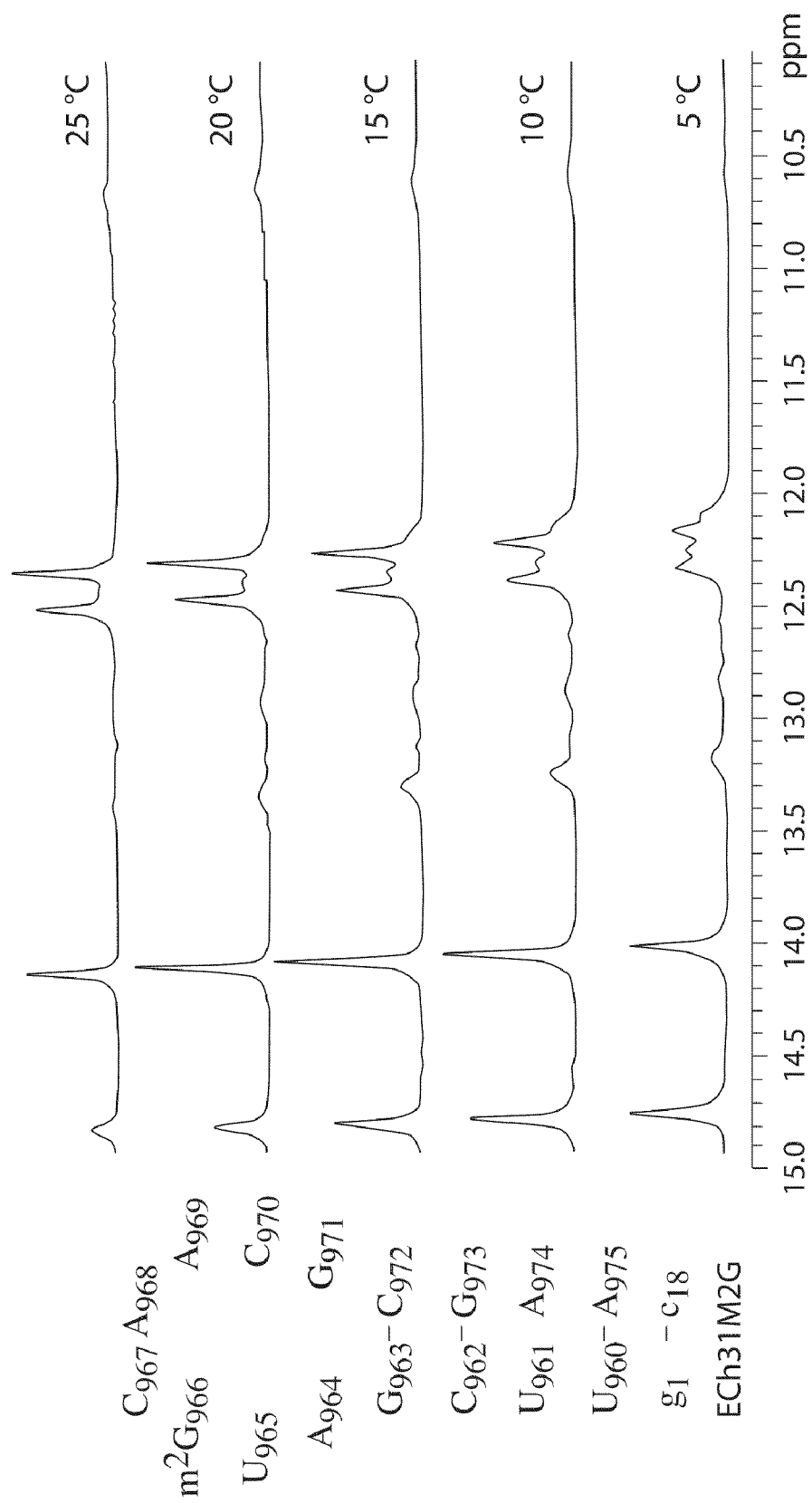

FIG. 18 depicts the temperature dependence of the imino region of ECh31M2G RNA sequence (SEQ ID NO: 18).

Figure 19:
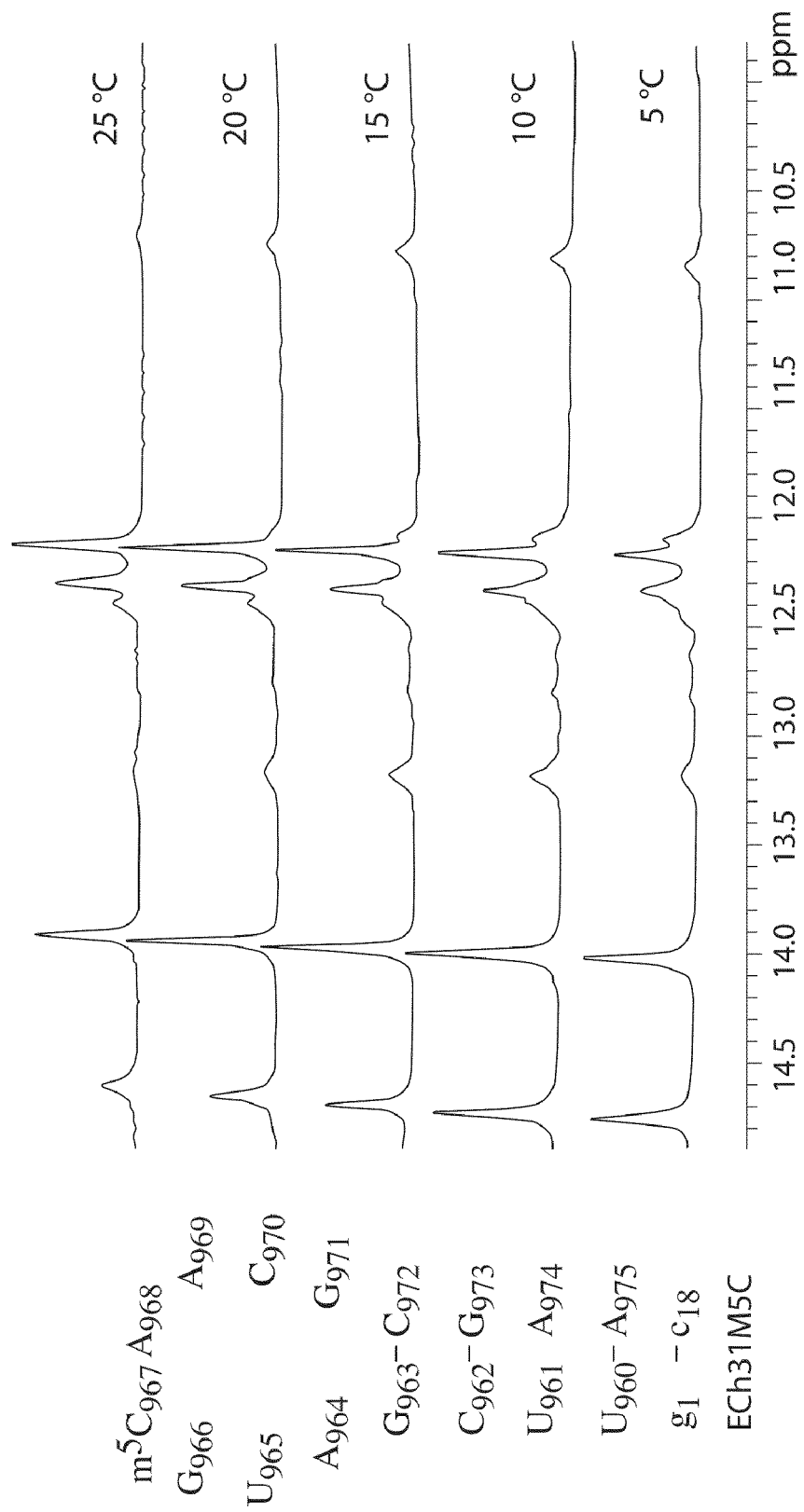

FIG. 19 depicts the temperature dependence of the imino region of ECh31M5C RNA sequence (SEQ ID NO: 17).

Figure 20:
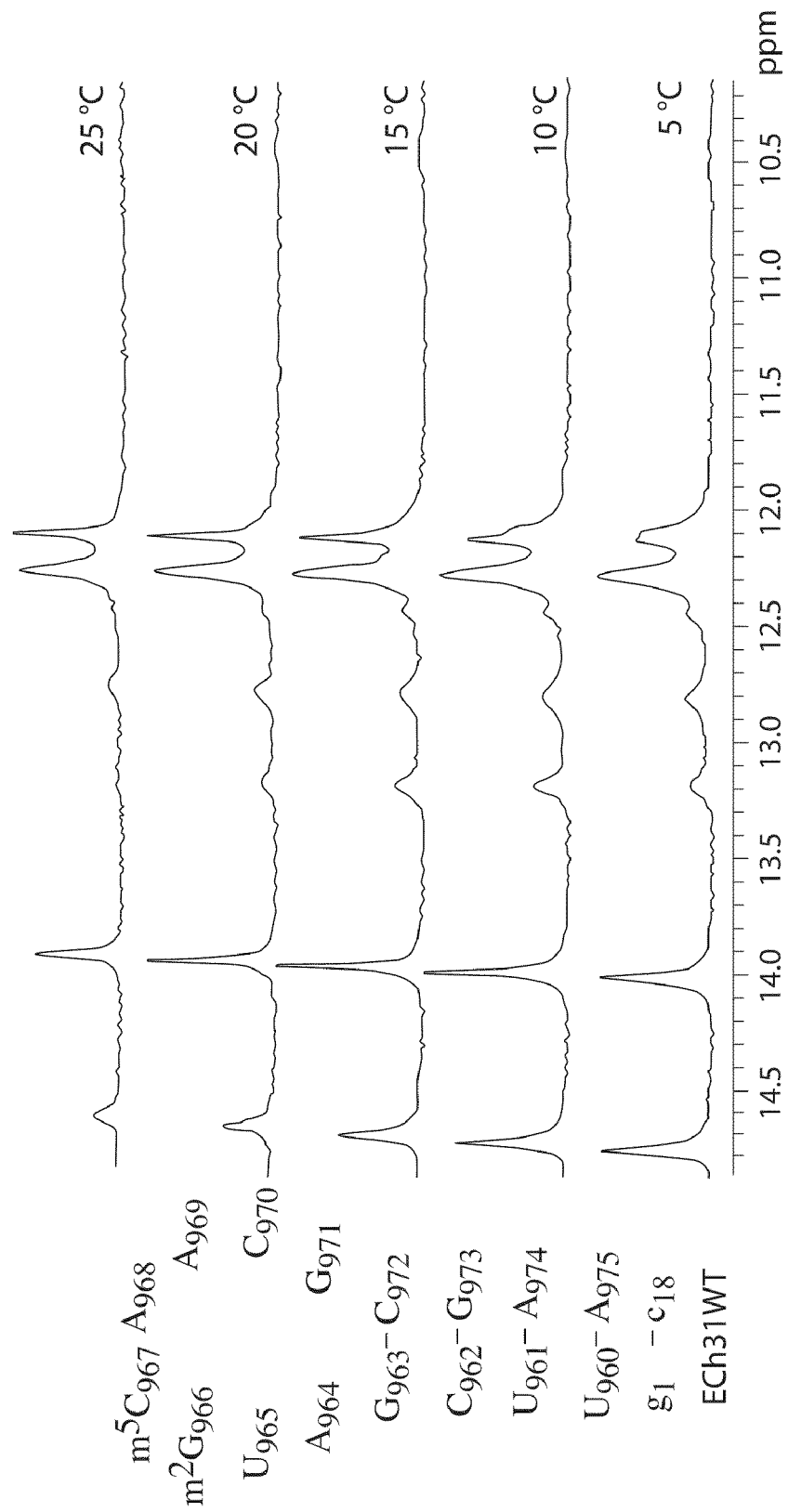

FIG. 20 depicts the temperature dependence of the imino region of ECh31WT RNA sequence (SEQ ID NO: 15).

Figure 21:
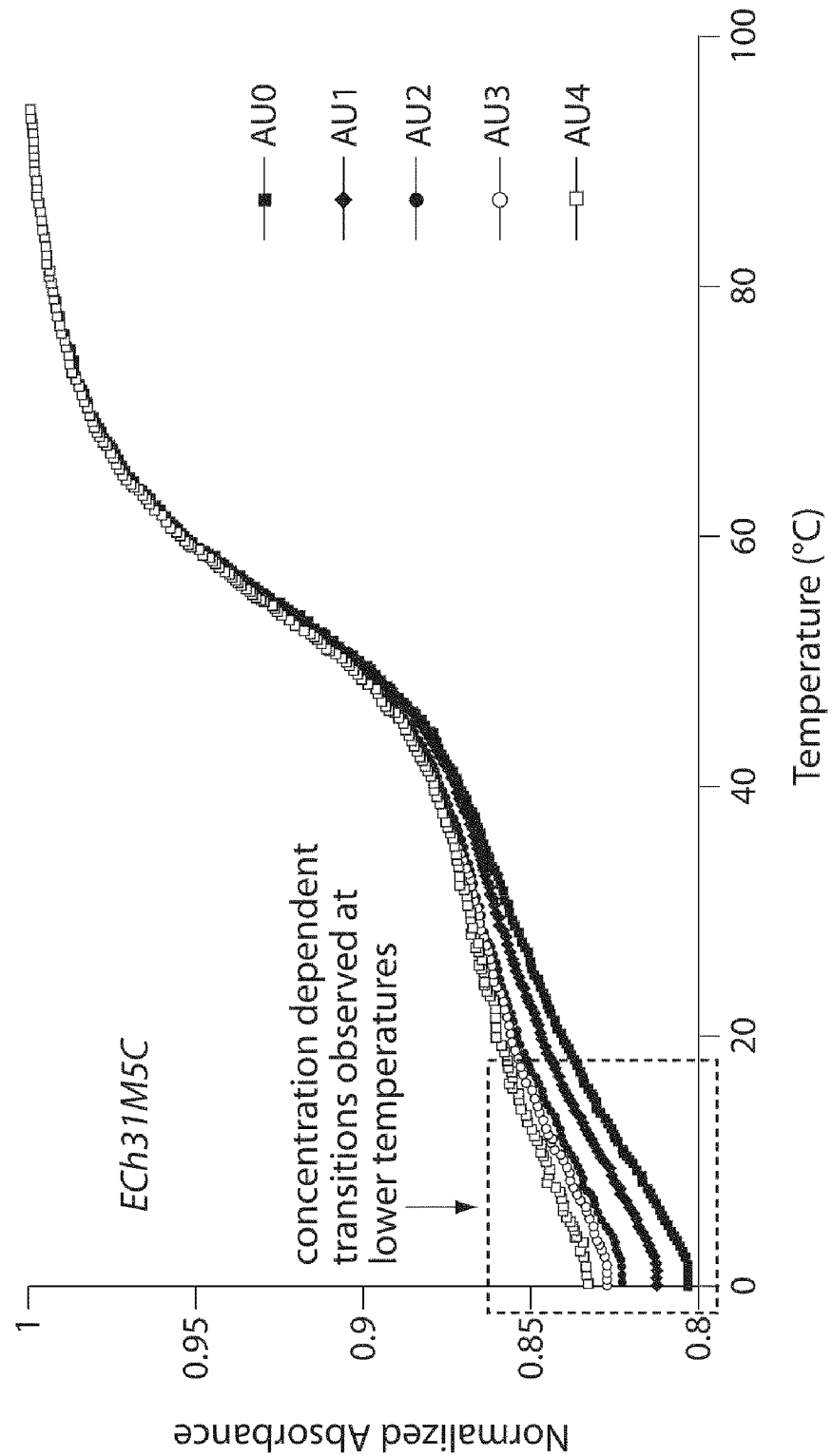

FIG. 21 depicts an example of the biphasic nature of the melting transition observed by helix 31 RNAs.

Figure 22:
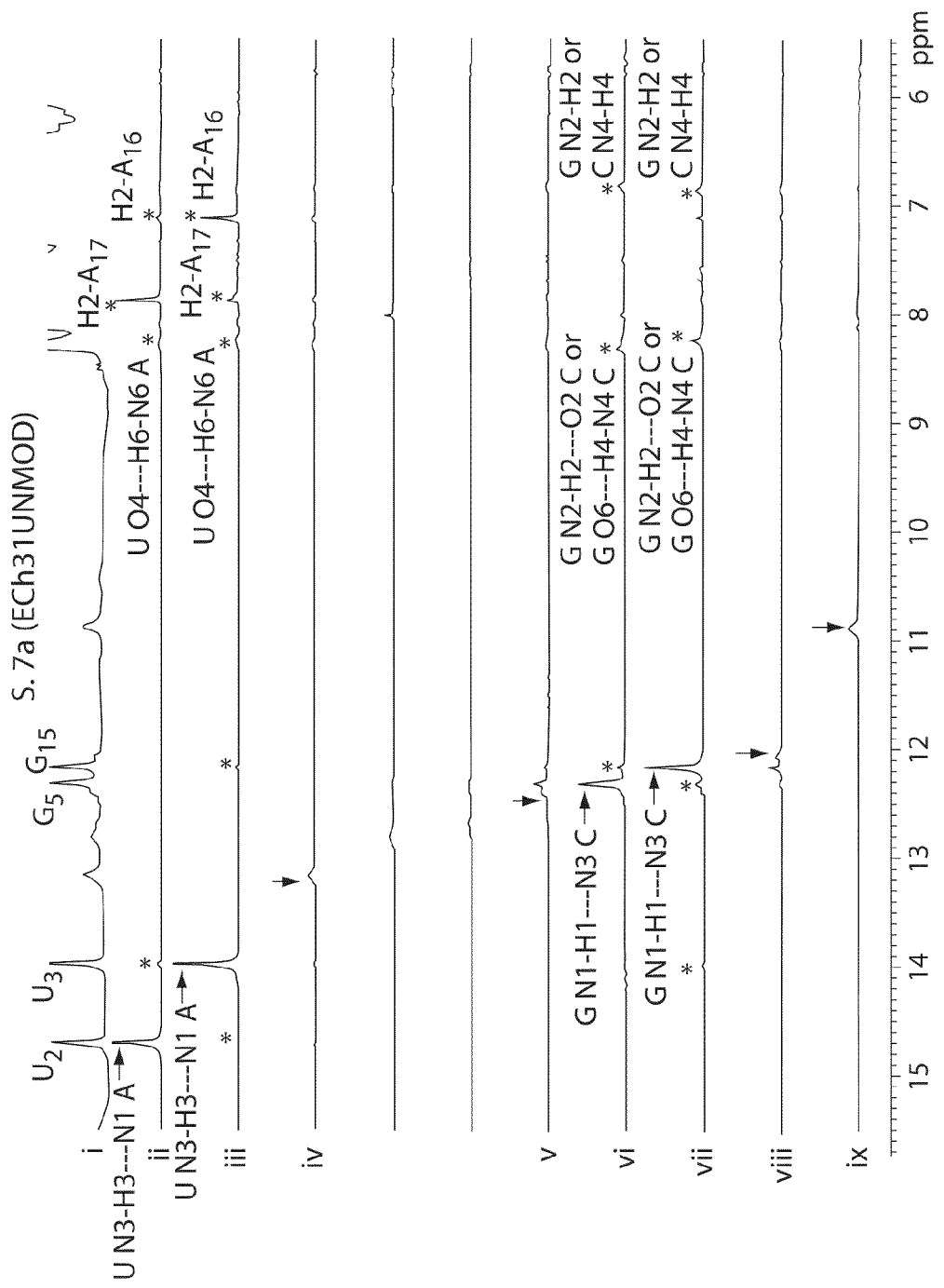

FIG. 22 depicts the imino proton spectrum and NOE difference spectra of ECh31UNMOD RNA construct.

Figure 23:
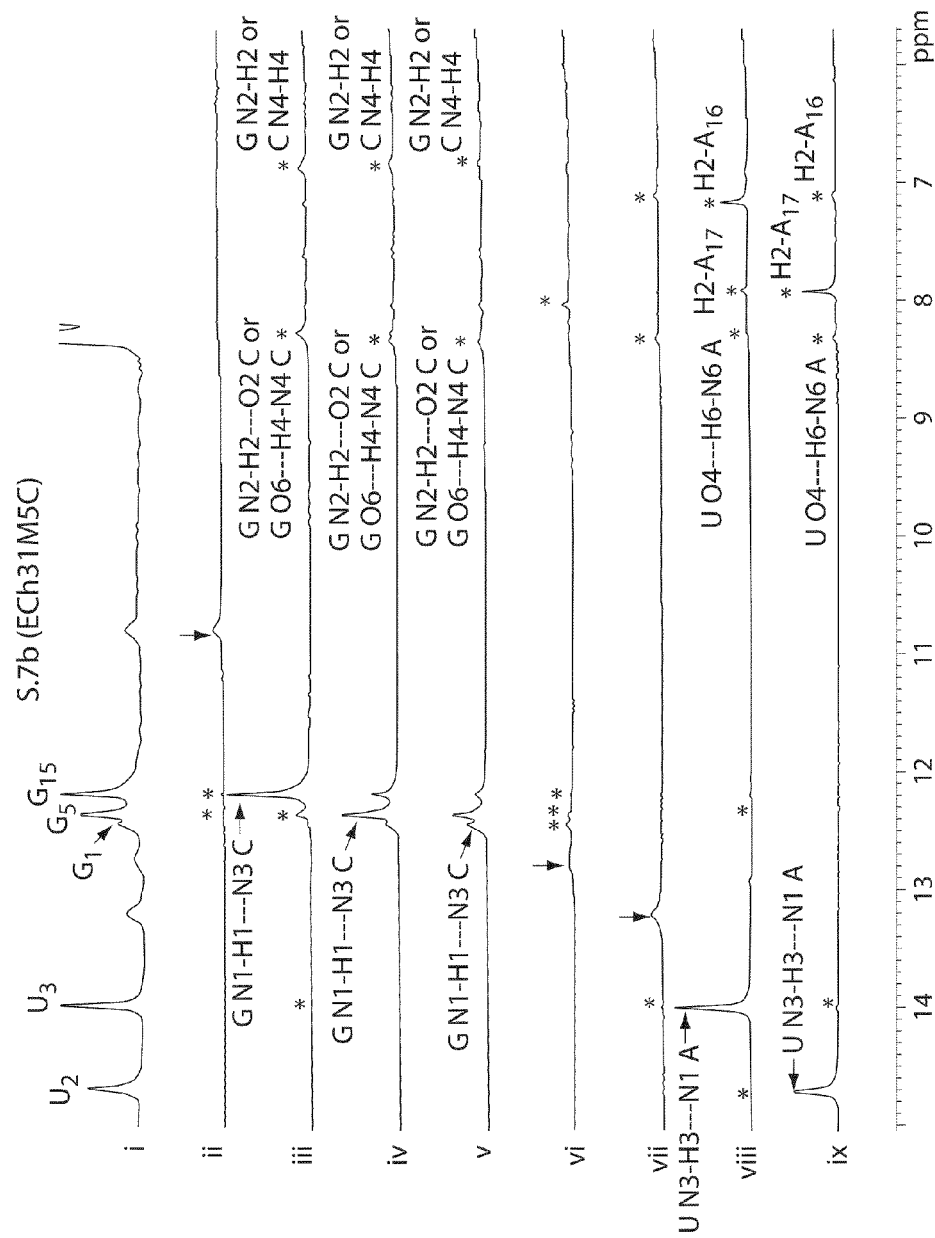

FIG. 23 depicts the imino proton spectrum and NOE difference spectra of ECh31M5C RNA construct.

Figure 24:
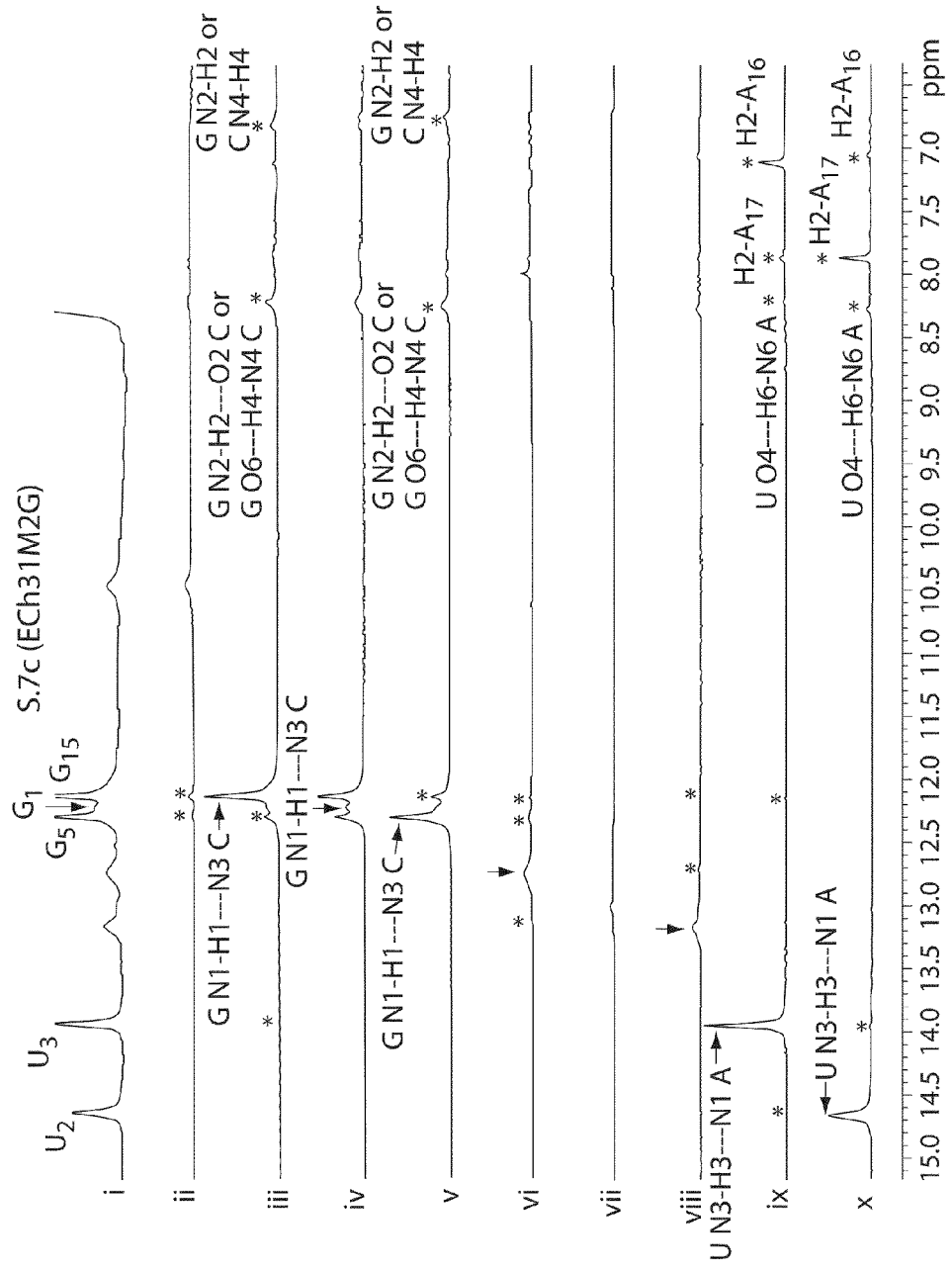

FIG. 24 depicts the imino proton spectrum and NOE difference spectra of ECh31M2G RNA construct.

Figure 25:
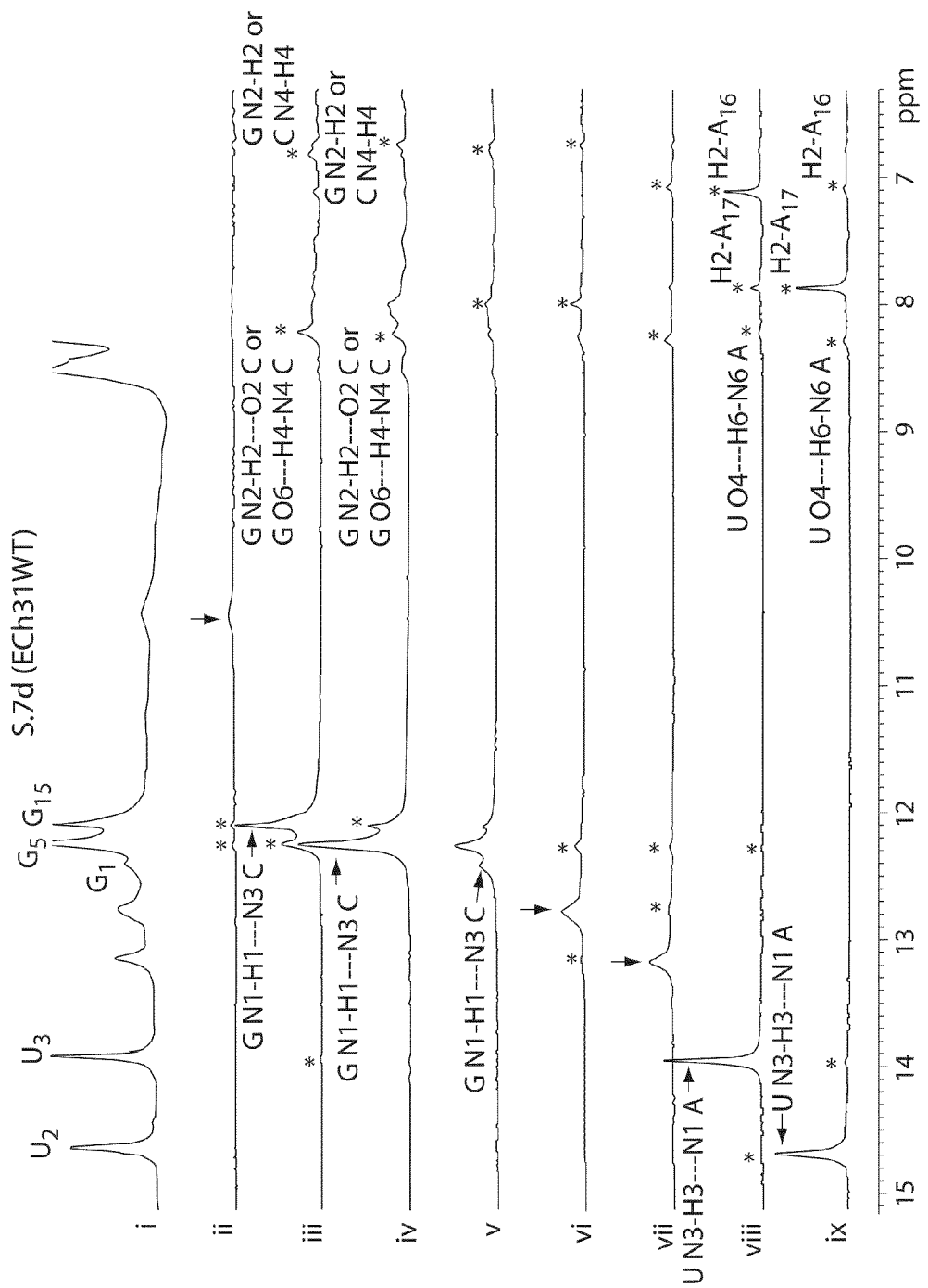

FIG. 25 depicts the imino proton spectrum and NOE difference spectra of ECh31WT RNA construct.

Figure 26:
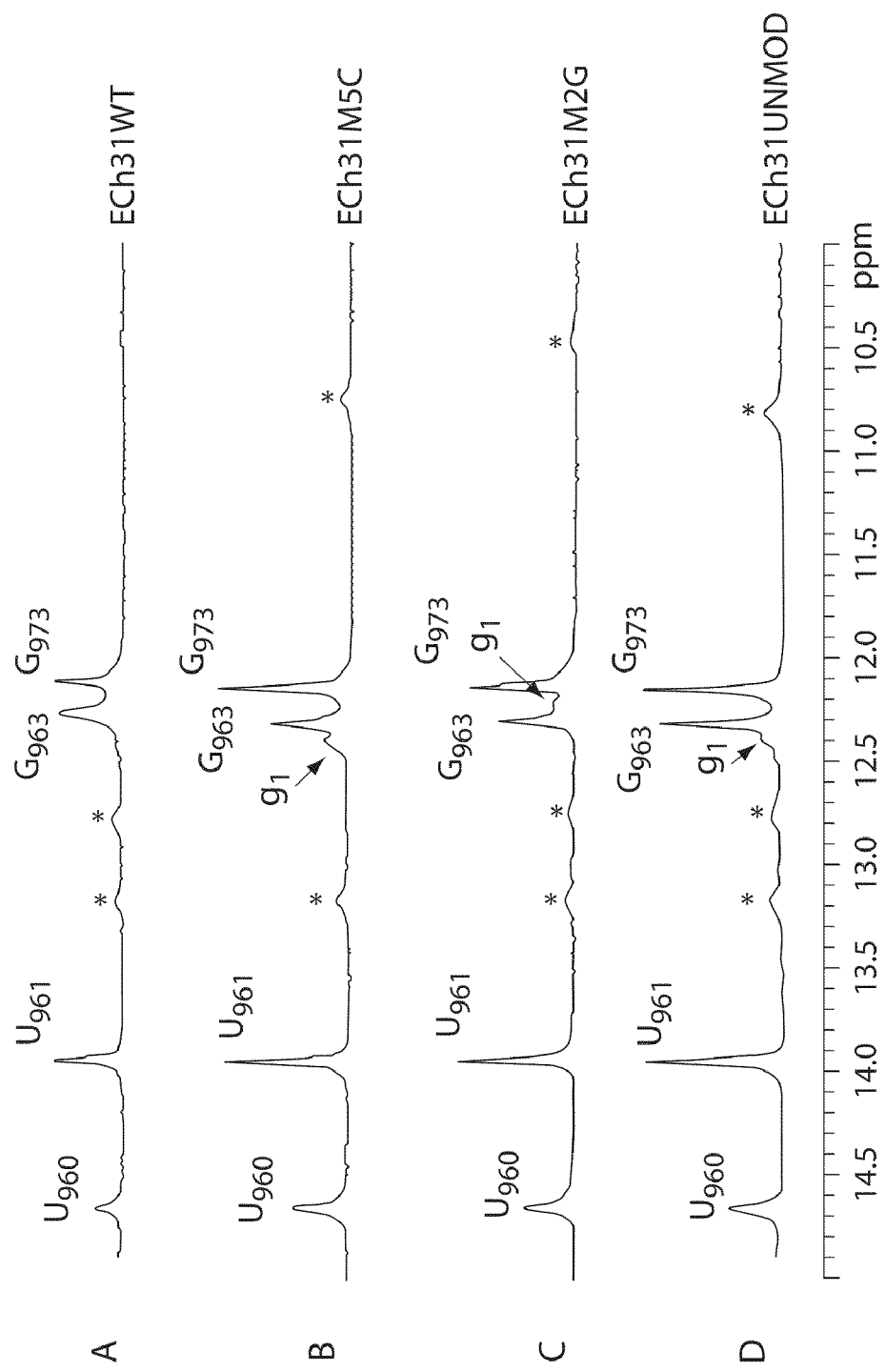

FIG. 26 depicts the ID imino proton (uridine H3/guanine H1) NMR spectra at 20° C. of ECh31WT, ECh31M5C, ECh31M2G and ECh31WT RNA sequences.

Figure 27:
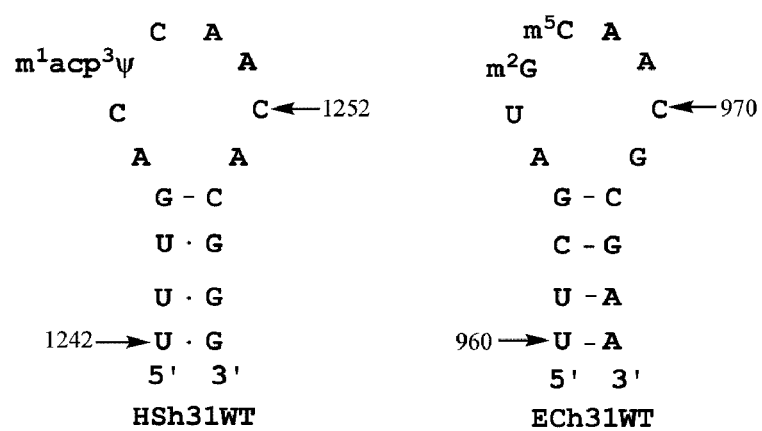

FIG. 27 depicts the helix 31 (h31) RNA hairpins from *H. sapiens* (SEQ ID NO: 20) and *E. coli* (SEQ ID NO: 19), highlighting the wild-type sequences and numbering.

Figure 28:
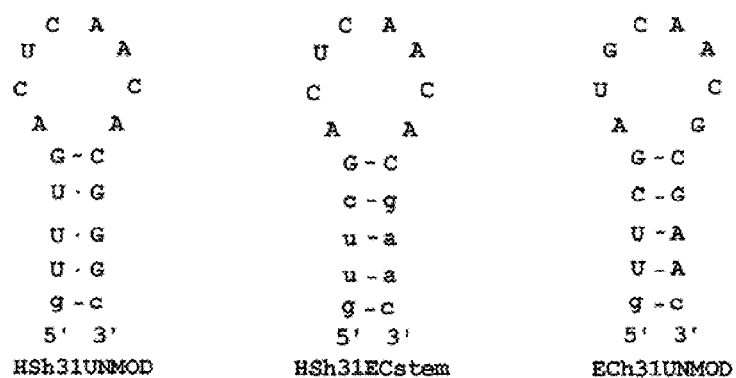

FIG. 28 depicts the unmodified helix 31 (h31) RNA hairpins from *H. sapiens* (SEQ ID NOS 21 and 22, respectively) and *E. coli* (SEQ ID NO: 16), highlighting the sequences and terminal G-C base-pair.

Figure 29:
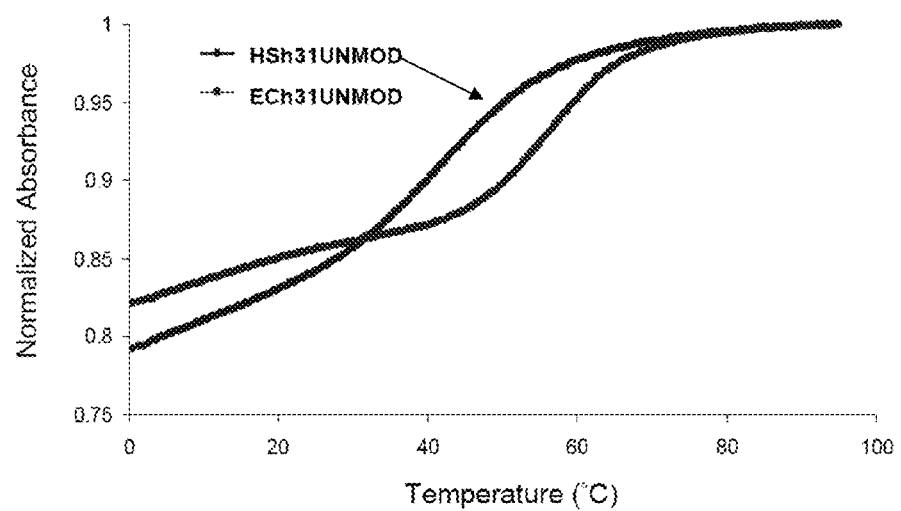

FIG. 29 depicts representative normalized UV melting curves for the unmodified *E. coli* (blue) and *H. sapiens* (red) helix 31 analogues taken in 15 mM NaCl, 20 mM sodium cacodylate, and 0.5 mM EDTA at pH 7.0.

Figure 30:
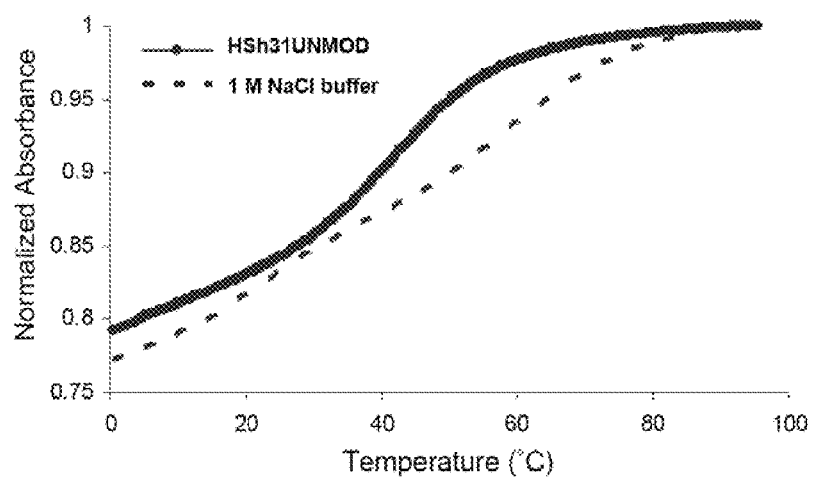

FIG. 30 depicts a representative normalized UV melting curve for HSh31UNMOD, taken in 1 M NaCl, 20 mM sodium cacodylate and 0.5 mM EDTA at pH 7.0 (dotted line), compared to the lower salt condition (solid line).

Figure 31:
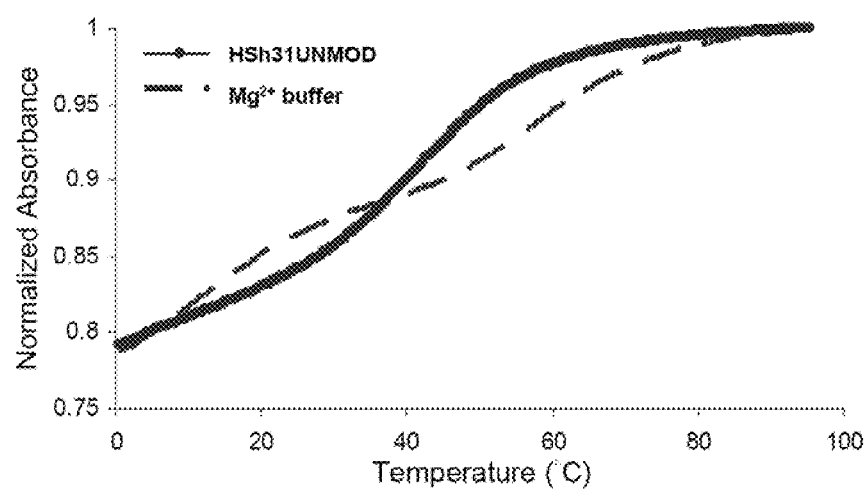

FIG. 31 depicts a representative normalized UV melting curve for HSh31UNMOD, taken in 15 mM NaCl, 20 mM sodium cacodylate, 0.5 mM EDTA, and 5 mM MgCl$_2$ at pH 7.0 (dashed line).

Figure 32:
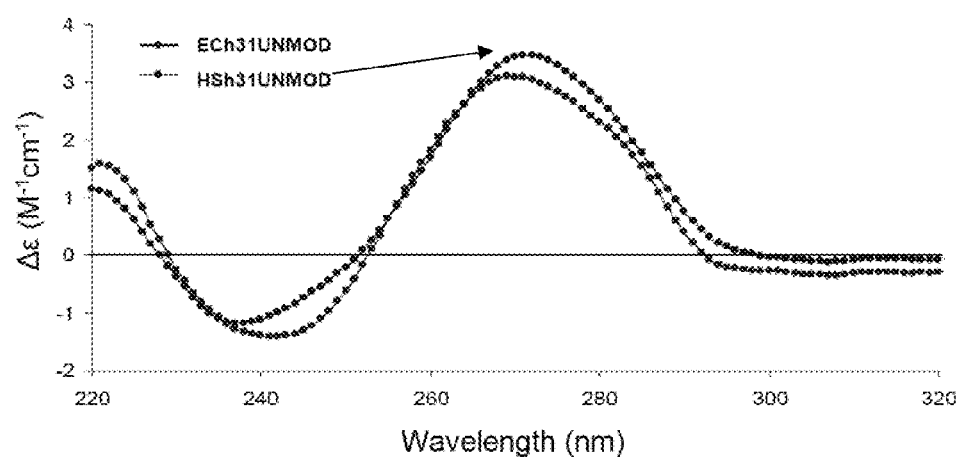

FIG. 32 depicts CD spectra of unmodified analogues from *E. coli* (ECh31UNMOD) and *H. sapiens* (HSh31UNMOD) h31 RNAs (15 mM NaCl, 20 mM sodium cacodylate and 0.5 mM EDTA at pH 7.0).

Figure 33:
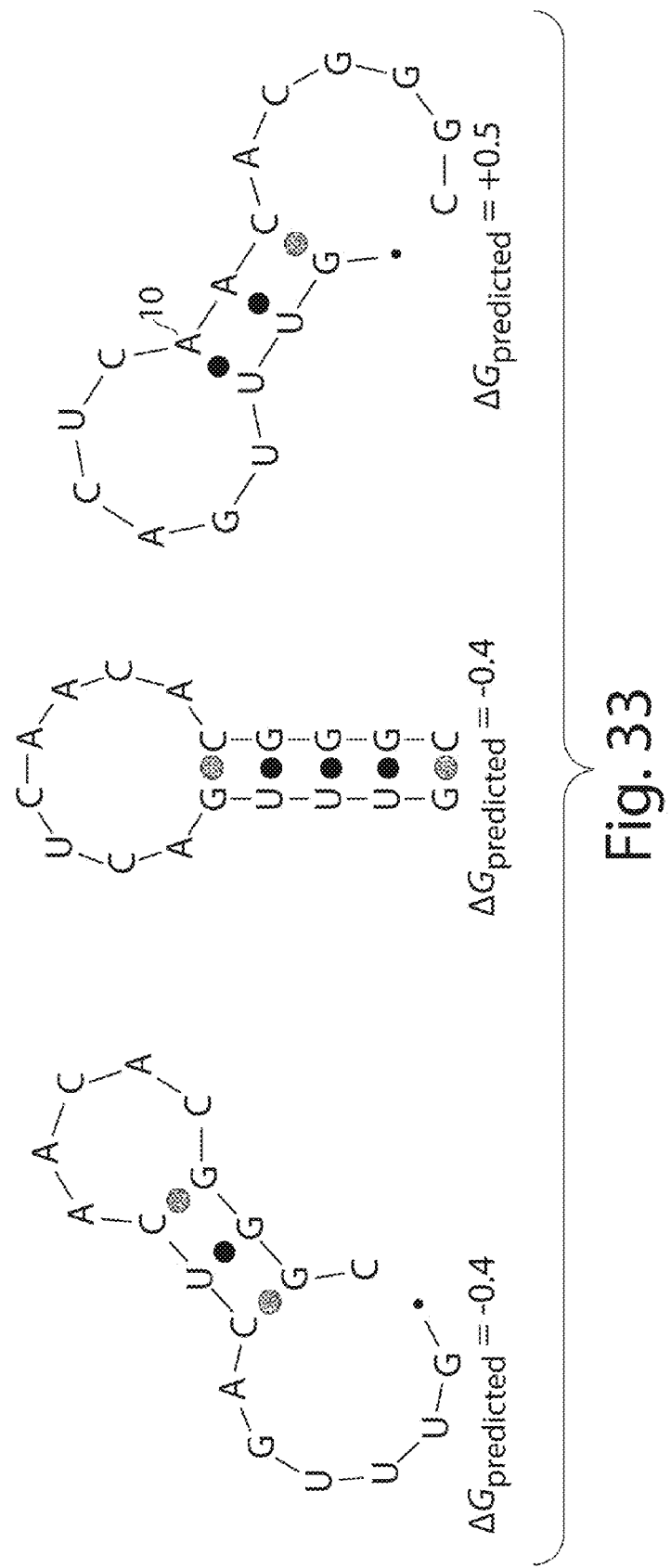

FIG. 33 depicts MFOLD data for HSh31UNMOD RNA (SEQ ID NO: 21).

Figure 34:
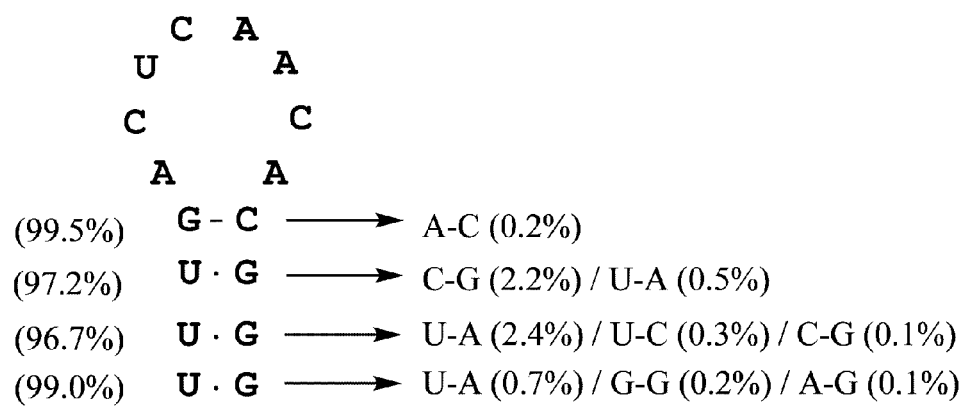

FIG. 34 depicts base-pair distribution of helix 31 stem regions among eukaryotes (SEQ ID NO: 23)

FIG. 35 depicts helix 31 base pair conservation in the stem region aligned with the *E. coli* 16S rRNA reference sequence. The abbreviations T, 3, A, B, C, E, and M represent Three Phylogenetic Domains/Two organelles, Three Phylogenetic Domains, Archaea, (eu)Bacteria, Chloroplasts, Eukarya, and Mitochondria, respectively.

FIG. 36 depicts a new model oligonucleotide analogue (ECh31ECstem) for the *H. sapiens* h31, compared with the *E. coli* (SEQ ID NO: 16) and *H. sapiens* sequences (SEQ ID NOS 21-22, respectively).

FIG. 37 depicts representative normalized UV melting curves for the h31 analogues: A) HSh31UNMOD (red) vs HSh31ECstem (green) and B) HSh31ECstem (green) vs ECh31UNMOD (blue).

Figure 38:
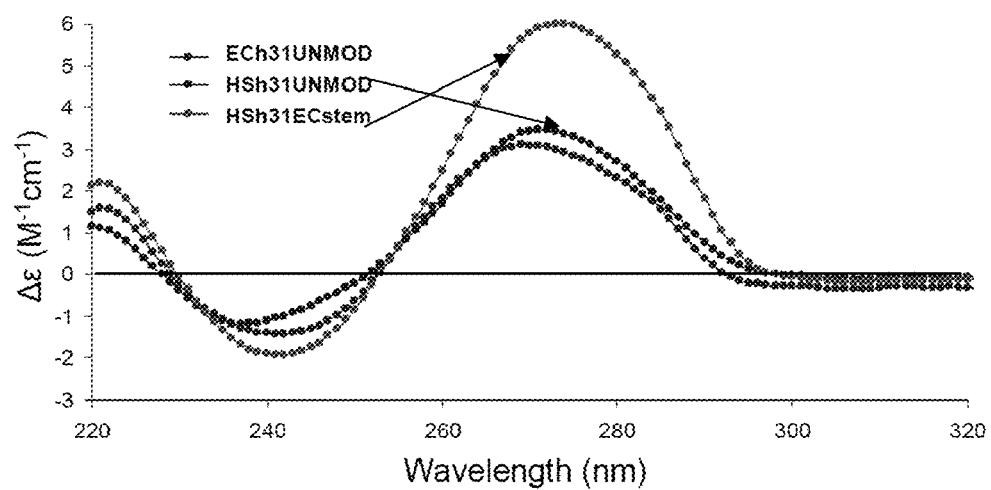

FIG. 38 depicts CD spectra of unmodified analogues of ECh31UNMOD (blue), HSh31UNMOD (red), and HSh31ECstem (green) of h31 RNAs.

FIG. 39 depicts peptides isolated from modified h31 as a target (round 3). FIG. 39 discloses SEQ ID NOS 24-33, 5, 34-37, 6, 38-47, 14, 7, 48-73, 11 and 74-76, respectively, in order of appearance.

FIG. 40A depicts peptides isolated from modified h31 as a target (round 3). FIG. 40A discloses SEQ ID NOS 77-108, 3, 109-110, 107, 111-112, 2, 113-118 and 118-121, respectively, in order of appearance. FIG. 40B depicts peptides isolated from modified h31 as the target. Unmodified h31 was used in the counter selection step (round 3). FIG. 40B discloses SEQ ID NOS 4, 122-123, 3 and 124, respectively, in order of appearance.

FIG. 41 depicts peptides isolated from unmodified h31 as the target (round 3). FIG. 41 discloses SEQ ID NOS 125-143, 8, 144-147, 147, 148-156, 9, and 157-203, respectively, in order of appearance.

FIG. 42 depicts peptides isolated from unmodified h31 as the target (round 3).

FIG. 42 discloses SEQ ID NOS 204-230, respectively, in order of appearance.

FIG. 43 depicts peptides isolated from screening streptavidin beads (control). The HPQ motif is a known binder for streptavidin. FIG. 43 discloses SEQ ID NOS 231-232, 54, 233, 54, 234-238, 235, 239-244, 242, 245, 237, 235, 243, 237, 246, 237, 244, 247-249, 235, 246, 240, 247, 240, 244, 240, 235, 244, 244, 250, 240, 244, 240, 237, 235, 247, 247, 243, 242, 244, 251, 242, 244, 235, 252-253, 236, 244, 237, 240, 243, 254-255, 244, 256, 256, 252, 247, 252, 237, 237, 249, 257, 248, 244, 235, 257-266, respectively, in order of appearance.

FIG. 44 depicts sequence homology of selected peptides with different proteins of *E. coli*. Most of the peptide sequences showed homology with motifs representing RNA-binding proteins. FIG. 44 discloses SEQ ID NOS 2, 267-269, 269, 14, 270, 270, 3, 271, 271, 4, 272, 272, 6, 273, 273, 274, 275, 5, 276, 276, 8, 277, 277, 9, 278 and 279, respectively, in order of appearance.

Figure 45:
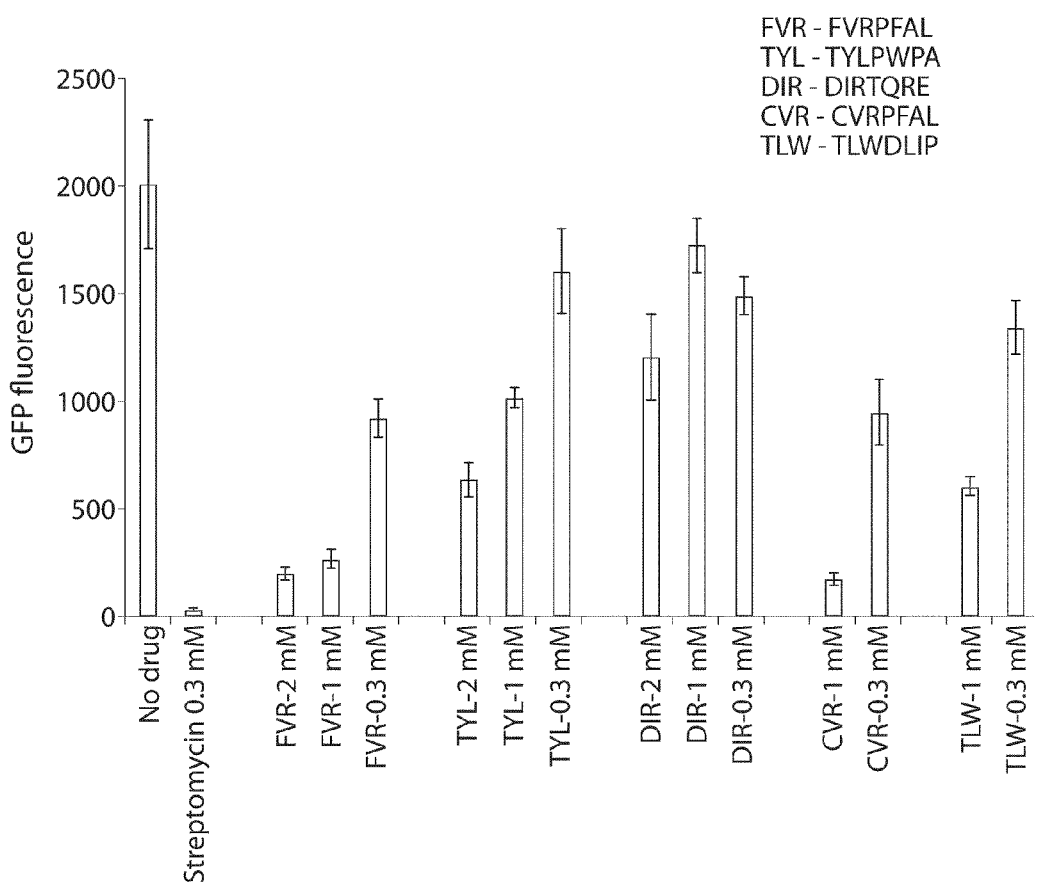

FIG. 45 depicts results of the coupled in vitro transcription-translation inhibition assay of different peptides. FIG. 45 discloses SEQ ID NOS 7, 2, 6, 4 and 3, respectively, in order of appearance.

Figure 46:
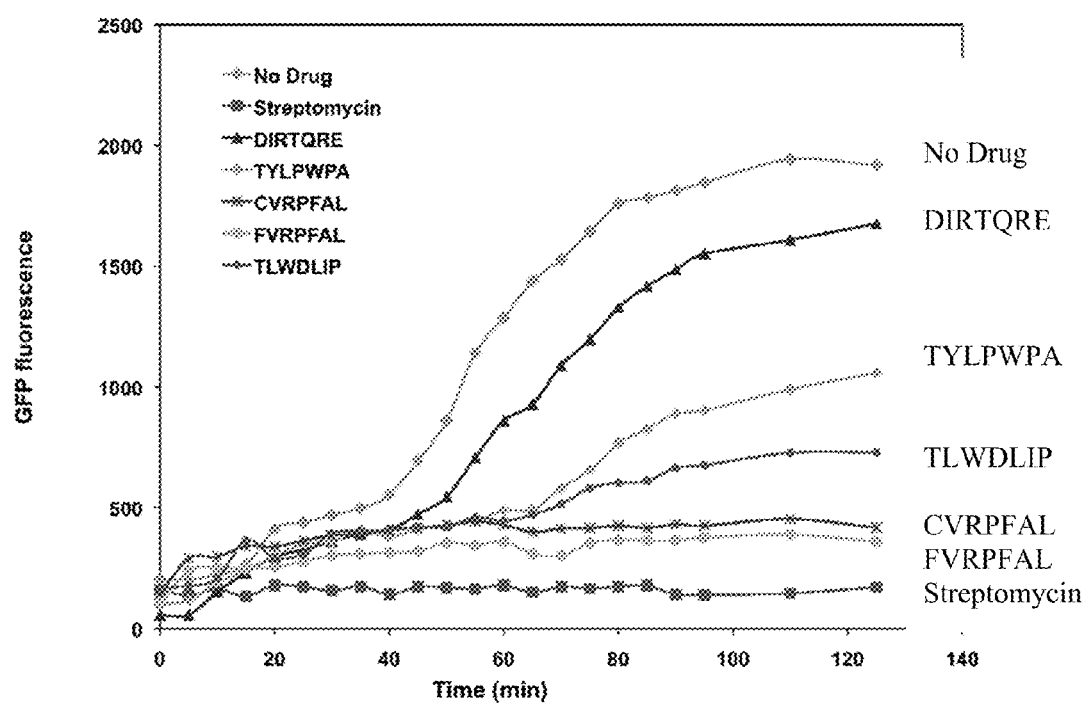

FIG. 46 depicts the rates of translation inhibition by different peptides at 1 mM.

FIG. 46 discloses "DIRTQRE" as SEQ ID NO: 6, "TYLPWPA" as SEQ ID NO: 2, "CVRPFAL" as SEQ ID NO: 4, "FVRPFAL" as SEQ ID NO: 7 and "TLWDLIP" as SEQ ID NO: 3.

Figure 47:
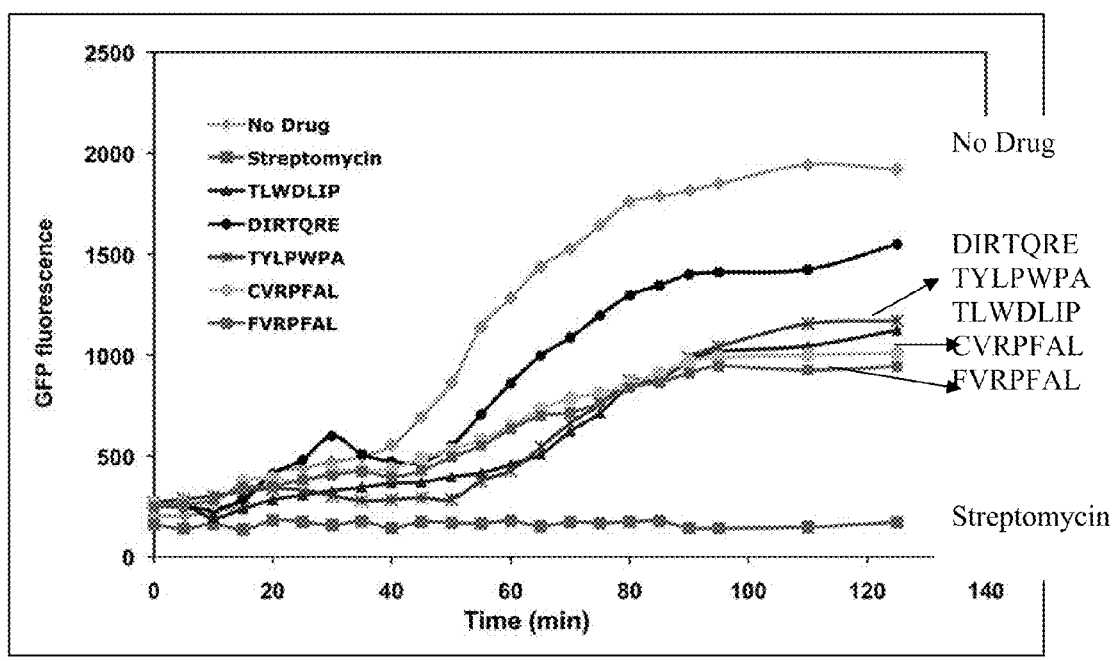

FIG. 47 depicts the rates of translation inhibition by different peptides at 0.3 mM FIG. 47 discloses "TLWDLIP" as SEQ ID NO: 3, "DIRTQRE" as SEQ ID NO: 6, "TYLPWPA" as SEQ ID NO: 2, "CVRPFAL" as SEQ ID NO: 4 and "FVRPFAL" as SEQ ID NO: 7.

Figure 48:
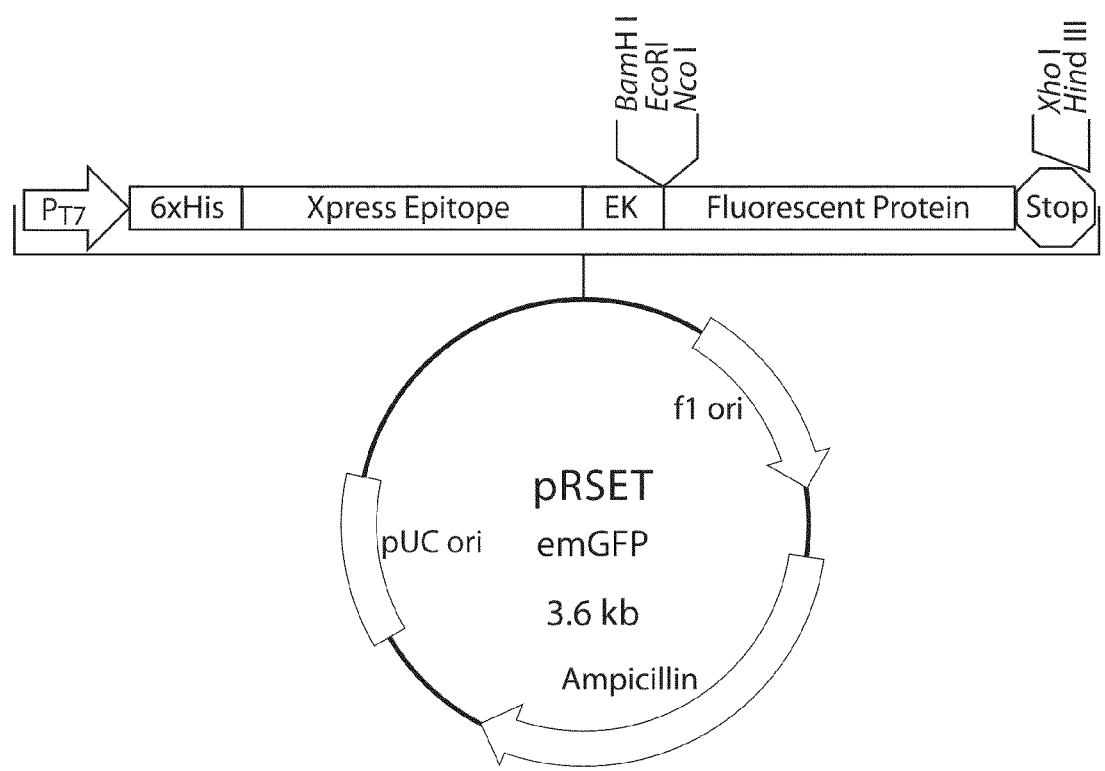

FIG. 48 depicts the plasmid used as template for in vitro transcription-translation inhibition reaction. The T7 promoter is shown as PT7 and is located just before the six histidine residues (SEQ ID NO: 1). The detail information of this plasmid can be obtained at www.invitrogen.com.

Figures 1, 49:
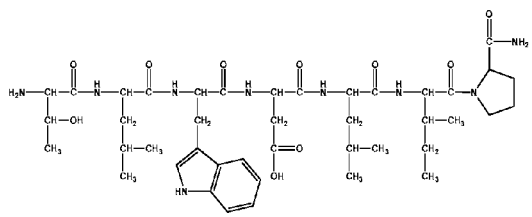
Figures 2, 49:
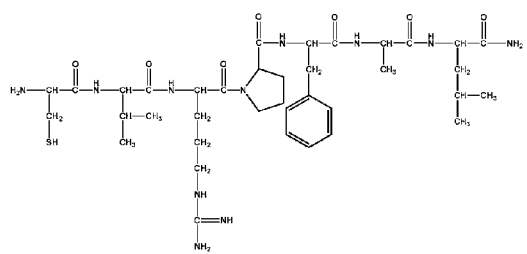
Figures 3, 49:
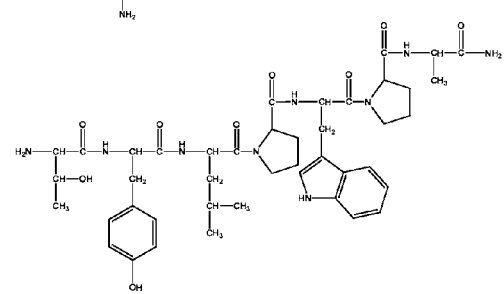
Figures 4, 49:
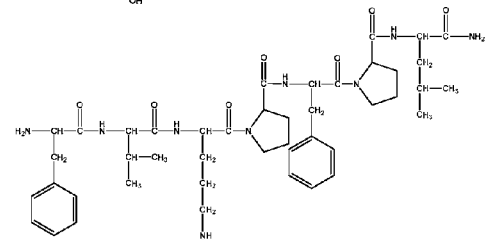
Figures 5, 49:
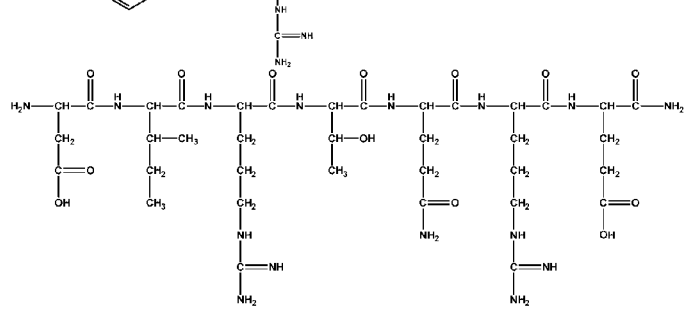

FIG. 49 depicts the chemical structures of the 7-mer peptide sequences numbered 14 (FIGS. 49-1), 15 (FIGS. 49-2), 16 (FIGS. 49-3), 17 (FIGS. 49-4) and 18 (FIGS. 49-5) (SEQ ID NOS 3-4, 7, 2 and 6, respectively, in order of appearance).

Figure 50:
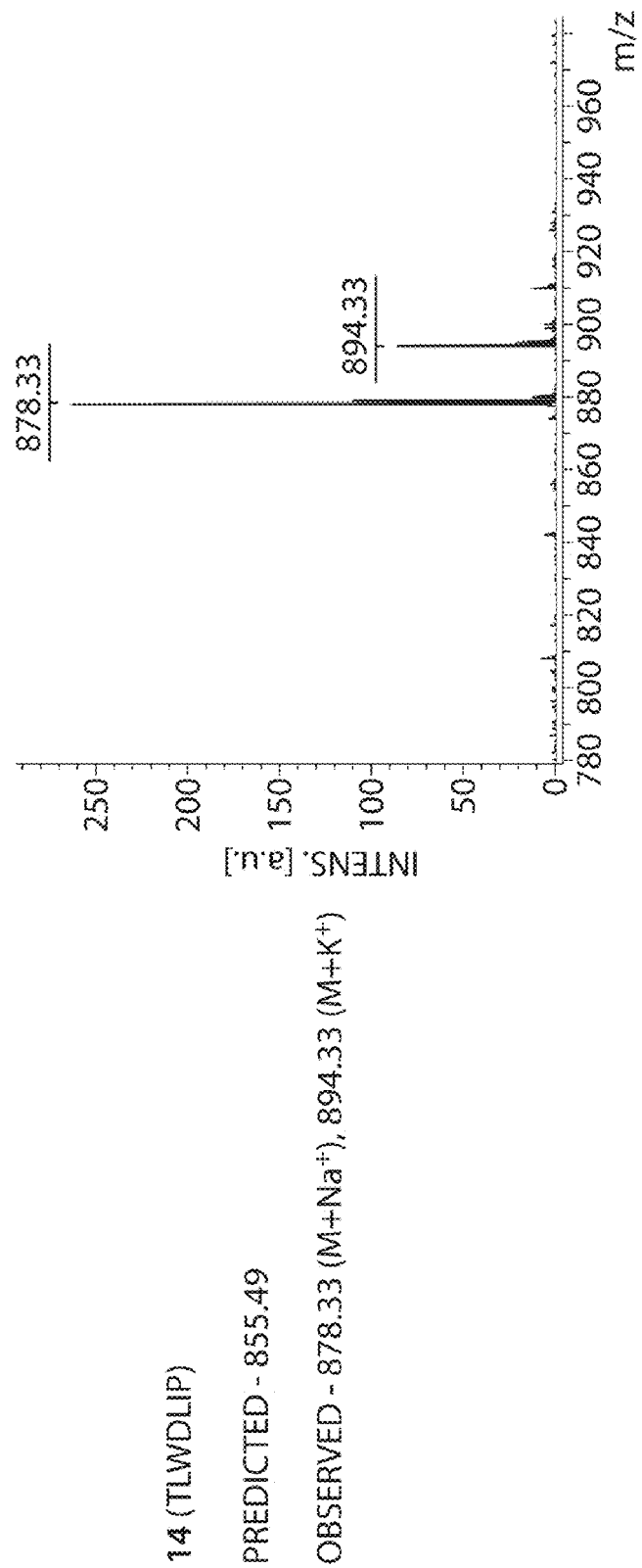

FIG. 50 depicts characterization of peptides by MALDI-TOF mass spectrometry. FIG. 50 discloses SEQ ID NO: 3.

Figure 51:
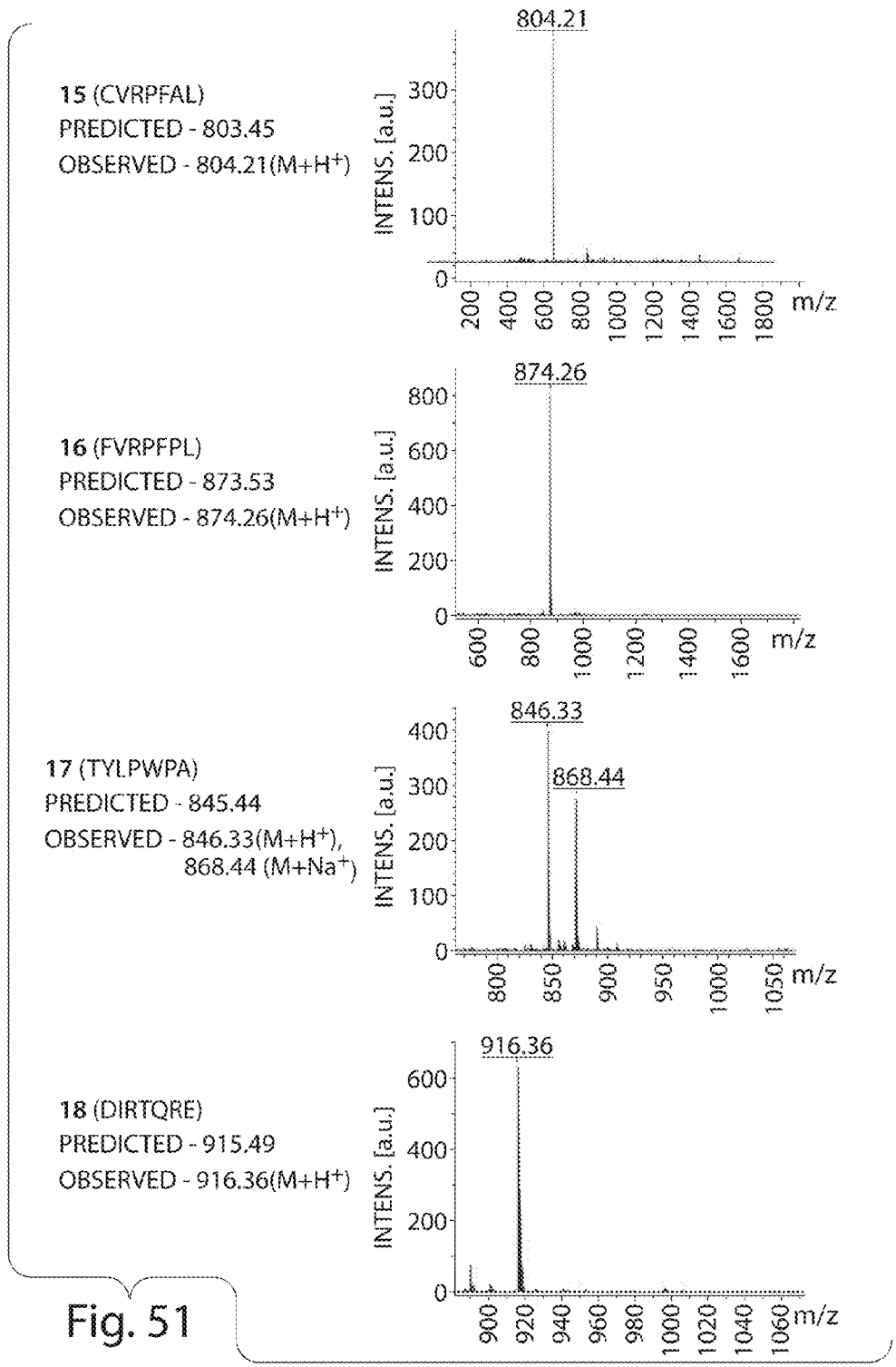

FIG. 51 depicts characterization of peptides by MALDI-TOF mass spectrometry. FIG. 51 discloses SEQ ID NOS 4, 7, 2 and 6, respectively, in order of appearance.

Figure 52:
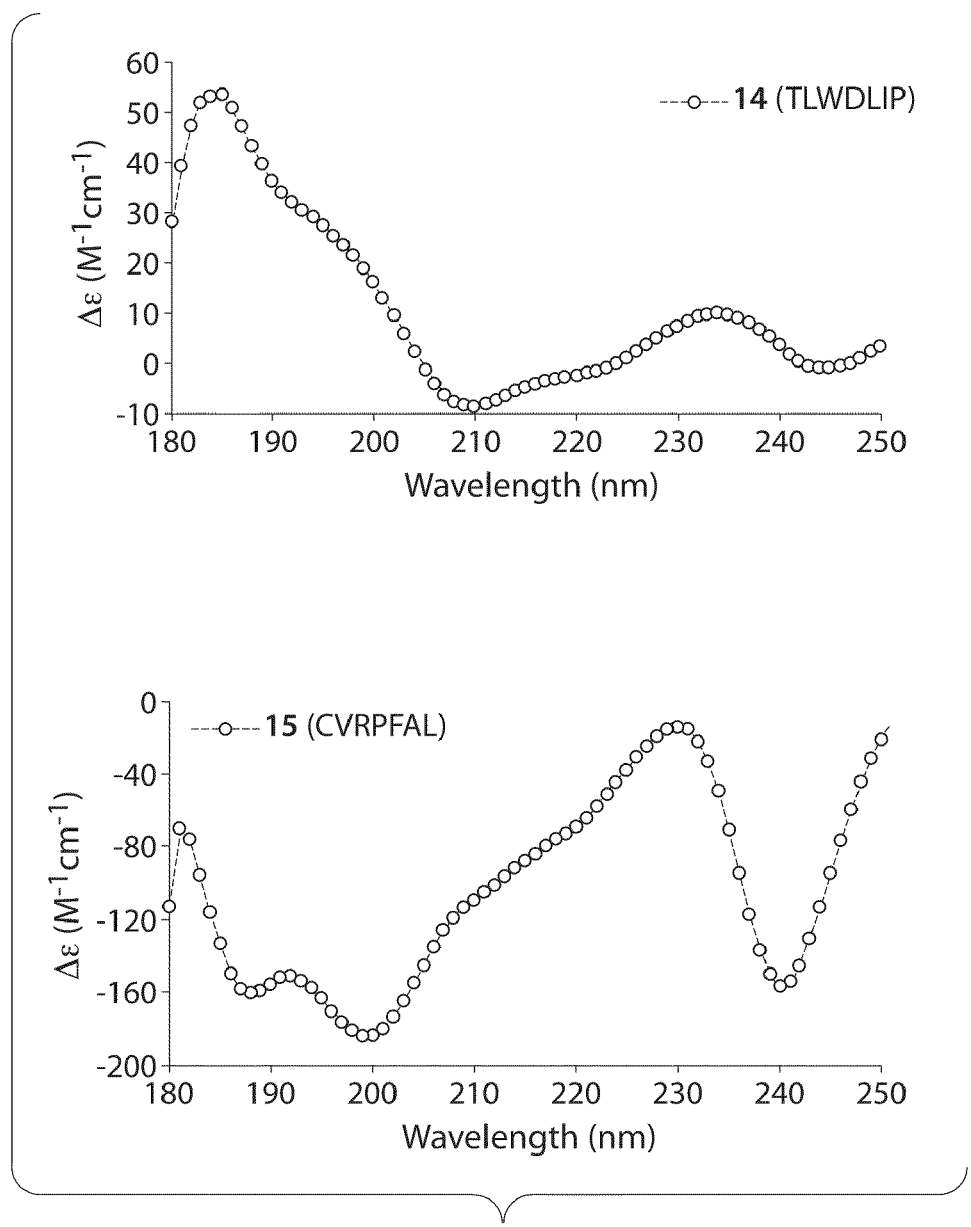

FIG. 52 depicts circular dichroism spectra of the synthetic peptides. FIG. 52 discloses SEQ ID NOS 3-4, respectively, in order of appearance.

Figure 53:
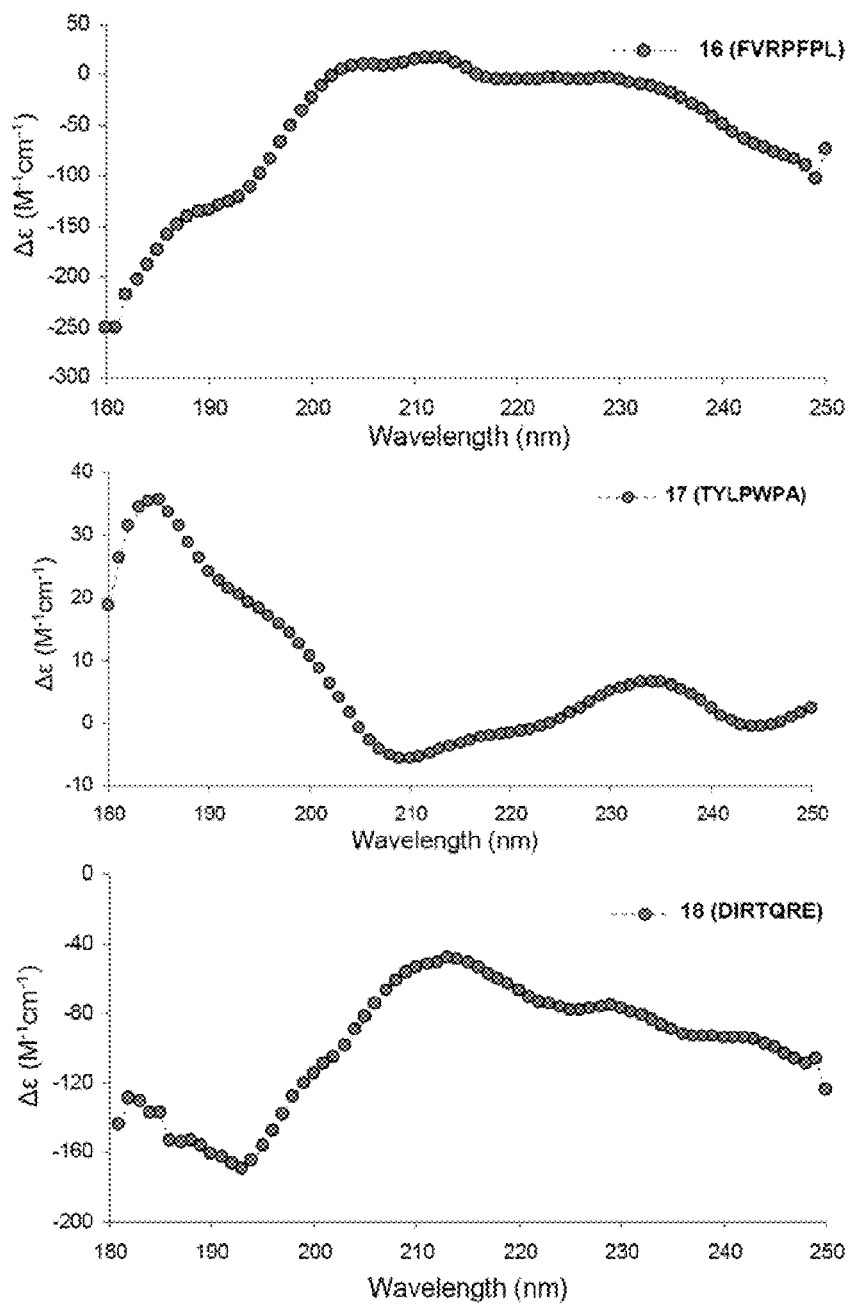

FIG. 53 depicts circular dichroism spectra of the synthetic peptides. FIG. 52 discloses SEQ ID NOS 7, 2 and 6, respectively, in order of appearance.

Figure 54:
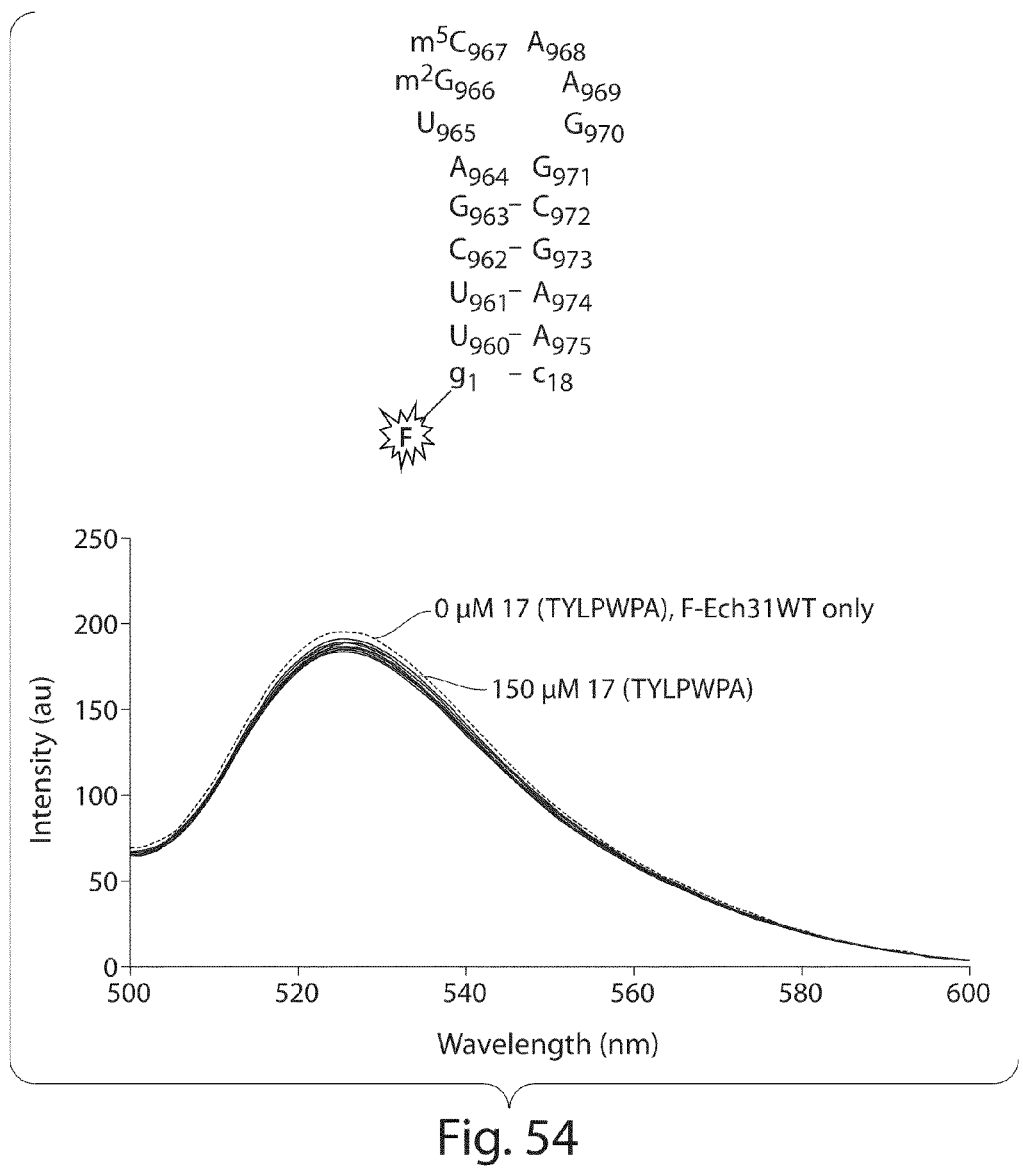

FIG. 54 depicts fluorescence changes in h31 observed for the titration with peptide 17 (TYLPWPA (SEQ ID NO: 2)). The buffer contained 10 mM HEPES at pH 7.5, 50 mM NaCl, 1 mM Na2EDTA. FIG. 54 discloses SEQ ID NO: 15.

Figure 55A:
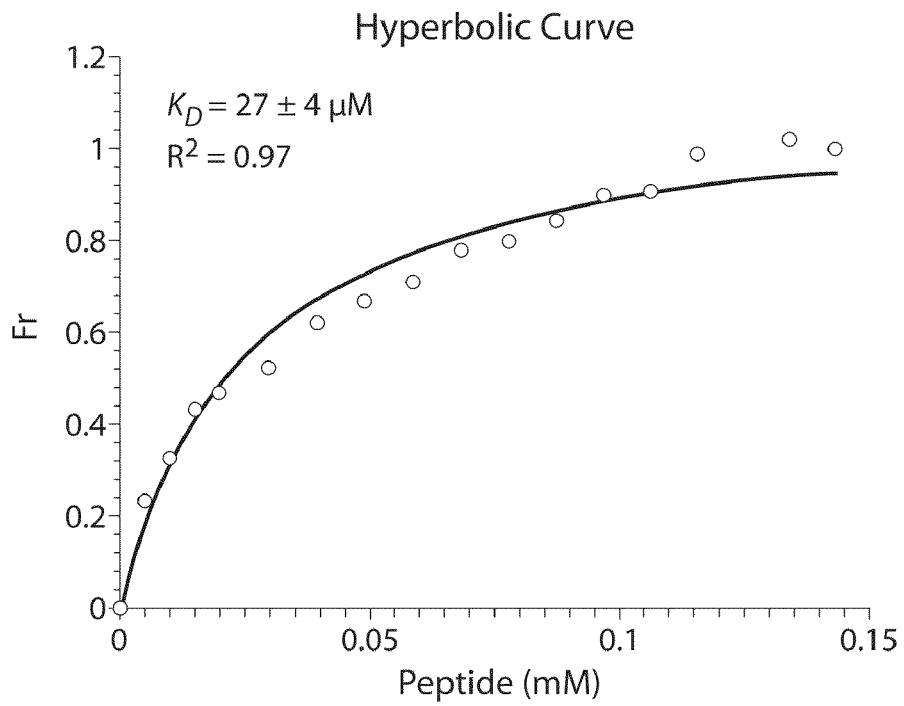
Figure 55B:
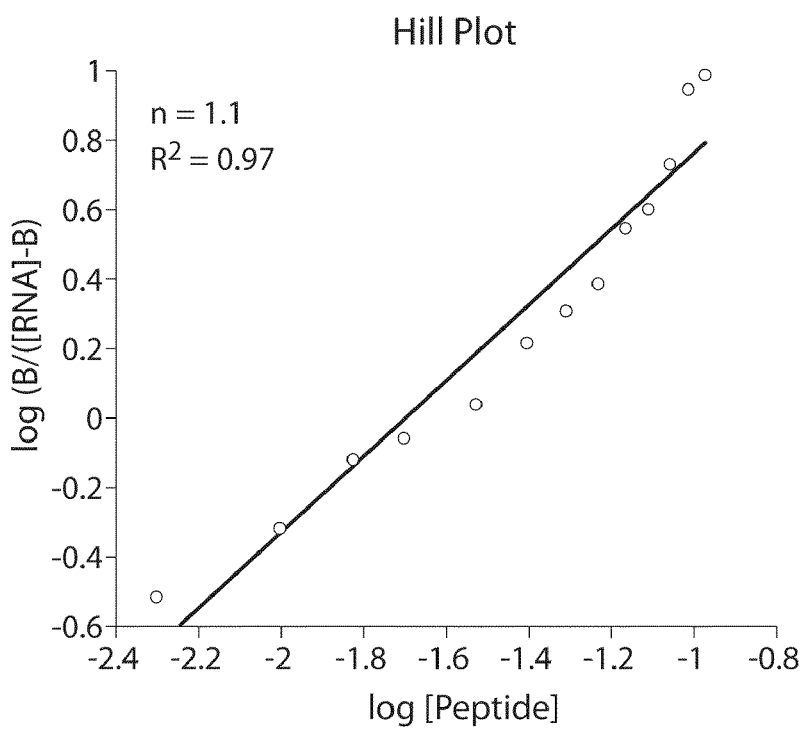

FIG. 55 depicts determination of the apparent KD for the titration of peptide 17 (TYLPWPA (SEQ ID NO: 2)) with h31 (A) and the Hill plot (B).

FIG. 56 depicts CD changes in h31 observed for the titration of peptide 17 (TYLPWPA (SEQ ID NO: 2)) (A) and curve fitting for the determination of an apparent KD (B). The buffer contained 10 mM sodium phosphate at pH 7.0, 100 mM NaCl, and 0.1 mM Na2EDTA.

Figure 57:
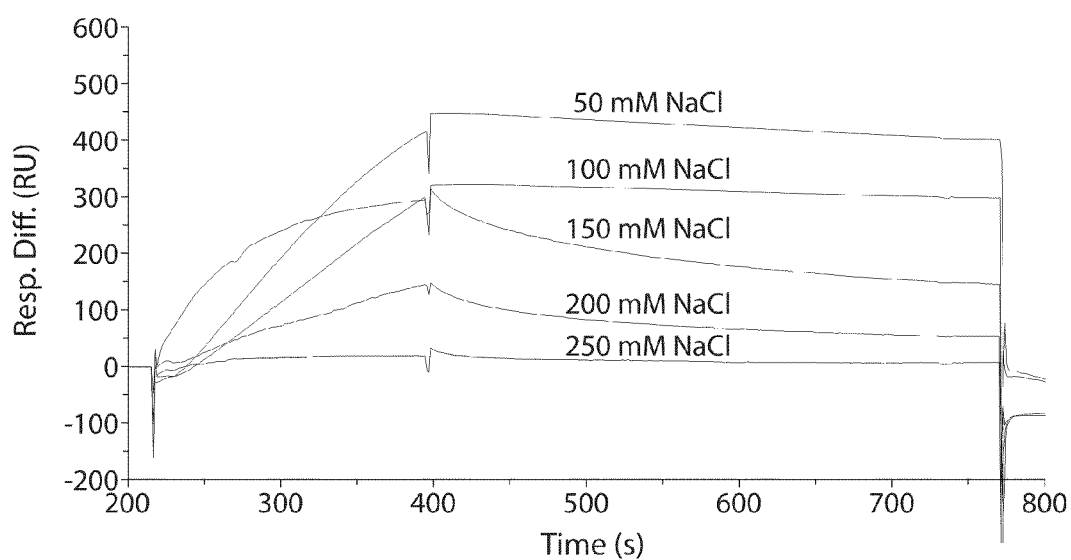

FIG. 57 depicts an overlay of sensorgrams showing the interaction of 17 (TYLPWPA)-GFP ("TYLPWPA" disclosed as SEQ ID NO: 2) with h31 RNA in varying salt concentrations.

Figure 58:
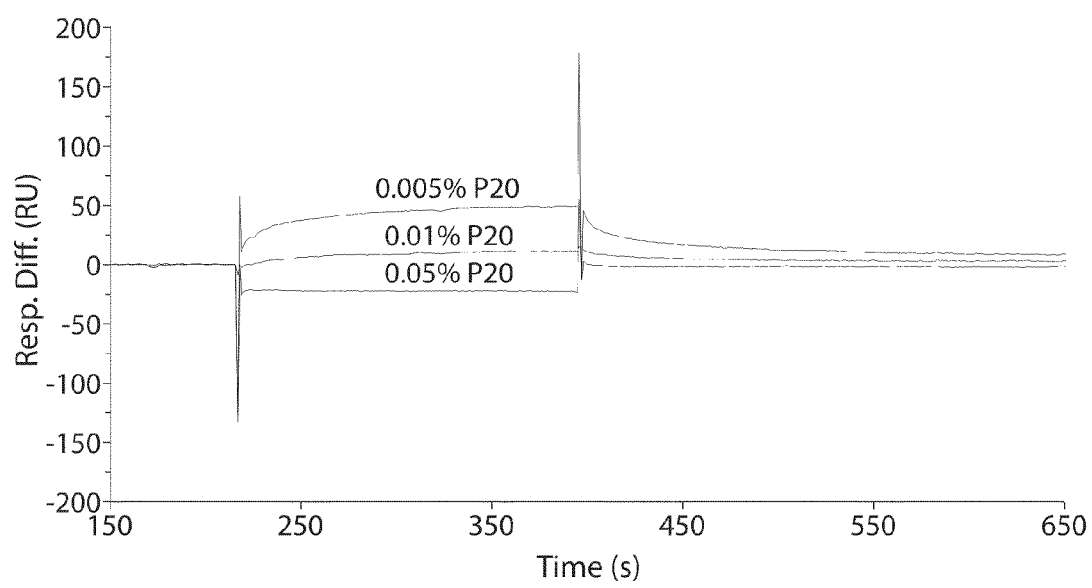

FIG. 58 depicts an overlay of sensorgrams showing the interaction of 17 (TYLPWPA)-GFP ("TYLPWPA" disclosed as SEQ ID NO: 2) with h31 RNA under varying detergent concentrations.

Figure 59:
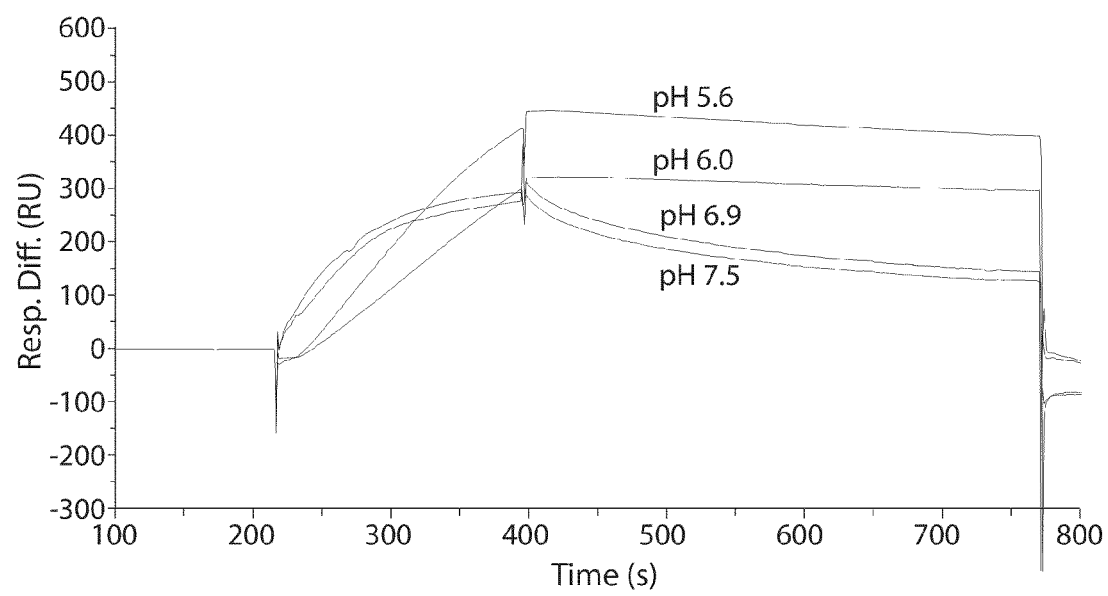

FIG. 59 depicts an overlay of sensorgrams showing the interaction of 17 (TYLPWPA)-GFP ("TYLPWPA" disclosed as SEQ ID NO: 2) with h31 RNA under varying pH-buffers (10 mM Tris.HCl, 150 mM NaCl, 10 mM MgCl2, 1 mM DTT, 0.005% (v/v) surfactant P20).

Figure 60:
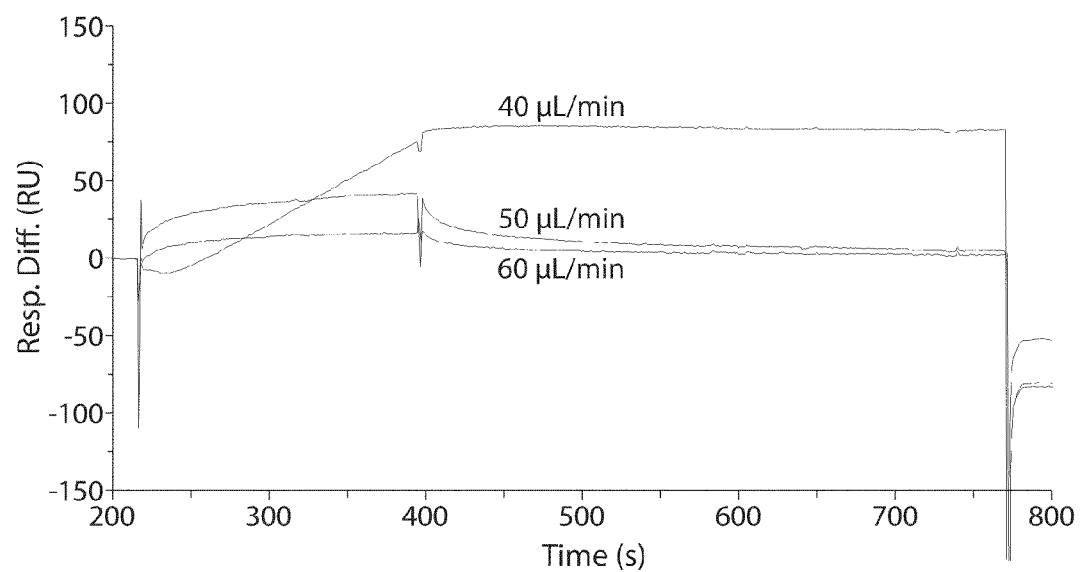

FIG. 60 depicts an overlay of sensorgrams showing the interaction of 17 (TYLPWPA)-GFP ("TYLPWPA" disclosed as SEQ ID NO: 2) with h31 RNA at different flow rates in 10 mM Tris.HCl, 150 mM NaCl, 10 mM MgCl2, 1 mM DTT, 0.005% (v/v) P20 at pH 7.5.

Figure 61:
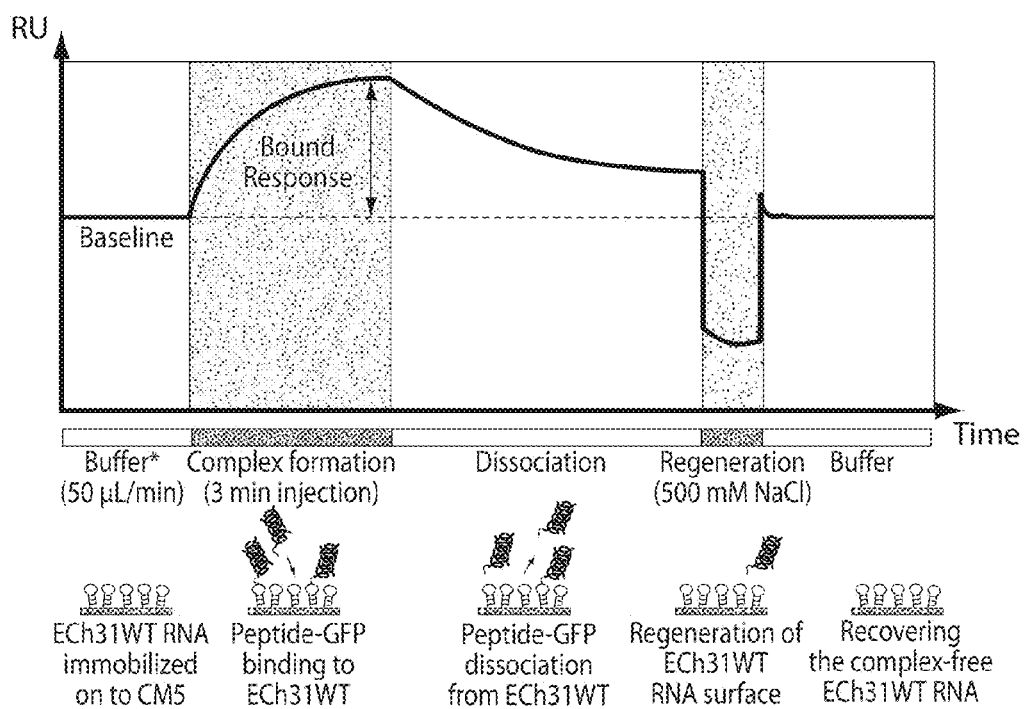

FIG. 61 depicts a schematic diagram of a typical sensorgram to highlight the events pertaining to h31 RNA and GFP-fused peptide binding.

Figure 62:
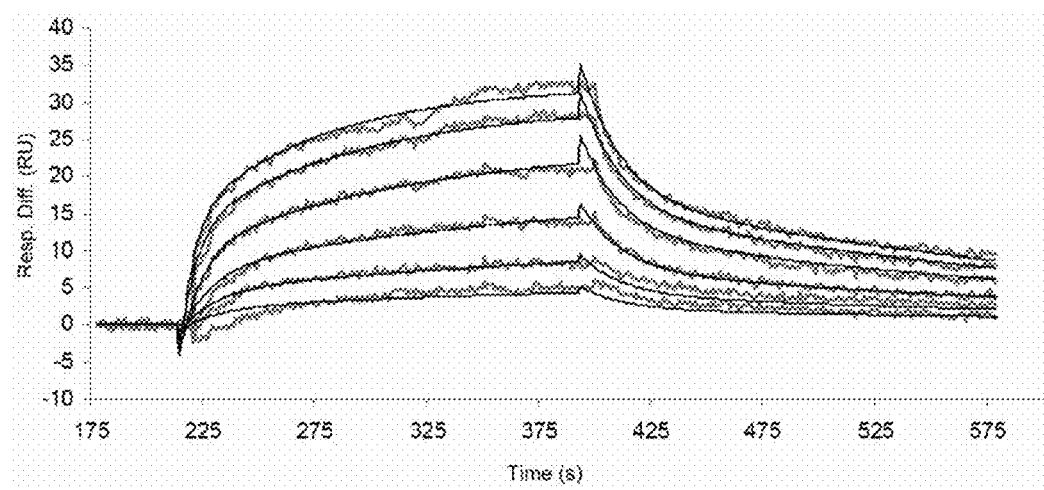

FIG. 62 depicts SPR binding curves and the curve fittings obtained from the kinetic analysis of h31 binding to 17 (TYLPWPA)-GFP ("TYLPWPA" disclosed as SEQ ID NO: 2).

Figure 63:
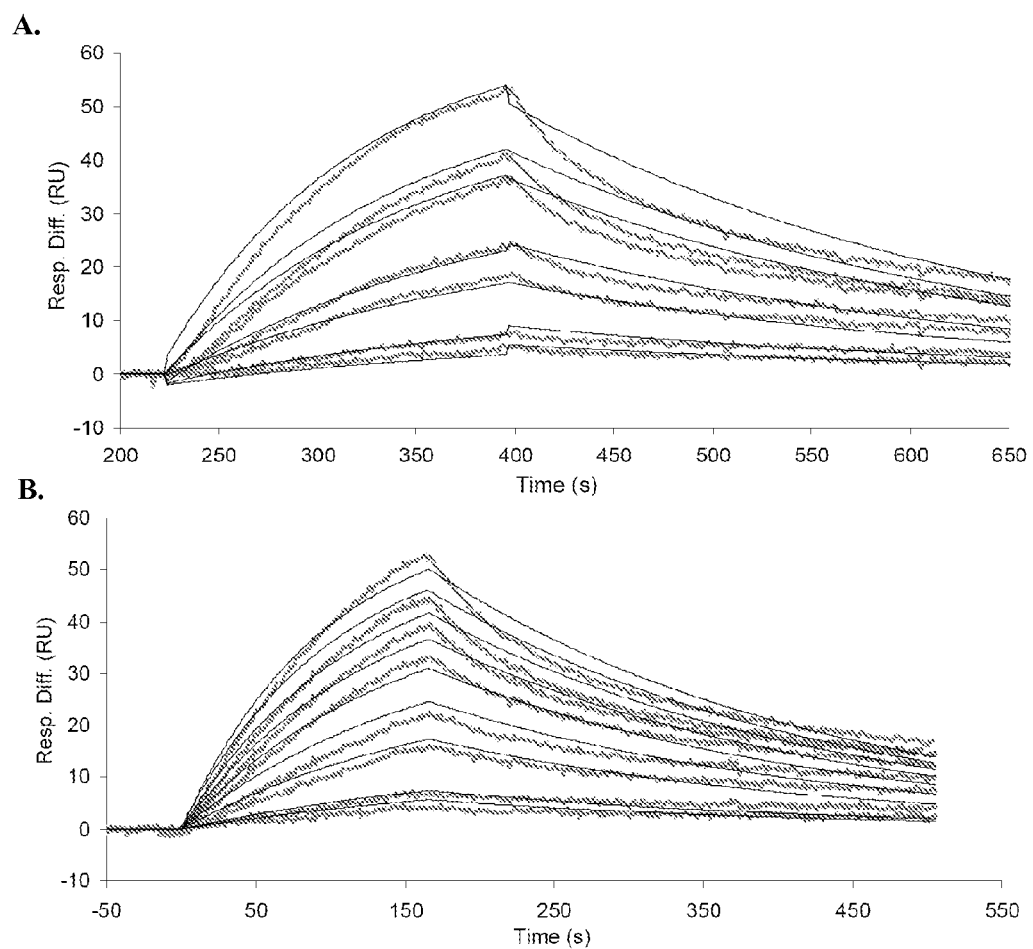

FIG. 63 depicts SPR binding curves obtained from the kinetic analysis of h31 binding to 14 (TLWDLIP)-GFP ("TYLPWPA" disclosed as SEQ ID NO: 3) (FIG. 63A) and 15 (CVRPFAL)-GFP ("TYLPWPA" disclosed as SEQ ID NO: 4) (bottom FIG. 63B).

Figure 64:
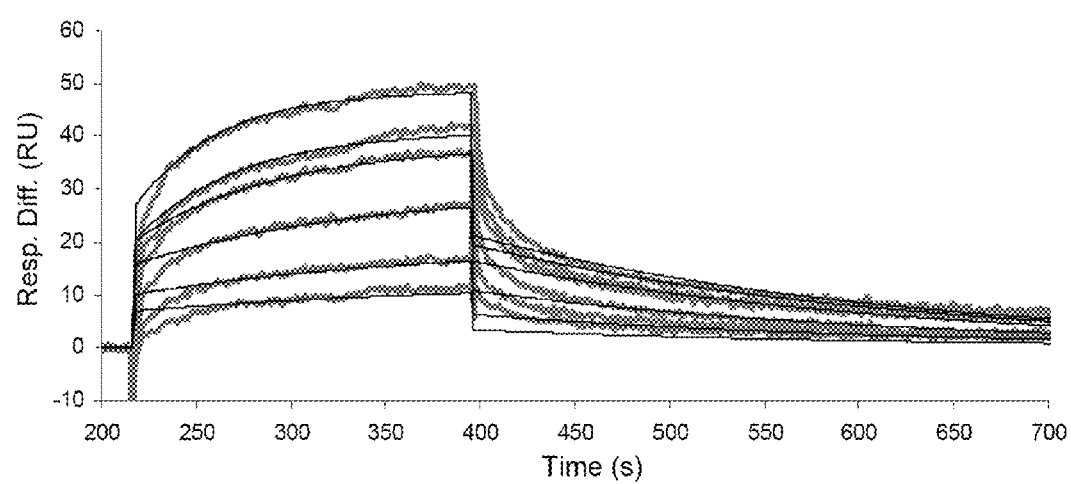

FIG. 64 depicts SPR binding curves obtained from the kinetic analysis of h31 binding to GFP.

Figure 65C:
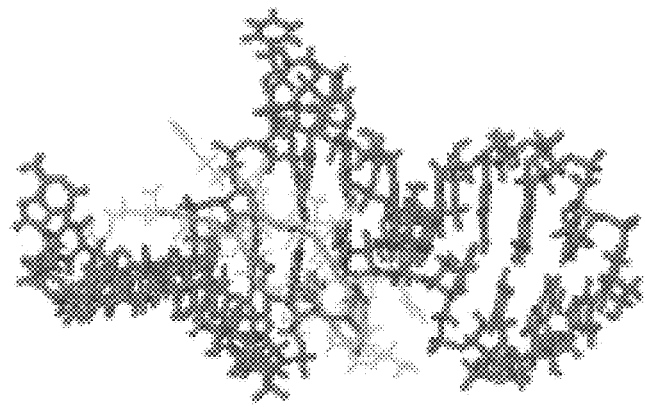
Figure 65B:
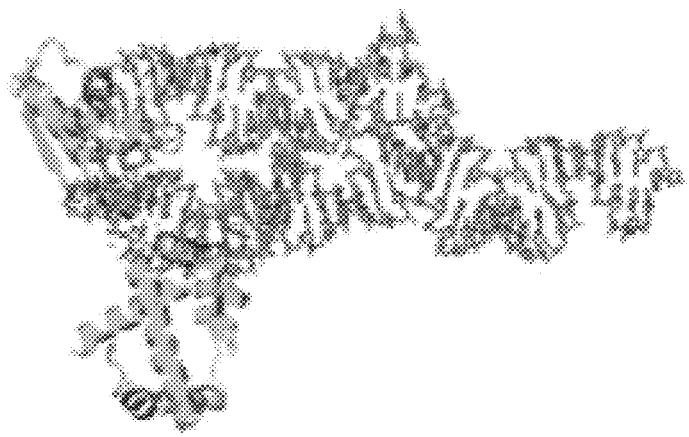
Figure 65A:
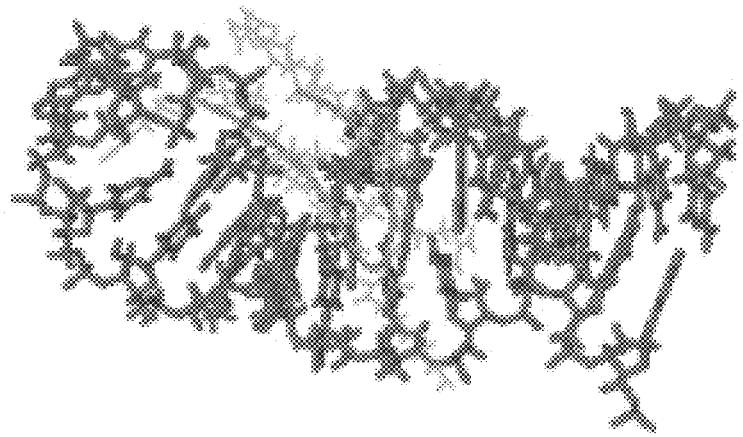

FIG. 65 depicts NMR and X-ray structures of peptide domains bound to different types of RNA. The RNA and proteins are shown in pink and green color, respectively: (A) the bovine immunodeficiency virus (BIV) Tat-Tar peptide-RNA complex, PDB ID: 1MNB (4); (B) U1A spliceosomal protein complexed with an RNA hairpin, PDB ID: 1ETG (6); and (C) the Rev peptide RRE RNA complex, PDB ID: IMFQ (7).

Figure 66:
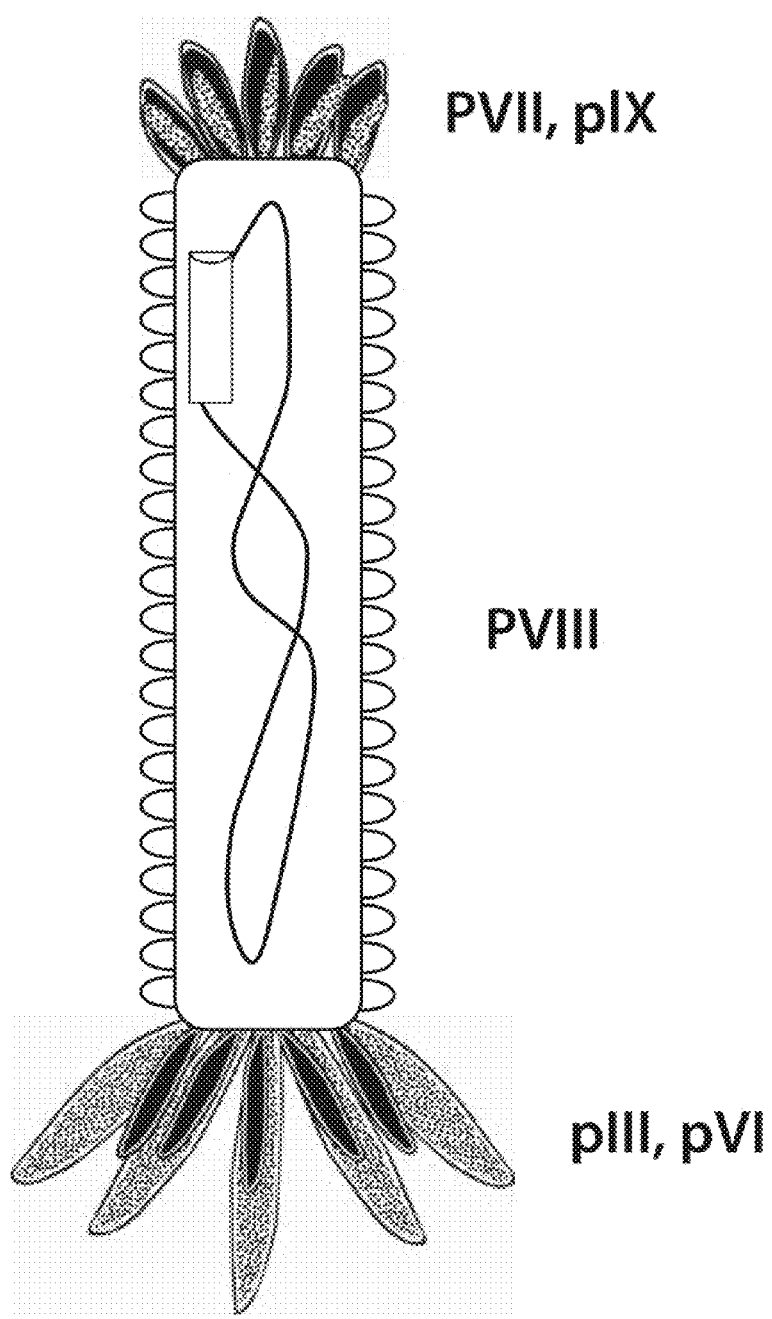

FIG. 66 depicts M13 bacteriophage with the major coat protein, pVIII, covering the entire phage. The minor coat proteins, pIII, pVI, pVII and pIX, are present at the two tips of the phage particle.

Figure 67:
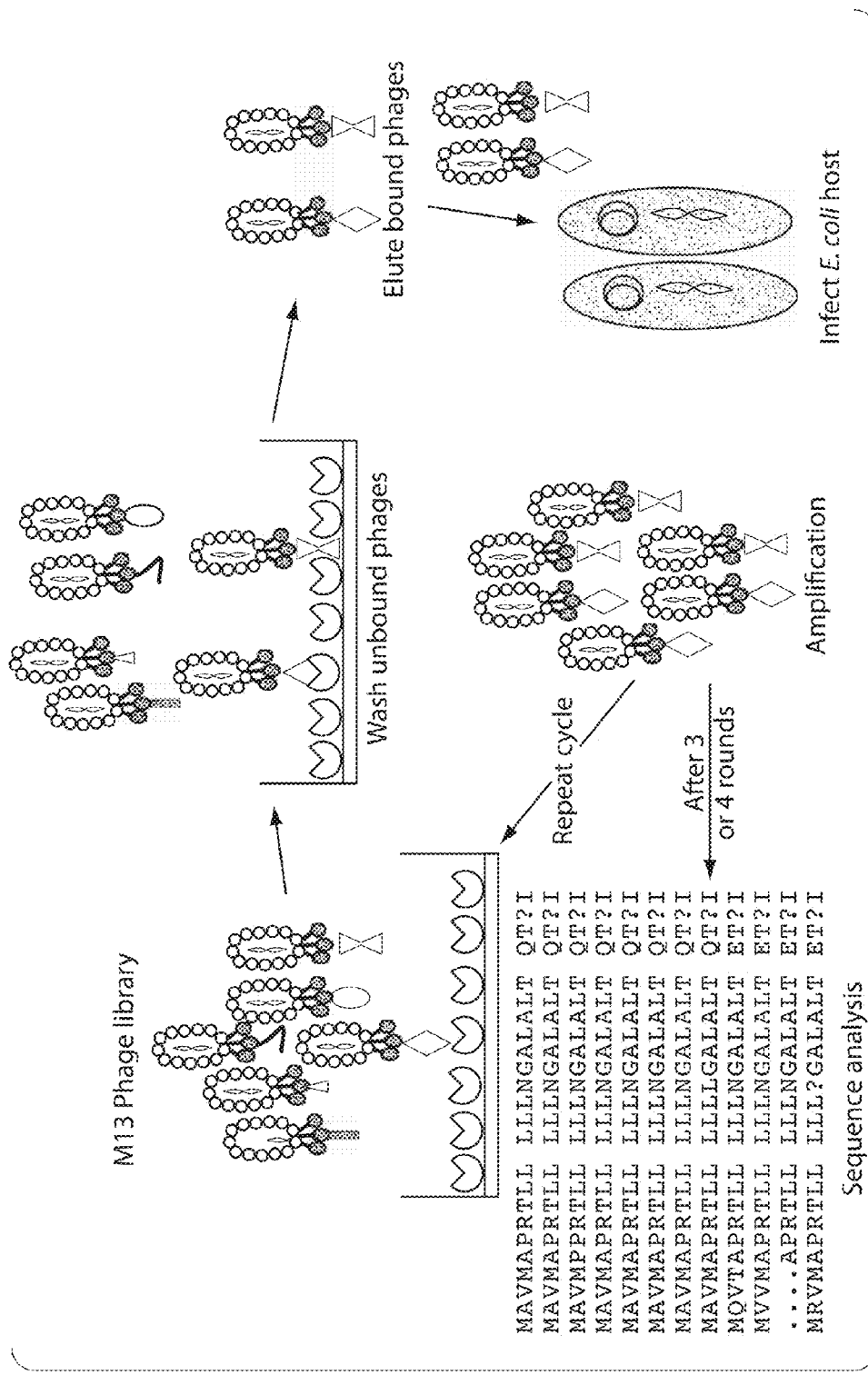

FIG. 67 depicts a schematic diagram of ligand selection by phage display. The cycle starts with the exposure of the phage display peptide library to the target molecules, which are immobilized on the surface. The unbound phage molecules are washed away and the bound ones are eluted by denaturation, which are later used to infect *E. coli* for amplification. The amplified library is again exposed to fresh target for further rounds of screening. Cycles are repeated until tightly bound, target-specific peptides are isolated.

Figure 68:
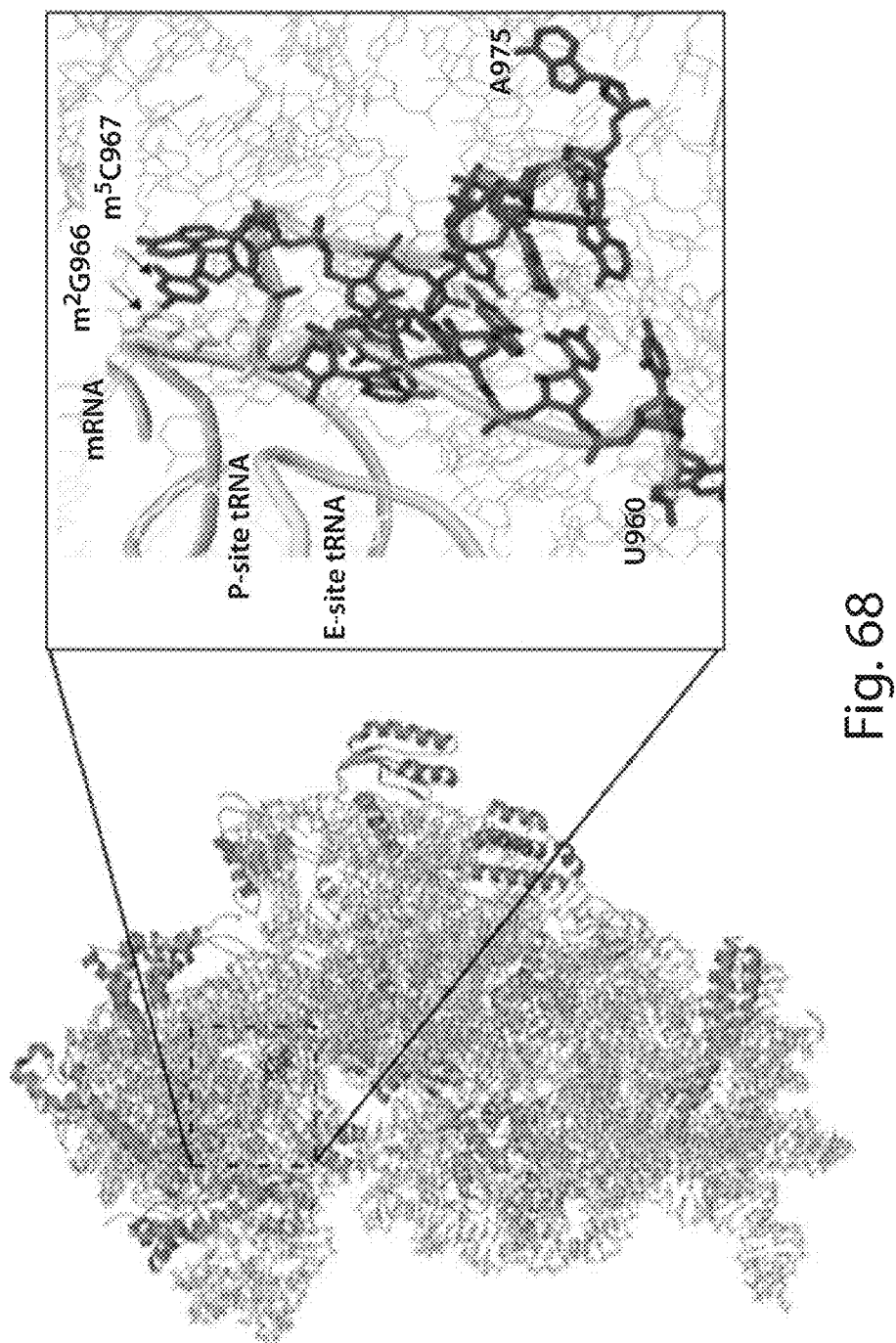
Figure 69:
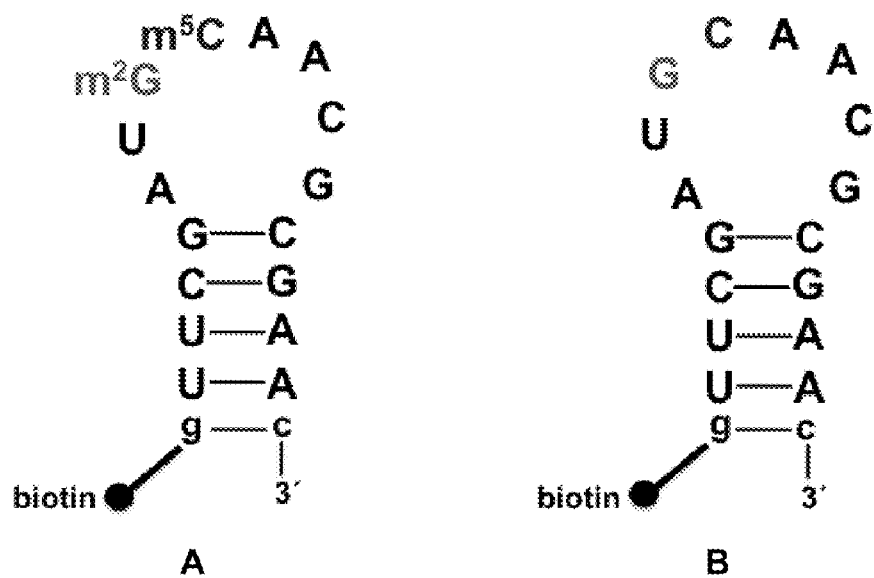

FIG. 68 depicts the location of helix 31 in the ribosome. The left side represents the 30S subunit with the location of h31 shown in the box. The expanded figure on the right shows h31 (970 loop) and positions of the P-site tRNA, E-site tRNA, and mRNA. Two modified nucleotides, $m^2G966$ and $m^5C967$, are located near the anticodon stem-loop of the P-site tRNA. PDB ID: 2I2P FIG. 69 depicts targets for phage display. The 5'-biotinylated wild-type (modified h31, A), and unmodified h31 (SEQ ID NO: 15) (B) constructs are shown (SEQ ID NO: 16). The extra closing g-c base pair at the end of the stem was added for stem stabilization.

FIG. 70 depicts the chemical structures of Fmoc and Boc protecting groups.

Figure 71:
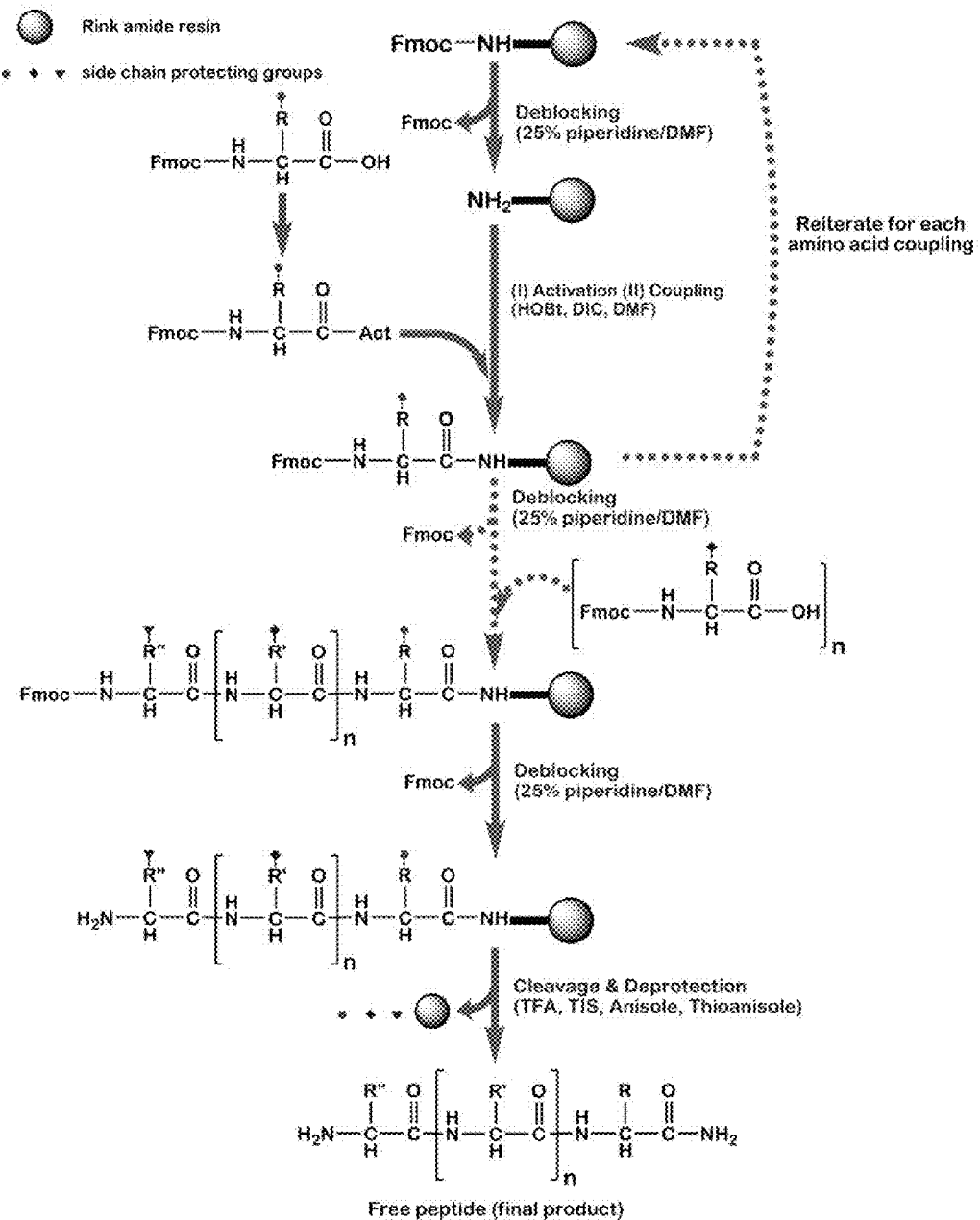

FIG. 71 depicts a general scheme for solid-phase peptide synthesis (SPPS).

Figure 72:
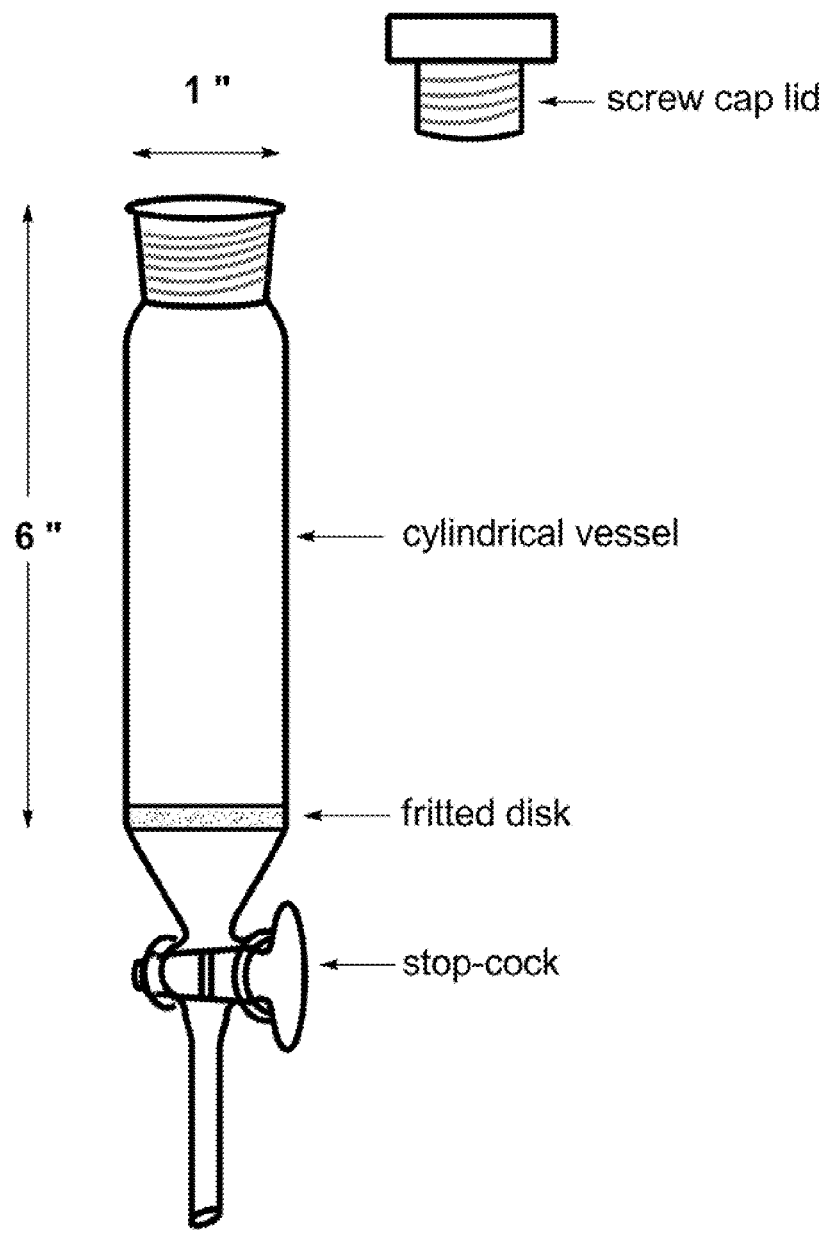

FIG. 72 depicts a schematic of the peptide synthesis vessel.

FIG. 73 depicts a few examples of SPPS resins.

Figure 74:
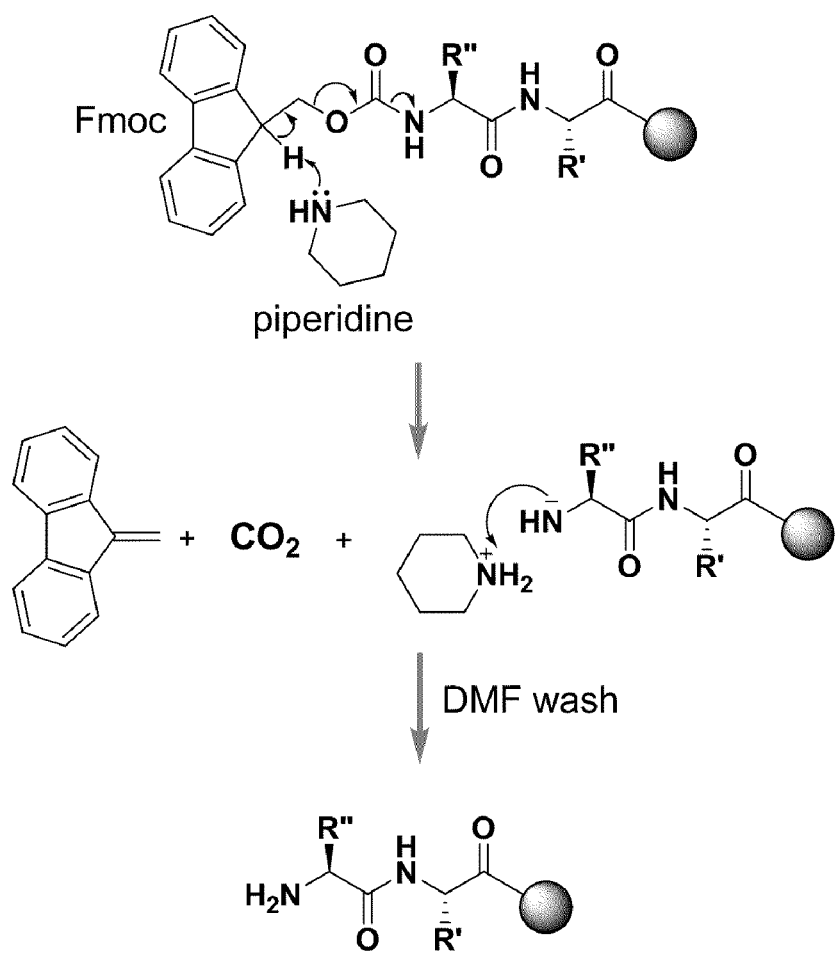

FIG. 74 depicts the Fmoc deprotection.

Figure 75:
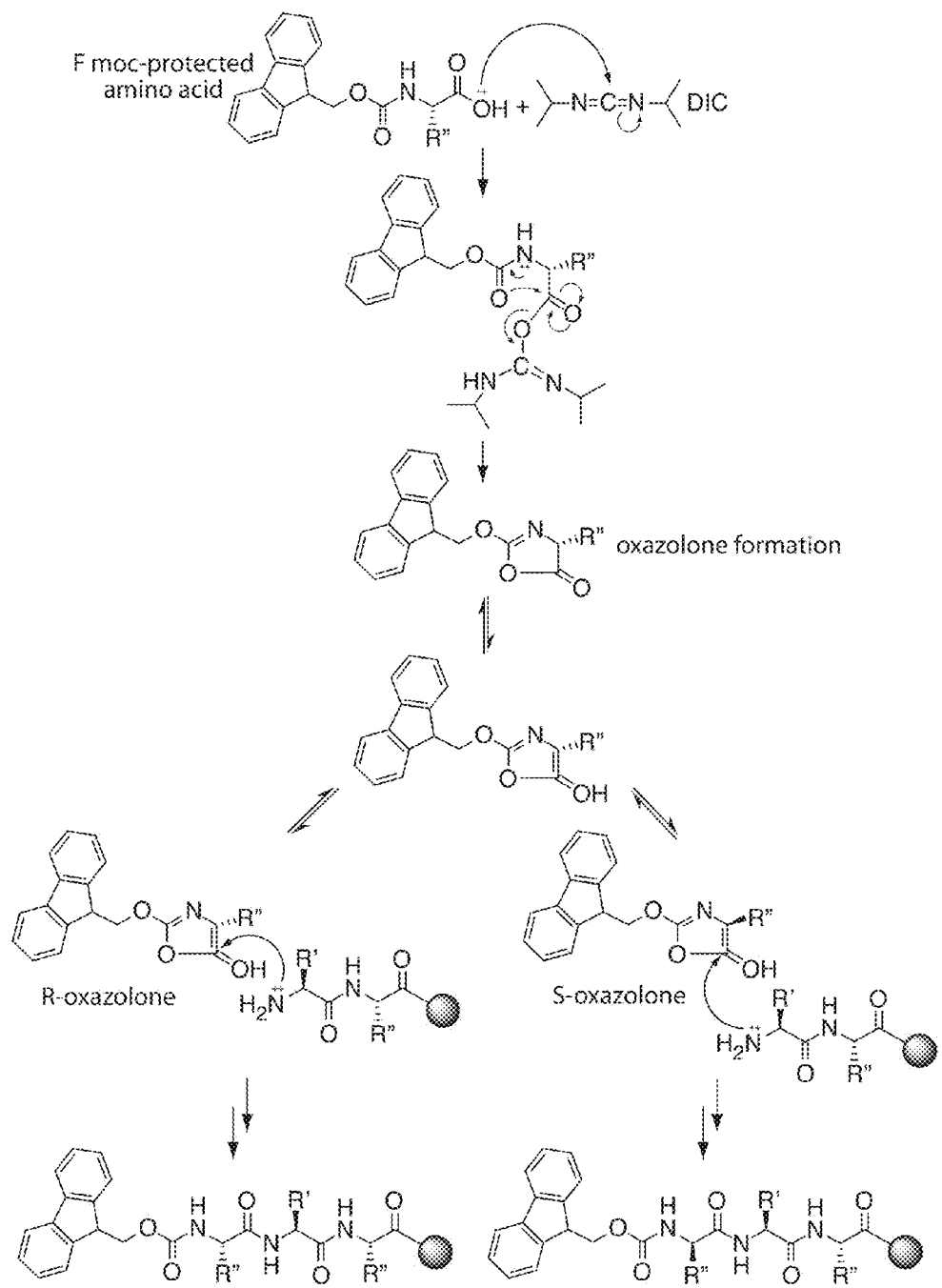

FIG. 75 depicts DIC-mediated racemization via oxazolone formation.

Figure 76:
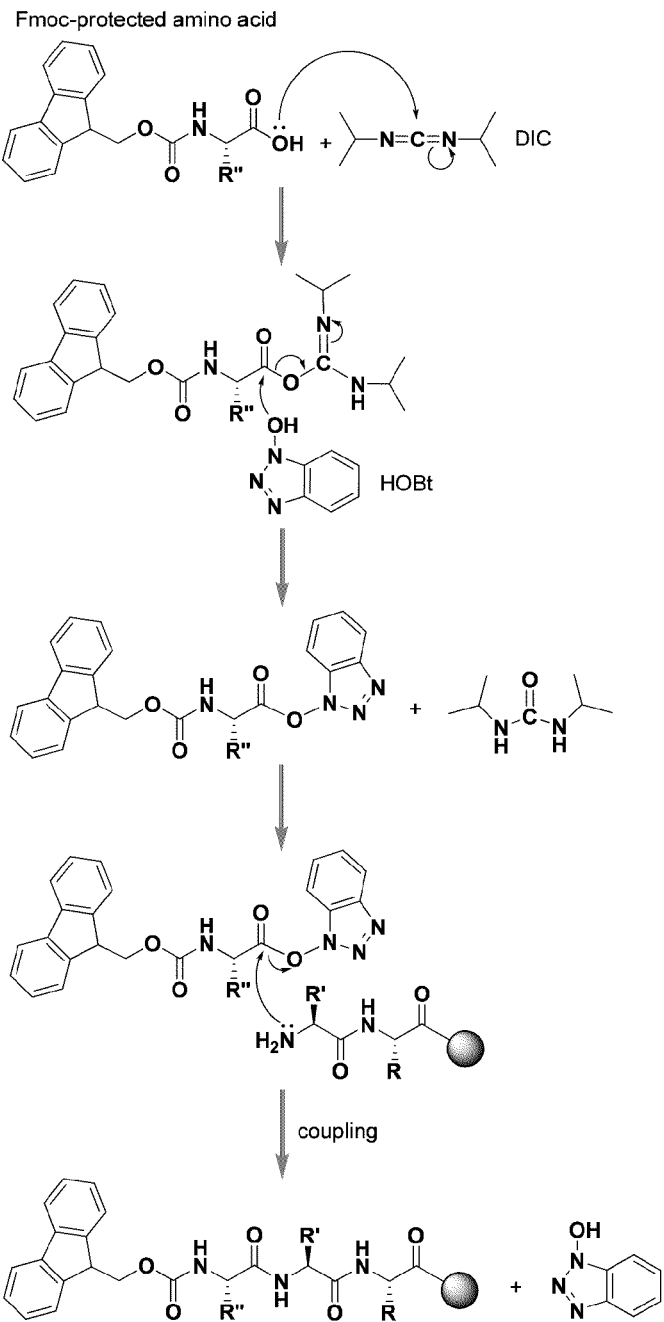

FIG. 76 depicts amino-acid coupling via DIC/HOBt activation.

Figure 77:
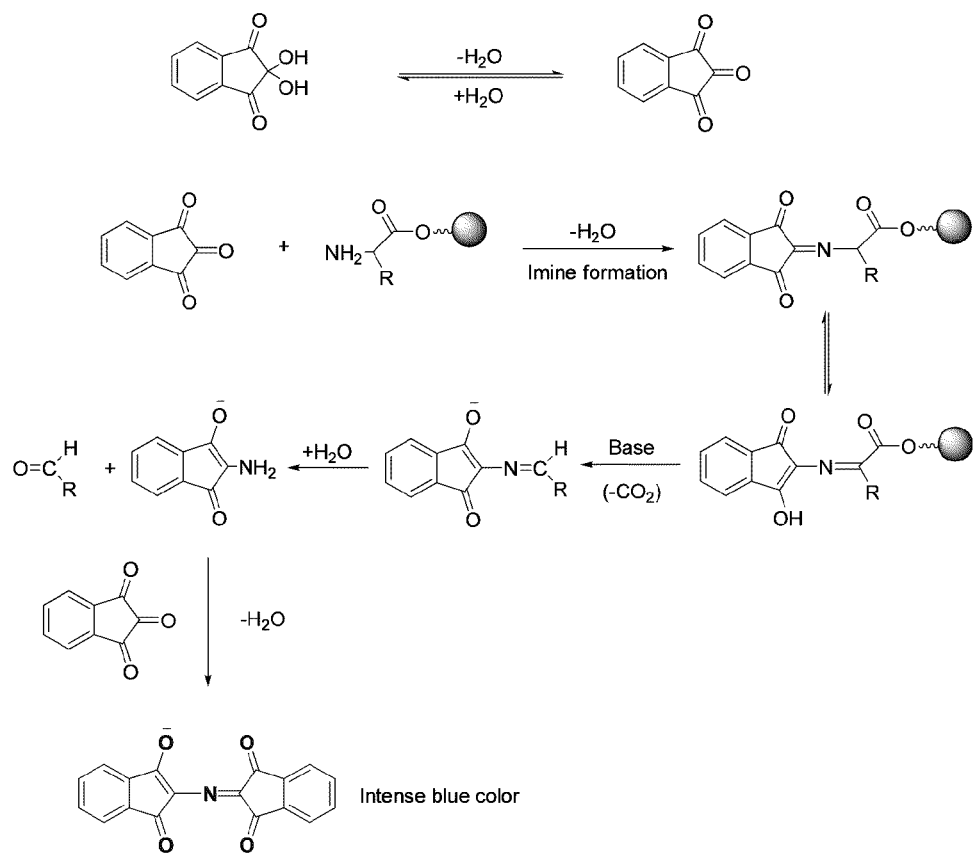

FIG. 77 depicts the ninhydrin reaction, the core reaction of the Kaiser test.

Figure 78:
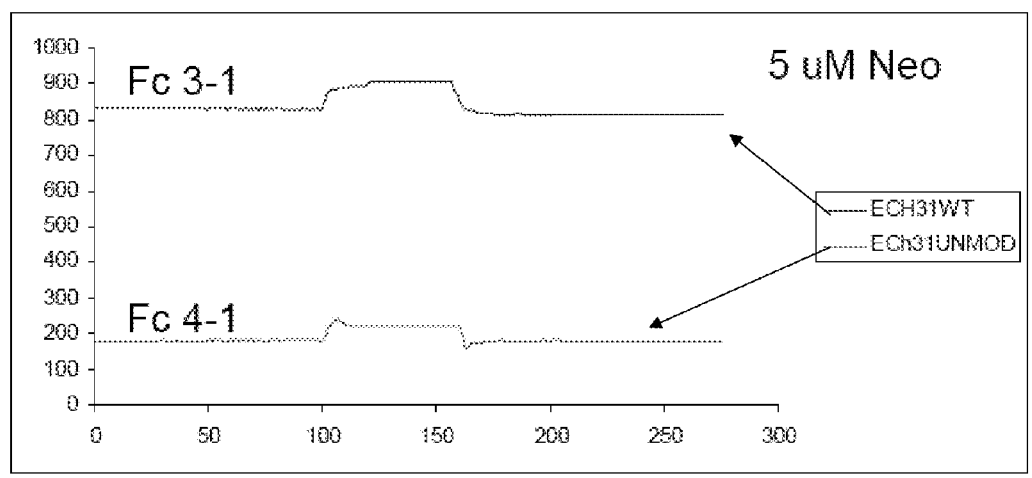

FIG. 78 depicts the affinity for ECh31WT RNA (Fc 3-1) and ECh31UNMOD (Fc 4-1) of 5 μM neomycin (positive control).

Figure 79:
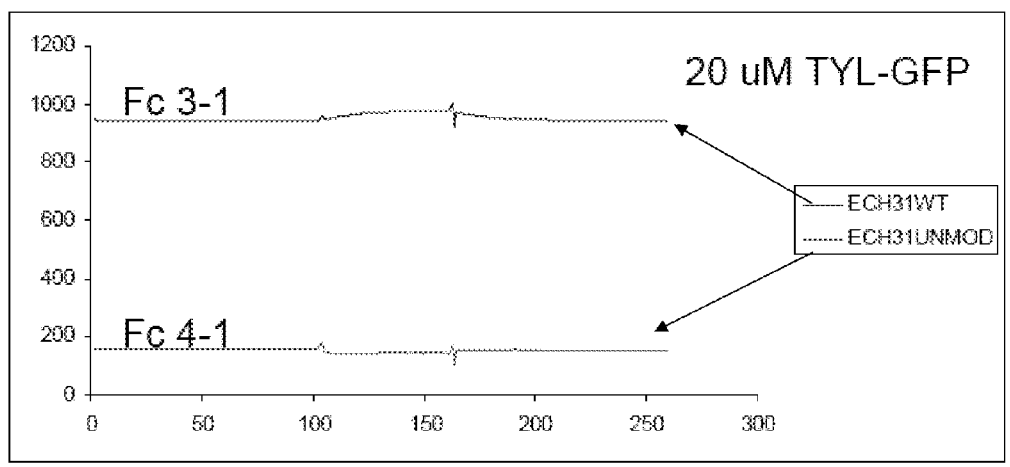

FIG. 79 depicts the affinity for ECh31WT RNA (Fc 3-1) and ECh31UNMOD (Fc 4-1) of 20 μM TYL-GFP.

Figure 80:
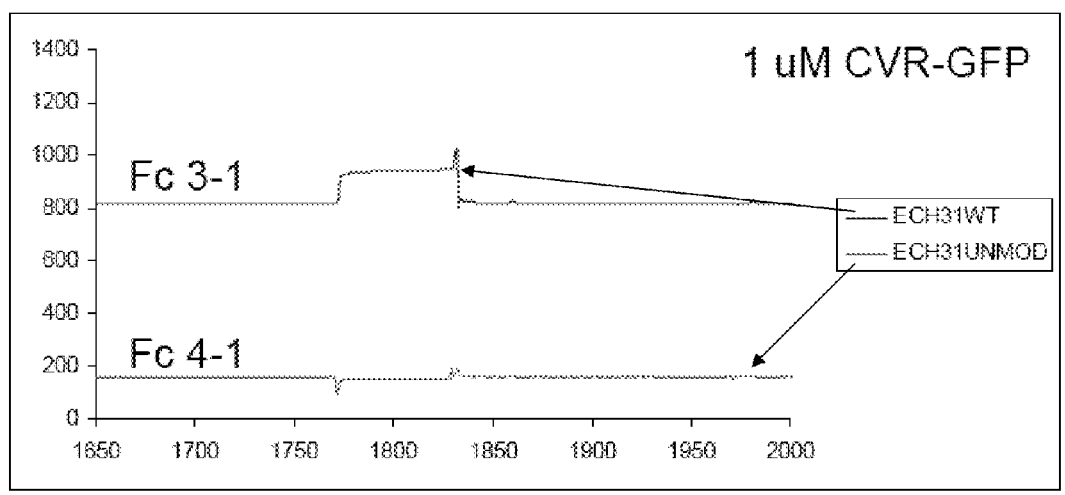

FIG. 80 depicts the affinity for ECh31WT RNA (Fc 3-1) and ECh31UNMOD (Fc 4-1) of 1 μM CVR-GFP.

Figure 81:
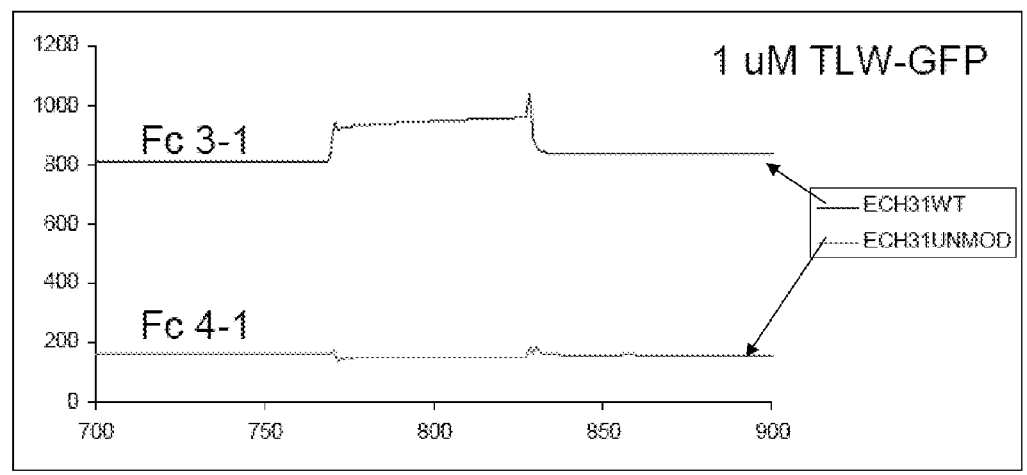

FIG. 81 depicts the affinity for ECh31WT RNA (Fc 3-1) and ECh31UNMOD (Fc 4-1) of 1 μM TLW-GFP.

Figure 82:
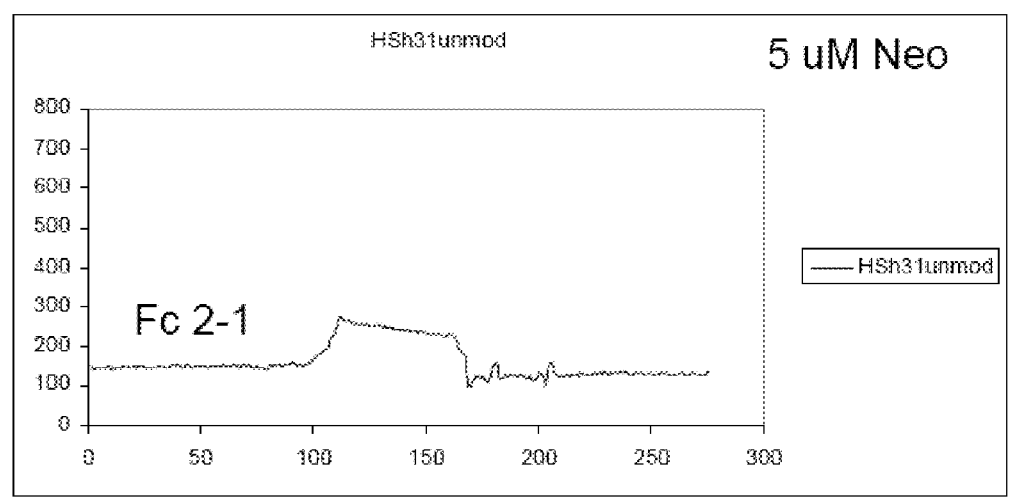

FIG. 82 depicts the affinity for HSh31ECstem RNA (Fc 2-1) of 5 μM neomycin (positive control).

Figure 83:
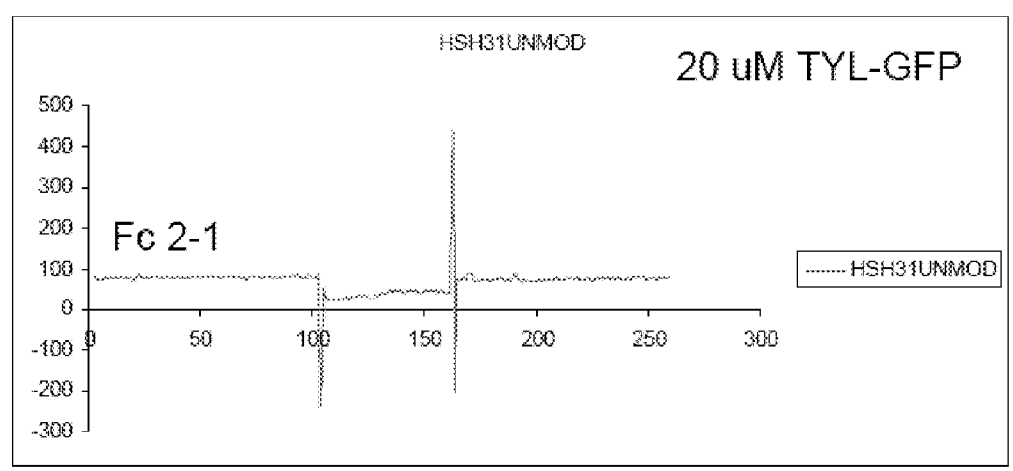

FIG. 83 depicts the affinity for HSh31ECstem RNA (Fc 2-1) of 20 μM TYL-GFP.

Figure 84:
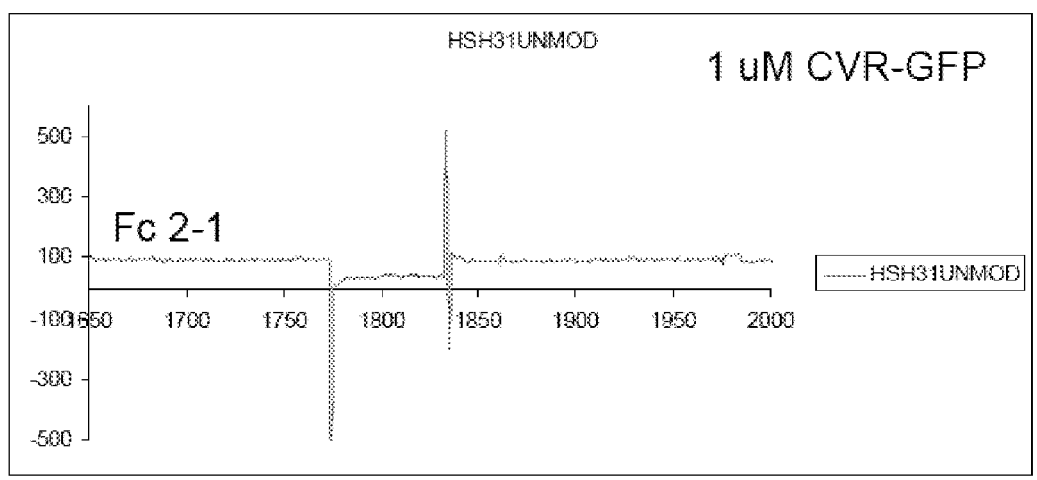

FIG. 84 depicts the affinity for HSh31ECstem RNA (Fc 2-1) of 1 μM CVR-GFP.

Figure 85:
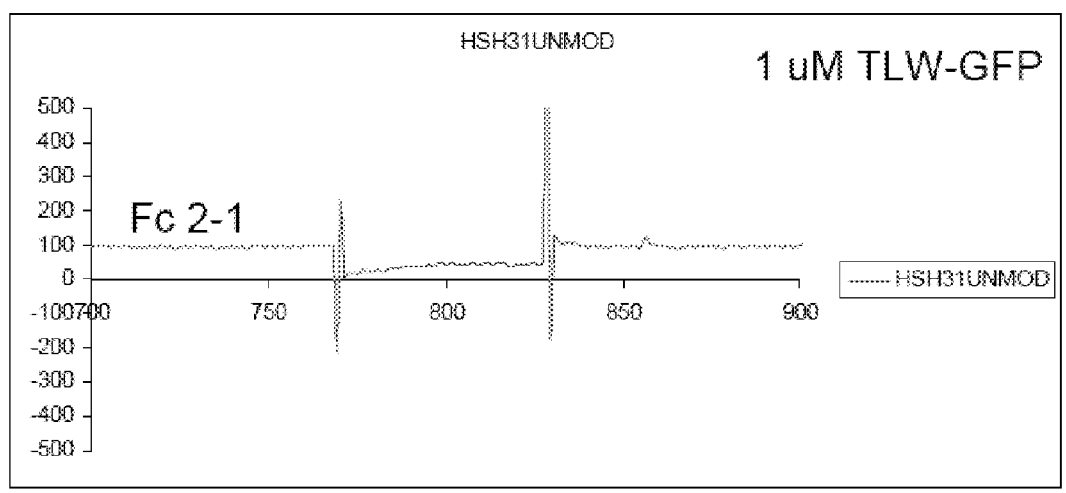

FIG. 85 depicts the affinity HSh31ECstem RNA (Fc 2-1) of 1 μM TLW-GFP.

Figure 86:
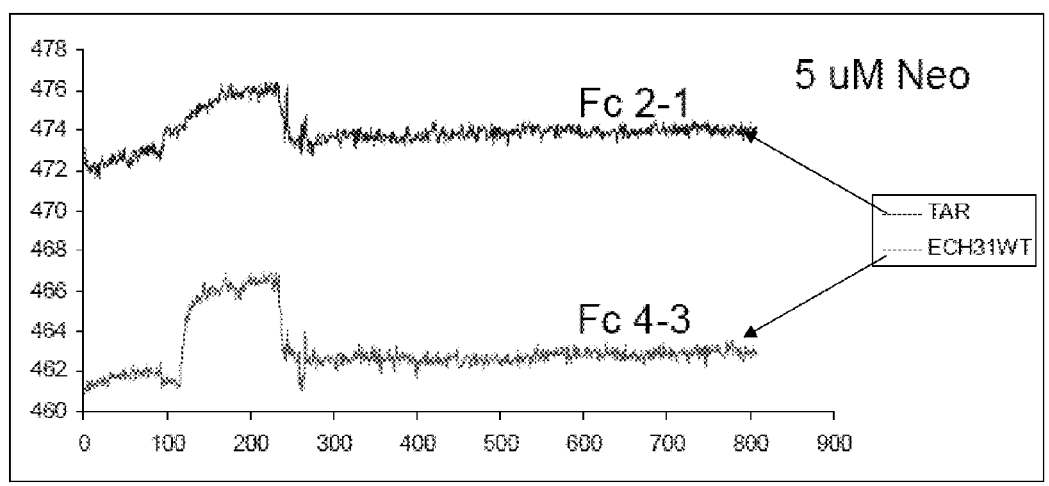

FIG. 86 depicts the affinity for TAR RNA (Fc 2-1) and ECh31WT (Fc4-3) of 5 μM neomycin (positive control).

Figure 87:
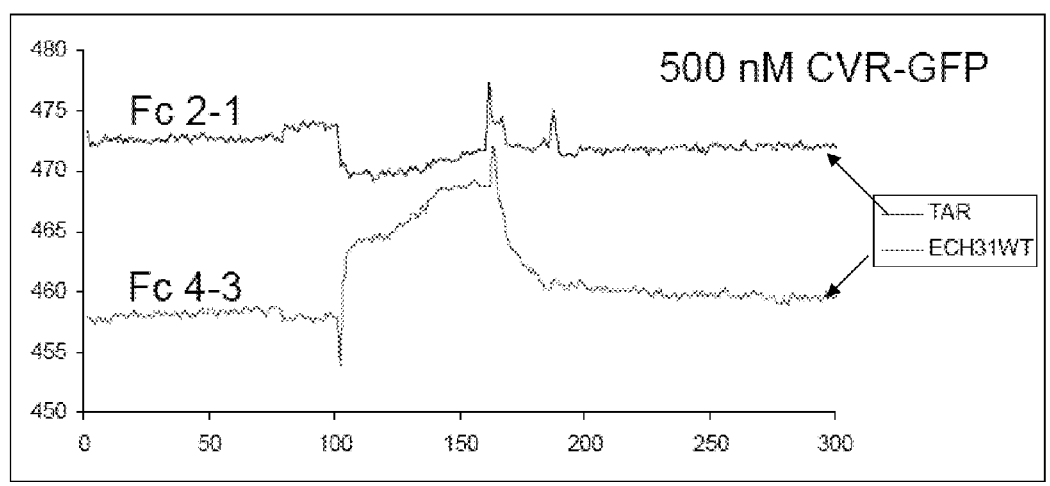

FIG. 87 depicts the affinity for TAR RNA (Fc 2-1) and ECh31WT (Fc4-3) of 500 nM CVR-GFP.

DETAILED DESCRIPTION

Definitions

The articles "a" and "an" are used herein to refer to one or more than one (i.e., to at least one) of the grammatical object of the article.

The term "amino acid" is known in the art. In general the abbreviations used herein for designating the amino acids and the protective groups are based on recommendations of the IUPAC-IUB Commission on Biochemical Nomenclature (see Biochemistry (1972) 11:1726-1732). In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term "amino acid" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups. For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (d) and (l) stereoisomers of such amino acids when the structure of the amino acid admits of stereoisomeric forms. The configuration of the amino acids and amino acid residues herein are designated by the appropriate symbols (d), (l) or (dl), furthermore when the configuration is not designated the amino acid or residue can have the configuration (d), (l) or (dl). It will be noted that the structure of some of the compounds of this invention includes asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (d) or (l) stereoisomers. D- and L-α-Amino acids are represented by the following Fischer projections and wedge-and-dash drawings. In the majority of cases, D- and L-amino acids have R- and S-absolute configurations, respectively.

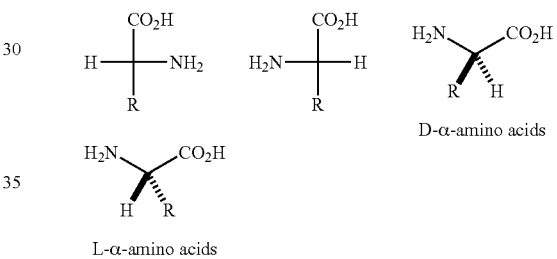

In certain embodiments, polypeptides of the invention may be synthesized chemically, ribosomally in a cell free system, or ribosomally within a cell. Chemical synthesis of polypeptides of the invention may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Schnolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

Certain compounds of the present invention may exist in particular geometric or stereoisomeric forms. The present invention contemplates all such compounds, including cis- and trans-isomers, R- and S-enantiomers, diastereomers, (d)-isomers, (l)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The term "conservative substitutions" refers to changes between amino acids of broadly similar molecular properties. For example, interchanges within the aliphatic group alanine, valine, leucine and isoleucine can be considered as conservative. Sometimes substitution of glycine for one of these can also be considered conservative. Other conservative interchanges include those within the aliphatic group aspartate and glutamate; within the amide group asparagine and glutamine; within the hydroxyl group serine and threonine; within the aromatic group phenylalanine, tyrosine and tryptophan; within the basic group lysine, arginine and histidine; and within the sulfur-containing group methionine and cysteine. Sometimes substitution within the group methionine and leucine can also be considered conservative. Preferred conservative substitution groups are aspartate/glutamate; asparagine/glutamine; valine/leucine/isoleucine; alanine/valine; valine/leucine/isoleucine/methionine; phenylalanine/tyrosine; phenylalanine/tyrosine/tryptophan; lysine/arginine; and histidine/lysine/arginine.

"Equivalent" when used to describe nucleic acids or nucleotide sequences refers to nucleotide sequences encoding functionally equivalent polypeptides. Equivalent nucleotide sequences will include sequences that differ by one or more nucleotide substitution, addition or deletion, such as an allelic variant; and will, therefore, include sequences that differ due to the degeneracy of the genetic code. For example, nucleic acid variants may include those produced by nucleotide substitutions, deletions, or additions. The substitutions, deletions, or additions may involve one or more nucleotides. The variants may be altered in coding regions, non-coding regions, or both. Alterations in the coding regions may produce conservative or non-conservative amino acid substitutions, deletions or additions.

"Homology" or alternatively "identity" refers to sequence similarity between two peptides or between two nucleic acid molecules. Homology may be determined by comparing a position in each sequence, which may be aligned for purposes of comparison. When a position in the compared sequence is occupied by the same base or amino acid, then the molecules are homologous at that position. A degree of homology between sequences is a function of the number of matching or homologous positions shared by the sequences.

The term "percent identical" refers to sequence identity between two amino acid sequences or between two nucleotide sequences. Identity may be determined by comparing a position in each sequence, which may be aligned for purposes of comparison. When an equivalent position in the compared sequences is occupied by the same base or amino acid, then the molecules are identical at that position; when the equivalent site is occupied by the same or a similar amino acid residue (e.g., similar in steric and/or electronic nature), then the molecules may be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and may be used with, e.g., default settings. ENTREZ is available through the National Center for Biotechnology Information, National Library of Medicine, National Institutes of Health, Bethesda, Md. In one embodiment, the percent identity of two sequences may be determined by the GCG program with a gap weight of 1, e.g., each amino acid gap is weighted as if it were a single amino acid or nucleotide mismatch between the two sequences. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See *Meth. Mol. Biol.* 70: 173-187 (1997). Also, the GAP program using the Needleman and Wunsch alignment method may be utilized to align sequences. An alternative search strategy uses MPSRCH software, which runs on a MASPAR computer. MPSRCH uses a Smith-Waterman algorithm to score sequences on a massively parallel computer. This approach improves the ability to pick up distantly related matches, and is especially tolerant of small gaps and nucleotide sequence errors. Nucleic acid-encoded amino acid sequences may be used to search both protein and DNA databases. Databases with individual sequences are described in *Methods in Enzymology*, ed. Doolittle, supra. Databases include Genbank, EMBL, and DNA Database of Japan (DDBJ).

The terms "polynucleotide", and "nucleic acid" are used interchangeably to refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term "recombinant" polynucleotide means a polynucleotide of genomic, cDNA, semi-synthetic, or synthetic origin, which either does not occur in nature or is linked to another polynucleotide in a non-natural arrangement. An "oligonucleotide" refers to a single stranded polynucleotide having less than about 100 nucleotides, less than about, e.g., 75, 50, 25, or 10 nucleotides.

The terms "polypeptide", "peptide" and "protein" (if single chain) are used interchangeably herein to refer to polymers of amino acids. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The term "specifically hybridizes" refers to detectable and specific nucleic acid binding. Polynucleotides, oligonucleotides and nucleic acids of the invention selectively hybridize to nucleic acid strands under hybridization and wash conditions that minimize appreciable amounts of detectable binding to nonspecific nucleic acids. Stringent conditions may be used to achieve selective hybridization conditions as known in the art and discussed herein. Generally, the nucleic acid sequence homology between the polynucleotides, oligonucleotides, and nucleic acids of the invention and a nucleic acid sequence of interest will be at least 30%, 40%, 50%, 60%, 70%, 80%, 85%, 90%, 95%, 98%, 99%, or more. In certain instances, hybridization and washing conditions are performed under stringent conditions according to conventional hybridization procedures and as described further herein.

The terms "stringent conditions" or "stringent hybridization conditions" refer to conditions, which promote specific hybridization between two complementary polynucleotide strands so as to form a duplex. Stringent conditions may be selected to be about 5° C. lower than the thermal melting point (Tm) for a given polynucleotide duplex at a defined ionic strength and pH. The length of the complementary polynucleotide strands and their GC content will determine the Tm of the duplex, and thus the hybridization conditions necessary for obtaining a desired specificity of hybridization. The Tm is the temperature (under defined ionic strength and pH) at which 50% of a polynucleotide sequence hybridizes to a perfectly matched complementary strand. In certain cases it may be desirable to increase the stringency of the hybridization conditions to be about equal to the Tm for a particular duplex.

A variety of techniques for estimating the Tm are available. Typically, G-C base pairs in a duplex are estimated to contribute about 3° C. to the Tm, while A-T base pairs are estimated to contribute about 2° C., up to a theoretical maximum of about 80-100° C. However, more sophisticated models of Tm are available in which G-C stacking interactions, solvent effects, the desired assay temperature and the like are taken into account. For example, probes can be designed to have a dissociation temperature (Td) of approximately 60° C., using the formula: Td=(((((3×#GC)+(2×#AT))×37)−562)/#bp)−5; where #GC, #AT, and #bp are the number of guanine-cytosine base pairs, the number of adenine-thymine base pairs, and the number of total base pairs, respectively, involved in the formation of the duplex.

Hybridization may be carried out in 5×SSC, 4×SSC, 3×SSC, 2×SSC, 1×SSC or 0.2×SSC for at least about 1 hour, 2 hours, 5 hours, 12 hours, or 24 hours. The temperature of the hybridization may be increased to adjust the stringency of the reaction, for example, from about 25° C. (room temperature), to about 45° C., 50° C., 55° C., 60° C., or 65° C. The hybridization reaction may also include another agent affecting the stringency, for example, hybridization conducted in the presence of 50% formamide increases the stringency of hybridization at a defined temperature.

The hybridization reaction may be followed by a single wash step, or two or more wash steps, which may be at the same or a different salinity and temperature. For example, the temperature of the wash may be increased to adjust the stringency from about 25° C. (room temperature), to about 45° C., 50° C., 55° C., 60° C., 65° C., or higher. The wash step may be conducted in the presence of a detergent, e.g., 0.1 or 0.2% SDS. For example, hybridization may be followed by two wash steps at 65° C. each for about 20 minutes in 2×SSC, 0.1% SDS, and optionally two additional wash steps at 65° C. each for about 20 minutes in 0.2×SSC, 0.1% SDS.

Exemplary stringent hybridization conditions include overnight hybridization at 65° C. in a solution comprising, or consisting of, 50% formamide, 10×Denhardt (0.2% Ficoll, 0.2% Polyvinylpyrrolidone, 0.2% bovine serum albumin) and 200 µg/ml of denatured carrier DNA, e.g., sheared salmon sperm DNA, followed by two wash steps at 65° C. each for about 20 minutes in 2×SSC, 0.1% SDS, and two wash steps at 65° C. each for about 20 minutes in 0.2×SSC, 0.1% SDS.

Hybridization may consist of hybridizing two nucleic acids in solution, or a nucleic acid in solution to a nucleic acid attached to a solid support, e.g., a filter. When one nucleic acid is on a solid support, a prehybridization step may be conducted prior to hybridization. Prehybridization may be carried out for at least about 1 hour, 3 hours or 10 hours in the same solution and at the same temperature as the hybridization solution (without the complementary polynucleotide strand).

Appropriate stringency conditions are known to those skilled in the art or may be determined experimentally by the skilled artisan. See, for example, Current Protocols in Molecular Biology, John Wiley & Sons, N.Y. (1989), 6.3.1-12.3.6; Sambrook et al., 1989, Molecular Cloning, A Laboratory Manual, Cold Spring Harbor Press, N.Y.; S. Agrawal (ed.) Methods in Molecular Biology, volume 20; Tijssen (1993) Laboratory Techniques in biochemistry and molecular biology-hybridization with nucleic acid probes, e.g., part 1 chapter 2 "Overview of principles of hybridization and the strategy of nucleic acid probe assays", Elsevier, New York; and Tibanyenda, N. et al., Eur. J. Biochem. 139:19 (1984) and Ebel, S. et al., Biochem. 31:12083 (1992).

The term "substantially homologous" when used in connection with a nucleic acid or amino acid sequences, refers to sequences which are substantially identical to or similar in sequence with each other, giving rise to a homology of conformation and thus to retention, to a useful degree, of one or more biological (including immunological) activities. The term is not intended to imply a common evolution of the sequences.

The term "patient" refers to a mammal in need of a particular treatment. In a preferred embodiment, a patient is a primate, canine, feline, or equine. In another preferred embodiment, a patient is a human.

Synthesis of Model Constructs of the 970 Hairpin Loop

The syntheses of the 6-O-DPC-2-N-methylguanosine ($m^2G$) nucleoside and the corresponding phosphoramidite are reported. Among the two approaches used for the phosphoramidite synthesis, the 5'-O-DMT-2'-O-TOM-protected 6-O-DPC-2-N-methylguanosine phosphoramidite [DMT, 4,4'-dimethoxytrityl; TOM, [(triisopropylsilyl)-oxy]methyl; DPC, diphenyl carbamoyl] gave much higher yields. The availability of the phosphoramidite in sufficiently large quantities allowed for syntheses of hairpin RNAs with selective incorporation of 2-N-methylguanosine modification. Four 18-nt hairpin RNA analogues representing the 970-loop region (helix 31; U960-A975) of *Escherichia coli* 16S rRNA were synthesized with and without modifications in the loop region.

Figure 1:
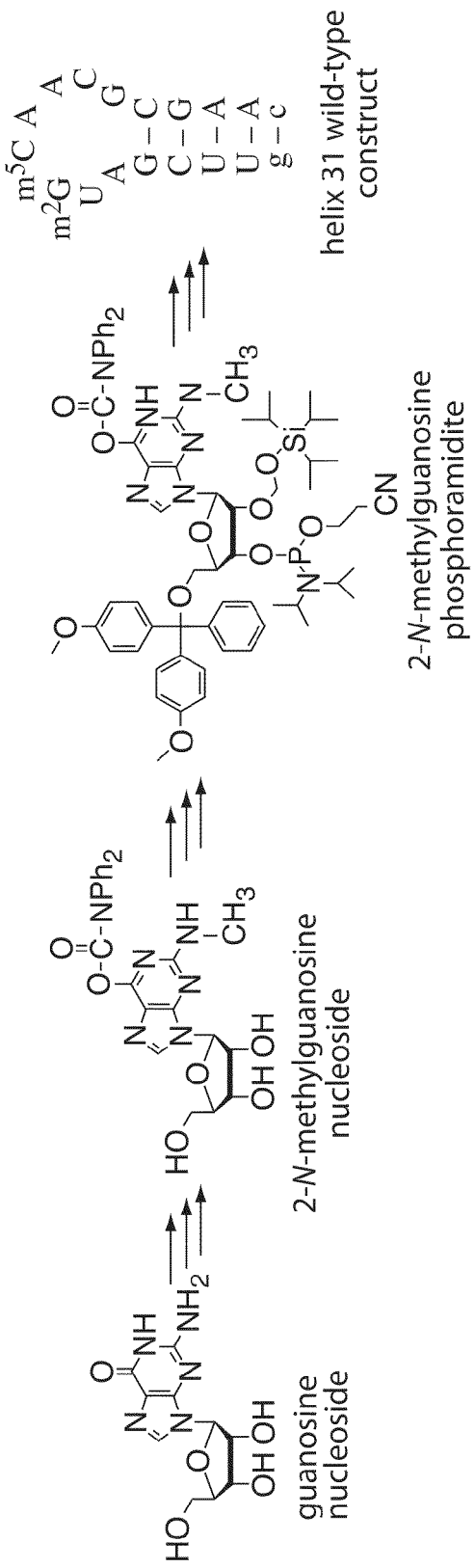
FIG. 1 depicts the synthesis of helix 31 RNA construct (SEQ ID NO: 15) in a stepwise manner.

The 970 loop of helix 31 (h31) of *E. coli* 16S rRNA is located near the ribosomal P site and therefore believed to be intimately involved in translation.[1-3] *E. coli* h31 contains two modified nucleotides, 2-N-methylguanosine at position 966 ($m^2G966$) and 5-methylcytidine at position 967 ($m^5C967$). The chemical synthesis of *E. coli* helix 31 therefore involves the incorporation of $m^2G$ and $m^5C$ modified phosphoramidites, in addition to the standard A, U, C, and G phosphoramidites. The $m^5C$ phosphoramidite is commercially available and was purchased along with standard (A, U, C, and G) phosphoramidites, while the $m^2G$ phosphoramidite was synthesized, which will be discussed in this chapter. Hence, chemical synthesis of the helix 31 RNA construct can be illustrated by a stepwise manner, which involves two major synthetic challenges as shown (FIG. 1).

The first challenge was the synthesis of the methylated guanosine nucleoside, 2-N-methylguanosine ($m^2G$). From the organic chemists' perspective, synthesizing $m^2G$ is challenging due to solubility problems encountered throughout the synthesis and purification steps. Commercially available $m^2G$ has a consistently high price. Currently, one milligram of $m^2G$ costs $40 at Sigma-Aldrich compared to $37 for 25 g of G. The commercially available $m^2G$ also requires further protection at the $O^6$-position prior to phosphoramidite synthesis. In this work, the synthesis of $m^2G$ was achieved by using a combination of several published procedures. The next step was to synthesize the phosphoramidite of $m^2G$ in order to incorporate it into the oligonucleotide sequence of interest, namely helix 31. Two approaches were used to obtain the corresponding $m^2G$ phosphoramidite; one of which has given rise to higher yields in the $m^2G$ phosphoramidite synthesis than the methods reported previously. My first approach involved the synthesis of 5'-O-BzH-2'-O-ACE-6-O-DPC-2-N-methylguanosine phosphoramidite [BzH, benzhydryloxy-bis(trimethylsilyloxy)silyl; ACE, tris(2-acetoxyethoxy)orthoformate). Despite a successful small-scale synthesis, subsequent generation of this compound on a large scale was not achieved. In contrast, synthesis of the 5'-O-DMT-6-O-DPC-2-N-methyl-2'-O-TOM-guanosine-3'-(2-cyanoethyl)diisopropylphosphoramidite was accomplished on a large scale and therefore utilized in subsequent RNA syntheses. Since the $m^2G$ phosphoramidite of interest is not commercially available, its synthesis was quite useful for constructing the natural helix 31. The RNA hairpins used in this study were chemically synthesized at the W. M. Keck Foundation at Yale University, New Haven, Conn. USA. For RNAs containing $m^2G$, 50 µmoles from the corresponding phosphoramidite were provided.

The synthetic protocol is described in further detail in the Examples. In summary, the synthesis of 2-N-methylguanosine ($m^2G$) followed and adapted the methodologies from Matsuda and Reeses.[4,5] The lactam function ($O^6$-position) of the guanine residue is protected according to a widely used procedure originally devised by Kamimura.[8] In addition to the successful $O^6$-protection of the guanine residue, introduction of DPC (diphenylcarbamoyl chloride) improves the solubility and chromatographic purification properties of the resultant derivatives. From this strategy, we were able to generate gram quantities of $m^2G$ from guanosine, which is relatively a cheap starting material.

Two approaches were used to obtain the corresponding $m^2G$ phosphoramidite, one of which gave high yields, allowing for gram quantities to be made. My first approach involved synthesis of the 5'-O-BzH-2'-O-ACE-6-O-DPC-2-N-methylguanosine phosphoramidite. Despite a successful small-scale synthesis, subsequent utilization of this compound in RNA synthesis was not achieved due to the inability to obtain the compound in sufficiently large amounts. Consequently, the synthesis of the 5'-O-DMT-6-O-DPC-2-N-methyl-2'-O-TOM-guanosine-3'-(2-cyanoethyl)diisopropylphosphoramidite was accomplished on a large scale and allowed us to generate RNAs for subsequent biophysical studies. Both MALDI-TOF mass spectrometric analyses and reverse-phase HPLC analyses of the enzyme digest products confirmed that the methyl group at the $N^2$-position of guanosine remained intact during the chemical synthesis and deprotection strategies of helix 31 synthesis Biophysical Characterization of the Helix 31 RNA Model Constructs Biophysical investigations with model constructs representing helix 31 of *E. coli* and *H. sapiens* small subunit ribosomal RNA are discussed. Three types of biophysical techniques, namely circular dichroism, thermal melting, and nuclear magnetic resonance spectroscopy, were employed. The chemically synthesized *E. coli* RNA constructs were subjected to detailed biophysical analyses in order to reveal the possible roles of the modified nucleosides. Studies with an *H. sapiens* unmodified helix 31 RNA construct are also discussed. This work has led to the discovery of a novel and stable hairpin construct that can be used for future ligand-binding experiments.

Four constructs representing the helix 31 region of *E. coli* 16S rRNA, with and without modifications, were synthesized, as discussed above and in the examples. Our next goal was to reveal the ability of those constructs to represent helix 31 of 16S rRNA. Three different biophysical techniques were employed. UV melting experiments were performed to determine the stability of the stem regions; whereas, circular dichroism and 1D NMR spectroscopy were used to study structural features of the h31 RNAs. The imino proton peaks observed in 1D NMR spectra of the *E. coli* constructs were assigned using a 1D NOE difference spectroscopic analysis. The UV melting experiments also helped us to assign structural roles for the modified nucleosides present in this region.

The two methylated bases ($m^2G966$ and $m^5C967$) of *E. coli* helix 31 occur at the same or adjacent site as the hypermodified nucleotide 1-methyl-3-(3-amino-3-carboxypropyl)-pseudouridine ($acp^3m^1\Psi$) in the *H. sapiens* small subunit rRNA. Preliminary biophysical experiments were carried out with the unmodified version of human helix 31 in order to determine its ability to represent the natural hairpin structure. The stability of the original hairpin loop design was unusually low, generating reasonable doubt about its ability to represent the *H. sapiens* helix 31 region. This observation led us to perform a phylogenetic analysis to determine with other possible base pairs for the stem region of *H. sapiens* helix 31 RNA. The discovery of a novel construct to represent the *H. sapiens* helix 31 region and biophysical studies pertaining to this hairpin RNA will also be discussed in this chapter.

In summary, the significance of the *E. coli* modifications in h31 was explored by using various biophysical techniques. Modifications in the loop region of *E. coli* helix 31 are slightly destabilizing. Destabilization may allow helix 31 to be more flexible and to enhance its biological function.

The CD data indicate that the unmodified, singly modified, and fully modified RNAs all exist in solution as A-form helices and they display similar conformations. The presence of modifications at specific locations does not appear to influence the ability to form a hairpin structure. Furthermore, $^1$H NMR spectra of the h31 RNAs confirm the formation of three G-C base pairs and two A-U base pairs in the stem region; however, the presence of additional imino proton peaks in the NMR spectra with differing chemical shifts for each h31 model RNA suggests the formation of alternate loop conformations or dimerization artifacts. The residual peaks (marked by * in FIG. 26) are not apparent at temperatures >20° C., indicating greater solvent accessibility of these protons at higher temperatures. Detailed NMR studies with the fully modified RNAs are currently in progress and will be helpful in order to gain a complete understanding of the structure of helix 31 in solution.

Overall, there is good agreement between the ID NMR data and the thermal melting data. Loss of the imino peak corresponding to the $g_1$-$c_{18}$ base pair of ECh31WT is consistent with a lowering of the $T_m$ and hence the decreased stability of the RNA construct.

The exact functional role of the modifications at positions 966 and 967 of h31 is still unknown. Ribosomes carry out the essential biochemical process of translation, which requires an exquisite array of highly specific interactions between rRNA, mRNA, tRNAs, and ribosomal proteins. Modifications are believed to help fine-tune ribosome function.[18] Since proper ribosome function depends on the correct balance of speed and accuracy of tRNA binding, peptide-bond formation and tRNA release, methylations in h31 could play a role in maintaining proper interactions within the ribosome.[19, 20] Mutational analyses revealed that a loss of methylation at either position 966 or 967, leads to increased protein production by the mutant ribosomes.[21] Our data would therefore suggest that methylations destabilize h31 in order to maintain the proper interactions with tRNA, rRNA, or proteins. A lack of modification at residues 966 or 967 in h31 could reduce the ability of base 966 to flip and regulate tRNA affinity, positioning, or accuracy.

Reconstruction of the human analogues of helix 31 with the *E. coli* stem made it more stable for biophysical studies and hence proved to be suitable for the future ligand binding studies. According to CD studies, differences in both peak maxima and peak minima for HSh31ECstem and ECh31UNMOD are significant even though they both have the same stem sequences. This result implies that the loop regions are influencing the structures of these two analogues. UV melting data suggest that the loop region corresponding to the *H. sapiens* rRNA h31 exerts a destabilizing effect on the stem relative to the *E. coli* loop region, irrespective of the fact that they have the same number of nucleotides (eight) in their loop regions and both share the same base-pairing schemes in the stem region. These data are consistent with the CD results.

Identification of Peptides Targeting Helix 31

The ribosome is a protein-synthesis machine that has been used as a drug target for decades. Ribosomal RNA is the catalytic part of the ribosome. It can undergo different conformational changes during translation, which can be facilitated by modified nucleotides. A phage-display experiment was carried out to select for peptides that bind to helix 31 of the 16S ribosomal RNA of *Escherichia coli*. Helix 31 harbors two modified nucleotides, $m^2G966$ and $m^5C967$, which are conserved in each of the phylogenetic domains. The degree and nature of modification is different in prokaryotes and eukaryotes. By using modified and unmodified variants of h31 as targets in a phage-display experiment, consensus peptide sequences were isolated after several rounds of screening. Their inhibitory effects on protein synthesis were identified by using in vitro protein translation assays.

Intermolecular interactions are important in all cellular processes, such as transcription, translation, and cell signaling. Protein-protein, protein-DNA and protein-RNA interactions are crucial events in the cell. As soon as the RNA is transcribed, ribonucleoproteins (RNPs) bind to the nascent transcript and carry out RNA processing, nuclear export, transport and localization (5). Understanding the basic principles of RNA-protein interactions is important for the identification of ligands that recognize specific structures, or motifs of RNA.

RNA-protein interactions. RNA-protein interactions are a fundamental process of gene regulation in every living organism (8). Such types of interactions are facilitated by RNA's ability to form diverse secondary structures such as bulges, hairpins, pseudoknots, and A-form helices. The ribosome contains many examples of RNA-protein interactions in which the functional conformations of ribosomal RNA (rRNA) are achieved only after interactions with ribosomal proteins. In many cases, although RNA recognition is mediated by highly basic stretches of amino acids that are rich in arginine and lysine residues, the presence of these residues is not usually sufficient to recognize specific RNA motifs (9, 10). Among the 11 different types of RNA-binding domains present in nature, the single-stranded RNA-binding domain (ssRBD) and double-stranded RNA-binding domain (dsRBD) are the most abundant (11). The RNA-recognition motif (RRM), the K homology domain (KH), and the oligonucleotide/oligosaccharide binding-fold domain (OB-fold) are common examples of ssRBDs. RRM is a well-characterized domain. More than 6000 RRM sequences have been discovered, and almost 2% of the human genome has RRM motifs (12). Double-stranded RNA-binding proteins contain 70-90 amino-acidlong, RNA-binding-motifs and are found in both bacteria and eukaryotes. The dsRBD binds across two successive minor grooves and an intervening major groove on one face of double-stranded RNA helices (13) (FIG. 65). Most of the interactions are sequence independent and do not involve any specific contacts with nucleobases. The major contacts include interactions with 2'-OH group and phosphate backbone of the RNA. The presence of multiple dsRBDs helps to increase the specificity due to their ability to recognize particular conformations of the RNA helix (14-16).

Identification of molecules targeting RNA. Regions in the RNA where there are perturbations in the A-form helices are optimal sites for RNA targeting. The standard major and minor grooves of RNA are not optimal binding sites for small molecules. Once an ideal targeting site is identified, the next goal is to determine the class of compounds to consider for potential ligands. Clinical trials of many small molecules have been unsuccessful due to their toxicity, even if they have low costs, long half lives, and are easy to synthesize (18). With the development of new technologies, peptide-based drugs are taking the leading role in drug discovery and are now viable alternatives to antibodies and small molecules as potential drugs. Peptides have some advantages over small molecules such as ease of tissue penetration, high specificity, and low toxicity (19).

Some drawbacks such as short half life, susceptibility to protease degradation, low permeability through cell membranes, and low transport through the blood-brain barrier limit their usefulness as drug candidates (19). By using peptidomimetic chemistry, the functional groups and backbones of the peptides can be changed to overcome these problems. Highly structured peptides including cyclic, α helical, and β sheet-like motifs usually have higher affinities for their targets. Usually, heterodimer peptides have better abilities to block protein-protein or protein-RNA interactions because they occupy larger surface areas, enough to disrupt the bridges between two molecular surfaces (20). These dimer peptides could be better therapeutic agents than small molecules and antibodies because of such desirable properties (21).

High-throughput screening (HTS) methodologies have been used to identify peptides from synthetic or biological libraries (22). Today, more than 140 peptides have been used as drugs and more than 400 peptides are in various phases of clinical trials (Table 1) (1). The number of peptides being used as drugs increases by approximately 15% per year (1). Without prior knowledge of their structures, the peptides can be screened for better affinity to the target (23). Different biological peptide libraries can be constructed by using molecular genetics and recombinant display technologies, such as ribosome display (24), phage display (25), mRNA display (26), and cell display (27). These techniques enable the identification of high affinity peptides with a $K_{ds}<10$ nM against different targets (21, 28).

Phage display. Since discovery of the phage-display technology by George Smith in 1985 (25), it has been used extensively in the pharmaceutical industry for drug discovery. It has been used to isolate ligands for drug discovery (29), affinity chromatography (30, 31), Since it does not lyse the bacterial cells, there is minimal chance of contamination due to bacterial proteases and nucleases during the course of selection. Other advantages of M13 are its stability and resistance to high temperature (55° C.) and acidic conditions (pH 3.0) (43). M13 phage is composed of circular ssDNA (6407 nucleotides) that is encapsulated by different major and minor coat proteins (FIG. 66) (44). The pVIII is a major coat protein that is arranged in a helical manner covering the entire length of the bacteriophage. It carries 2700 copies of its gene. The proteins pIII, pVI, pVII, and pIX (minor coat proteins) are arranged at the phage tip and carry only five copies of the minor coat protein genes. The bacteriophage infects $E.$ $coli$ by attaching the N-terminus of the pIII coat protein to the F-pilus of the host bacterium (45). When the host bacterium retracts the F-pilus, the phage genome (ssDNA) is translocated into the bacterial cytoplasm. It is later converted into a replicative form of dsDNA inside the host (41). The phage and phagemid vector consists of an Ff origin of replication to allow single-stranded DNA production. The random peptide library is cloned with the genes of the major or minor coat protein and displayed along with the coat protein (41, 46). The pIII is the protein of choice for most phage-display fusions due to its tolerance for large insertions, compatibility with monovalent display, and wide availability of suitable vectors (45). Some peptide sequences may be toxic to $E.$ $coli$ or interfere with phage assembly or be sensi-

TABLE 1

Examples of therapeutic peptides used in clinical trials are listed. This table is adapted from Huther A et al; 2007.

| Peptide drugs | Company | Peptide length | Therapy | Clinical status |
| --- | --- | --- | --- | --- |
| Enfuvirtide | Trimeris/Roche | 36 | Anti-HIV Fusion inhibitor | Approved |
| Hematide | Affymax | 20 | Erythropoietin mimetic Anemia | Phase II |
| Dentonin | Acologix Inc. | 23 | Stimulation of dental pulp stem cell proliferation | Phase II |
| Insulin | Eli Lilly | 51 | Type I diabetes | Approved |
| Byetta | Amylin/Eli Lilly | 39 | Type II diabetes | Approved |
| Ostabolin C | Zelos Therapeutics | 31 | Osteoporosis | Phase II |
| DiaPep277 | DeveloGen AG | 24 | Type II diabetes | Phase II |
| Exubera | Pfizer | ??? | Type I & II diabetes (Non-injectable insulin) | Phase II | epitope mapping of antibodies (32, 33), protein-protein interactions (34-36), isolating antibody fragments (35, 36), engineering the binding affinity of displayed proteins (37, 38), identification of peptides that target organs or tissues (39, 40), enzyme inhibition (29), as well as many other applications. The basis of this technology is the construction of a library of various peptides fused to one of the coat proteins of bacteriophage. The DNA encoding the peptide resides inside the bacteriophage genome providing a linkage between a phenotype and genotype, in which peptide sequences can be easily identified by sequencing the phage DNA (41). Highly diverse phage-displayed peptide libraries (approximately $10^9$) are commercially available. A library with randomization of codons of seven amino acids contains approximately $3.4 \times 10^{10}$ unique sequences ($32^7$, NNK=$4^1 \times 4^1 \times 2^1$, where K=C, T), which represents $1.39 \times 10^9$ ($20^7$) unique amino acid combinations. Even a library with $10^{10}$ unique members is unlikely to provide complete coverage of all possible sequences.

M13 and T7 bacteriophage are commonly used in phage display. M13 is a non-lytic, filamentous bacteriophage (42).

tive to bacterial proteases. Therefore, every clone theoretically contained within the library might not be obtained in the selection.

The typical procedure for affinity selection includes immobilization of target molecule on the surface of beads or in the wells of microtiter plates (FIG. 67). The phage library is mixed with the target and binding takes place. The unbound phage are removed by washing; whereas, bound phage are eluted out by denaturing the peptide-target interactions.

The eluted phage are infected into specific bacterium to amplify the sub-population of phage before going to the next cycle of selection. After three to five cycles of selection, target-specific and tightly bound peptides are isolated (2).

Identification of peptide ligands using RNA as a drug target. After the discovery of phage display in 1985, most of the work that followed involved the isolation of ligands using protein as the target. The use of phage display to target RNA picked up momentum nearly one decade after its discovery (47, 48). Peptides isolated from the library can mimic the specific motifs of proteins, which are important for recognization of RNAs such as Tar and RRE from HIV (49, 50).

Under physiological conditions, the shorter peptides may lack any secondary structure; however, they may still have specific interactions with RNA (51). X-ray crystallography and NMR structures of peptide-RNA complexes have provided further insights into peptide-RNA interactions (52). U1 RNA-binding antibody fragments were isolated from autoimmune human-derived bacteriophage display libraries (53, 54). Peptide ligands for psi RNA from the HIV-1 packaging signal were identified and their specificity was characterized (55, 56). Agris' lab isolated modified-nucleotide-specific peptides by using the anticodon stem-loop region of different tRNAs as the targets (57-60). To date, no work has been published on targeting the modified nucleotides of ribosomal RNA.

Modified rRNA as a drug target. It has been shown that the absence of certain modifications in tRNA abolishes the recognition of tRNA-synthetase as well as initiation and elongation factors. The presence of modified nucleotide 1-methylguanosine at residue 37 ($m^1G37$) in tRNA$^{Asp}$ and lysidine in the anticodon of E. coli tRNA$^{Ile}$ prevents mis-aminoacylation of near-cognate amino acid (61, 62). In some cases, loss of modifications in bacterial ribosomal RNA leads to resistance or sensitivity to antibiotics, indicating that ligand-RNA interactions are mediated either directly or indirectly by modified nucleotides (63, 64). These facts highlight the possibility of using modified RNA as a potential drug target.

Helix 31 (970 loop) of the bacterial 16S ribosomal RNA, which contains two modified nucleotides, $m^2G966$ and $m^5C967$ (FIG. 68), can be a unique target The modified nucleotides in this loop are conserved in each of the phylogenetic domains; however, the complexity of modification increases from bacteria to eukaryotes (65). The archaea contain $acp^3U$ and eukaryotes contain $m^1acp^3\psi$ (65, 66) at position 966 of the small subunit rRNA (E. coli numbering). In bacteria, these modified nucleotides reside at or near the binding sites for initiation factor 3, tetracycline, and the anticodon stem-loop of the P-site tRNA (67, 68). The aim of this project is to identify peptide ligands that have high selectivity and affinity to h31 of the bacterial 16S ribosomal RNA. The peptides isolated from this screening could be used as leads and formulated into drug molecules in the future. A commercially available seven-amino-acid random peptide library (New England Biolabs, Ph.D.-7™) was used for selection. The actual size of the peptide library was $2\times10^{13}$ pfu/mL.

Using both modified and unmodified h31 as targets (FIG. 69), different peptides were isolated after several rounds of screening. The inhibitory effects of selected peptides were characterized by using a cell-free translation assay. Thus, bacteriophage libraries with random amino acids can be a good source for ligands to screen against modified RNA targets.

In summary, RNA-protein interactions are very crucial for biological processes. RNA function is regulated by RNA-binding proteins, which also control gene expression. A peptide that can disrupt critical interactions by binding to a specific RNA motif inside the cell can be a potential drug lead. Several RNA-binding peptides have been discovered by phage display, and it was found that they recognize and bind to specific motifs of RNA structure (10). RNA modifications play a significant role in efficient protein-RNA interactions (80). Several studies (including this thesis work, Chapters 2, 3 and 4) have shown the importance of modifications in different aspects of protein synthesis, such as translational fidelity, ribosome assembly, stability and initiation.

One of the current challenges in medicine is the rapid development of drug resistance due to target-site mutations. Therefore, if we can identify new drugs that target essential modified nucleotides or RNA regions, this problem might be solved in the future. By using phage display, peptide motifs recognizing the RNA with modified nucleotides can be identified and they can be used as drug leads.

Helix 31 plays an important role in protein synthesis (81, 82). From several biochemical and structural studies, it has been shown that modified nucleotides $m^2G966$ and $m^5C967$ are close to the P-site tRNA and mRNA (83, 84). This helix also interacts with S9 and S10 ribosomal proteins and initiation factor 3 (1F3) (67, 81, 85). The loss of modifications affects translational fidelity and interactions with initiation factors. One more significant feature of this loop is the domain-specific phylogenetic conservation of modifications (65, 66), suggesting its importance as a potential drug target. If we can identify ligands (peptides) that can interrupt the essential interactions of h31 and tRNA, mRNA, or initiation factors by specific recognition of this bacterial rRNA loop, those molecules could potentially be used as drug leads.

Synthesis and Characterization of Peptides that Target Helix 31

Solid-phase syntheses of peptides that were selected against helix 31 in the bacterial ribosome are discussed. Availability of the chemically synthesized peptides allowed us to characterize their affinities with helix 31 using various biophysical techniques. Biophysical characterizations by circular dichroism, fluorescence spectroscopy, and surface plasmon resonance are discussed. This work revealed two high-affinity peptides that have nanomolar affinities toward bacterial helix 31 RNA.

The chemical syntheses of bacterial h31 model constructs allowed us to reveal not only the possible roles of the modifications present in this region, but also allowed us to subject this construct to phage-display screening experiments (performed by Tek Lamichhane in collaboration with the Cunningham lab). Phage display is a selection method that allows for the identification of peptides from a random library of sequences that have affinity for a chosen target.[1-3] Consequently, several peptide sequences were obtained with potential for recognition of the h31 region in the bacterial ribosome. In order to further investigate the peptide affinities and specificity towards h31, it was necessary to obtain those peptides via a chemical synthetic strategy. Two major methods are reported in the literature for the chemical synthesis of peptides, namely solution-phase and solid-phase peptide synthesis.[4] Among the two methods, solid-phase peptide synthesis (SPPS) has become the most useful methodology due to its simplicity. SPPS was first established by Robert Bruce Merrifield in 1963,[5] and he was awarded the Nobel prize for his outstanding work in 1984.[4]

SPPS has become our choice for obtaining the phage-display selected peptides, not only due to its simplicity, but also due to its compatibility with our system and the ability to obtain large amounts of peptide with few by-products. In order to achieve successful SPPS, it is desirable to choose an adequate combination of protecting groups/solid support before commencing a synthesis. For routine syntheses, the choice is generally limited to Fmoc/tBu-[6-7] or Boc/benzyl[5,8]-based methodologies [Fmoc, 9-fluorenylmethoxycarbonyl chloride (Fmoc-Cl); Boc, di-tert-butyl pyrocarbonate]. The chemical structures of Fmoc and Boc protecting groups are given in FIG. 70.

During our syntheses, we used the Fmoc/tBu-type chemistry. The Fmoc/tBu-based SPPS process is summarized in FIG. 71. Fully automated instrumentation has been developed to carry out the steps shown in FIG. 71, with delivery of solvents, measured quantities of the appropriate reagents, and protected amino acids according to pre-written protocols.

Once started, these synthesizers require minimal intervention by an operator. Less sophisticated man-made systems are also available for manual solid-phase synthesis by an operator.

During our experiments, the peptides were obtained by SPPS using a manual synthetic apparatus in which the reactor consists of a cylindrical vessel with a fritted disk and a screw cap lid (FIG. 72) equipped with a mechanical stirrer.

A typical vessel used in our synthesis is six inches in height and has an internal diameter of one inch. These are custom-made glass vessels and proper care must be used during handling. The upper-end can be capped with a Teflon screw-cap lid; whereas, the solvent flow through the bottom is controlled by a stop-cock. Just above the stop-cock, there is a fritted-disk that retains the resin. When the stop-cock is in the closed position, the vessel can retain both the resin and the solvent containing other reagents. A constant shaking is applied by a mechanical stirrer. This step allows the coupling reaction to take place. But when the stop-cock is open and the bottom end is connected to a vacuum generator, the solvent and reagents are filtered through while leaving the resin on the surface of the fritted disk. This step allows a new round of amino-acid coupling to be performed on the resin with a new set of reagents. In order to perform an effective synthesis, an appropriately functionalized resin (polymer support) is chosen. The resin is made out of polystyrene, and is often functionalized with linkers that serve as actual coupling ends.[9] The choice of the linker, and hence the resin, depends on the conditions necessary for the synthesis, the cross reactivity with different reactant functionalities, and special requirements for the particular synthetic route, etc. The most common functionalities on the linkers are alcohols, aldehydes, acids, amines, thiols, and chlorines.[9] FIG. 73 shows some commonly used resins and the original Merrifield resin, which was the first SPPS resin.

During the phage-display screening process, the C-termini of the peptides are not free. On M13 phage, the peptides are displayed with free N-termini exposed to the environment. The C-termini are linked to the minor coat protein (P3) of M13 phage through a short spacer forming an amide bond. In order to mimic this type of display, the peptides were chemically synthesized on Rink Amide resin (FIG. 73) and obtained in their amidated form. This step was done in order to mimic the conformation of the peptide displayed on the phage surface.

The Rink amide resin was obtained in its Fmoc-protected form for our syntheses. Therefore, the first step of the synthesis involved removal of the Fmoc protecting group under mild basic conditions with 25% piperidine in DMF.[9] A similar strategy was used to remove Fmoc protections from all amino acids immediately after their coupling step (FIG. 74).

Fmoc deprotection exposes the free amino terminus for subsequent coupling with the incoming Fmoc-protected amino acid. Coupling reactions were performed with a 0.05 M solution of the Fmoc-protected amino acid, 1-hydroxy-1H-benzotriazole (HOBt),[10] and N,N'-diisopropylcarbodiimide (DIC)[11] in DMF. The addition of DIC activates the carboxylic group of the incoming amino acid, while HOBt is used as the catalyst. In the absence of HOBt, the situation is totally different. Racemization can occur due to high reactivity of the carboxylic acid activator, DIC.[10] This causes cyclization of the activated species to an oxazolone, which racemizes via enolization and subsequent reopening by the amino component to yield epimers (FIG. 75).

For this reason, a second reagent (HOBt) is added which displaces DIC upon activation of the incoming amino acid (FIG. 76).[10] HOBt acts as an auxiliary nucleophile. It forms an O-acyl-1-hydroxy-benzotriazone upon transesterification of the highly active amino-acyl-isourea species formed by the reaction between the amino acid and DIC. This step suppresses the racemization by shortening the lifetime of the amino-acyl-isourea species.[10] A detailed mechanism for the HOBt/DIC mediated amino acid coupling is given in FIG. 76. Alternatively, N,N'-diisopropylethylamine (DIEA) and 2-(1H-benzotriazole-1-yl)-1,1,3,3-tetramethyluronium hexafluorophosphate (HBTU) are also commonly used in amino-acid coupling reactions.

The progress of the coupling reactions and deblocking steps are monitored by the Kaiser test (FIG. 77).[13, 14] It is based on the reaction between ninhydrin and amine groups. This is a qualitative test for the detection of primary amines, visualized by an intense blue color (Ruhemann's blue), and therefore may not provide reliable information in the presence of secondary amines such as proline and other N-substituted amino acids. Those may generate a brownish red color from the test.

The Kaiser test provides a negative result only when the coupling reaction has gone to completion. Otherwise, it shows an intense blue color indicating that the reaction is in an intermediate stage. This particular feature of the Kaiser test is rather useful in peptide synthesis, as it is indicative of the 100% efficiency in each coupling step.

The coupling step is repeated until the desired peptide sequence is obtained. Then, peptide cleavage from the resin and deprotection of the amino-acid side chains are achieved with a mixture of trifluoroacetic acid (TFA)/triisopropylsilane (TIS)/anisole/thioanisole (94:2:2:2, vol:vol:vol:vol).[15, 16] During the final cleavage step, highly reactive carbocations are generated; it is therefore necessary to trap them in order to avoid side reactions with sensitive amino acids such as Cys, Met, Ser, Thr, Trp, and Tyr.[15] This step is achieved by the addition of scavengers such as water, anisole, thioanisole, TIS, etc. At the final step, the resin is filtered off and the solution containing the crude product is drained into cold diethylether ($Et_2O$). The resulting cloudy mixture is centrifuged and lyophilized. The crude peptides are purified by semi-preparative HPLC. Characterization of the peptides is done by MALDI-TOF mass spectrometry.

Several conclusions can be drawn from the work reported in this chapter. Among the methods utilized for the peptide-RNA binding characterization, CD and fluorescence have provided good starting points for the future peptide binding experiments. Despite the poor curve fit obtained for the fluorescence titration experiment, the data gave us some hope for the subsequent experiments. Several reasons can be put forward for the low reliability of the fluorescence data. Problems associated with the RNA construct (fluorescein is attached to the guanosine residue at 5' end of the RNA) might have caused the fluorescence intensity to be quenched, hence resulting in a small percentage of reduction in the fluorescence intensity. On the other hand, peptide aggregation effects at higher concentrations might have resulted in poor curve fitting. Data analyses assuming a coorporative binding mode generated inferior fits than the one that is reported.

Circular dichroism data has provided a comparable value for the dissociation constant with a greater margin of error. That may possibly be due to the discrepancies in the isodichroic point, which is indicative of peptide aggregation effects. Despite a greater margin of error, both of the above-mentioned techniques provided a comparable dissociation constant for the interaction of 17 (TYLPWPA (SEQ ID NO: 2)) with h31 RNA.

When the same system, 17 (TYLPWPA (SEQ ID NO: 2)) with h31 RNA, was further analyzed to reveal the kinetics of the interaction, the dissociation constant was comparable to that obtained from CD and fluorescence. In the SPR analysis, the peptide was cloned with GFP to gain a better signal-to-noise ratio. Despite the presence of GFP, the dissociation constant of 17 (TYLPWPA (SEQ ID NO: 2)) with h31 RNA was found to be consistent with the values obtained from other two techniques. The SPR analysis provided a dissociation constant with a lower margin of error. Therefore, SPR has provided a better platform for the studies of peptide-RNA interactions with greater reliability. One intriguing question is the affinity of GFP itself towards h31 RNA. This affinity might presumably be required in this kinetic investigation to bring the peptide towards the RNA. This situation would be comparable to that one might observe in the phage-display technique, in which the peptide is associated with the phage during the selection process. Therefore, we can argue that a similar scenario has been created for the peptide when it is attached to GFP. The GFP may not only bring the peptide close to its target, but it may also be limiting the conformational flexibility of the peptide in a favorable manner for the observed binding. The utility of SPR technology in the peptide-RNA binding studies was further revealed by studies with peptides 14 (TLWDLIP (SEQ ID NO: 3)) and 15 (CVRPFAL (SEQ ID NO: 4)) with h31 RNA. The two peptide conjugates have nanomolar affinities for h31. This result was further validated by a coupled in vitro transcription-translation assay performed by Tek Lamichhane (in collaboration with the Cunningham lab). Based on the results of this experiment, the two nanomolar affinity peptides (14 and 15) have shown greater inhibitory effects on in vitro protein synthesis than other peptides that were obtained from the phage-display selection (FIG. 5. 23). The in vitro assay has also shown that h31 in the bacterial ribosome is located in an accessible region for the peptide inhibitors. All these data suggest that h31 in the bacterial ribosome has the potential to become a target for anti-infectives.

A peptide ligand/s that can bind specifically to the h31 region of *E. coli* 16S rRNA was discovered. Therefore this region may be utilized as a potential drug target in the bacterial ribosome. The availability of the wild-type h31 RNA construct allowed us to discover peptide sequences that possess high affinity and specificity towards this region, may lead to the discovery of yet another anti-infective target in the bacterial ribosome.

Peptides of the Invention

In certain embodiments, the invention relates to peptides discussed in the Examples.

In certain embodiments, the invention relates to a peptide with the sequence: TLWDLIP (SEQ ID NO: 3).

In certain embodiments, the invention relates to a peptide with the sequence: CVRPFAL (SEQ ID NO: 4).

In certain embodiments, the invention relates to a peptide with the sequence: ATPLWLK (SEQ ID NO: 5).

In certain embodiments, the invention relates to a peptide with the sequence: TYLPWPA (SEQ ID NO: 2).

In certain embodiments, the invention relates to any one of the aforementioned peptides, wherein the conventional single letter abbreviations are used.

In certain embodiments, the inventino relates to the D-, Beta, or peptoid verions of any one of the aforementioned peptides.

Structural Studies of Targets and Compounds

Interactions of the hits (peptides and compounds) and drug leads with their *E. coli* rRNA targets are characterized using NMR spectroscopy to determine key functional groups important in the interaction. This data is helpful in modifying the drug leads using rational drug design and medicinal chemistry to improve bioavailability, pharmacodynamics, and to reduce toxicity.

NMR studies provide several types of critical information. First, NMR is used to verify whether the structure of isolated RNA targets taken out of the context of the ribosome resemble their structure in the ribosome and will therefore be valid targets for screening compound libraries. NMR spectroscopy also provides detailed stereochemical information on the mechanism of binding of small-molecule ligands with RNA targets. Lastly, NMR studies reveal crucial differences between the *E. coli* and the human small subunit rRNAs. Comparison of the wild-type and mutant structures will reveal the essential functional groups and structural folds required for ribosome function, thereby focusing the design of drugs to these critical residues. Structural characterization of RNA-ligand complexes will reveal how each compound recognizes the essential target motifs. Further, characterization of RNA dynamics by NMR in the presence and absence of bound drug leads will reveal the role of induced fit in RNA recognition. [Chow, C. S. & Bogdan, F. M. (1997). A Structural Basis for RNA-Ligand Interactions. *Chem. Rev.* 97, 1489-1513.]

Target Validation

Potential drug compounds are tested in eukaryotic and bacterial in vitro protein synthesis assays. Compounds that inhibit wild-type and mutant bacterial ribosomes but not eukaryotic ribosomes are further developed, and allow in vitro validation of the selected targets.

In another embodiment, the functionally important regions identified above are divided into groups based upon whether or not they occur in closely related groups of organisms. For instance, some regions of rRNA are found in all bacteria but not in other organisms. Other areas of rRNA are found only in closely related groups of bacteria, such as all of the members of a particular species, e.g., members of the genus *Mycobacterium* or *Streptococcus*.

In a further embodiment, the regions found in very large groups of organisms, e.g., all bacteria or all fungi, are used to develop broad-spectrum antibiotics that may be used to treat infections from a large number of organisms within that group. The methods of the present invention may be performed on these regions and functional mutant ribosomes identified. These functional mutant ribosomes may be screened, for example, with compound libraries.

In yet another embodiment, regions that are located only in relatively small groups of organisms, such as all members of the genus *Streptococcus* or all members of the genus *Mycobacterium*, may be used to design narrow spectrum antibiotics that will only inhibit the growth of organisms that fall within these smaller groups. The methods of the present invention may be performed on these regions and functional mutant ribosomes identified. These functional mutant ribosomes will be screened with, e.g., compound libraries.

Methods of the Invention

One aspect of the present invention relates to a peptide obtained as described herein. Yet another aspect of the present invention relates to a method of administering to a patient in need thereof a peptide and/or compound obtained by any one of the aforementioned methods, wherein said patient is suffering conditions associate with a microbial infection, such as an infection caused by, for example, *E. coli, P. aeruginosa*, or the like. In certain embodiments said microbial infections is a bacterial infection.

Exemplification

The invention now being generally described, it will be more readily understood by reference to the following examples, which are included merely for purposes of illustration of certain aspects and embodiments of the present invention, and are not intended to limit the invention.

Example #1

General Procedures for Examples 2-5

Most reagents and solvents were either purchased from Aldrich (St. Louis, Mo.) or Across (Morris Plains, N.J.). Benzhydryloxy-bis(trimethylsiloxy)silyl chloride (BzHCl), 4-(tert-butyldimethylsilyloxy)-3-penten-2-one (TBDMS-pent), and tris(2-acetoxyethoxy)-orthoformate (ACE) were purchased from Dharmacon, Inc. (Lafayette, Colo.). All other reagents and solvents were purchased form commercial sources and used as received. Anhydrous pyridine was purchased in a sure-seal bottle from Aldrich. Methylene chloride ($CH_2Cl_2$) was distilled over $CaH_2$. Methanol and triethylamine was purchased dry from Aldrich in a sure-seal bottle. Moisture sensitive reactions involved flame-drying equipment (syringes, round-bottom flasks, stir-bars, etc.) under vacuum and performing reactions under dry argon. TLC analyses were accomplished with precoated silica gel (0.25 mm thickness) glass plates. Reactions were monitored by visualizing the TLC plates under UV light and/or by staining with phosphomolybdic acid (PMA) solution (10% w/v in absolute ethanol). Flash chromatography was performed with silica gel 60 (0.038-0.063 mm). Flash columns were neutralized with 0.5-1% triethylamine (TEA) prior to purification of pH sensitive intermediates/compounds. $^1H$ NMR and $^{13}C$ NMR spectra were recorded on either a Varian Unity 300, Mercury 400, or Varian Unity 500 spectrometer and referenced to tetramethylsilane as an internal standard. ESI spectra were recorded on a Quattro LC (Bruker Daltonics) in the positive ion mode unless otherwise noted.

NMR methods. Sample (20-40 mg) was dissolved in the deuterated NMR solvent (~3 mL) to obtain a clear solution. The samples were either sonicated or filtered through a cotton plug, when ever insoluble particles were observed. $CDCl_3$ was neutralized by passing through basic alumina to avoid any degradation of acid-sensitive compounds.

MALDI-TOF mass spectrometric methods. The sizes of the chemically synthesized RNAs and the presence of the methyl modifications were confirmed using MALDI-TOF mass spectrometry. The samples were prepared by mixing 5 µl supersaturated matrix solution (3-hydroxypicolinic acid in $dH_2O$/acetonitrile, 50/50 V/V), 0.5 µl RNA (5-10 pmol), and 0.5 µl 100 mM NH4OAc. Next, 1 µl of the mixture was spotted on a MALDI plate and dried in the air. The RNA samples were then analyzed on a Bruker Ultraflex MALDI-TOF under negative ion mode and linear acquisition operation mode.

HPLC methods. Confirmation of nucleosides present in the synthetic RNAs were obtained by digestion of ~0.5 ODs of RNAs to their corresponding nucleotides with P1 nuclease [1.5 units], 0.5 M NaOAc [$C_f$=37.5 mM], 5 mM $ZnCl_2$ [$C_f$=0.25 mM], at 37° C. overnight. The mixtures were then heated at 70° C. for 15 min (to inactivate P1). Then, the samples were cooled on ice. The corresponding nucleosides were then obtained by treating the resulting nucleotides with CIP (calf intestinal phosphatase) [1.5 units], 0.5 M Tris.HCl, pH 8.3 [$C_f$=56 mM], at 37° C. for 2 h. Then, the mixtures were heated to inactivate CIP, and the resulting mixtures were filtered through microcon (Millipore, MWCO 30,000) and analyzed by reverse-phase HPLC on a Supelco C18 column. Approximately 0.25 OD were injected for each analysis. A linear gradient in 0.1 M TEAA buffer, pH 6.0 from 0 to 30% methanol over 17 min at a flow rate of 1 mL/min was employed. The retention times of the nucleosides were confirmed by injection of authentic standards (C=6.7 min, U=9.6 min, $m^5C$=12.7, G=16.1 min, $m^2G$=19.4 min, A=19.9 min).

The RNAs were purified by HPLC on an XTerra MS C18 column (2.5 µm, 10×50 mm, Waters) in which the eluent was 0.1 M TEAA buffer, pH 7.0, with a 5-15% linear gradient of acetonitrile over 25 min. at a flow rate of 4.0 mL/min. The column was pre-equilibrated with 80% of buffer A (5% acetonitrile in TEAA) and 20% of buffer B (15% acetonitrile in TEAA) prior to sample introduction. The elution of RNA was monitored by a photodiode array (PDA) detector scanning at a wavelength of 254 nm.

Example #2

Synthesis of the 6-O-DPC-2-N-methylguanosine modified nucleoside

Figure 2:
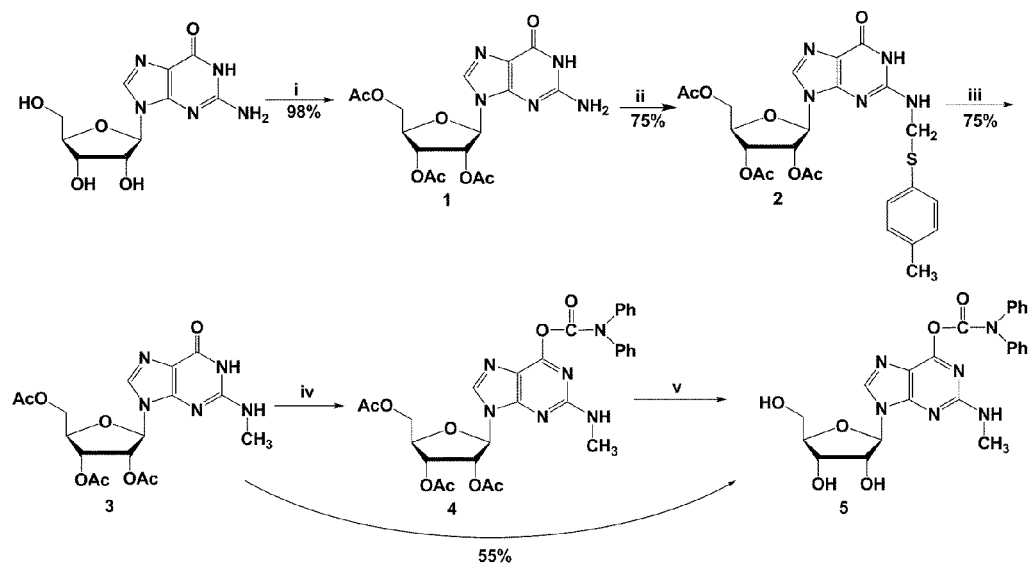
FIG. 2 depicts the synthesis of the $O^6$-DPC-$N^2$-methylguanosine 5: (i) acetic anhydride, DMAP, $Et_3N$, acetonitrile, 0.5 h;[4] (ii) p-thiocresol, acetic acid, formaldehyde, ethanol, reflux;[5] (iii) $NaBH_4$, DMSO, 100° C.;[6] (iv) DPCCl, diisopropylethylamine, pyridine; (v) a) 2 M NaOH, 20 min. b) acetic acid.

In general, the methylated guanosine nucleoside, $m^2G$, was synthesized by using a combination of several published procedures (FIG. 2). The first step involved the acetylation of guanosine to give compound 1.[4] The second and third steps to generate N-methylated intermediate 3 were adapted from Bridson and Reese's method using a p-thiocresol intermediate.[7] The generation of compounds 2 and 3 was accomplished with 75% yields for each step. To avoid solubility problems typically encountered during the phosphoramidite synthesis, we used a strategy that involves protection at the lactam function of the guanine residue according to a procedure devised by Kamimura[8] and used by others.[9] The DPC-protected intermediate 4 was obtained in 80% yield from 3. Deprotection of 4 under mild basic conditions gave compound 5 in reasonably good yield (55%). Strong basic conditions were not applied to the above step, since significant deprotection of the DPC group was observed under such conditions. Alternatively, several silyl ether type protecting groups are available, which could be considered as reasonable candidates for sugar hydroxyl protection. Trimethylsilyl (TMS),[10] tert-butyldiphenylsilyl (TBDPS),[11] tert-butyldimethylsilyl (TBS/TBDMS),[12] triisopropylsilyl (TIPS),[13] and triethylsilyl (TES)[14] are some of the commonly used sugar protecting groups; however, their utility in the case of guanosine protection requires greater optimization to achieve higher yields. The lower yields are mainly due to the insoluble nature of guanosine in solvents that are typically used for the silyl protections. In contrast, Matsuda's method[4] gave almost quantitative yields in the first step. In order to avoid solubility problems typically encountered during the phosphoramidite synthesis, we used a strategy that involves protection at the lactam function of the guanine residue by the diphenylcarbamoyl (DPC) protecting group. In addition to the successful $O^6$-protection of the guanine residue, the presence of DPC improved the solubility and chromatographic purification properties of the resulting derivative.

Specifically, the synthesis was carried out as follows:

2',3',5'-Tri-O-acetylguanosine [1]. To a colloidal suspension of guanosine nucleoside (105 mg, 0.37 mmol, 1.0 eq) and 4-dimethylaminopyridine (4 mg, 0.03 mmol, 0.08 eq) in acetonitrile (5 mL) and triethylamine (0.2 mL, 1.51 mmol, 4 eq) was added the acetic anhydride (0.12 mL, 1.3 mmol, 3.6 eq) at room temperature. The suspension was stirred for 30 min. Then methanol (5 mL) was added to the mixture and stirring was continued for another 5 min. The mixture was evaporated to dryness under reduced pressure. The residue was chromatographed on a column of silica gel to give 1 as an off-white solid in 99% yield (152 mg, 0.37 mmol). TLC ($CH_2Cl_2$:MeOH, 9:1 v/v): $R_f$=0.37; $^1H$ NMR (DMSO-$d^6$, 400 MHz) δ (ppm): 2.01 (s, 3H), 2.02 (s, 3H), 2.08 (s, 3H), 4.22-4.28 (m, 1H), 4.33-4.37 (m, 1H), 5.48 (dd, J=4, 6 Hz, 1H), 5.76 (t, 1H), 5.95 (d, J=6 Hz, 1H), 6.5 (br.s, 1H), 7.85 (s, 1H), 8.2 (s, 1H), 10.7 (br.s, 1H); $^{13}$C NMR (DMSO-d$^6$, 400 MHz) δ (ppm): 20.1, 20.3, 20.4, 62.95, 70.25, 72.04, 84.46, 116.85, 135.41, 150.97, 153.79, 156.65, 168.96, 169.13, 169.79; ESI-MS (ES$^+$) calculated for $C_{16}H_{19}N_5O_8$ 409.1234, found 410.2 (M+H$^+$), 432.1 (M+Na$^+$), 448.1 (M+K$^+$), 841.3 (2M+Na$^+$).

2',3',5'-Tri-O-acetyl-2-N-(p-methylphenylthiomethyl)guanosine [2]. 2',3',5'-Tri-O-acetylguanosine 1 (4.6 g, 11.2 mmol, 1.0 eq), 37% aqueous formaldehyde (4.7 mL, 156 mmol, 14 eq), p-thiocresol (4.6 g, 37 mmol, 3.3 eq), and acetic acid (2 mL) were added into 50 mL of ethanol. The mixture was heated under reflux for 4 h. The mixture was cooled and the white precipitate was collected by filtration. Product was recrystallized from water to obtain the pure solid compound 2 in 75% yield (4.58 g, 8.4 mmol). TLC (CH$_2$Cl$_2$:MeOH, 9:1 v/v): R$_f$=0.57; $^1$H NMR (DMSO-d$^6$, 400 MHz) δ (ppm): 2.03 (s, 6H), 2.09 (s, 3H), 2.25 (s, 3H), 4.26-4.29 (m, 1H), 4.30-4.34 (m, 1H), 4.9 (br.s, 2H), 5.48 (br.s, 1H), 5.77 (t, 1H), 5.97 (d, J=6.4 Hz, 1H), 6.1 (br.s, 1H), 6.54 (br.s, 1H), 7.11 (d, J=7.2 Hz, 2H), 7.3 (d, J=7 Hz, 2H), 7.9 (s, 1H), 10.7 (br.s, 1H); $^{13}$C NMR (DMSO-d$^6$, 400 MHz) δ (ppm): 20.2, 20.4, 20.5, 63.5, 67.2, 70.3, 72.06, 79.55, 84.44, 129.53, 129.54, 135.67, 153.94, 156.69, 169.31, 169.49.

2',3',5'-Tri-O-acetyl-2-N-methylguanosine [3]. Sodium borohydride (625 mg, 16.5 mmol, 1.82 eq) was added to a solution of 2',3',5'-tri-O-acetyl-2-N-(p-methylphenylthiomethyl)guanosine 2 (5.0 g, 9.2 mmol, 1.0 eq) in dimethyl sulfoxide (25 mL). The mixture was heated at 100° C. for 1 h and then cooled to room temperature. Reaction products were neutralized with 1 M aqueous potassium dihydrogen phosphate solution. The precipitate obtained was collected by filtration and further washed with acetone. The residue was chromatographed on a column of silica gel to give 3 in 75% yield (2.93 g, 6.93 mmol). TLC (CH$_2$Cl$_2$:MeOH, 9:1 v/v): R$_f$=0.45; $^1$H NMR (DMSO-d$^6$, 400 MHz) δ (ppm): 1.92 (s, 3H), 2.03 (s, 3H), 2.04 (s, 3H), 2.8 (d, J=4 Hz, 3H), 4.11-4.15 (dd, J=6, 11.6 Hz, 1H), 4.23-4.25 (m, 1H), 4.33-4.37 (dd, J=4, 11.6 Hz, 1H), 5.7 (t, 1H), 5.8 (t, 1H), 5.9 (d, J=4 Hz, 1H), 6.4 (q, 1H), 7.79 (s, 1H), 10.79 (s, 1H); $^{13}$C NMR (DMSO-d$^6$, 400 MHz) δ (ppm): 20.2, 20.3, 27.7, 40.4, 62.7, 69.7, 72.1, 78.5, 86.4, 117.3, 136.9, 150.2, 153.3, 156.6, 169.3, 169.4, 169.9; ESI-MS (ES$^+$) calculated for $C_{17}H_{21}N_5O_8$ 423.139, found 424.2 (M+H$^+$), 446.2 (M+Na$^+$), 847.3 (M+H$^+$), 869.3 (2M+Na$^+$).

2-N-Methyl-6-O-(diphenylcarbamoyl)guanosine [5]. To a solution of 2',3',5'-tri-O-acetyl-2-N-methylguanosine 3 (3.0 g, 7.1 mmol, 1.0 eq) in dry pyridine (50 mL) were added diphenylcarbamoyl chloride (3.45 g, 15 mmol, 2.1 eq) and diisopropylethylamine (1.9 mL, 11.4 mmol, 1.6 eq). The dark brown reaction mixture was then stirred at room temperature for 1 h to obtain 2',3',5'-tri-O-acetyl-6-O-(diphenylcarbamoyl)-2-N-methylguanosine 4. TLC showed complete conversion at this stage of the reaction. The reaction mixture was then diluted with pyridine (15 mL) and EtOH (30 mL). To this solution cooled at 0° C. was added 2 M NaOH (25 mL), which was precooled at 0° C. The reaction mixture was stirred for 10 min at 0° C. Acetic acid (c.a. 5 mL) was then added to neutralize the solution. Extraction with CH$_2$Cl$_2$ followed by chromatography on silica gel afforded 5 in 55% yield (1.92 g). TLC (CH$_2$Cl$_2$:MeOH, 9:1 v/v): R$_f$=0.5; $^1$H NMR (DMSO-d$^6$, 400 MHz) δ (ppm): 2.81 (d, 3H), 3.51-3.56 (m, 1H), 3.61-3.66 (m, 1H), 3.90 (m, 1H), 4.02 (q, 1H), 4.15 (br.d, 1H), 4.62 (br.s, 1H), 4.99 (br.s, 1H), 5.21 (d, J=4.8 Hz, 1H), 5.48 (d, J=5.6 Hz, 1H), 5.82 (d, J=5.6 Hz, 1H), 7.28-7.32 (m, 4H), 7.4-7.44 (m, 6H), 8.19 (s, 1H); $^{13}$C NMR (DMSO-d$^6$, 400 MHz) δ (ppm): 28.3, 61.5, 70.5, 73.1, 85.5, 116.4, 127.1, 129.4, 140.9, 141.8, 150.4, 155.6, 155.9, 159.6; ESI-MS (ES$^+$) calculated for $C_{24}H_{24}N_6O_6$ 492.1757, found 493.2 (M+H$^+$), 515.2 (2M+Na$^+$), 1007.4 (2M+Na$^+$).

Example #3

Synthesis of 5'-O-BzH-2'-O-ACE-O$^6$-DPC-N$^2$-methylguanosine phosphoramidite

Figure 3:
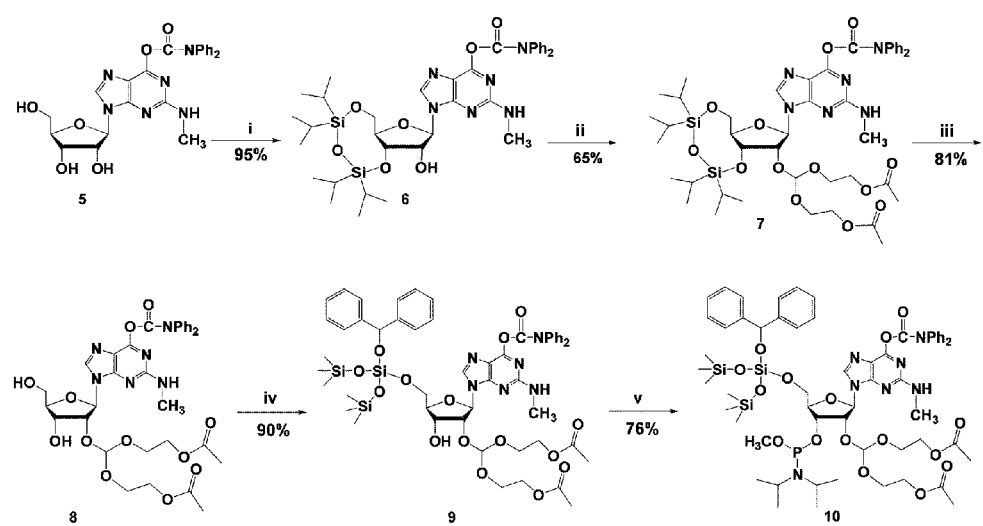
FIG. 3 depicts the synthesis of the 5'-O-BzH-2'-O-ACE-6-O-DPC-2-N-methylguanosine phosphoramidite 10: (i) TIPDSCl$_2$, pyridine, 0° C. to room temperature; (ii) tris(2-acetoxyethyl)orthoformate, pyridinium p-toluenesulfonate, 4-(tert-butyldimethyl-silyloxy)-3-penten-2-one, dioxane, 55° C.; (iii) HF/TMEDA,$CH_3CN$; (iv) BzH-Cl, di isopropylamine, $CH_2Cl_2$, 0° C.; (v) methyl tetraisopropylphosphorodiamidite, tetrazole, $CH_2Cl_2$, room temperature.

In general, two approaches were used to obtain the corresponding m$^2$G phosphoramidite. My first approach involved the synthesis of 5'-O-BzH-2'-O-ACE-6-O-DPC-2-N-methylguanosine phosphoramidite (FIG. 3). We were following the methodology introduced by Scaringe,[15] the chemistry now employed by Dharmacon Research Inc. for producing synthetic RNAs. The first step in Scheme 2.2 involves protection of the 3'- and 5'-hydroxyl groups using Markiewicz's disiloxane reagent (TIPDSCl$_2$) to obtain compound 6 in 95% yield. The TIPDS-protected compound was then subjected to 2'-O-ACE protection with tris(2-acetoxyethoxy)orthoformate (ACE) to yield compound 7. The removal of disiloxane by HF/TMEDA gave compound 8 in 81% yield. The 5'-OH protection was achieved by the reaction with benzhydryloxy-bis(trimethylsilyloxy)silyl chloride (BzH—Cl) to obtain compound 9 in 90% yield. Finally, the reaction between 9 and methyl tetraisopropylphosphorodiamidite gave the target molecule 10 in 76% yield. Despite a successful small-scale synthesis, subsequent generation of this compound on a large scale was not achieved due to problems encountered in the second step with ACE protection.

Specifically, the synthesis was carried out as follows:

3',5'-O-(1,1,3,3-Tetraisopropyl-1,3-disiloxanediyl)-2-N-methyl-6-O-(diphenylcarba-moyl)guanosine [6]. Compound 5 (1.88 g, 3.8 mmol, 1 eq) was azeotroped with benzene in vacuo overnight. This compound was dissolved in 75 mL of dry pyridine. The suspension was stirred for 30 min to give a clear solution and then cooled to 0° C. 1,3-Dichloro-1,1,3,3-tetraisopropyldisiloxane (TIPDSCl$_2$) (1.34 mL, 4.2 mmol, 1.1 eq) was added dropwise (while stirring) to the cold solution over a period of 1 h. Stirring was continued at room temperature for 12 h. The solvent was evaporated, and the light yellow residue was taken up in CH$_2$Cl$_2$, washed with 5% NaHCO$_3$, and then washed with water. The organic layers were combined and washed with brine, dried over Na$_2$SO$_4$, filtered, and concentrated. The crude product was purified by flash column chromatography on silica gel to yield 6 as a pale yellow solid (2.65 g, 95%). TLC (CH$_2$Cl$_2$:MeOH, 12:1 v/v): R$_f$=0.69; $^1$H NMR (CDCl$_3$, 400 MHz) δ (ppm): 1.01-1.09 (m, 24H), 1.24 (br.s, 1H), 1.57 (br.s, 4H), 2.98 (d, J=4.8 Hz, 3H), 3.09 (br.s, 1H), 4.04-4.07 (m, 3H), 4.53 (d, J=4.8 Hz, 1H), 4.71 (t, 1H), 5.06 (br.s, 1H), 5.90 (d, J=1.6 Hz, 1H), 7.18-7.22 (m, 4H), 7.29-7.34 (m, 4H), 7.4-7.42 (m, 2H), 7.8 (s, 1H); $^{13}$C NMR (DMSO-d$^6$, 400 MHz) δ (ppm): 12.04, 12.27, 12.46, 12.79, 16.82, 16.86, 16.89, 16.98, 17.09, 17.15, 17.31, 28.17, 61.31, 70.33, 73.11, 81.23, 93.99, 116.26, 127.06, 129.30, 139.70, 141.74, 150.34, 155.16, 155.57, 159.59; ESI-MS (ES$^+$) calculated for $C_{36}H_{50}N_6O_7Si_2$ 734.328, found 735.5 (M+H$^+$), 773.4 (M+K$^+$), 1507.7 (2M+K$^+$).

2'-O-[Bis(2-acetoxyethoxy)methyl]-3',5'-O-(1,1,3,3-tetraisopropyl-1,3-disiloxanediyl)-2-N-methyl-6-O-(diphenylcarbamoyl)guanosine [7]. Compound 6 (0.75 g, 1 mmol, 1 eq) was dried by azeotropic removal of water with anhydrous dioxane in vacuo overnight and then dissolved in 10 mL of anhydrous 1,4-dioxane to give a clear solution. Pyridinium p-toluenesulfonate (0.1 g, 0.41 mmol, 0.4 eq) and tris(2- acetoxyethoxy)-orthoformate (1.3 mL, 4.7 mmol, 4.6 eq) were then added in the given order to give a clear pale yellow solution. The reaction was stirred for 1 h at room temperature and then 4-(tert-butyldimethylsilyloxy)-3-penten-2-one (0.7 mL, 2.8 mmol, 2.8 eq) was added. The solution was stirred and heated at 55° C. with a condenser for 48 h. The reaction progress was monitored by TLC and showed efficient product conversion. The reaction was quenched with N,N,N',N',-tetramethylethylenediamine (TMEDA; 0.1 mL, 0.61 mmol, 0.6 eq) and stirring was continued for another 15 min at room temperature. The crude mixture was evaporated and purified by flash chromatography on silica gel to yield 7 as a pale yellow oil (0.5 g, 55%). TLC ($CH_2Cl_2$:MeOH=20:1 and TEA=0.5% v/v): $R_f$=0.7; $^1$H NMR ($CDCl_3$, 400 MHz) δ (ppm): 0.98-1.08 (m, 28H), 2.1 (q, 1H), 2.19-2.22 (m, 1H), 2.24 (s, 6H), 2.41 (s, 4H), 3.4 (s, 4H), 4.06-4.12 (m, 5H), 4.44-4.46 (m, 1H), 4.57-4.6 (m, 1H), 6.01 (d, 1H), 7.21-7.25 (m, 4H), 7.32-7.36 (m, 4H), 7.40-7.42 (m, 2H), 8.11 (s, 1H), 9.81 (s, 1H); $^{13}$C NMR ($CDCl_3$, 400 MHz) δ (ppm) 12.87, 13.22, 13.29, 13.68, 17.21, 17.30, 17.38, 17.57, 17.64, 17.71, 28.62, 45.99, 57.64, 61.72, 70.77, 75.07, 82.48, 89.43, 118.05, 121.22, 122.08, 127.86, 129.48, 129.59, 142.12, 150.66, 154.27, 154.83, 156.32, 163.59; ESI-MS (ES$^+$) calculated for $C_{45}H_{64}N_6O_{13}Si_2$ 952.407, found 953.4 (M+H$^+$), 975.5 (M+Na$^+$).

2'-O-[Bis(2-acetoxyethoxy)methyl]-2-N-methyl-6-O-(diphenylcarbamoyl)guanosine [8]. Acetonitrile (3 mL), TMEDA (0.76 mL, 5.2 mmol, 10 eq) and HF (48% aq stock solution, 0.12 mL, 3.15 mmol, 6 eq) were added slowly via syringe to a 25 mL round-bottom flask at 0° C. The HF/TMEDA mixture was stirred at 0° C. for 15 min and then transferred to a clear solution of 7 (0.5 g, 0.53 mmol, 1 eq, in 3 mL of acetonitrile) at 0° C. dropwise over 5 min by cannula. The resulting light yellow solution was stirred at 0° C. for 0.5 h and then at room temperature for 3 h. The solvent was evaporated and the crude product was purified by flash chromatography on silica gel with 0.5% TMEDA to yield 8 as yellow oil (0.25 g, 70%). TLC ($CH_2Cl_2$:MeOH=20:1 and TEA=0.5% v/v): $R_f$=0.3; $^1$H NMR ($CDCl_3$, 400 MHz 2.06-2.15 (m, 6H), 3.05-3.15 (m, 1H), 3.4 (s, 1H), 3.63-3.7 (m, 1H), 3.75-3.79 (m, 4H), 3.79-3.81 (d, 3H), 4.05-4.15 (m, 1H), 4.18-4.25 (m, 4H), 4.25-4.3 (m, 1H), 4.31-4.4 (m, 1H), 4.5 (m, 1H), 5.05-5.12 (m, 1H), 6.01 (d, 1H), 7.21-7.25 (m, 4H), 7.32-7.36 (m, 4H), 7.40-7.42 (m, 2H), 8.11 (s, 1H), 9.71 (s, 1H); ESI-MS (ES$^+$) calculated for $C_{33}H_{38}N_6O_{12}$ 710.255, found 711.1 (M+H$^+$), 733.2 (M+Na$^+$), 749.2 (M+K$^+$).

5'-O-[Benzhydryloxybis(trimethylsilyloxy)silyl]-2'-O-[Bis(2-acetoxyethoxy)methyl]-2-N-methyl-6-O-(diphenylcarbamoyl)guanosine [9]. Solution A was prepared by adding diisopropylamine (0.01 mL, 0.07 mmol, 1 eq) dropwise to benzhydryloxybis(trimethylsiloxy)silyl chloride (BzHCl; 0.07 mL, 0.17 mmol, 2.5 eq) in 2 mL of anhydrous $CH_2Cl_2$ at 0° C. Solution B was made by adding diisopropylamine (0.01 mL, 0.07 mmol, 1 eq) dropwise to a solution of 8 (50 mg, 0.07 mmol, 1 eq, in 2 mL of anhydrous $CH_2Cl_2$) and cooling the resulting mixture to 0° C. Solution A (0.6 mL, 0.5 eq) was added to solution B dropwise, and thereafter every 20 min, 0.3 eq aliquots were added. Reaction was stirred for 3 h at 0° C. The reaction was quenched with 5% $NaHCO_3$ and extracted with $CH_2Cl_2$. The organic layer was washed with brine, dried over $Na_2SO_4$, concentrated, and purified by silica gel flash chromatography to yield 9 as pale yellow oil in 91% yield (66 mg). TLC ($CH_2Cl_2$:MeOH=20:1 and TEA=1% v/v): $R_f$=0.4; $^1$H NMR ($CDCl_3$, 400 MHz) δ (ppm): 0.02-0.2 (m, 18H), 1.33 (t, 6H), 2.03 (s, 4H), 3.04 (m, 4H), 3.3 (m, 1H), 3.4 (d, J=5.6 Hz, 3H), 3.74-3.76 (m, 1H), 3.78-3.84 (m, 1H), 4.05 (t, 1H), 4.15 (m, 1H), 4.23 (m, 1H), 4.35 (br.s, 1H), 5.8-6.01 (m, 2H), 7.15-7.46 (m, 20H), 8.21 (s, 1H), 9.79 (s, 1H); $^{13}$C NMR ($CDC_3$, 400 MHz) δ (ppm): 1.27, 1.37, 1.46, 20.82, 28.26, 45.96, 60.96, 62.8, 65.16, 71.30, 75.42, 76.17, 85.02, 88.84, 121.51, 126.23, 126.34, 126.44, 126.52, 126.92, 127.02, 127.09, 127.13, 127.19, 127.49, 128.02, 128.12, 128.18, 128.23, 128.43, 129.15, 141.78, 142.22, 143.82, 143.89, 144.08, 144.22, 150.44, 154.24, 154.43, 155.91, 163.39; ESI-MS (ES$^+$) calculated for $C_{52}H_{66}N_6O_{15}Si_3$ 1098.389, found 1099.5 (M+H$^+$).

5'-O-[Benzhydryloxybis(trimethylsilyloxy)silyl]-2'-O-[Bis(2-acetoxyethoxy)methyl]-2-N-methyl-6-O-(diphenylcarbamoyl)guanosine-3'-(methyl-N,N-diisopropyl)phosphoramidite [10]. Compound 9 (0.08 g, 0.07 mmol, 1.0 eq) was dissolved in 2 mL of anhydrous $CH_2Cl_2$ at room temperature under Ar atmosphere. To the stirring solution, 1H-tetrazole (0.01 g, 0.07 mmol, 1.0 eq) dissolved in diisopropylamine (0.05 mL) was added. After stirring the solution for ~2 min, the methyl tetraisopropyl phosphoramidite (0.06 mL, 0.2 mmol, 2.8 eq) was added dropwise and the reaction was stirred overnight. The solution initially appeared as a cloudy mixture. The mixture became a pale yellow clear solution after 0.5 h. After 16 h, the TLC showed proper product conversion. The reaction was quenched with 5% $NaHCO_3$ and extracted with $CH_2Cl_2$. The organic layer was further washed with saturated NaCl and dried over $Na_2SO_4$. The concentrated product was purified on silica gel with 2% TEA in 20:1 mixture of $CH_2Cl_2$: MeOH to afford 10 as colorless oil (0.07 g) in 76% yield. TLC ($CH_2Cl_2$: MeOH=20:1 and TEA=2% v/v): $R_f$=0.48; $^1$H NMR (400 MHz, $CD_2Cl_2$) δ (ppm): 0.03-0.06 (m, 60H), 1.12-1.26 (m, 22H), 1.42 (t, 12H), 3.25-3.62 (m, 24H), 5.61 (s, 2H), 5.95 (t, 4H), 7.19-7.37 (m, 40H); $^{31}$P NMR (400 MHz, $CD_2Cl_2$): δ (ppm): (mixture of diastereomers) 135.35, 150.58; ESI-MS (ES$^+$) calculated for $C_{59}H_{82}N7O_{16}PSi_3$ 1259.486, found 1260.6 (M+H$^+$), 1298.5 (M+K$^+$).

Example #4

Figure 4:
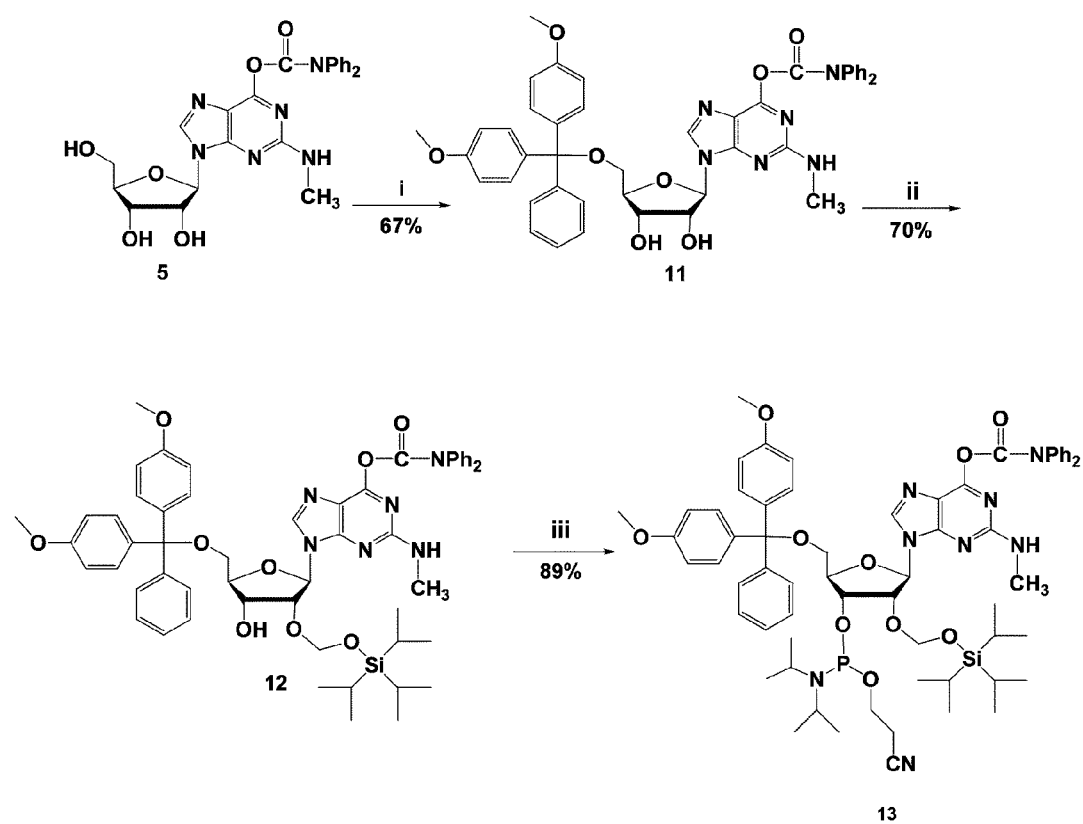
FIG. 4 depicts the synthesis of 5'-O-DMT-2'-O-TOM-6-O-DPC-2-N-methylguanosine phosphoramidite 13: (i) DMTCI, DMAP, pyridine, room temperature, 24 h; (ii) a) tert-Bu$_2$SnCl$_2$, iPr$_2$NEt, dichloroethane, 70° C., 15 min.; b)

Synthesis of the 5'-O-DMT-6-O-DPC-2-N-methyl-2'-O-TOM-guanosine-3'-(2-cyanoethyl)diisopropylphosphoramidite In general, since our main goal was to synthesize enough modified RNA for biophysical and biochemical studies, the phosphoramidite was needed in sufficient quantities (>100 mg). Therefore, a different approach was taken in which the phosphoramidite was generated using 5'-O-DMT-2'-O-TOM chemistry.[17] The first step involved the reaction between DMT-Cl and 5'-OH of compound 5 to yield compound 11 (FIG. 4). In the second step, 2'- and 3'-OH groups were subjected to reaction with ditertiarybutyl tin chloride (t-$Bu_2SnCl_2$) under basic conditions to form a cyclic 2',3'-O-dibutylstannylidene intermediate which activates the diol for the subsequent nucleophilic addition to the TOM-Cl protecting group to give 2'-(compound 12) and 3'-TOM isomers in 70% and 30% yields, respectively. The two isomers can be identified by the $R_f$ values and proton coupling constants ($J_{H1',H2}$'). The 2'-isomer is less polar compared to the 3'-isomer hence eluted first.[18, 19] The 2'-O-TOM protected intermediate, 12 was converted to the corresponding phosphoramidite building block, 13 by treating with 2-cyanoethyldiisopropylphosphoramidochloridite under basic conditions.

In our hands, compound 5 has lead to higher yields in the $m^2G$ phosphoramidite synthesis than the methods reported previously.[17, 20] DPC protection at the $O^6$-position enhanced solubility of the $m^2G$ nucleoside in solvents used during the phosphoramidite synthesis. It also protected the $O^6$-position from side reactions. The synthesis could be performed on a reasonably high scale to produce sufficient amounts of amidite 13 for multiple couplings.

Specifically, the synthesis was carried out as follows:

5'-O-(4,4'-Dimethoxytrityl)-2-N-methyl-6-O-(diphenylcarbamoyl)guanosine [11]. Compound 5 (0.51 g, 1.05 mmol, 1.0 eq) and 4,4'-dimethoxytritylchloride (0.39 g, 1.14 mmol, 1.09 eq) were azeotroped three times with toluene for ~15 h. To the dried compound 5, anhydrous pyridine (5 mL) was added. The mixture was stirred at room temperature under Ar atmosphere for 4 h. 4-Dimethylaminopyridine (0.09 g, 0.7 mmol, 0.7 eq) was subsequently added and stirring was continued for 17 h. The reaction was quenched with methanol (1 mL) and evaporated to dryness. The crude residue was dissolved in 50 mL of dichloromethane and washed with 5% sodium bicarbonate followed by saturated sodium chloride. The organic layer was dried over sodium sulfate and filtered. The product was then purified via silica gel chromatography using a solvent mixture of 90% dichloromethane, 9% methanol, 1% triethylamine to give 11 as a light yellow crystalline solid (0.56 g, 67%). TLC ($CH_2Cl_2$:MeOH, 9:1 v/v): $R_f$=0.4; $^1H$ NMR ($CD_3OD$, 400 MHz) 2.71 (br.s, 1H), 2.98-3.03 (q, 1H), 3.21 (d, J=3.2 Hz, 3H), 3.25-3.27 (m, 1H), 3.29-3.32 (m, 1H), 3.60 (d, J=4.8 Hz, 6H), 3.66 (m, 1H), 4.07-4.10 (m, 1H), 4.45 (m, 1H), 4.83 (m, 1H), 5.87 (d, J=4.8 Hz, 1H), 6.64-6.69 (m, 5H), 7.05-7.38 (m, 18H), 8.0 (s, 1H); $^{13}C$ NMR (($CD_3$)$_2SO$, 500 MHz) 28.8, 55.6, 72.2, 74.9, 82.3, 85.3, 87.7, 113.8, 114.0, 126.3, 127.8, 128.5, 128.7, 129.1, 129.2, 129.3, 129.9, 130.2, 130.4, 131.2, 141.2, 149.2, 159.9; ESI-MS ($ES^+$) calculated for $C_{45}H_{42}N_6O_8$ 794.3064, found 795.7 ($M+H^+$), 303.4 ($[(MeO)_2Tr]^+$).

5'-O-(4,4'-Dimethoxytrityl)-2'-O-[[(triisopropylsillyl)oxy]methyl]-2-N-methyl-6-O-(diphenylcarbamoyl)guanosine [12]. Di-tert-butyltindichloride (0.26 g, 0.846 mmol, 1.2 eq) was added to a solution of dry 1,2-dichloroethane (6.5 mL) containing compound 11 (0.56 g, 0.705 mmol, 1.0 eq) and ethyldiisopropylamine (0.36 mL, 2.82 mmol, 4.0 eq). The reaction mixture was heated to 70° C. for 15 min under reflux conditions. Then, the mixture was allowed to cool to room temperature. Upon cooling down, the mixture became cloudy and light brown in color. The crude reaction mixture was then stirred with [(triisopropylsilyl)oxy]methylchloride (0.18 mL, 0.776 mmol, 1.1 eq) for 3 h at room temperature. After 3 h, the mixture was evaporated to dryness. The resulting crude residue was dissolved in 20 mL of dichloromethane and washed with saturated sodium bicarbonate followed by saturated sodium chloride. The organic layer was dried over sodium sulfate and filtered. The product was then purified via silica gel column chromatography using a solvent mixture of dichloromethane: methanol (20:1) and triethylamine (0.5%) to give 12 as a light yellow oil (0.49 g, 70%). TLC ($CH_2Cl_2$:MeOH, 9:1 v/v): $R_f$=0.7; $^1H$ NMR ($CD_3OD$, 400 MHz) 0.89-1.05 (m, 18H), 1.25-1.3 (m, 3H), 2.79-2.8 (m, 7H), 3.1 (br.s, 1H), 3.3-3.5 (m, 2H), 3.70 (d, J=4.8 Hz, 3H), 4.15-4.25 (m, 1H), 4.65-4.7 (m, 1H), 4.85 (s, 2H), 5.05-5.15 (m, 1H), 6.1 (d, J=5 Hz, 1H), 6.79-6.83 (m, 5H), 7.17-7.5 (m, 18H), 8.05 (s, 1H), ESI-MS ($ES^+$) calculated for $C_{55}H_{64}N_6O_9Si$ 980.4504. found 981.9 ($M+H^+$), 1003.9 ($M+Na^+$), 1019.9 ($M+K^+$)

5'-O-(4,4'-Dimethoxytrityl)-2'-O-[[(triisopropylsilyl)oxy]methyl]-2-N-methyl-6-O-(diphenylcarbamoyl)guanosine 3'-(2-cyanoethyldiisopropylphosphoramidite) [13]. Compound 12 (0.25 g, 0.25 mmol, 1.0 eq) was dried extensively under vacuum. Then, it was dissolved in 5 mL of anhydrous dichloromethane. Next, N,N-diisopropylethylamine (0.3 mL, 2.5 mmol, 10 eq) and 2-cyanoethyldiisopropylchlorophosphoramidite (0.08 mL, 0.38 mmol, 1.5 eq) were added and the mixture was stirred for 2 h at room temperature. The reaction was quenched with 5% aqueous sodium bicarbonate, and then it was extracted with 2×50 mL of dichloromethane. Combined extracts were dried over anhydrous sodium sulfate and evaporated. The crude mixture was purified by silica gel column chromatography (hexane:ethyl acetate, 3:1 and triethylamine, 0.5%) to yield 13 as a white form (0.285 g, 95%). TLC (hexane:EtOAc:$Et_3N$=75%:24.5%:0.5%): $R_f$=0.23; $^1H$ NMR (($CD_3$)$_2CO$, 400 MHz) (mixture of diastereoisomers) 0.89-1.05 (2 m, 60H), 1.18-1.30 (2 m, 10H), 1.45 (t, 4H), 2.49 (br.s, 2H), 2.79-2.84 (m, 8H), 3.39-3.41 (m, 2H), 3.66-3.75 (m, 14H), 4.17-4.19 (m, 2H), 4.69 (m, 2H), 5.12-5.14 (m, 8H), 6.11 (d, J=5.2 Hz, 2H), 6.79-6.83 (m, 10H), 7.17-7.50 (2 m, 36H), 8.04 (s, 2H); $^{13}C$ NMR (($CD_3$)$_2CO$, 400 MHz) 12.56, 18.04, 18.08, 20.7, 20.75, 24.76, 24.82, 24.89, 24.95, 28.97, 43.82, 43.91, 43.96, 44.06, 55.45, 59.0, 59.16, 59.89, 60.02, 64.39, 72.59, 84.4, 84.7, 87.14, 87.71, 90.03, 90.36, 113.86, 127.54, 128.54, 128.58, 128.91, 128.98, 129.91, 130.85, 130.93, 130.99, 136.57, 136.69, 143.38, 145.96, 151.43, 157.33, 159.58, 160.82, 206.15; $^{31}P$ NMR (($CD_3$)$_2CO$, 400 MHz) (mixture of diastereoisomers) 150.96, 151.14; ESI-MS ($ES^+$) calculated for $C_{64}H_{81}N_8O_{10}PSi$ 1180.5583. found 1181.5 ($M+H^+$), 1203.5 ($M+Na^+$), 1219.4 ($M+K^+$); High resolution ESI-MS ($ES^+$) calculated for $C_{64}H_{81}N_8O_{10}PSi$ 1180.5583. found 1181.5634 ($M+H^+$), 1203.5439 ($M+Na^+$), 1219.5358 ($M+K^+$)

Example #5

970 Loop Model Constructs

Chemical synthesis of 970 loop model constructs. Four RNA analogues representing the 970 stem-loop region (h31) of *E. coli* 16S rRNA, were chemically synthesized at the W. M. Keck Foundation at Yale University, New Haven, Conn., USA (FIG. 5).

For RNAs containing 2-N-methyl-guanosine, 50 µmoles from the corresponding phosphoramidite were provided. The 5-methylcytidine phosphoramidite was purchased from Glen Research along with the standard A, U, C, and G amidites. The numbering system is based on the full-length *E. coli* rRNA sequence.[21] A G-C base pair was added at the end of the stems (denoted by lower case g-c) to stabilize the hairpin structure. Residues in all four constructs are numbered from $g_1$ to $c_{18}$ for the ends and $U_{960}$ through $A_{975}$ for the component representing the natural *E. coli* h31 sequence. Two h31 RNAs (ECh31UNMOD and ECh31M5C) were obtained using commercial amidites. The other two h31 analogues (ECh31M2G and ECh31WT) were synthesized using the 5'-O-DMT-2'-O-TOM-6-O-DPC-2-N-methylguanosine phosphoramidite along with commercially available amidites. The doubly modified h31 analogue (ECh31WT) represents the wild-type sequence of *E. coli* 16S rRNA helix 31.

Post-synthetic processing of RNA constructs. Upon completion of coupling on an automated synthesizer, the CPG-bound RNA was cleaved from the solid support and deprotected with 1:3 (v/v) $EtOH/NH_4OH$ and TBAF (tetrabutylammonium fluoride solution, 1 M in THF) as described in the literature.[8, 18] These steps will remove the 6-O-DPC and 2'-TOM protections on the $m^2G$ modified nucleoside simultaneously. The 2'-silyl protections were then removed either by $Et_3N·3HF$ or TBAF (tetrabutylammonium fluoride solution, 1M in THF) as described in the literature.[8, 18] Basically, 1 mL of TBAF was added to the dried oligo and vortexed. The modified RNAs containing 2'-TOM protecting groups were less soluble than the RNAs containing only 2'-TBDMS protections. Therefore the 2'-TOM-protected RNAs were warmed to 50° C. with shaking for 10 min to completely dissolve the RNA. Then, the solutions were allowed to cool to 35° C. and shaken overnight to attain complete deprotection. The reaction was quenched by adding 1 mL of 1 M Tris.HCl buffer (pH 7.5). This step also removes the 2'-hemiacetals remaining from the 2'-TOM protections in the modified RNAs.

The RNAs were desalted over Poly-Pak II cartridges (Glen Research cat. 60-3100-01) to remove the fluoride ions present in the mixture. To avoid any adverse effects of THF on the RNA binding to the cartridge matrix, the mixture was first dried to about half the original volume to remove THF from the mixture. Then, 1 mL of 0.1 M TEAA (pH 7.0) was added to the mixture making the total volume up to ~2 mL. Prior to sample introduction, the cartridge was flushed with 4 mL of acetonitrile to swell the resin and to remove any organic impurities. It was then flushed with 4 mL of 2 M TEAA (pH 7.0) which acts as an ion pairing agent to enhance the binding of RNA to the matrix. After loading the RNA-containing mixture onto the cartridge, it was flushed with 6 mL of 0.1 M TEAA (pH 7.0) to remove the salts. Then, the RNA was eluted with 1-2 mL of 50% acetonitrile. It is essential to maintain a flow rate of ~1-2 drops per second throughout the desalting process in order to obtain a higher efficiency of RNA recovery.

The RNAs were purified by HPLC (see HPLC methods for more details). After HPLC purification, each oligomer was further desalted by ethanol precipitation and dialysis for 3 days against RNase-free, deionized water using a 1000 molecular weight cut-off membrane (Spectra-Por). RNA concentrations were calculated using Beer's law and a single-stranded extinction coefficient ($\epsilon$) of 176,900 M$^{-1}$ cm$^{-1}$.[22] The same extinction coefficients were used for guanosine and N$^2$-methylguanosine ($1.4\times10^4$ M$^{-1}$ cm$^{-1}$ at pH 7.0) and cytidine and 5-methylcytidine ($9.1\times10^3$ M$^{-1}$ cm$^{-1}$ at pH 7.0). These steps are summarized in FIG. 6.

Characterization of RNA constructs. It is quite important to verify that the methyl group of m$^2$G remains intact after carrying out all the RNA synthesis and deprotection steps. The incorporation of m$^2$G residues was first confirmed by MALDI-TOF mass spectrometric analysis of full-length RNA and then by P1 nuclease digestion and calf intestinal phosphatase (CIP) treatment of the RNAs, followed by reverse-phase HPLC analysis of the enzyme digest products. The results are shown in FIGS. 7-10. For the HPLC analysis, the nucleoside standards were examined first to determine the retention times ($t_R$), then the nucleoside mixtures from P1 and CIP treatment were examined. All samples were analyzed by reverse-phase HPLC on a Supelco C18 column.

For the HPLC characterization, retention time ($t_R$) values of the individual nucleoside standards were first obtained as shown in FIG. 8.

The above retention time ($t_R$) values (6.7, 9.5, 15.9, 19.2, 18.7, and 12.5 min. for C, U, G, A, m$^2$G, and m$^5$C, respectively) were then used to determine the peaks seen from the enzyme digested h31 RNA samples (FIG. 10). The retention times deviated slightly both in the standard mixture and in enzyme digested RNA sample mixtures from those observed for the authentic standards (±0.1 to 0.6 min). These differences could be due to systematic errors or due to the fact that certain components in the digestion mixtures cause slight shifts in retention times compared to the pure standards.

Example #6

General Procedures for Examples 7-13

RNA sample preparation. The four RNA hairpins used in this study were chemically synthesized at the W. M. Keck Foundation at Yale University, New Haven, Conn., USA. For RNAs containing N$^2$-methylguanosine, 50 µmoles of the corresponding phosphoramidite were provided. The 5-methylcytidine phosphoramidite was purchased from Glen Research. Upon completion of coupling on an automated synthesizer, the CPG-bound RNA was cleaved from the solid support and deprotected with 1:3 (v/v) EtOH/NH$_4$OH and TBAF (tetrabutylammonium fluoride solution, 1 M in THF) as described in the literature.[22, 23] The RNAs were desalted over Poly-Pak II cartridges (Glen Research), then purified by HPLC on an XTerra MS C18 column (2.5 µm, 10×50 mm, Waters) in which the eluent was 0.1 M TEAA (triethyl ammonium acetate) buffer, pH 7.0, with a 5-15% linear gradient of acetonitrile over 25 min at a flow rate of 4.0 mL/min. After HPLC purification, each oligomer was further desalted by ethanol precipitation and dialysis for 3 days against RNase-free, deionized water using a 1000 molecular weight cut-off membrane (Spectra-Por). RNA concentrations were calculated using Beer's law and a single-stranded extinction coefficient ($\epsilon$) of 176,900 M$^{-1}$ cm$^{-1}$.[24] The same extinction coefficients were used for guanosine and N$^2$-methylguanosine ($1.4\times10^4$ M$^{-1}$ cm$^{-1}$ at pH 7.0) and cytidine and 5-methylcytidine ($9.1\times10^3$ M$^{-1}$ cm$^{-1}$ at pH 7.0).

Thermal melting studies. The absorbance versus temperature profiles were obtained on an Aviv 14DS UV-vis spectrophotometer with a five-cuvette thermoelectric controller. Microcuvettes with two different pathlengths, 0.1 and 0.2 cm (60 and 120 µL volumes, respectively), were employed. Each set of measurements was done in triplicate. The buffer used in each experiment contained 15 mM NaCl, 20 mM sodium cacodylate, and 0.5 mM Na$_2$EDTA (pH 7.0) unless otherwise noted. Each oligomer was dissolved in a specific volume to yield an absorbance reading just below 2.0 in a 0.1 cm pathlength cuvette. The RNA concentrations were determined from the absorbance values (260 nm) at 95° C. The absorbance data were collected at 280 nm from 0 to 95° C. with a constant heating rate of 0.5° C./min. Thermodynamic parameters were obtained from the absorbance versus temperature profiles using the MELTWIN v. 3.5 melting curve program.[1] This program performs a van't Hoff analysis, assuming a two-state model for the transition between a native and a denatured (random coil) structure of a hairpin.

Circular dichroism studies. CD spectra were obtained on an Applied Photophysics Chirascan circular dichroism spectrometer (220-320 nm) at 25° C. in 15 mM NaCl, 20 mM sodium cacodylate, and 0.5 mM Na2EDTA at pH 7.0 unless otherwise noted. The RNA concentrations were maintained at 2.5-3.0 µM for all CD experiments. Based on the RNA strand concentration, the measured CD spectra were converted to molar ellipticity ($\Delta\epsilon$),[25] which denotes the moles of RNA molecules rather than moles of individual residues present in the sequence.

NMR experiments. The HPLC-purified RNAs (~150 µM) were further desalted by ethanol precipitation, followed by desalting in two steps: 1) dialysis against double-deionized water in the presence of 0.1 M NaCl and 0.1 mM EDTA for 1 day, and 2) dialysis against double-deionized water for 2 days. All four RNAs were dissolved in 40 mM NaCl, 10 mM sodium phosphate, 0.5 mM Na2EDTA, and 15 µM TSP-d$_4$ (sodium 3-(trimethylsilyl)tetradeuteriopropionate), in 90% H$_2$O and 10% D$_2$O at pH 6.8. The NMR spectra were obtained on a Bruker AVANCE-AQS 700 MHz spectrometer equipped with a 5 mm triple-resonance cryoprobe. All NMR spectra were acquired at 20° C., except for variable temperature experiments that ranged from 5 to 30° C. ID imino proton NMR spectra were acquired for all samples using Digital Quadrature Detection for at least 16,000 data points. The water samples in 9:1 H$_2$O/D$_2$O required additional Watergate solvent suppression pulse schemes to be included in the pulse program. 1D NOE difference spectra included a 500 msec presaturation pulse centered on imino peaks of interest. A reference spectrum was subtracted from the resulting selective saturation spectra to obtain the 1D NOE difference spectra for each construct. For each experiment, 256 scans×10 iterations were acquired in order to improve the signal to noise ratio. The data were further processed with solvent baseline correction, zero-filling one time and 3 Hz of line broadening.

Example #7

Effect of Modifications on the Stability of Helix 31 Hairpin from *E. coli* 16S rRNA Absorbance versus temperature profiles (melting curves) were obtained at pH 7.0 for all four RNA constructs. They were analyzed in terms of $\Delta G°_{37}$, $\Delta G°_{50}$, $\Delta H°$, $\Delta S°$, and melting temperature ($T_m$),[1,2] Representative normalized UV melting curves of the modified RNAs compared to the unmodified RNA, taken in 15 mM NaCl, 20 mM sodium cacodylate, 0.5 mM Na$_2$EDTA (pH 7.0), are shown in FIG. 11.

The curves represent an average of five sets of data at different concentrations of RNA obtained from a five-cuvette thermoelectric controller. The melting curves for the unmodified RNA (ECh31UNMOD, blue line in panels A-C) are compared to those for the modified RNAs (pink lines: (A) ECh31WT, (B) ECh31M2G, and (C) ECh31M5C). All of the melting curves were normalized at 95° C. and absorbance measurements were taken at 260 nm (see materials and methods, section 4.5).

The melting curves are biphasic for all four RNAs (FIG. 12) with transitions at 0 to 35° C. and 40 to 80° C. The low temperature transitions were concentration dependent, suggesting the formation of a bimolecular complex, such as a duplex or loop-loop interaction. The higher melting transitions were concentration independent, consistent with unimolecular unfolding of the hairpin structure.[3] The corresponding thermodynamic parameters for the four RNAs are given in Table 2. The data indicate slight destabilizing effects ($\Delta\Delta G°_{37}$ values of 0.2-0.5 kcal/mol) of the modifications on helix 31. The observed order of stability of the RNAs is ECh31UNMOD>ECh31M2G>ECh31M5C>ECh31WT.sup.a A conservative estimate of the standard error for $\Delta G°_{50}$ is 3% (.+-.0.2 kcal/mol)[4]

TABLE 3

Thermodynamics of the ECh31 WT RNA in Na$^+$ and K$^+$ buffers.

| | $\Delta G°_{37}$ (kcal/mol) | $\Delta H°$ (kcal/mol) | $\Delta S°$ (cal/K · mol) | $T_m$ (° C.) |
|---|---|---|---|---|
| ECh31WT - KCl buffer | −2.13 ± 0.03 | −39.37 ± 1.2 | −120.08 ± 3.8 | 54.7 |
| ECh31WT - NaCl buffer | −2.10 ± 0.07 | −37.26 ± 1.2 | −113.37 ± 3.6 | 55.5 |

The subtle destabilizing effects of the methylations were somewhat unexpected. In X-ray crystal structures of *E. coli* 70S ribosomes[5] and *T. thermophilus* 30S ribosomes,[6] m$^2$G and m$^5$C are involved in a base-triple stacking interaction with residue 968. One might expect the methyl groups in the modified nucleosides to facilitate stacking interactions;[7] however, both m$^2$G and m$^5$C are destabilizing relative to standard nucleotides G and C within the given sequence context. The presence of the h31 methylations might serve another purpose, such as stabilizing the ribosome through hydrophobic interactions with Arg128 of the S9 protein.[7] Furthermore, the slight destabilization caused by the base methylation may facilitate base flipping of m$^2$G966, which has been observed in ribosome crystal structures and likely plays an important role in protein synthesis.[8] The energetic penalty would then be overcome by contacts with various ribosome components such as 16S rRNA-helices, ribosomal proteins, and tRNA.[8] Furthermore, the X-ray crystal structure of the *T. thermophilus* 70S ribosome complexed with a model mRNA and two tRNAs revealed that the positions of the 16S rRNA P-site nucleotides in the vacant ribosome superimpose well with those in the tRNA-containing complex, with the exception of m$^2_2$G966.[8] Residue m$^2_2$G966 is flipped out in the crystal structure of the *T. thermophilus* 70S ribosome containing a model mRNA and two tRNAs (FIG. 14A)[8] or remains stacked in the 30S ribosomal subunit from *T. thermophilus* crystal structure (FIG. 14B).[6] The interaction with the anticodon loop of the P-site-bound tRNA appears to be stabilized by stacking interactions involving m$^2_2$G966 with ribose 34. Hence, the flipped-out base has been suggested to facilitate correct positioning of the tRNA during translation.[8,9] Therefore, the slight destabilizing effects of modifications in h31 may be important for facilitating the flipping movement of m$^2_2$G966, but at the same time stabilizing stacking interactions with the tRNA through the methyl group. Positioned in the middle of the stacked triplet, the m$^5$C967 residue has a greater destabilizing effect than m$^2$G966 (ECh31M5C vs ECh31M2G). This result may be due to a greater disruption of stacking by the methylated base of m$^5$C967.

TABLE 2

Thermodynamic data for ECh31WT, ECh31M5C, ECh31M2G, and ECh31UNMOD RNA sequences.

| | $\Delta G°_{50}$ (kcal/mol) | $\Delta G°_{37}$ (kcal/mol) | $\Delta H°$ (Kcal/mol) | $\Delta S°$ (cal/K · mol) | $T_m$ (° C.) |
|---|---|---|---|---|---|
| ECh31UNMOD | −0.9$^a$ | −2.6 ± 0.1 | −44.1 ± 1.0 | −133.8 ± 3.0 | 57 |
| ECh31M5C | −0.6$^a$ | −2.2 ± 0.1 | −40.5 ± 0.9 | −123.3 ± 3.1 | 55 |
| ECh31M2G | −0.7$^a$ | −2.4 ± 0.1 | −41.9 ± 1.1 | −127.5 ± 3.2 | 56 |
| ECh31WT | −0.5$^a$ | −2.1 ± 0.1 | −37.5 ± 2.2 | −114.4 ± 5.8 | 56 |

The RNA samples were analyzed as five different dilutions per experiment and UV melts were also performed in triplicate for each construct. AU0-AU4 represent profiles corresponding to different dilutions of each RNA taken in 15 mM NaCl, 20 mM sodium cacodylate, 0.5 mM Na$_2$EDTA at pH 7.0. Experiments in K$^+$ buffer (15 mM KCl, 20 mM cacodylic acid, 20 mM Tris [basic form], 0.5 mM Na$_2$EDTA, pH 7.0) gave similar results (Table 3, FIG. 13).

Example #8

Effect of Modifications on the Structure of Helix 31 Hairpin from *E. coli* 16S rRNA Circular dichroism studies. The CD spectra of the helix 31 analogues were obtained to analyze the effects of modifications on the folded structure (FIG. 15).

In FIG. 15, the unmodified RNA spectra are shown in blue color and that of modified RNAs are shown in pink color. The difference spectrum (panel D) is shown in black color triangles. The data indicate that the unmodified, singly modified, or doubly modified RNAs all exist in solution as A-form helices, and they display similar conformations. They all have peak maxima at 270 nm and minima at 240 nm, similar to other A-form RNAs. A difference spectrum was obtained using Equation 1 in order to determine if the structural changes induced by the modified nucleotides are additive. In Equation 1, the difference spectrum for the singly modified RNAs and unmodified RNA is set equal to the difference spectrum of fully modified (wild-type) and unmodified RNA. If the effects of the modifications on the structure are additive, then the total difference spectrum should be equal to zero (Equation 2).

$$ECh31M5C+ECh31M2G-(2\times ECh31UNMOD)=ECh31WT-ECh31UNMOD \quad (1)$$

$$\text{difference}=ECh31M5C+ECh31M2G-ECh31UNMOD-ECh31WT \quad (2)$$

Figure 15A:
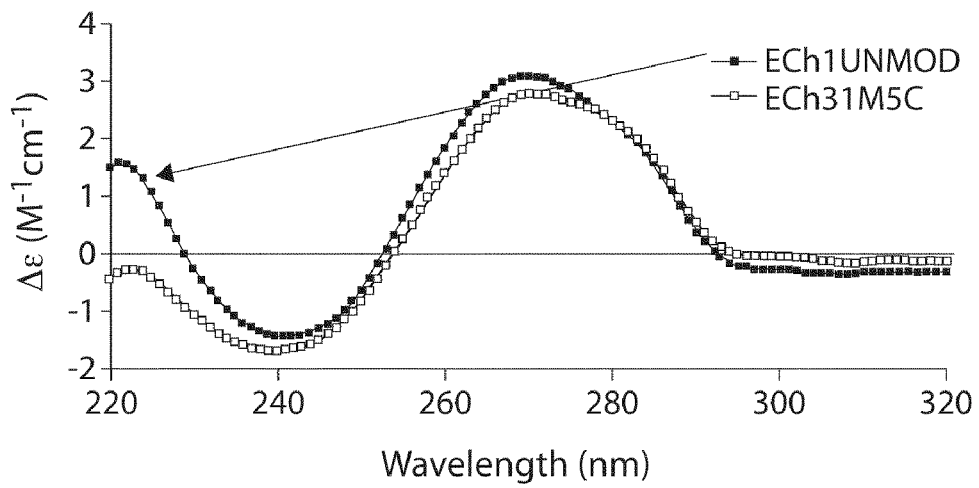
Figure 15B:
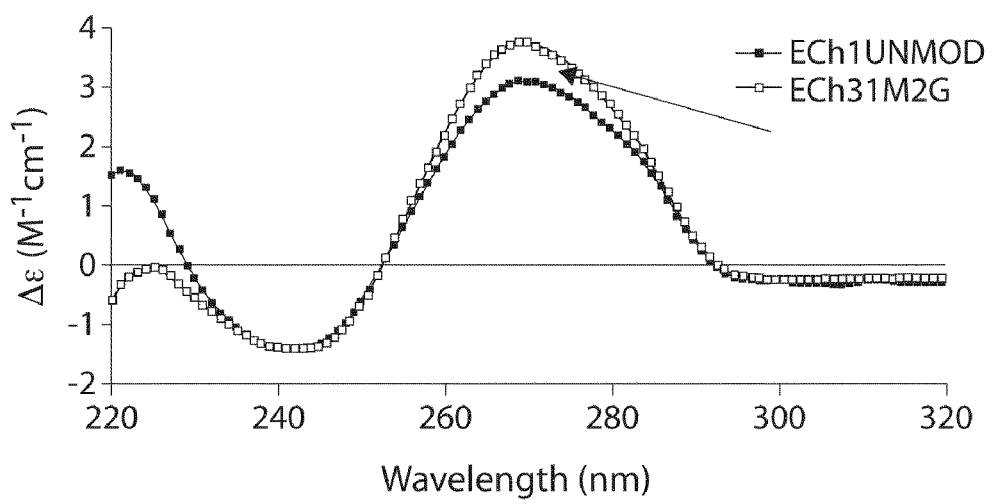
Figure 15C:
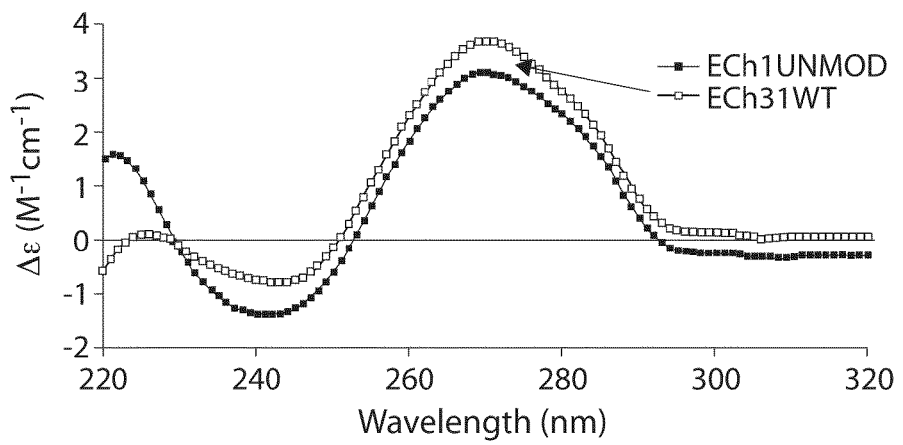
Figure 15D:
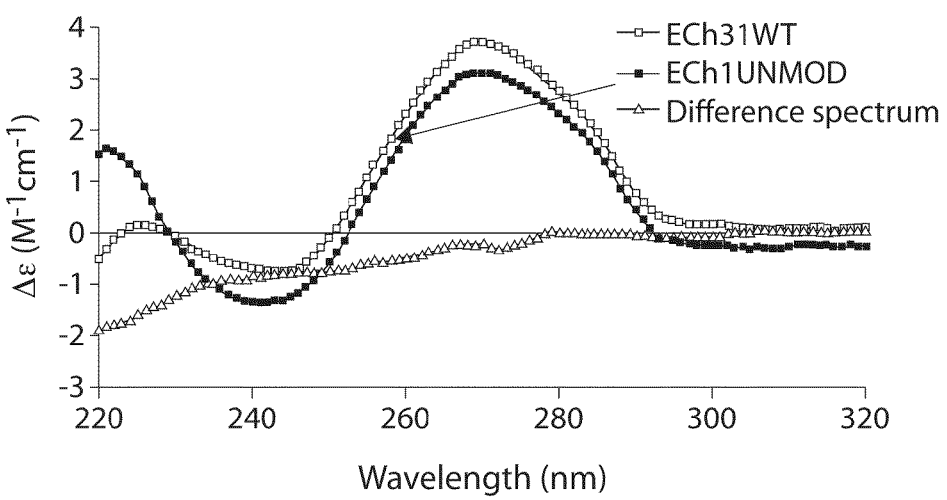

As shown in FIG. 15D, the total difference spectrum is close to zero except for slight changes in the lower wavelength range (<260 nm). Therefore, the data are interpreted as the presence of modifications in h31 having only subtle or no effects on the RNA structure.

The CD experiments were repeated for ECh31WT RNA in 35 mM K$^+$ buffer (KCl buffer) and salt concentrations that more closely mimic in vivo protein synthesis conditions[10] (25 mM cacodylic acid, 25 mM Tris [basic form], 30 mM KCl, 70 mM NH$_4$Cl, 3 mM MgCl2 at pH 7.0; Mg buffer). The spectra taken in K$^+$ and Mg$^{2+}$ containing buffers are similar (FIG. 16)

1D NMR studies. ID NMR spectroscopy was employed to examine hydrogen-bonding interactions in the four RNA constructs. The signals corresponding to the imino protons can be observed only when those protons are protected from exchange with the bulk solvent (water). That is generally possible when they are involved in hydrogen-bonding interactions. Other types of tertiary structures (including base stacking) may also lead to protection from solvent exchange. Simply by counting the number of imino proton resonances present in the region of 10 to 15 ppm, it is possible to determine the number of base pairs present in the stem region if only standard Watson-Crick base-pairs are present. Additional peaks may arise from non-standard base-pairing interactions such as base mismatches. In order to investigate the stability of the RNA-stem-regions, we performed 1D-experiments at temperatures ranging from 5 to 25° C. The 1 D imino-proton spectra were obtained at variable temperatures for each of the helix 31 RNA constructs (FIG. 17). The upper limit for the variable temperature experiment depends on the temperature of melting ($T_m$) of that particular RNA hairpin. The disappearance of some peaks at higher temperatures will therefore provide information about the stability.

The variable temperature experiments provided a suitable temperature for NOE difference experiments to be performed. The temperature at which all the imino proton peaks corresponding to the base-pairing interactions of the four RNA constructs was found to be 20° C. Also, this temperature (20° C.) gave rise to minimal effects from the spectral artifacts that would otherwise appear at lower temperatures as evident from the biphasic nature of the UV melting transitions (FIG. 21). These low temperature transitions may occur as a consequence of loop-loop interactions or duplex formation.

Peak assignments of the imino proton spectra were made using ID NOE difference spectroscopy. The corresponding analyses are shown in FIGS. 22-25.

The imino proton regions of the $^1$H NMR spectra of four RNA analogues and their peak assignments based on ID NOE difference spectroscopy are summarized in FIG. 26.

All four spectra in FIG. 26 show peaks at 14.7, 14.0, 12.3, and 12.1 p.p.m., corresponding to stem base pairs ($U_{960}$, $U_{961}$, $G_{963}$, and $G_{973}$, respectively). The NMR spectra for three RNAs (ECh31M5C, ECh31M2G and ECh31UNMOD) have a peak corresponding to the terminal base pair, $g_1$-$c_{18}$ (12.4 p.p.m.), although the peak is shifted upfield (12.2 p.p.m.) in the ECh31M2G spectrum. The imino proton peak corresponding to terminal $g_1$-$c_{18}$ pair of the wild-type RNA (FIG. 26A) was not observed at 20° C., presumably due to solvent exchange or overlap with the peak corresponding to $G_{963}$. The imino proton resonances marked by asterisks are most likely arising from loop residues. The chemical shifts of these peaks vary between the four RNAs, indicating differences in their loop structures. The ECh31WT spectrum (FIG. 26A) exhibits two additional peaks at 12.8 and 13.2 p.p.m. The ECh31M5C spectrum (FIG. 26B) exhibits two additional peaks at 10.8 and 13.2 p.p.m., as well as a slight feature at 12.8 p.p.m. The spectrum of ECh31M2G (FIG. 26C) has additional peaks at 10.4, 12.7, and 13.2 p.p.m. The unmodified RNA (ECh31UNMOD, FIG. 26D) $^1$H NMR spectrum exhibits three additional peaks at 10.8, 12.8, and 13.2 p.p.m. These additional resonances are not observed at temperatures >20° C. (FIGS. 17-20), indicating that they arise from weak interactions, such as base stacking. Further experiments are currently underway (in collaboration with the SantaLucia group) to make definitive assignments of these peaks.

Example #9

The helix 31 Corresponding to *H. sapiens* 18S rRNA

The 970 loop of helix 31 (h31) of *E. coli* 16S rRNA is located near the ribosomal P site and therefore believed to be intimately involved in translation.[8, 9, 11] *E. coli* h31 contains two modified nucleotides, N$^2$-methylguanosine at position 966 (m$^2$G966) and 5-methylcytidine at position 967 (m$^5$C967) as shown in FIG. 27. The two methylated bases, m$^2$G966 and m$^5$C967, occur at the same or adjacent site as the hypermodified nucleotide 1-methyl-3-(3-amino-3-carboxypropyl)-pseudouridine (acp$^3$m$^1$Ψ) in the human small subunit rRNA (FIG. 27).[12, 13] The ECh31WT construct is derived from positions 960-975 of *E. coli* 16S rRNA, while the corresponding HSh31WT construct containing the hypermodified nucleotide 1-methyl-3-(3-amino-3-carboxypropyl)-pseudouridine (acp$^3$m$^1$Ψ) is derived from positions 1242-1257 of the *H. sapiens* small subunit Rrna.

Example #10

Stability Studies on the Unmodified Helix 31 Corresponding to *H. sapiens* 18S rRNA.

Thermal melting studies. Preliminary experiments were performed with the unmodified human analogue (HSh31UNMOD) containing an additional G-C base-pair (denoted by g-c) similar to that of the ECh31UNMOD construct (FIG. 28). Preliminary UV melting studies based on the unmodified human analogue (HSh31UNMOD; FIG. 29) revealed a fairly low stability with respect to hairpin formation (Table 4).

TABLE 4

Thermodynamics of the unmodified RNA model constructs representing *E. coli* and *H. sapiens* h31

|  | $\Delta G°_{37}$ (kcal/mol) | $\Delta H°$ (kcal/mol) | $\Delta S°$ (cal/K · mol) | $T_m$ (° C.) |
|---|---|---|---|---|
| HSh31UNMOD | −0.6 ± 0.1 | −29.4 ± 1.6 | −92.8 ± 5.4 | 44 |
| ECh31UNMOD | −2.6 ± 0.1 | −44.1 ± 1.0 | −133.8 ± 3.0 | 57 |

The HSH31UNMOD analogue was unstable with respect to hairpin formation, as indicated by the relatively low negative value for the free energy ($\Delta G°_{37}$=−0.6 kcal/mol). Also, this value was not very reproducible, possibly due to formation of G quartets by the highly abundant guanine residues in the stem region. In order to alleviate this problem, we tried different buffer conditions used previously in the literature.[4, 14, 15] First, we increased the NaCl concentration to 1 M keeping the remaining components constant. Therefore, the buffer contained 1 M NaCl, 20 mM sodium cacodylate, and 0.5 mM EDTA at pH 7.0. In FIG. 30, the result obtained under high salt conditions (dotted line) is compared with that obtained under the normal buffer conditions (solid line).

In another attempt, we added 5 mM $MgCl_2$ to the buffer. The new buffer contained 15 mM NaCl, 20 mM sodium cacodylate, 0.5 mM EDTA, and 5 mM $MgCl_2$ at pH 7.0. The result obtained in the presence of $Mg^{2+}$ (dashed line) is compared with that obtained under the first set of buffer conditions (solid line) in FIG. 31. In both the cases, we observed fairly inconsistent melting curves with hardly reproducible thermodynamic parameters (data not shown). The lack of reproducibility in the thermodynamic parameters likely occurred due to inconsistencies in the data fitting process.

Example #11

Structural Studies on the Unmodified Helix 31 Corresponding to *H. sapiens* 18S rRNA Circular dichroism studies. CD experiments were carried out under the standard buffer conditions (15 mM NaCl, 20 mM sodium cacodylate, and 0.5 mM EDTA at pH 7.0). The HSH31UNMOD spectrum has a peak maximum at 270 nm with an increase in peak intensity at the maximum (~2 ellipticity units) compared to ECh31UNMOD, and a peak minimum at 240 nm and a crossover point at 252 nm. Differences in the CD spectra between the *E. coli* and *H. sapiens* RNAs were not surprising, because they have different stem sequences.

MFOLD analysis on the unmodified helix 31 of *H. sapiens* 18S rRNA. The above observations from UV melting and CD were further supported by MFOLD analysis[16] carried out on the given HSH31UNMOD RNA. The free energy data obtained from MFOLD revealed that hairpin formation from the given sequence is relatively unfavorable (FIG. 33). Alternative structures with comparable free energy values were predicted.

Phylogenetic analysis to reveal the base-pair conservation in the stem region of helix 31. The observed instability of the HSh31UNMOD hairpin raised doubts about its utility as a model construct to represent the human helix 31. Consequently, the requirement for a stable stem region for the study was recognized. In an attempt to determine other possible sequences for the stem region of helix 31, the sequences of rRNAs from a series of organisms were compared (FIG. 35). A total of 431 species of bacteria and 115 species of eukaryotes were examined using the comparative RNA Web (CRW) site.[17] The results are summarized in FIG. 34.

Example #12

Stability Studies: An Altered Oligonucleotide Sequence for the Helix 31 of *H. sapiens* 18S rRNA The aforementioned phylogenetic analysis revealed several other possible base pairs for the stem region of the *H. sapiens* model helix 31. It also revealed that replacement of the three consecutive G:U wobble pairs by the secondary possibilities provide a stem region similar to that of the *E. coli* helix 31 as shown by the construct HSh31ECstem (FIG. 36). The sequence HSh31ECstem is compared with that of HSh31UNMOD and ECh31UNMOD. The wild-type sequences are shown by upper-case letters, and the altered sequence positions are indicated by lower-case letters.

Thermal melting studies on the human unmodified helix 31 containing the altered sequence. The absorbance versus temperature profiles were obtained at pH 7.0 in low salt conditions (35 mM $Na^+$) for the new analogue of helix 31 (HSh31ECstem) and analyzed in terms of the melting temperature ($T_m$), $\Delta°$, $\Delta S°$ and $\Delta G°_{37}$. The melting curve for HSH31ECSTEM (green color curve) is biphasic with transitions at 0-35 and 45-80° C. (FIG. 37). The higher melting transition is concentration independent, consistent with unimolecular unfolding of a hairpin structure. In contrast, the lower temperature transition is concentration dependent, suggesting the formation of a bimolecular complex, such as a duplex or a loop-loop interaction (data not shown).

Figure 37A:
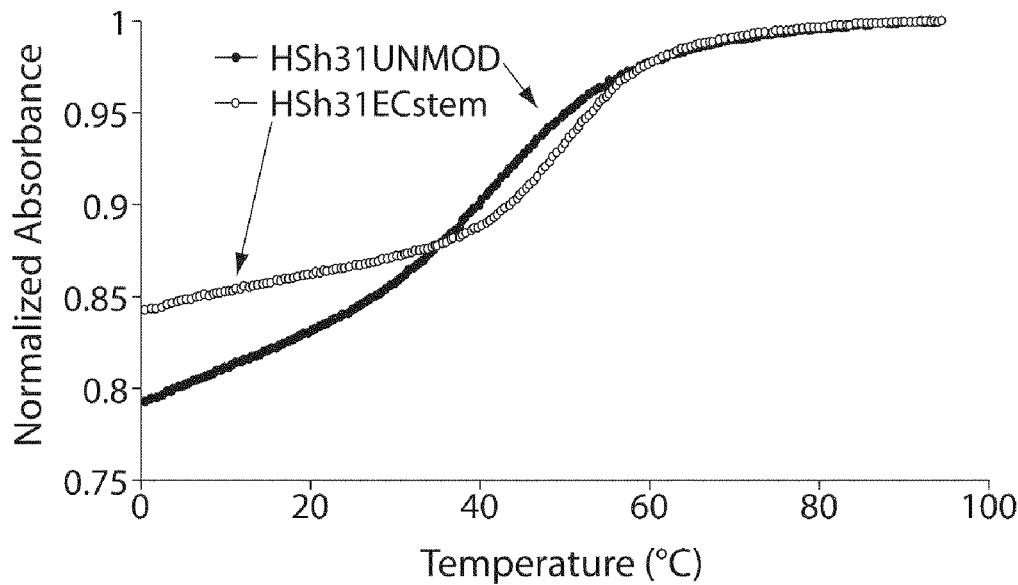
Figure 37B:
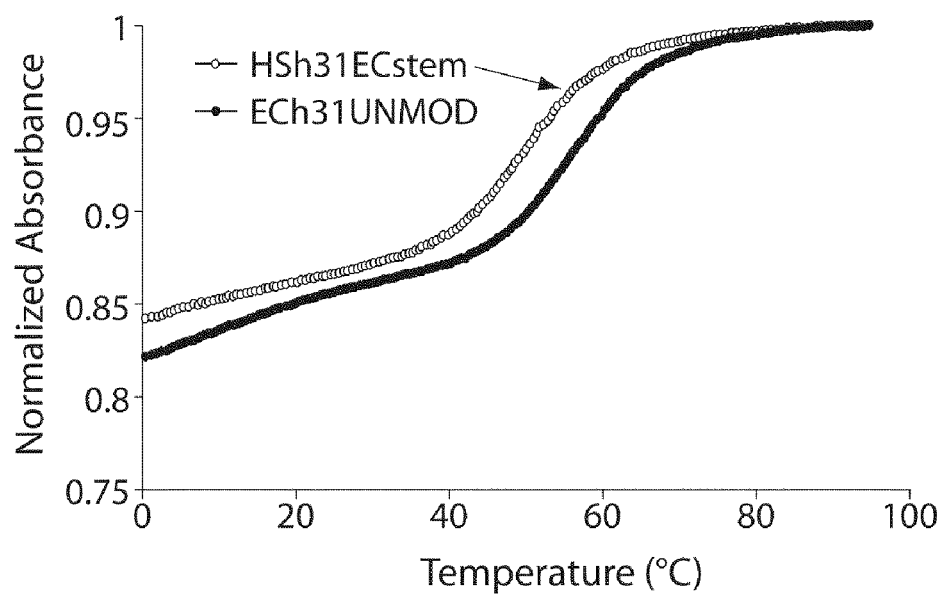

A comparison of HSh31UNMOD vs. HSh31ECstem (FIG. 37A; Table 5) shows the improvement in the melting profile of the HSh31ECstem with respect to the wild-type helix 31 ($\Delta G°_{37}$ of 0.6 vs. 1.8 kcal/mol, respectively) and shows a characteristic melting of the stem region from 0 to 100° C. The ECh31UNMOD vs. HSh31ECstem comparison (FIG. 37B; Table 5) suggests that the loop region corresponding to the *H. sapiens* exerts a destabilizing effect on the stem relative to the *E. coli* loop region, since they have the same number of nucleotides (eight) in their loop regions and they both share the same base-pairing schemes in the stem region.

TABLE 5

Thermodynamics of the HSh31ECstem RNA as compared with ECh31UNMOD and HSh31UNMOD RNAs.

|  | $\Delta G°_{37}$ (kcal/mol) | $\Delta H°$ (kcal/mol) | $\Delta S°$ (cal/K · mol) | $T_m$ (° C.) |
|---|---|---|---|---|
| HSh31UNMOD | −0.6 ± 0.1 | −29.4 ± 1.6 | −92.8 ± 5.4 | 44 |
| HSh31ECstem | −1.8 ± 0.1 | −43.1 ± 0.3 | −133.1 ± 1.0 | 51 |
| ECh31UNMOD | −2.6 ± 0.1 | −44.1 ± 1.0 | −133.8 ± 3.0 | 57 |

Example #13

Structural Studies on the Human Unmodified Helix 31 Containing the Altered Sequence.

Circular dichroism. The CD spectra of the helix 31 analogues show peak maxima around 265 nm and minima around 240 nm, similar to other A-form RNAs (FIG. 38); however, HSh31ECstem (green) shows shifts in peak maxima, peak minima, and crossover points towards slightly higher wavelengths compared to HSh31UNMOD (red) and ECh31UNMOD (blue) (FIG. 38). In the case of HSh31UNMOD vs. HSh31ECstem spectra, the difference in the peak maxima intensity and wavelength are quite significant. That result is most likely due to the difference in the base-pairing content in the stem regions. In the ECh31UNMOD vs. HSh31ECstem spectra, the differences in both peak maxima and peak minima are also quite significant even though they both have the same stem sequences. This result implies that the loop regions are influencing the structures of these two analogues.

Example #14

General Procedures for Examples 15-18

Media and bacterial strains. Cells were grown in LB media (10 g of bactotryptone, 0.5% (5 g) NaCl (instead of 1% in normal media) and 0.5% (5 g) yeast extract in 1 L) as suggested by New England Biolabs (NEB) (Beverly, Mass.). For plates, 18 g (1.8%) of agar was added to 1 L of LB. To make soft or top agar, 14 g (1.4%) of agar was added to 1 L of LB. The *E. coli* ER2738 strain (New England Biolabs) was used to infect M13 bacteriophage and amplify its population. Its genotype is: F'lacIq Δ(lacZ)M15, proA+B+zzf::Tn10(Tet$^R$)/ fhuA2, supE, thiΔ(lac-proAB), Δ(hsdMS-mcrB)5, ($r_k^-m_k^-$ McrBC$^-$).

Biotinylation of target RNA. The 18 mer wild-type h31 contains m$^2$G966 and m$^5$C967 modified nucleotides. Dinuka Abeydeera (Chow lab) prepared the m$^2$G phosphoramidite and its incorporation into RNA was done at the W. M. Keck Foundation, Yale University, CT. It was deprotected and purified by D. Abeydeera using manufacturer's instructions. The unmodified h31 was purchased from Dharmacon Inc, Lafayette, Colo. and it was deprotected and purified by 18% polyacrylamide denaturing gel (7 M urea, 29:1 acrylamide and bisacrylamide). The 5'-end of RNA was biotinylated as follows. One nmole of RNA oligo was mixed with 5 μl of polynucleotide kinase (PNK, 50 units), 3.5 μl of ATP-γ-S (final concentration, 0.2 mM), 5 μl of 10× polynucleotide kinase buffer and the mixture was incubated at 37° C. for 1.5 h. The PNK enzyme was inactivated by keeping the tubes at 70° C. in a water bath for 15 min. The reaction mixture was dried on speed vac evaporator before carrying out the coupling reaction. Coupling of the phosphorothioate RNA oligo with biotin was done by mixing 45 μl of potassium phosphate (KHPO$_4$), pH 8.0 buffer (final concentration, 90 mM), and 5 μl of NIBH (N-iodoacetyl-N'-biotinylhexyldiamine) (final concentration, 2 mM); then, the reaction was kept at 50° C. in a water bath in the dark for 1 h. The NIBH solution was prepared in dimethyl formamide (DMF) by warming to 50° C. in a water bath for 20 min. It was stored at 4° C. in the dark. The coupled biotinylated product was separated from uncoupled RNA on a denaturing 20% denaturing PAGE gel (7 M urea, 29:1 acrylamide:bisacrylamide). The RNA was recovered from the polyacrylamide gel by electroelution and ethanol precipitation. The molecular weight of product was confirmed by MALDI-TOF mass spectrometry.

Biopanning of rRNA (h31) target. Ph.D.-7® (New England Biolabs, Ipswich, Mass.), a 7 mer library, was used for screening. Before starting the screen, a culture of *E. coli* ER2738 cells was grown in LB+tetracycline [35 .mu.g/ml] media. Approximately 25 mu.L of Dynabeads (M–280 streptavidin beads—Dynal Biotech, Oslo, Norway) were added to a 0.1 mL PCR tube. Three tubes were used for both modified and unmodified h31 target. The target was run in 2 tubes (identical target) and the control in the 3rd tube. The PCR tubes were placed in a magnetic holder and bead storage buffer was removed. The beads were washed three times with 100 μL of buffer A (0.1 M NaOH, 0.05 M NaCl). During washing, tubes were set on the magnetic holder and the supernatant was removed by pipetting. Beads were then washed once with 100 μL of buffer B (0.1 M NaCl) followed by 1× Fish binding buffer (10 mM Tris-Cl, pH 8.0, 1 M NaCl). Fifty pmoles of biotinylated h31 (modified or unmodified) rRNA and 50 μl of 2× Fish binding buffer were added together with ddH$_2$O to give 100 μl total volume, and the mixture was incubated for ½ hr at RT. At the same time, another set of beads that were washed with buffer A and buffer B, were then washed with RNA/phage washing buffer (10 mM Tris-Cl, pH 7.5, 10 mM MgCl$_2$, 150 mM NaCl, 1 mM DTT). Ten microliters of phage library (2×10$^{11}$ phage particles) were added to the beads with 90 μl RNA/phage binding buffer and incubated for ½ hr at RT. The supernatant was taken out, which comprises the pre-screened phage library. This library was titered to quantify the phage concentration. This pre-screening step was carried out to remove phage with non-specific binding to beads and tubes. The tubes with beads in which target RNA was bound were washed twice with 100 μl of RNA/phage binding buffer to remove unbound biotinylated RNA. The pre-screened phage library was stored in RNA/phage binding buffer. Approximately 2×10$^{11}$/15 μl pre-screened phage library, 8 μl of E. c tRNA$^{Phe}$ (30 pmole), 10 μl of 10×RNA/ phage binding buffer, 67 μl of DEPC (diethylpyrocarbonate) treated water was added to h31 RNA-bound magnetic beads and incubated at room temperature for ½ hr. Thirty pmoles of tRNA$^{Phe}$ was added in every round as a competitor so that any non-specific RNA binding phage could be removed. Following incubation, the unbound phages were removed by washing the tubes with 200 μl of RNA/Phage washing buffer containing 0.1% Tween-20 (Fisher Scientific) 12 times as shown in Table 7. During washing, the tubes were kept in the magnetic holder and incubated for one minute after the addition of washing buffer. After washing was done, the bound phage were eluted from the beads non-specifically by incubation with 100 μl of elution buffer (0.2 M glycine-HCl, pH 2.2, 1 mg/ml BSA) for 9 min followed by mixing with 15 μl of neutralization buffer (1 M Tris-HCl, pH 9.1). The eluant represents the unamplified phage pool, which was amplified by infecting *E. coli* cells (described in next section). This step of enrichment ensured that the phage quantity was sufficient for the next round of selection. After the first round, the amplified phage library was not prescreened against magnetic beads/tubes before starting the round. The stringency of washing was increased by changing the number of washes and amount of Tween-20 in consecutive rounds (Table 7). The beads were washed 16 times in the second round and 24 times in the round 3 with buffer containing 0.3% Tween-20. The concentration of Tween-20 was increased to 0.5% in the fourth round with the same washing conditions as round 3.

Amplification of phage. The overnight culture of ER2738 cells was diluted to 1:100 in 20 mL of LB/Tet medium. Unamplified phage (10 μl) was added to the diluted cells and allowed to grow for 4.5 h at 37° C. in an air shaker. After transferring the culture into an Oakridge tube, it was centrifuged for 10 min at 10,000×g at 4° C. Almost two thirds of the supernatant was transferred into another tube and ⅙ volume of 20% PEG (polyethylene glycol)/2.5 M NaCl was added to precipitate the phage particles. The tubes was kept overnight at 4° C. and on the following day, it was centrifuged at 10,000×g for 15 min at 4° C. After removing the supernatant, the pellet was dissolved in 1 mL TBS buffer (50 mM Tris-Cl, pH 7.5, 150 mM NaCl). The pellet was completely dissolved by vortexing and transferred to a 1.7 ml microcentrifuge tube. Again, ⅙ volume of 20% PEG/2.5 M NaCl was added and the solution was kept on ice for 45 min. The phage particles were pelleted by centrifuging for 5 min at 10,000×g. Finally, the pellet containing the amplified phage was dissolved in 100 μl of TBS buffer and stored at 4° C. The number of phage particles was determined by a plaque assay.

Plaque assay. Phage were grown on LB-Xgal/IPTG/Tet plates. Due to the presence of the lacZ gene on the phage plasmid, the plaques turn blue in the presence of Xgal/IPTG. The plates were pre-warmed at 37 C. The low melting agar was prepared and aliquoted into 3 mL portions in 13 mM sterile tubes. The tubes with low melting agar were stored in a 50.degree. C. water bath until use. Serial dilutions of both amplified and unamplified phage was done. For unamplified phage, 10 μl of eluted phage were diluted up to $10^{-5}$, for amplified phage, the dilution was made up to $10^{-11}$. Next, 200 μL of 1:80 dilutions of overnight culture of ER2738 cells were added to each 0.7 mL microcentrifuge tube. Finally, 10 μL of diluted phage were added to the 0.7 mL microcentrifuge tube containing diluted ER2738 cells. After mixing serially diluted phage with ER2738 cells, they were kept at room temperature for 1-3 minutes. The warm top agar was mixed with phage infected *E. coli*, vortexed briefly, and immediately poured on top of the pre-warmed LB/X-gal/IPTG/Tet plate. The plates were kept for 10-15 minutes for complete solidification and were incubated at 37° C. incubator for about 15-18 hrs. The next day, blue plaques of phage were observed. For each dilution, the number was counted from each plate and plaque-forming units (pfu) were determined by multiplying the dilution factor by the number of colonies. The plaque assay for the unamplified phage was done in a similar way using only five dilutions from $10^{-1}$ to $10^{-5}$. From unamplified phage plaque assay, we can determine the input and output ratio (Tables 6, 8, and 10). Plaque assays were performed before and after each round of selections.

Sequencing of phage clones. Phage were amplified and sequenced at the end of rounds three and four. First, the blue phage plaques were removed from LB/Tet/IPTG/X-Gal plate and dipped into 10 .mu.1 of PCR master mix. The region of peptide in the plasmid was amplified using the appropriate primers (bind in the flanking region of peptide) (Table 6) with the following conditions: denaturation (5 min, 95° C.); cycle: denaturation (15 sec, 95° C.); annealing (15 sec, 55° C.); polymerization (15 sec, 72° C.). This cycle was repeated 29 times and the final polymerization step was carried out for 5 minutes. The amplification step was carried out in 96-well plate (thin wall PCR plate, GENE Mate, Kaysville, Utah). The amplified PCR product was cleaned up using a robotic program. The program was designed in this way: The PCR product (10 mu.1) was mixed with 18 mu.1 of magnetic beads (Agencore® Ampure® beads, Agencourt Bioscience Corporation, Beverly, Mass.) in 96-well PCR plate (Thin wall PCR plate, GENE Mate, Kaysville, Utah) and incubated for 5 min to allow for binding. The plate was then transferred to the 96-well magnetic plate (Agencourt SPRIPlate® 96R—Ring Magnet Agencourt Bioscience Corporation, Beverly, Mass.) and kept for 5 min. The DNA is bound to the magnetic beads and which adhere to the side of tube so that the buffers and reagents from PCR (dNTP, buffers, Ampli Taq polymerase) can be removed. One hundred microliters of 70% ethanol were added, incubated for 5 min, and then removed. This step was repeated twice. Finally, in the elution step, 100 μl of water was added to the beads and the plate was transferred to the non-magnetic holder. The beads were mixed well with water and incubated for 10 min so that DNA would be eluted from the beads. The plate was again transferred to the 96-well magnetic plate and incubated for 10 min to separate the magnetic beads from DNA. The DNA (at the bottom of tube) was transferred to a new 96-well plate. All of these steps were performed on the Biomek® FX instrument, Beckman Coulter Inc. Fullerton, Calif. Finally sequencing reactions were performed by using the primers shown in Table 6.

TABLE 6

Primer sequences used for PCR and sequencing of peptides are shown.

| Primers | Description | Sequence (5' to 3') |
|---|---|---|
| PCR M13 PD1 | Forward primer to amplify peptide region n M13 phage | GCA AGC TGA TAA ACC GAT ACA AT |
| PCR M13 PD2 | Reverse primer to amplify peptide region in M13 phage | CCC TCA TAG TTA GCG TAA CG |
| M13 pd3 (700) | Primer to sequence petide region (700 channel primer) | TCC AGA CGT TAG TAA ATG AA |
| M13 pd3 (800) | Primer to sequence the peptide region (800 channel primer) | TCC AGA CGT TAG TAA ATG AA |

Example #15

Target Preparation

The 18-nucleotide wild-type and unmodified h31 constructs were used as bait for peptide screening in phage display (FIG. 5). The RNA having $m^2G$ and $m^5C$ modified nucleotides was synthesized at the W.M. Keck Foundation, Yale University, CT. The unmodified h31 RNA was purchased from Dharmacon, Inc. The phosphoramidite of $m^2G$ was synthesized and used for the chemical synthesis of modified h31. The RNA was deprotected using manufacturer's instructions and purified by using gel electrophoresis. The purity of the deprotected RNA was confirmed by MALDI-TOF mass spectrometry. The 5'-end of the RNA was biotinylated of a slight modification from published procedure. The 5'-OH group of RNA was phosphorothiolated by reacting with ATP-γ-S and polynucleotide kinase. The 5'-biotinylated RNA was obtained by the coupling of NIBH (N-iodoacetyl-N'-biotinylhexyldiamine) with phosphorothiolated RNA. The product was purified by 15% denaturing polyacrylamide gel electrophoresis and its molecular weight was confirmed by MALDI-TOF mass spectrometry.

Example #16

Screening of Phage Display Peptide Library Using Modified h31 as a Target

Two identical targets of h31 (T1h31, T2h31) and one control with no target (beads only) were freshly prepared for each round of selection. Pre-washed, streptavidin-coated magnetic beads (M-280) were mixed with 5'-biotinylated h31 RNA and allowed to bind in polypropylene PCR tubes at room temperature. The peptide library (Ph.D.-7™, 10 .mu.1, $2 \times 10^{13}$ pfu/ml) was pre-selected against the beads to remove non-specifically binding phage. The supernatant (unbound phage with low affinity for beads and plastic PCR tubes) was titered to quantify the number of phage. After the removal of excess unbound RNA from the RNA-streptavidin complex, about $2 \times 10^{11}$ M13 phage particles from the pre-selected library were added to RNA-streptavidin complex and incubated with TNMD (10 mM Tris-C1, pH 7.5, 50 mM NaCl, 10 mM $MgCl_2$ and 1 mM DTT) buffer. The unbound and weakly bound phage were removed by washing with the same buffer. The bound phage were then eluted and amplified for the next rounds of screening by infecting into a specific E. coli strain. The number of washes and concentration of detergent (Tween-20) were increased in the subsequent rounds of selection to remove any weakly bound and non-specific peptides (Table 7). In each round, 30 pmole of free tRNA was added as a competitor to remove non-specific RNA-binding peptides. In the third round, the biopanning was carried out with and without free unmodified h31 as a counter-selection method. This strategy was used to remove peptides with affinity to unmodified h31 and retain those with affinity for modified h31. The number of bound phage increased with each round of selections, indicating successful enrichment of target-specific peptides (Table 8).

A random peptide library was screened against modified h31 (970 loop) of 16S rRNA to identify peptide ligands. The library was pre-screened to remove non-specific peptides that have higher affinity to beads and plasticware so that they would not get enriched in further rounds of selection. In every round of selection, tRNA was added as a competitor that would help to bypass non-specific RNA-binding peptides. This step helps to obtain target-specific peptides. The number of bound phage was increased with each round of selection (Table 8), indicating the successful enrichment of target-specific peptides. The selection procedure was validated by screening the library against streptavidin beads without adding any target. The number of peptides having-HPQ motifs, which are known binders for streptavidin, were about 65% of the total peptides in the third round and their number increased to approximately 85% in the fourth round of selection (FIG. 43). No peptides isolated from the target have same sequence or motif as peptides isolated from control beads.

TABLE 7

Biopanning conditions using wild-type h31 RNA as a target

| Cycle no. | Cycle 1 | Cycle 2 | Cycle 3 |
| --- | --- | --- | --- |
| No. of washes (200 μl/wash) | 12 | 18 | 24 |
| Tween-20 | 0.10% | 0.10% | 0.30% |
| Target RNA (unmodified h31) | 50 pmole | 50 pmole | 30 pmole |
| Competitor RNA (tRNA) | 30 pmole | 30 pmole | 30 pmole |
| Competitor RNA (tRNA + unmodified h31) | — | — | 30 pmole, each |

In the third round of selection with modified h31 as the target, specific peptides were isolated by using the unmodified h31 as a counter-selection agent. The counter-selection was designed to isolate peptides that have higher affinity to modified nucleotides or regions of h31 than to unmodified h31. Based upon sequence analysis, peptides having-TLW- and -VRP motifs were found in the screens using modified h31 as a target with and without counter-selection against unmodified h31. These peptides are expected to display specific binding to modified h31 and interact with residues m2G966 and m5C967. Out of the five major peptides selected for further study, three of them (DIRTQRE (SEQ ID NO: 6), CVRPFAL (SEQ ID NO: 4), FVRPFAL (SEQ ID NO: 7)) contain arginine at the third position of the seven-amino-acid peptide. The presence of R and Q might enhance interactions with the phosphodiester backbone. Two other peptides (TLWDLIP (SEQ ID NO: 3) and TYLPWPA (SEQ ID NO: 2)) contain aromatic tryptophan and tyrosine residues, which might intercalate with nucleobases of h31.

Peptide clones were sequenced after completion of the third round of screening. For each target, 100 plaques (peptide-bearing phage) were sequenced, so altogether for modified h31 target, 300 clones (including with and without counter-selections) were sequenced. The sequences were analyzed by RELIC software, which is a bioinformatics server for combinatorial peptide analysis (74). The peptides obtained repeatedly in the isolated sequences were TLWDLIP (SEQ ID NO: 3), TYLPWPA (SEQ ID NO: 2), ATPLWLK (SEQ ID NO: 5), DIRTQRE (SEQ ID NO: 6), and FVRPFAL (SEQ ID NO: 7) (FIGS. 39 and 40). The TLWDLIP (SEQ ID NO: 3) and CVRPFAL (SEQ ID NO: 4) peptides were also obtained in the selection in which unmodified h31 was used in the counter-selection step.

TABLE 8

Plaque-forming titration units (pfu) against modiifed h31 in each rounds of screening

| Rounds | Input PFU | Output PFU | % yield |
| --- | --- | --- | --- |
| Pre-screen with beads | $2.0 \times 10^{11}$ | $2.5 \times 10^{10}$ | 0.0125 |
| I | $2.8 \times 10^{11}$ | $2.2 \times 10^{6}$ | $0.08 \times 10^{-4}$ |
| II | $2.5 \times 10^{11}$ | $4.3 \times 10^{6}$ | $0.17 \times 10^{-4}$ |
| III | $2.2 \times 10^{11}$ | $3.1 \times 10^{6}$ | $0.14 \times 10^{-4}$ |

Example #17

Screening of Peptides by Using Unmodified h31 as a Target

A random peptide library was screened against unmodified h31 (970 loop) of 16S rRNA to identify peptide ligands. The library was pre-screened to remove non-specific peptides that have higher affinity to beads and plasticware so that they would not get enriched in further rounds of selection. In every round of selection, tRNA was added as a competitor that would help to bypass non-specific RNA-binding peptides. This step helps to obtain target-specific peptides. The number of bound phage was increased with each round of selection (Table 10), indicating the successful enrichment of target-specific peptides. The selection procedure was validated by screening the library against streptavidin beads without adding any target. The number of peptides having-HPQ motifs, which are known binders for streptavidin (75), were about 65% of the total peptides in the third round and their number increased to approximately 85% in the fourth round of selection (FIG. 43). No peptides isolated from the target have same sequence or motif as peptides isolated from control beads.

We wanted to determine if any common peptide sequences (motifs) would emerge from screening both modified and unmodified h31. The 5'-biotinylated unmodified h31 was used as the target and the selection conditions were similar to those used for modified h31 (Table 9). The number of bound phage increased with each round of selection, indicating successful enrichment of target-specific peptides (Table 10). Peptides were sequenced after the third and fourth round of screening. After analyzing the peptide sequences, two major peptides (HHHPPLA and KPFHNST) were the most abundant (FIGS. 41 and 42). Both peptides are rich in polar residues. None of the peptides isolated from the unmodified h31 target matched those from the modified h31 screen.

TABLE 9

Biopanning conditions using unmodified h31 RNA as a target

| Cycle no. | Cycle 1 | Cycle 2 | Cycle 3 | Cycle 4 |
|---|---|---|---|---|
| No. of washes (200 µl/wash) | 12 | 18 | 24 | 24 |
| Tween-20 | 0.10% | 0.10% | 0.30% | 0.50% |
| Target RNA (unmodified h31) | 50 pmole | 50 pmole | 30 pmole | 30 pmole |
| Competitor RNA (tRNA) | 30 pmole | 30 pmole | 30 pmole | 30 pmole |

TABLE 10

Plaque-forming titration units (pfu) against unmodiifed h31 in each rounds of screening

| Rounds | Input PFU | Output PFU | % of yield |
|---|---|---|---|
| I | $2.1 \times 10^{11}$ | $3.2 \times 10^5$ | $0.015 \times 10^{-4}$ |
| II | $3.6 \times 10^{11}$ | $4.3 \times 10^6$ | $0.12 \times 10^{-4}$ |
| III | $2.3 \times 10^{12}$ | $5.2 \times 10^7$ | $0.22 \times 10^{-4}$ |
| IV | $2.5 \times 10^{11}$ | $2.6 \times 10^6$ | $0.010 \times 10^{-4}$ |

In control experiments, peptides were isolated from screening against streptavidin beads. The conditions used for screening and total input and output ratios of phage are shown in Tables 9 and 10, respectively. Sequence analysis showed a consensus sequence with the conserved HPQ motif (FIG. 43). The S/T/N L L/IN H P Q peptide is a known binding sequence for streptavidin. A BLAST (basic alignment search tool) search of the selected peptides revealed motifs that are found in different classes of RNA enzymes (FIG. 44). The SILPYPY peptide was seen in some of the selections with modified h31 RNA target (third round) and unmodified h31 RNA target (fourth round) respectively. They were also found in selection against the h9 and h23 of 16S rRNA and S20 protein of 30S subunit. Peptide sequences, LPLTPLP and HAIYPRH identified in the fourth round of screening of unmodified h31 (data not shown) and were considered as non-specific RNA-binding peptides because they were also found in selection against the A-site of 16S rRNA.

Screening with unmodified h31 revealed two major peptides, HHHPPLA (SEQ ID NO: 8) and KPFHNST (SEQ ID NO: 9) in round 3. They are mostly polar and rich in histidine residues. The —HHP or —HPP motifs were also seen in some other peptide sequences (FIGS. 41 and 42) indicating unique recognition motifs for the unmodified h31. Interestingly, we did not find any identical peptides between modified and unmodified h31. This difference might be due to altered RNA loop structures for modified and unmodified h31. The peptides might have shown specificity to either modified or unmodified h31, depending on the structure and dynamics their loop regions. From biophysical studies, it has been shown that the modified nucleotides of the h310f *E. coli* slightly destabilize the loop. A high resolution crystal structure of *T. thermophilus* in the presence of tRNA and mRNA shows a flipped out conformation of $m^2_2G966$. The loop needs to be mobile for accommodation of P-site tRNA as revealed by the *E. coli* 70S ribosome structure complexed with tRNA and mRNA. From sequence alignment of peptides with other known proteins of *E. coli*, slight homology with several RNA modifying enzymes and tRNA synthetases was found. Those peptide motifs might be important for the recognition of target RNA for modification, whereas other amino acids in the peptide contribute to specificity to the modified nucleotides.

TABLE 11

Biopanning conditions using beads (no target)

| Cycle no. | Cycle 1 | Cycle 2 | Cycle 3 | Cycle 4 |
|---|---|---|---|---|
| No. of washes (200 µl/wash) | 12 | 18 | 24 | 24 |
| Tween-20 | 0.10% | 0.10% | 0.30% | 0.50% |
| Target RNA | — | — | — | — |
| Competitor RNA (tRNA) | 30 pmole | 30 pmole | 30 pmole | 30 pmole |

TABLE 12

Plaque-forming titration units (pfu) against beads (no target)

| Rounds | Input PFU | Output PFU | % of yield |
|---|---|---|---|
| I | $2.0 \times 10^{11}$ | TNTC up to $10^{-5}$ dilution | — |
| II | $2.7 \times 10^{11}$ | Lawn up to $10^{-5}$ dilution | — |
| III | $2.1 \times 10^{12}$ | Lawn up to $10^{-5}$ dilution | — |
| IV | $3.1 \times 10^{11}$ | $1.0 \times 10^7$ | $0.32 \times 10^{-4}$ |

(TNTC—too many too count)

Example #18

Coupled in vitro Transcription-Translation Inhibition Assay

Peptides with high frequency in the screening against wild-type h31 were synthesized. The peptides (DIRTQRE (SEQ ID NO: 6), CVRPFAL (SEQ ID NO: 4), FVRPFAL (SEQ ID NO: 7), TLWDLIP (SEQ ID NO: 3) and TYLPWPA (SEQ ID NO: 2)), were synthesized and their sequences were determined from the phage display experiments. The inhibitory effects of these peptides on cellular processes were determined by in vitro coupled transcription-translation inhibition assay. The PURExpress™ in vitro protein synthesis kit # E6800S from New England Biolabs (NEB) was used for this purpose. This kit contains all of the necessary components for the transcription and translation, except for the DNA template. The amounts of reagents from the kit were added according to the NEB manual. We used a DNA template for GFP (pRSETEmGFP plasmid) at a concentration of 10 µg/ml in a 15 µl of reaction volume. Different concentrations of peptides were added, ranging from 300 µM to 2 mM. The DNA template was added only after mixing of the peptides or streptomycin so that they can bind to their target region. For the control, streptomycin was added at a final concentration of 300 µM. The reaction was incubated in 384-well, Costar, clear-well, black plates and in situ incubated at 37° C. in the fluorometer. The amount of GFP translation was monitored at different intervals of time from 0 min to 2 h by fluorescence (excitation at 487 nm, emission at 509 nm) using a Gemini XPS microplate spectrofluorometer, (Molecular Devices).

A cell-free translation assay was used to test the inhibitory effects of the peptides on protein synthesis. The pRSETEmGFP plasmid that was used as template has an EmGFP gene under control of the T7 promoter (FIG. 48). Upon transcription with T7 polymerase, EmGFP mRNA was formed and undergoes translation by ribosomes to produce the green fluorescent protein (GFP). The degree of inhibition on transcription and translation due to the presence of peptide could be determined by measuring the level of GFP fluorescence. *Escherichia coli* S30 extracts were used, which contained all of the necessary factors and supplements for translation. The rate of GFP translation in the presence or absence of peptide was measured at different time intervals. Streptomycin was used as a positive control and no GFP translation was observed upon treatment with 300 μM of the antibiotic. Five different peptides were tested, and out of them, FVRPFAL (SEQ ID NO: 7) and CVRPFAL (SEQ ID NO: 4) showed the best inhibitory effects and the DIRTQRE (SEQ ID NO: 6) did not inhibit transcription or translation even up to 2 mM (FIG. 45). All of the peptides showed a concentration-dependent inhibition of transcription and translation (FIGS. 46 and 47).

From in vitro protein translation inhibition assays, CVRPFAL (SEQ ID NO: 4) and FVRPFAL (SEQ ID NO: 7) showed strong inhibitory effects as compared to others. They showed similar level of inhibition, which could be due to the presence of a common motif. They are different only in first amino acid position. DIRTQRE (SEQ ID NO: 6) showed the least inhibitory effect. The order of translation inhibition by peptides (from high to low) is as follows: CVRPFAL (SEQ ID NO: 4), FVRPFAL (SEQ ID NO: 7)>TLWDLIP (SEQ ID NO: 3)>TYLPWPA (SEQ ID NO: 2)>DIRTQRE (SEQ ID NO: 6). Concentration-dependent inhibitory effects of the peptides were observed for all peptides. Therefore, peptides targeting h31 of 16S rRNA have been identified and could be used as future drug molecules after refinement by peptidomimetics.

Example #19

General Procedures for Examples 20-22

HPLC purification methods. The crude peptides required HPLC purification prior to binding studies. This step eliminated salt as well as other contaminants, such as failed sequences, organic reagents, etc., which may otherwise interfere with the binding studies. Purification was performed on a Luna® (Phenomenex) C18 reverse-phase column (250×10 mm) with water (0.05% TFA) as the mobile phase A and acetonitrile (0.05% TFA) as the mobile phase B at a flow rate of 5 μL/min. As a starting point, the lyophilized peptide was dissolved in water to form a 8-10 mg/ml solution, and a portion of it was then subjected to a test run at a gradient from 90% to 40% mobile phase A over a period of one hour. The subsequent method was then optimized based on the gradient at which the peptide was eluted in the test run. For the bulk purification, the lyophilized peptide was dissolved in water to give a 50-100 mg/mL solution, depending on the peptide solubility. The relevant fraction was collected and lyophilized to obtain the pure peptide. The HPLC traces corresponding to crude and purified peptides are given in the Appendix 5.

MALDI-TOF mass spectrometric methods. The synthetic peptides were characterized by MALDI-TOF mass spectrometry. A saturated matrix was made by dissolving 10 mg of α-cyano-4-hydroxycinnamic acid (α-cyano CHCA: Sigma-Aldrich®) in 1 mL of 50% acetonitrile in 0.05% TFA solution. This solution, in general, can be used for a long period of time (~one year). The sample can be prepared by dissolving the purified peptide in 25% acetonitrile to give a 3-5 mg/mL solution. First, 10 μL from the saturated matrix was transferred to a small tube. To this, 1-10 μL of sample was added depending on its concentration and vortexed. Then, 2 μL from the resulting mixture was spotted onto the MALDI plate. Once the liquid was evaporated, the sample was used for the analysis.

RNA sample preparation. The RNA samples (ECh31WT) used in this study were chemically synthesized and purified as described in Chapter 4, Section 4.5.1. Three different versions of the ECh31 WT construct were employed for the binding experiments.

For circular dichroism experiments, h31 RNA was directly used without further processing or labeling. For the fluorescence experiments, the ECh31WT construct was 5' labeled with fluorescein as described in Chapter 3, Section 3.5.2. For the SPR kinetic experiments, the ECh31WT construct was 5' labeled with biotin as described in Chapter 3, Section 3.6.2.

Quantification of peptides. The concentration of the peptide sequences containing tryptophan or tyrosine was calculated based on the molar extinction coefficients ($\epsilon_{280}$) of these residues ($\delta^{Trp}$=5560 and $\epsilon^{Tyr}$=1200 AU/mmole/mL).[22] Since the extinction coefficients of chromophores in a given peptide sequence are additive, the overall molar extinction coefficient (e) of the peptide depends on the types and number of chromophores. Therefore, the milligrams (mg) of peptide in one milliliter (mL) of solution is given by the equation ($A_{280}$× MW×DF)/ε, where $A_{280}$ is the absorbance of the peptide, MW is the molecular weight of the peptide, DF is the dilution factor, and E is the total molar extinction coefficient of the peptide. For example, if the peptide has two tryptophan residues and one tyrosine residue, then the value ε is given by [(2×5560)+(1×1200)].

The concentration of GFP-fused peptides were determined by using a Micro BCA protein assay kit (Pierce™).[23] This method of detection is based on the reduction of $Cu^{2+}$ by protein in an alkaline medium, a strategy similar to the biuret assay.[24] Then, the reduced $Cu^+$ is colorimetrically detected by bicinchoninic acid (BCA).[25]

Circular dichroism (CD) studies. All CD measurements were done on a Chirascan™ circular dichroism spectrophotometer at 25° C. using a 1 cm pathlength quartz CD cuvette.

Structural characterization of peptides by CD. The peptides were dissolved in 10 mM HEPES-KOH, 100 mM KCl, 1 mM $MgCl_2$, 0.5 mM EDTA, and 0.01% Triton-X-100 at pH 7.5 to obtain a 0.5 mg/mL solution. The spectra were obtained by scanning in the range of 180 nm to 250 nm.

Binding studies with CD. The titration was performed by adding increasing concentrations of peptide (10-80 μM) to 1 mL of 0.5 μM ECh31WT RNA in 10 mM sodium phoshate, 100 mM NaCl, 0.1 mM $Na_2$EDTA at pH 7, and incubated for 2 min for each concentration point followed by spectrum scanning. Prior to titration, the RNA was renatured as described in Chapter 3, Section 3.2.2. RNA-peptide binding was determined by observing CD changes at 270 nm upon addition of peptide to the sample. The CD at 270 nm was converted to a fraction bound ratio and the dissociation constant ($K_D$) of RNA-peptide binding was determined by curve fitting using the Kaleidagraph™ 3.0 program, as described in Chapter 3, Section 3.2.4.

Fluorescence methods. Fluorescence measurements were taken on a RF-5301PC spectrofluorometer (Shimadzu) at 25° C. using a 1 cm path-length quartz fluorometer cell. The emission spectra were acquired by scanning between 500 and 600 nm with an excitation wavelength of 494 nm, slit widths of 3 nm for excitation and emission. The fluorescent titrations were performed by adding increasing concentrations of peptide (5-150 μM) to 350 μl of 0.5 μM 5'-fluorescein-labeled helix 31 RNA in HEPES buffer (10 mM HEPES, 50 mM NaCl, 1 mM Na2EDTA at pH 7.5) and incubated for 2 min for each concentration point followed by spectrum scanning. Prior to titration, the RNA was renatured as described in Chapter 3, Section 3.5.2. RNA-peptide binding was determined by quenching of the fluorescence intensity upon addition of peptide to the sample. The fluorescence intensity at 523 nm was converted to a fraction bound ratio and the dissociation constant ($K_D$) of RNA-peptide binding was determined by curve fitting using the Kaleidagraph™ 3.0 program, as described in Chapter 3, Section 3.5.3

SPR methods. All immobilization and subsequent binding studies were performed using a BIAcore 2000 instrument set at a temperature of 25° C. Standard dextran surface BIAcore sensorchips (Sensor chip CM5) were purchased from BIAcore. Standard desorb and sanitize routines were performed according to the BIAcore guidelines before docking a new CM5 sensor chip. All buffers were filtered through sterile 0.2 µm nylon membranes (Millipore™) under vacuum. Before derivatizing the flow cells with streptavidin, the CM5 sensor chip was pre-conditioned using three successive 10 µl injections of chip-preparation solution (10 mM NaOH, 500 mM NaCl) at 100 µl/min, followed by a normalization routine using BIAnormalizing solution (40% glycerol). Streptavidin derivatization was performed as described in Chapter 3. Prior to immobilization, the solution of biotinylated RNA in HBS-EP buffer (10 mM HEPES, 3 mM EDTA, 150 mM NaCl, 0.005% P20 at pH 7.4) was renatured by heating to 90° C. for 2 min followed by placing on ice. Flow cells were functionalized by injecting 30 µl of RNA at a time using the MANUAL INJECT command at a flow rate of 10 µl/min, until the desired immobilization level is reached. One of the flow cells was used to immobilize RNA (typically FC4), while another one adjacent to it (FC3) remained unmodified to serve as a blank-control for matrix effects. Levels of RNA captured were calculated by subtracting response units after injection from response units before injection for each flow cell. After RNA immobilization, FC3 and FC4 were blocked with 100 µL of 1 mg/mL biotin at 5 µL/min.

Peptide samples were prepared by serial dilutions from stock solutions into micro-centrifuge tubes. Dilutions are made by the same running buffer to avoid buffer mismatches. All procedures for binding were automated, as optimized methods using repetitive cycles of sample injection and regeneration. Typically, running buffer (10 mM Tris.HCl, 150 mM NaCl, 10 mM $MgCl_2$, 1 mM DTT, 0.005% (v/v) P20 at pH 7.5) was injected for ~30 min prior to experiment to establish a stable baseline value. Peptide solutions (200 µL) were injected at a kinetic flow rate (50 µL/min), using the KINJECT command. All peptide samples were injected from 7 mm plastic vials (BIAcore) that were capped with pierceable plastic-crimp-caps to minimize carry-over and sample evaporation. Samples were injected in order of increasing concentration. The surface was regenerated using 150 µL of 500 mM NaCl solution. The data were fit to a 1:1 binding Langmuir model using BIAevaluation 3.0.

Example #20

Fmoc SPPS of Phage-Display Selected Peptides 7-Mer Peptides

Phage display is a biological system that facilitates the cloning and rapid selection of peptides from large combinatorial libraries.[1, 17] The phage display library is a large, heterogeneous mixture of phage clones, each carrying a different foreign DNA insert, and therefore displaying a different peptide on the surface.[2] An in vitro selection process called biopanning allows rapid identification of peptide ligands from this library. Biopanning was carried out by incubating the phage peptide library with the immobilized target (in this case the above-mentioned helix 31 wild-type construct), removing the unbound phage and eluting the target-bound phage. The eluted phage were amplified in cells to obtain a large crop of progeny phage, and these were then subjected to additional binding/amplification cycles to enrich the pool with the best binders.[3] This phage-display procedure was carried out by Tek Lamichhane, in collaboration with the Cunningham laboratory.

In order to accomplish the above strategy, we constructed the wild-type *E. coli* h31 with its 5' end biotinylated (Chapter 3). This step allowed the hairpin RNA to be immobilized onto a streptavidin-coated plate. Counterselection of ligands that can bind preferably to *E. coli* h31 over the h31 of *H. sapiens* has allowed us to come up with lead peptides as potential new bacterial anti-infectives (Table 13). The selected peptides were chemically synthesized or cloned so that they could be studied further. The chemical structures of the five peptides are shown in FIG. 49.

Individual peptides based on the sequence from phage display were prepared so that they can be further characterized for their affinities by biophysical techniques. During the screening process, the C-termini of peptides are not free. The peptides were displayed with the free N-termini exposed to the environment and the C-termini linked to the minor coat protein (P3) of M13 phage through a short spacer forming an amide bond. Therefore, the peptides were chemically synthesized on Rink Amide AM resin and obtained in their amidated forms as shown in FIG. 49. This modification was done in order to mimic the conformation of peptide displayed on phage surface.

General procedure for the Fmoc 7-mer SPPS. All syntheses utilized Rink amide resin (Novabiochem®) preloaded with a 4-(2',4'-dimethoxyphenyl-Fmoc-aminomethyl)-phenoxyacetamido-norleucylaminomethyl linker. This resin has a theoretical substitution level of 0.68 mmol/g. Generally, 250 mg of resin was used for each synthesis. Therefore, 0.17 (0.68× 0.25) mmol of theoretical sites are available for coupling. First, 250 mg of resin was loaded into the peptide synthesis reaction vessel mounted on a wrist-action shaker. The initial suspension and swelling of the resin (45 min) took place with shaking using dichloromethane (DCM) followed by washing with dimethyl formamide (DMF). The procedure consisted of iterative deprotection, coupling, and washing steps. Fmoc deprotection was accomplished by treatment with piperidine-DMF (25% (v/v); 10× the resin volume) for 10 min with shaking, and a repeat with fresh deprotection solvent for 10 min, followed by DMF (5 times with 10× the resin volume) and DCM (5 times with 10× the resin volume) washing. Sequential coupling of residues involved mixing of Fmoc amino acid (3×0.68×0.25 mmol), DIC (4×0.68×0.25 mmol), HOBt (6×0.68×0.25 mmol), and DMF (5× the resin volume) with gentle shaking for 2 h. The side-chain protected Fmoc amino-acids were purchased from Novabiochem® (Appendix 3 and 4). The Kaiser test was used to confirm complete coupling, as indicated by a negative result; if the coupling was incomplete, additional DIC (4×0.68×0.25 mmol) was added and the vessel was shaken for an additional 2 h. If the coupling was complete, then the solution was drawn off, and the resin was washed with DMF (10× the resin volume). Coupling and deprotection steps were repeated for each added residue, with intervening washing steps (DMF, 10× the resin volume). After the final Fmoc deprotection, the resin was washed with DCM, DMF, ethyl ether, and acetone (twice each, 10× the resin volume). Finally, resin cleavage solution [5× the resin volume, TFA/TIS/thioanisole/anisole, 92:4:2:2 (v/v)] was added with shaking for 2 h. The solution was collected and separated equally into two 50 mL Falcon™ tubes, followed by addition of ethyl ether (−80° C.) to reach 80% of the total tube capacity. The solution was mixed, and the peptide precipitate formed immediately. After centrifugation (8 min at 6000 rpm), the supernatant was decanted, fresh ether was added, and the pelleted peptide was mixed prior to another round of centrifugation (repeated three additional times). Finally, the peptide was dissolved in distilled water (5-10 mL), frozen, and lyophilized for 24 to 48 h until a white powder was obtained.

As mentioned, the Kaiser test was used for the qualitative determination of coupling and deblocking. The Kaiser-test solutions contained the following components: Solution A—ninhydrin in ethanol (5% w/v), Solution B—phenol in ethanol (4:1, w/v), and Solution C—potassium cyanide in pyridine (2% v/v from a 1 mmol/L aqueous solution). The test was performed by adding 4 drops of solution A, 2 drops of solution B, and 2 drops of solution C to a tiny amount (<0.5 mg) of pre-washed resin contained in a small test tube. The test tube was heated to 100° C. for ~2 minutes. A blue color in the beads was considered as a positive result, indicative of an incomplete coupling reaction.

TABLE 13

The round-4 sequences obtained after biopanning ECH31WT RNA against a 7-mer phage library are summarized.

| Peptide (sequence) | Frequency |
|---|---|
| 14 (TLWDLIP) | 5 |
| 15 (CVRPFAL) | 5 |
| 16 (FVRPFPL) | 6 |
| 17 (TYLPWPA) | 5 |
| 18 (DIRTQRE) | 4 |

Example #21

Characterization of Peptides

The chemically synthesized peptides were purified by semi-preparative reverse-phase HPLC. Subsequently, the peptides were characterized using MALDI-TOF mass spectrometry and circular dichroism spectroscopy.

MALDI-TOF mass spectrometry. The peptide sequences were confirmed by checking for the correct molecular weights as shown in FIGS. 50 and 51.

Circular dichroism studies. In order to gain some information about the peptide behavior in solution, we investigated the peptide conformation by circular dichroism (CD) spectroscopy. The CD spectra were acquired in 10 mM HEPES-KOH, 100 mM KCl, 1 mM $MgCl_2$, 0.5 mM EDTA, and 0.01% Triton-X-100 at pH 7.5 (FIGS. 52 and 53).

The data indicate the formation of α-helices by 14 (TLWDLIP (SEQ ID NO: 3)) and 17 (TYLPWPA (SEQ ID NO: 2)); where as the other three peptides appear to have random coil or other undefined structures. The presence of proline in many of the sequences has made the peptides behave more like polyproline type structures.

Example #22

Determination of the Affinity of Phage-Display-Selected Peptides for h31

Once the peptides were synthesized, our goal was to find a suitable biophysical method to characterize the peptide-RNA interactions. These studies involved determination of binding affinities (equilibrium constants (Kd)) of peptides with the *E. coli* helix 31 hairpin RNA. Fluorescence, circular dichroism, and surface plasmon resonance (SPR) methods were employed to obtain Kd values for selected peptide-RNA interactions. Primarily, experiments were carried out with 17 (TYLPWPA (SEQ ID NO: 2)), because preliminary experiments with this peptide gave the most promising results.

Fluorescence titration assay. Helix 31 RNA was 5'-labeled with fluorescein (as described in Chapter 3) to monitor conformational changes in helix 31 upon binding of the peptide. A sample containing 0.5 µM of helix 31 was titrated with increasing concentrations of 17 (TYLPWPA (SEQ ID NO: 2)) (0-150 µM) in 10 mM HEPES, 50 mM NaCl, 1 mM Na2EDTA at pH 7.5. In this experiment, the fluorescence intensity decreased upon increases in the peptide concentration (FIG. 54); however, the percent change in the observed fluorescence intensity was fairly small (7%). One possible reason for this observation may be due to the quenching of fluorescein by the 5'-guanosine residue to which it is attached.

Hyperbolic curve fitting gave an apparent $K_D$ value of 27±4 µM ($R^2$=0.97) and the Hill plot analysis indicated a single binding site (n=1.1) on the h31 target RNA (FIG. 55). The relatively poor fits may be a result of the fact that the fluorescence changes are quite small leading to greater error. For these reasons, we decided to attempt for other methods to verify or confirm the fluorescence results. Alternatively, the curve shapes indicate possible coorperativity in the peptide-RNA interactions.

Figure 56A:
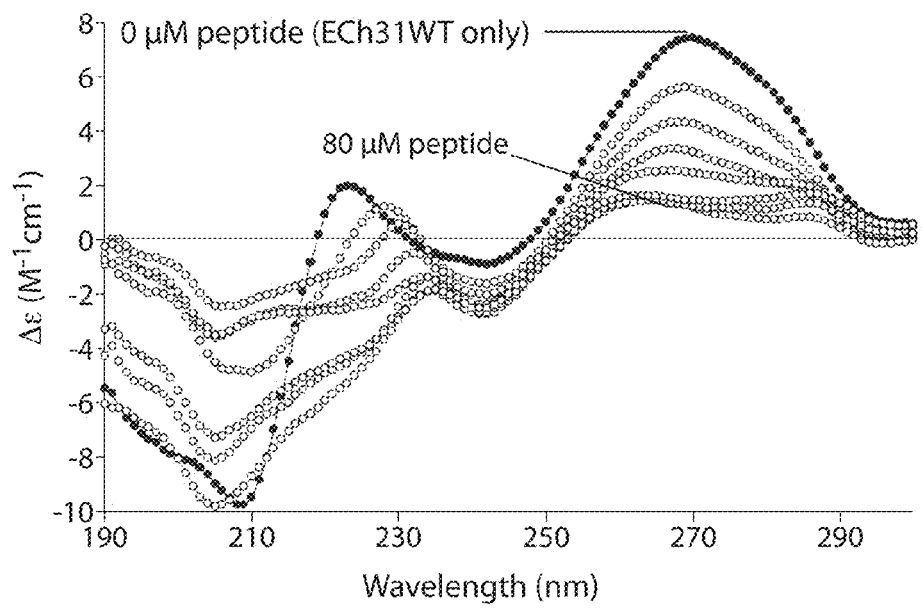
Figure 56B:
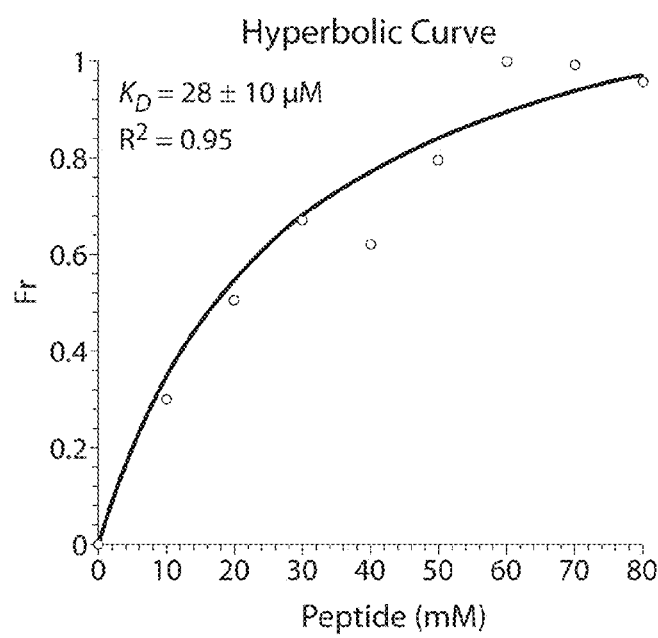

Circular dichroism studies. CD was employed to assess the conformational changes in helix 31 upon binding of the peptide. A sample containing 0.5 µM helix 31 was titrated with increasing concentrations of 17 (0-80 µM) to obtain the spectra as shown in FIG. 56A. Conformational changes in helix 31 measured by circular dichroism spectroscopy was performed in 100 mM NaCl, 10 mM sodium phosphate, and 0.1 mM $Na_2EDTA$ at pH 7. The observed CD at 270 nm was converted to a fraction bound ratio using $Fr=(F_0-F_i)/(F_0-F_f)$ where $F_r$ is the fraction of RNA bound, $F_0$ is the CD of free RNA, $F_i$ is the CD at a given titration point, and $F_f$ is the CD at the end point of the titration. The dissociation constant (KD) of RNA-peptide binding was determined by plotting $F_r$ versus peptide concentration, and by curve fitting to Equation, $F_r=[P]^n/([P]^{n+K_D^n})$ where [P] is the peptide concentration, n is the Hill coefficient, and $K_D$ is the apparent dissociation constant (FIG. 56B). The hyperbolic curve fitting gave an apparent $K_D$ value of 28±10 µM ($R^2$=0.95) for the peptide-RNA interaction, consistent with the result from fluorescence spectroscopy. The curve fittings for the CD data also gave poor fits. That may possibly be due to coorperative binding or peptide aggregation effects.

The decrease in RNA CD signal upon increasing the peptide concentration implies a decrease in the helicity of the hairpin RNA. Interestingly, this may be due a destabilization of the hairpin RNA upon peptide binding. Further studies are underway (in collaboration with the SantaLucia group) to verify this effect by NMR spectroscopy.

SPR spectroscopic analysis. Helix 31 RNA was labeled with biotin (as described in Chapter 3) to determine the kinetics of peptide binding by SPR. Initial experiments performed with peptide 17 (TYLPWPA (SEQ ID NO: 2)) as the analyte gave negligible responses due to binding. In order to enhance the signal-to-noise ratio, a GFP-protein-fused peptide (17 (TYLPWPA)-GFP ("TYLPWPA" disclosed as SEQ ID NO: 2)) was used as the analyte (GFP, green fluorescent protein). The fusion protein was obtained by cloning the DNA sequence corresponding to 7-mer peptide sequence with the N-terminus of the GFP gene. The tobacco etch virus (TEV) protease-recognizing sequence was also cloned into the same construct, up field of the peptide gene sequence. Then, the protein was expressedin bacteria. Upon expression, TEV protease enzyme in the cell binds and cleaves the TEV—recognizing peptide sequence, generating the 7-mer peptide attached to the N-terminus of the GFP. This cloning procedure was performed by Tek Lamichhane in collaboration with the Cunningham lab.

Due to its larger size, a peptide fused with GFP has a greater change in refractive index on the SPR surface, hence generating a significant signal response upon binding to RNA. Biotinylated helix 31 RNA was immobilized onto a streptavidin-coated CM5 chip and differing concentrations of 17 (TYLPWPA)-GFP ("TYLPWPA" disclosed as SEQ ID NO: 2) were injected as the analyte. Control experiments were performed by varying the salt concentrations, detergent levels, pH conditions, and flow rates, since these factors could affect the peptide-RNA complex formation in solution. Finally, the apparent dissociation constants were determined under optimized conditions.

A) Salt Concentration Effects

Preliminary experiments were performed with varying salt concentrations (50 to 250 mM NaCl) to determine the salt effects on 17 (TYLPWPA)-GFP ("TYLPWPA" disclosed as SEQ ID NO: 2) binding to h31 RNA. Salt concentration is an important factor that could affect the RNA-peptide interactions. The buffer used for these experiments contained 10 mM Tris.HCl at pH 7.5, 10 mM MgCl2, 1 mM DTT, 0.005% (v/v) surfactant P20, and varying concentrations of NaCl. The results obtained by injecting 50 µM concentration of 17 (TYLPWPA)-GFP ("TYLPWPA" disclosed as SEQ ID NO: 2) are shown in FIG. 57.

The results suggest that there is an enhanced binding of the peptide to the RNA at lower salt concentrations (<150 mM NaCl), possibly due to increased non-specific interactions under such conditions. That is evident from the fast association as well as the very slow dissociation of the peptide (FIG. 57). On the other hand, at higher salt concentrations (>150 mM NaCl), a significant decrease in the response was observed, indicating an overall decrease in the interactions upon increasing salt concentration. Therefore, it was decided to maintain a 150 mM NaCl concentration during the binding studies.

B) Effects of Detergent

Another common way to avoid non-specific binding in SPR is the addition of detergents. These detergents also prevent aggregation of proteins at high concentrations. Varying amounts of polysorbate 20 (P20) were added to the SPR buffer (10 mM Tris.HCl at pH 7.5, 150 mM NaCl, 10 mM MgCl2, 1 mM DTT) to observe any effects from the detergents. The results obtained by injecting 50 µM concentration of 17 (TYLPWPA)-GFP ("TYLPWPA" disclosed as SEQ ID NO: 2) are shown in FIG. 58.

The results indicate a significant decrease in signal upon increasing the detergent concentration, despite the fact that higher amounts of detergent are known to decrease the non-specific binding of the proteins.[19] Therefore, the level of P20 was maintained at 0.005% (V/V) in the subsequent experiments.

C) Effects of Buffer pH

The pI of 17 (TYLPWPA)-GFP ("TYLPWPA" disclosed as SEQ ID NO: 2) is predicted to be 6.20 therefore, if the pH is <6.0 there will be a net positive charge on the protein. In order to observe the effects of buffer-pH on the peptide binding, a series of buffers with varying pH (5.6 to 7.5) were employed (FIG. 59). The resulting sensorgrams showed an enhanced binding at lower pH values, due to enhanced electrostatic interactions between RNA and peptide. This causes an increase in the non-specific binding of the peptide.

The sensorgrams at pH>6.0 showed no significant changes in the response units (RUs). Therefore, it was decided that pH 6.9 to 7.5 is an effective pH range within which the binding experiments could be performed. The above result also suggests that the interaction between 17 (TYLPWPA)-GFP ("TYLPWPA" disclosed as SEQ ID NO: 2) and h31 RNA may be governed by a dominant electrostatic component along with stacking, hydrogen bonding, or metal-mediated binding. Further investigations are necessary to determine these effects conclusively.

D) Effects of Flow Rate

The flow rate is considered as another important parameter that should be investigated in SPR analysis.[21] The reason for this optimization is to eliminate any mass transfer issues during the binding experiments (discussed in Section 3.6.4). Sensorgrams were obtained at different flow rates (40, 50 and 60 µL/min) to determine a suitable flow rate at which the experiments can be performed (FIG. 60).

The results in FIG. 60 clearly indicate mass transfer issues at flow rates of 40 and 60 µL/min, but not at 50 µL/min. At 40 µL/min, the flow provides too many analytes per unit time causing faster binding. Also, the bound species tend to remain bound even at the dissociation phase, because the flow is not high enough to remove the bound analyte (see FIG. 5.18). On the other hand, 60 µL/min flow rate provides lesser amount of analyte per unit time causing less intense signal response. Therefore, a 50 µL/min flow rate was applied throughout the SPR kinetic analysis.

From this point onwards, all the data reported on kinetic analyses of peptide binding to RNA were obtained in 10 mM Tris.HCl, 150 mM NaCl, 10 mM MgCl$_2$, 1 mM DTT, 0.005% (v/v) P20 at pH 7.5 as the running buffer at a flow rate of 50 µL/min.

E) SPR kinetic analysis of the interaction between 17 (TYLPWPA)-GFP ("TYLPWPA" disclosed as SEQ ID NO: 2) and helix 31 RNA By making use of the information gained from the above control experiments, an optimized set of conditions were revealed to investigate the affinity of the peptides to helix 31 RNA. In addition to the aforementioned general control experiments, several specific controls (such as injection time, dissociation time, regenerating salt concentration, etc.) were also performed with respect to each peptide that was employed. Based on the above information, a typical sensorgram that is observed in this study is shown in FIG. 61.

Biotinylated helix 31 RNA was immobilized onto a streptavidin-coated CM5 chip and increasing concentrations of 17 (TYLPWPA)-GFP (0-100 µM) were injected in the KINJECT mode to obtain the data in FIG. 62. The sensorgrams generated were transformed and overlay plots were prepared using the BiaEvaluation software. The data were fit to a Langmuir 1:1 binding model to obtain the kinetic data given in Table 14. Kinetic constants were determined by integration of the experimental data using the differential rate equation $dRU/dt = k_a C(RU_{max} - RU) - k_d Ru$ to obtain $k_a$ and $k_d$ values simultaneously (RU=observed response, $RU_{max}$=maximum response upon saturation, C=analyte concentration, $k_a$=association rate constant, $k_d$=dissociation rate constant). Then, the ratio between $k_d$ and $k_a$ gives the reported dissociation constants ($k_d/k_a = K_D$).

TABLE 14

Affinity data obtained through SPR kinetic analysis of a 1:1 interaction between h31 and 17 (TYLPWPA)-GFP.

| | 17 (TYLPWPA)-GFP |
|---|---|
| $k_a$ (M$^{-1}$s$^{-1}$) | 150 |
| SE | 2.0 |
| $k_d$ (s$^{-1}$) | 4.2 × 10$^{-3}$ |
| SE | 3.8 × 10$^{-5}$ |

TABLE 14-continued

Affinity data obtained through SPR kinetic analysis of
a 1:1 interaction between h31 and 17 (TYLPWPA)-GFP.

|  | 17 (TYLPWPA)-GFP |
|---|---|
| $K_D$ (µM) | 28 ± 1 |
| $\chi^2$ | 0.5 |

Consistent $K_D$ values were obtained for the interaction of 17 (TYLPWPA) with helix 31 from fluorescence, CD, and SPR experiments as summarized in Table 15. The results reveal that the binding of 17 (TYLPWPA) to helix 31 has not been affected by the presence of GFP. From these experiments, peptide 17 (TYLPWPA) is found to have moderate affinity for helix 31.

TABLE 15

The binding affinity of 17 (TYLPWPA) towards h31 RNA
obtained through different biophysical techniques.

| Technique | Observed $K_D$ (µM) |
|---|---|
| fluorescence | 27 ± 4 |
| circular dichroism | 28 ± 10 |
| SPR | 28 ± 1 |

F) SPR kinetic analyses to reveal the interactions of 14 (TLWDLIP)-GFP ("TLWDLIP" disclosed as SEQ ID NO: 3) and 15 (CVRPFAL)-GFP ("CVRPFAL" disclosed as SEQ ID NO: 4) with helix 31 RNA In our next attempt, we extended the SPR kinetic analysis to two other peptides discovered from the phage display technology, namely 14 (TLWDLIP)-GFP and 15 (CVRPFAL)-GFP. Biotinylated helix 31 RNA was immobilized onto a streptavidin-coated CM5 chip and increasing concentrations of 14 (TLWDLIP)-GFP (0-1 µM) and 15 (CVRPFAL)-GFP (0-1 µM) were injected in the KINJECT mode to obtain the data shown in FIG. 63. The sensorgrams generated were transformed and overlay plots were prepared using the BiaEvaluation software. The data were fit to a Langmuir 1:1 binding model to obtain the kinetic data given in Table 16. Quite interestingly, 14 (TLWDLIP)-GFP and 15 (CVRPFAL)-GFP were able to bind to E. coli h31 RNA with relatively high affinities (nM range) compared to 17 (TYLPWPA)-GFP.

TABLE 16

Affinity data obtained through SPR kinetic analysis
of 14 (TLWDLIP)-GFP and 15 (CVRPFAL)-GFP are shown.

|  | 14 (TLWDLIP)-GFP | 15 (CVRPFAL)-GFP |
|---|---|---|
| $k_a$ (M$^{-1}$s$^{-1}$) | 9.3 × 10$^3$ | 1.2 × 10$^4$ |
| SE | 156 | 112 |
| $k_d$ (s$^{-1}$) | 3.1 × 10$^{-3}$ | 2.6 × 10$^{-3}$ |
| SE | 3.3 × 10$^{-5}$ | 1.8 × 10$^{-5}$ |
| $K_D$ (nM) | 330 ± 7 | 230 ± 3 |
| $\chi^2$ | 2.1 | 1.4 |

G) SPR Kinetic Analysis of GFP-Affinity Towards Helix 31 RNA

In order to improve the signal-to-noise ratio in the SPR studies, the peptides were cloned to GFP by molecular cloning techniques (performed by Tek Lamichhane in collaboration with the Cunningham lab) as mentioned earlier. Adequate control experiments were also performed to minimize the non-specific binding of GFP to helix 31. Despite these efforts, a reasonable non-specific interaction was still observed for GFP alone. Therefore, it was necessary to evaluate the affinity of GFP towards helix 31. A control kinetic experiment was performed with free GFP. Biotinylated helix 31 RNA was immobilized onto a streptavidin-coated CM5 chip and increasing concentrations of GFP (0-100 µM) were injected in the KINJECT mode to obtain the data shown in FIG. 64. The data were fit to a Langmuir 1:1 binding model to obtain the kinetic data as given in Table 17.

TABLE 17

Affinity data obtained through SPR kinetic analysis
of a 1:1 interaction between h31 and GFP protein.

|  | GFP |
|---|---|
| $k_a$ (M$^{-1}$s$^{-1}$) | 222 |
| SE | 3.1 |
| $k_d$ (s$^{-1}$) | 4.4 × 10$^{-3}$ |
| SE | 3.6 × 10$^{-5}$ |
| $K_D$ (µM) | 20 ± 1 |
| $\chi^2$ | 1.3 |

Example #23

The Specificity of the Phage display Peptides for ECh31WT RNA—Preliminary Studies The GFP fused peptides were tested for their specificity to ECh31WT RNA by a SPR analysis. The biotinylated RNA constructs were attached to the SA chip in the following order.
Chip A Fc 1=Reference cell (biotin blocked)
  Fc 2=HSh31ECstem
  Fc 3=ECh31WT
  Fc 4=ECh31UNMOD The sensorgrams were acquired in the 2-1, 3-1, 4-1 detection mode.

The affinities for ECh31WT RNA (Fc 3-1) were compared with ECh31UNMOD (Fc 4-1) (FIGS. 79-81). 5 µM neomycin was used as a positive control (FIG. 78).

Additionally, the affinities for HSh31ECstem RNA (Fc 2-1) were studied (FIGS. 82-85).

The affinities for TAR RNA (Fc 2-1) were compared with ECh31WT (Fc 4-3). The RNA constructs were immobilized in the following order:
Chip B Fc 1=Reference cell
  Fc 2=TAR RNA
  Fc 3=Reference cell
  Fc 4=ECh31WT The sensorgrams were acquired in the 2-1, 4-3 detection mode (FIG. 87). 5 µM neomycin was used as a positive control (FIG. 86).

INCORPORATION BY REFERENCE

All of the references including, without limitation, U.S. patents, U.S. patent application publications, published international applications and journal articles cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A peptide consisting of the sequence of SEQ ID NO: 3.
2. A peptide consisting of the sequence of SEQ ID NO: 4.
3. A peptide consisting of the sequence of SEQ ID NO: 5.

* * * * *